United States Patent
Kannan et al.

(10) Patent No.: US 11,576,873 B2
(45) Date of Patent: Feb. 14, 2023

(54) COMPOSITIONS FOR THE TREATMENT OF DRUG-RESISTANT TUMORS AND METHODS OF USE THEREOF

(71) Applicant: THE CURATORS OF THE UNIVERSITY OF MISSOURI, Columbia, MO (US)

(72) Inventors: Raghuraman Kannan, Columbia, MO (US); Dhananjay Suresh, Columbia, MO (US); Soumavo Mukherjee, Columbia, MO (US); Ajit P Zambre, Columbia, MO (US); Anandhi Upendran, Columbia, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 87 days.

(21) Appl. No.: 16/498,234

(22) PCT Filed: Mar. 30, 2018

(86) PCT No.: PCT/US2018/025544
§ 371 (c)(1),
(2) Date: Sep. 26, 2019

(87) PCT Pub. No.: WO2018/183944
PCT Pub. Date: Oct. 4, 2018

(65) Prior Publication Data
US 2021/0100752 A1    Apr. 8, 2021

Related U.S. Application Data

(60) Provisional application No. 62/479,931, filed on Mar. 31, 2017.

(51) Int. Cl.
| | | |
|---|---|---|
| *A61K 9/51* | (2006.01) | |
| *A61K 47/68* | (2017.01) | |
| *A61K 47/69* | (2017.01) | |
| *A61P 35/04* | (2006.01) | |
| *A61K 31/506* | (2006.01) | |
| *A61K 31/517* | (2006.01) | |
| *A61K 31/5377* | (2006.01) | |
| *A61K 33/243* | (2019.01) | |
| *A61K 9/00* | (2006.01) | |
| *A61K 9/19* | (2006.01) | |
| *B82Y 5/00* | (2011.01) | |

(52) U.S. Cl.
CPC .......... *A61K 9/5169* (2013.01); *A61K 31/506* (2013.01); *A61K 31/517* (2013.01); *A61K 31/5377* (2013.01); *A61K 33/243* (2019.01); *A61K 47/6849* (2017.08); *A61K 47/6857* (2017.08); *A61K 47/6935* (2017.08); *A61P 35/04* (2018.01); *A61K 9/0019* (2013.01); *A61K 9/19* (2013.01); *B82Y 5/00* (2013.01)

(58) Field of Classification Search
CPC .............. A61K 9/5169; A61K 47/6857; A61K 47/6935; A61K 47/6849; A61K 31/506; A61K 31/517; A61K 31/5377; A61K 33/243; A61K 9/0019; A61K 9/19; A61P 35/04; B82Y 5/00
See application file for complete search history.

(56) References Cited

U.S. PATENT DOCUMENTS

| | | |
|---|---|---|
| 2011/0034538 A1 | 2/2011 | Croce et al. |
| 2014/0121126 A1 | 5/2014 | Bivona et al. |

FOREIGN PATENT DOCUMENTS

| | | |
|---|---|---|
| WO | 2016/193680 A1 | 12/2016 |
| WO | 2017/011618 A1 | 1/2017 |

OTHER PUBLICATIONS

Vincent et al. (Current Oncology 19(1); S33-S34; 2012).*
Martinez-Aranda et al. (Oncotarget, 6(42); 44254-44274).*
Babu et al. (Nanoparticles for siRNA based gene slicing in tumor therapy (IEEE Trans Nanobioscience. Dec. 2016; 15(8): 849-863).*
Kohn et al. (Gene Expression and Molecular Interactions (2012); 7(5); 18 pages.*
Mukherjee et al., "Dual Inhibition of AXL and FN14 Sensitizes Cisplatin in Resistant Non-Small Cell Lung Carcinoma by Inducing Higher Caspase 3 Cleavage Through FHIT Upregulation, Both in vivo and in vitro", Annals of Oncology, Abstract, 2018, vol. 29.
Whitsett et al., "Mcl-1 Mediates TWEAK/Fn14-Induced Non-Small Cell Lung Cancer Survival and Therapeutic Response", Molecular Cancer Research, Apr. 2014, pp. 550-559, vol. 12, No. 4, American Association for Cancer Research.
Willis et al., "The Fibroblast Growth Factor-Inducible 14 Receptor in Highly Expressed in HER2-Positive Breast Tumors and Regulates Breast Cancer Cell Invasive Capacity", Molecular Cancer Research, May 2008, pp. 725-734, American Association for Cancer Research.
Winkles, "The TWEAK-Fn 14 Cytokine-Receptor Axis: Discovery, Biology and Therapeutic Targeting", Nature Reviews, May 2008, pp. 411-425, vol. 7, Nature Publishing Group.
Wu et al., "AXL Kinase as a Novel Target for Cancer Therapy", Oncotarget, Oct. 16, 2014, pp. 9546-9563, vol. 5, No. 20.
Xiao et al., "IFNy Promotes Papilloma Development by Up-Regulating Th17-Associated Inflammation", Cancer Research, 2009, pp. 2010-2017, vol. 69, American Association for Cancer Research.

(Continued)

*Primary Examiner* — Shirley V Gembeh
(74) *Attorney, Agent, or Firm* — Thompson Coburn LLP; William A. Holtz

(57) ABSTRACT

Provided herein are methods and compositions for sensitizing a cancer cell to a cancer treatment, for example to an anticancer drug by the inhibition of at least two cancer biomarkers. Further provided are methods of treating and/or preventing a cancer including reducing the size of a tumor. Also provided are compositions comprising nanopartides associated with inhibitory molecules, such as siRNA, and/or anti-cancer drugs.

Figure 1:
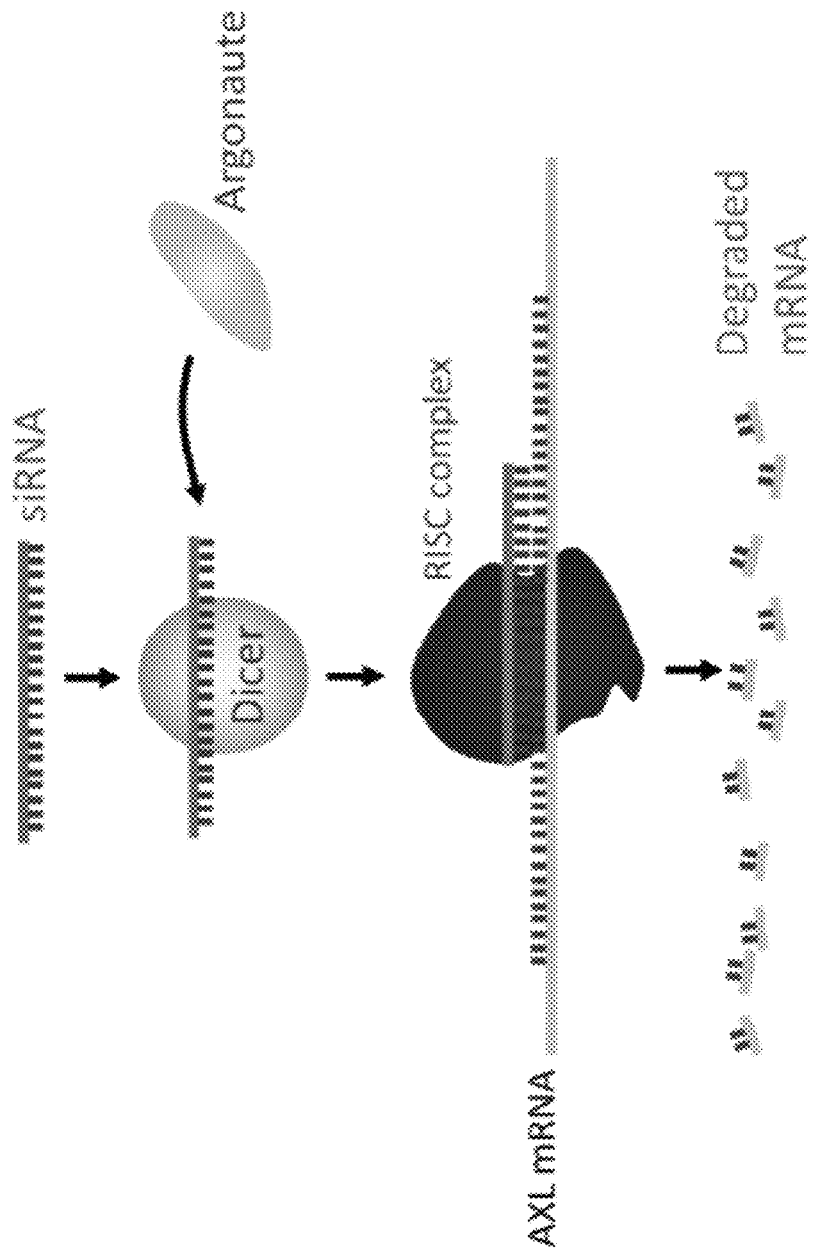

15 Claims, 73 Drawing Sheets
Specification includes a Sequence Listing.

(56) References Cited

OTHER PUBLICATIONS

Xu et al., "Acquired Resistance of Lung Adenocarcinoma to EGFR-Tyrosine Kinase Inhibitors Gefitinib and Erlotinib", Cancer Biology & Therapy, Apr. 15, 2010, pp. 572-582, vol. 9, Issue 8, Landes Bioscience.
Zhang et al., "Activation of the AXL Kinase Causes Resistance to EGFR-Targeted Therapy in Lung Cancer", Nature Genetics, Aug. 2012, pp. 852-862, vol. 44, No. 8, Nature America, Inc.
Zhang et al., "Mcl-1 is Critical for Survival in a Subgroup of Non-Small-Cell Lung Cancer Cell Lines", Oncogene, 2011, pp. 1963-1968, vol. 30.
Zhou et al., "The TWEAK Receptor Fn14 is a Therapeutic Target in Melanoma: Immunotoxins Targeting Fn14 Receptor for Malignant Melanoma Treatment", Journal of Investigative Dermatology, 2013, pp. 1052-1062, vol. 133, The Society for Investigative Dermatology.
Zhu et al., "Peroxisome Proliferator-Activated Receptor-γ Agonist Troglitazone Suppresses Transforming Growth Factor-B1 Signalling Through miR-92b Upregulation-Inhibited Axl Expression in Human Keloid Fibroblasts In Vitro", American Journal of Translational Research, 2016, pp. 3460-3470, vol. 8, No. 8.
Albanese et al., "The Effect of Nanoparticle Size, Shape, and Surface Chemistry on Biological Systems", Annual Review of Biomedical Engineering, 2012, pp. 1-16, vol. 14.
Asiedu et al., "AXL Induces Epithelial-to-Mesenchymal Transition and Regulates the Function of Breast Cancer Stem Cells", Oncogene, 2014, pp. 1316-1324, Macmillan Publishers Limited.
Blanco-Colio, "TWEAK/Fn 14 Axis: A Promising Target for the Treatment of Cardiovascular Diseases", Frontiers in Immunology, Jan. 20, 2014, pp. 1-13, vol. 5, Article 3.
Bonaldo et al., "Cellular and Molecular Mechanisms of Muscle Atrophy", Disease Models & Mechanisms, 2013, pp. 25-39, vol. 6, The Company of Biologists Ltd.
Brown et al., "TWEAK-Independent Fn14 Self-Association and NF-kB Activation is Medicated by the C-Terminal Region of the Fn14 Cytoplasmic Domain", PLOS One, Jun. 2013, pp. 1-11, vol. 8, Issue 6.
Cardnell et al., "Activation of the PI3K/mTOR Pathway Following PARP Inhibition in Small Cell Lung Cancer", PLOS One, Apr. 7, 2016, pp. 1-17.
Chen et al., "Fn14, a Downstream Target of the TGF-B Signaling Pathway, Regulates Fibroblast Activation", PLOS One, Dec. 1, 2015, pp. 1-17.
Chiu et al., "Protumoral Effect of Macrophage Through Axl Activation on Mucoepidermoid Carcinoma", Journal of Oral Pathology & Medicine, 2014, pp. 538-544, vol. 43.
Chorianopoulos et al., "FGF-Inducible 14-kDa Protein (Fn14) is Regulated via the RhoA/ROCK Kinase Pathway in Cardiomyocytes and Mediates Nuclear Factor-KappaB Activation by TWEAK", Basic Research in Cardiology, 2010, pp. 301-313, vol. 105.
Culp et al., "Antibodies to TWEAK Receptor Inhibit Human Tumor Growth Through Dual Mechanisms", Clinical Cancer Research, Jan. 12, 2010, pp. 497-509, vol. 16 No. 2.
Elkabets et al., "AXL Mediates Resistance to PI3Kα Inhibition by Activating the EGFR/PKC/mTOR Axis in Head and Neck and Esophageal Squamous Cell Carcinomas", Cancer Cell, Apr. 13, 2015, pp. 533-546, vol. 27.
Engels, "Gene Silencing by Chemically Modified siRNAs", New Biotechnology, Mar. 2013, pp. 302-307, vol. 30, No. 3, Elsevier Inc.
Enwere et al., "Role of the TWEAK-Fn14-cIAP1-NF-kB Signaling Axis in the Regulation of Myogenesis and Muscle Homeostasis", Frontiers in Immunology, Feb. 5, 2014, pp. 1-13, vol. 5, Article 34.
Feng et al., "The Fn14 Immediate-Eariy Response Gene is Induced During Liver Regeneration and Highly Expressed in Both Human and Murine Hepatocellular Carcinomas", American Journal of Pathology, Apr. 2000, pp. 1253-1261, vol. 156, No. 4.

Fortin Ensign, "The TWEAK-Fn14 Ligand Receptor Axis Promotes Glioblastoma Cell Invasion and Survival Via Activation of Multiple GEF-Rho GTPase Signaling Systems", The University of Arizona, 2013, pp. 2-243.
Fortin et al., "Tumor Necrosis Factor-Like Weak Inducer of Apoptosis (TWEAK) Stimulation of Glioma Cell Survival is Dependent Upon Akt2 Function", Molecular Cancer Research, Nov. 2009, pp. 1871-1881, vol. 7 No. 11.
Giovannetti et al., "Molecular Mechanisms Underlying the Synergistic Interaction of Erlotinib, an Epidermal Growth Factor Receptor (EGFR) Tyrosine Kinase Inhibitor, with the Multitargeted Antifolate Pemetrexed in Non-Small-Cell Lung Cancer Cells", Molecular Pharmacology Fast Forward, Jan. 10, 2008, pp. 1-39, American Society for Pharmacology and Experimental Therapeutics.
Han et al., "Emerging Roles of MicroRNAs in EGFR-Targeted Therapies for Lung Cancer", BioMed Research International, May 20, 2015, pp. 1-10, vol. 2015, Hindawi Publishing Corporation.
Jandova et al., "Fn14 Receptor Promotes Invasive Potential and Metastatic Capacity of Non-Small Lung Adenocarcinoma Cells Through the Up-Regulation of Integrin a6", Neoplasma, 2015, pp. 41-52, vol. 62 No. 1.
Johnston et al., "Targeting of Fn14 Prevents Cancer-Induced Cachexia and Prolongs Survival", Cell, Sep. 10, 2015, pp. 1365-1378, vol. 162, Elsevier Inc.
Karlin et al., "Applications and Statistics for Multiple High-Scoring Segments in Molecular Sequences", Proceedings of the National Academy of Sciences USA, Jun. 1993, pp. 5873-5877, vol. 90.
Khan et al., "Targeting the PI3K-AKT-mTOR Signaling Network in Cancer", Chinese Journal of Cancer, 2013, pp. 253-265, vol. 32, Issue 5, Chinese Anti-Cancer Association.
Kohn et al., "Differential Effects of Cystathionine-γ-lyase-Dependent Vasodilatory H2S in Periadventitial Vasoregulation of Rat and Mouse Aortas", PLoS One, Aug. 2012, pp. 1-9, vol. 7, Issue 8.
Kwon et al., "TWEAK/Fn14 Signaling Mediates Gastric Cancer Cell Resistance to 5-Fluorouracil Via NF-kB Activation", International Journal of Oncology, 2014, pp. 583-590, vol. 44.
Lee et al., "Akt is Required for Axl-Gas6 Signaling to Protect Cells from E1A-Mediated Apoptosis", Oncogene, 2002, pp. 329-336, vol. 21, Nature Publishing Group.
Lopes et al., "Identifying Activating Mutations in the EGFR Gene: Prognostic and Therapeutic Implications in Non-Small Cell Lung Cancer," J. Bras Pneumol, Aug. 1, 2015, pp. 365-375, vol. 41, No. 4.
Madrigal-Matute et al., "TWEAK/Fn14 Interaction Promotes Oxidative Stress through NADPH Oxidase Activation in Macrophages", Cardiovascular Research, 2015, pp. 139-147, vol. 108, European Society of Cardiology.
Martinez-Aranda et al., "FN14 and GRP94 Expression are Prognostic/Predictive Biomarkers of Brain Metastasis Outcome that Open Up New Therapeutic Strategies," Oncotarget, Dec. 29, 2015, pp. 44254-44273, vol. 6, No. 42.
Mouraviev et al., "Clinical Prospects of Long Noncoding RNAs as Novel Biomarkers and Therapeutic Targets in Prostate Cancer", Prostate Cancer and Prostatic Diseases, 2016, pp. 14-20, vol. 19, Macmillan Publishers Limited.
Mudduluru et al., "Myeloid Zinc Finger 1 Induces Migration, Invasion, and In Vivo Metastasis through Axl Gene Expression in Solid Cancer", Molecular Cancer Research, Feb. 9, 2010, pp. 159-170, American Association for Cancer Research.
Papadakis et al., "Axl Promotes Cutaneous Squamous Cell Carcinoma Survival through Negative Regulation of Pro-Apoptotic Bcl-2 Family Members", Journal of Investigative Dermatology, 2011, pp. 509-517, vol. 131, The Society for Investigative Dermatology.
Poveda et al., "TWEAK/Fn14 and Non-Canonical NF-kappaB Signaling in Kidney Disease", Frontiers in Immunology, Dec. 10, 2013, pp. 1-7, vol. 4, Article 447.
Reichl et al., "Axl Activates Autocrine Transforming Growth Factor-B Signaling in Hepatocellular Carcinoma", Hepatology, 2015, pp. 930-941, vol. 61, No. 3.
Rho et al., "MET and AXL Inhibitor NPS-1034 Exerts Efficacy Against Lung Cancer Cells Resistant to EGFR Kinase Inhibitors

(56) References Cited

OTHER PUBLICATIONS

Because of MET or AXL Activation", Cancer Research, Jan. 1, 2014, pp. 253-262, vol. 74, No. 1, American Association for Cancer Research.

Ruan et al., "Axl is Essential for VEGF-A-dependent Activation of PI3K/Akt", The EMBO Journal, 2012, pp. 1692-1703, vol. 31, No. 7, European Molecular Biology Organization.

Srikar et al., "Targeted Nanoconjugate Co-Delivering siRNA and Tyrosine Kinase Inhibitor to KRAS Mutant NSCLC Dissociates GAB1-SHP2 Post Oncogene Knockdown", Scientific Reports, 2016, pp. 1-14.

Srikar et al., "Three-Dimensional Nancomposites: Fluidics Driven Assembly of Metal Nanoparticles on Protein Nanostructures and Their Cell-Line-Dependent Intracellular Trafficking Pattern", Langmuir, 2016, pp. 4877-4885, vol. 32, American Chemical Society.

Sun et al., "Correlation of EGFR Del 19 with Fn14/JAK/STAT Signaling Molecules in Non-Small Cell Lung Cancer", Oncology Reports, 2016, pp. 1030-1040, vol. 36.

Tai et al., "Axl Promotes Cell Invasion by Inducing MMP-9 Activity through Activation of NF-kB and Brg-1", Oncogene, 2008, pp. 4044-4055, vol. 27, Nature Publishing Group.

Thress et al., "Acquired EGFR C797S Mutation Mediates Resistance to AZD9291 in Non-Small Cell Lung Cancer Harboring EGFR T790M", Nature Medicine, Jun. 2015, pp. 560-564, vol. 21, No. 6, Nature America, Inc.

Tran et al., "Increased Fibroblast Growth Factor-Inducible 14 Expression Levels Promote Glioma Cell Invasion via Rac1 and Nuclear Factor-?B and Correlate with Poor Patient Outcome", Cancer Research, 2006, pp. 9535-9542, vol. 66, American Association for Cancer Research.

Tran et al., "The Human Fn14 Receptor Gene is Up-Regulated in Migrating Glioma Cells in Vitro and Overexpressed in Advanced Glial Tumors", American Journal of Pathology, Apr. 2003, vol. 162, No. 4, American Society for Investigative Pathology.

Tran et al., "The Tumor Necrosis Factor-Like Weak Inducer of Apoptosis (TWEAK)-Fibroblast Growth Factor-Inducible 14 (Fn14) Signaling System Regulates Glioma Cell Survival Via NFkB Pathway Activation and BCL-X?/BCL-W Expression", The Journal of Biological Chemistry, Feb. 4, 2005, pp. 3483-3492, vol. 280, No. 5, The American Society for Biochemistry and Molecular Biology, Inc.

Uramoto et al., "Epithelial-Mesenchymal Transition in EGFR-TKI Acquired Resistant Lung Adenocarcinoma", Anticancer Research, 2010, pp. 2513-2518, vol. 30.

Wang et al., "Axl-Altered MicroRNAs Regulate Tumorigenicity and Gefitinib Resistance in Lung Cancer", Cell Death and Disease, 2014, pp. 1-11, vol. 5, Macmillan Publishers Limited.

Wang et al., "Transcriptional Profiling Suggests that Barrett's Metaplasia is an Early Intermediate Stage in Esophageal Adenocarcinogenesis", Oncogene, 2006, pp. 3346-3356, vol. 25, Nature Publishing Group.

Watts et al., "Identification of Fn14/TWEAK Receptor as a Potential Therapeutic Target in Esophageal Adenocarcinoma", International Journal of Cancer, 2007, pp. 2132-2139, vol. 121.

Whitehead et al., "Knocking Down Barriers: Advances in siRNA Delivery", Nature Reviews, Feb. 2009, pp. 129-138, vol. 8, Macmillan Publishers Limited.

Whitsett et al., "Elevated Expression of Fn14 in Non-Small Cell Lung Cancer Correlates with Activated EGFR and Promotes Tumor Cell Migration and Invasion", The American Journal of Pathology, Jul. 2012, pp. 111-120, vol. 181, No. 1.

Whitsett et al., "FN14 Expression Correlates with MET in NSCLC and Promotes MET-Driven Cell Invasion", Clinical and Experimental Metastasis, Apr. 2014, pp. 613-623, vol. 31.

* cited by examiner

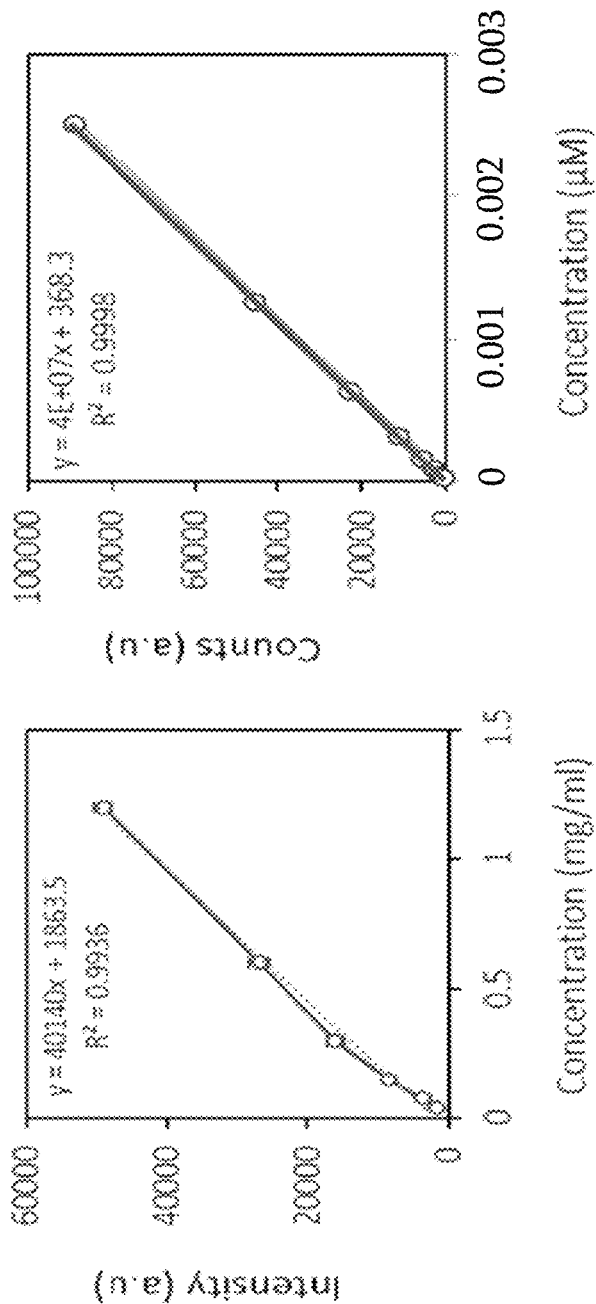
Figure 5A,B

Figure 7A:
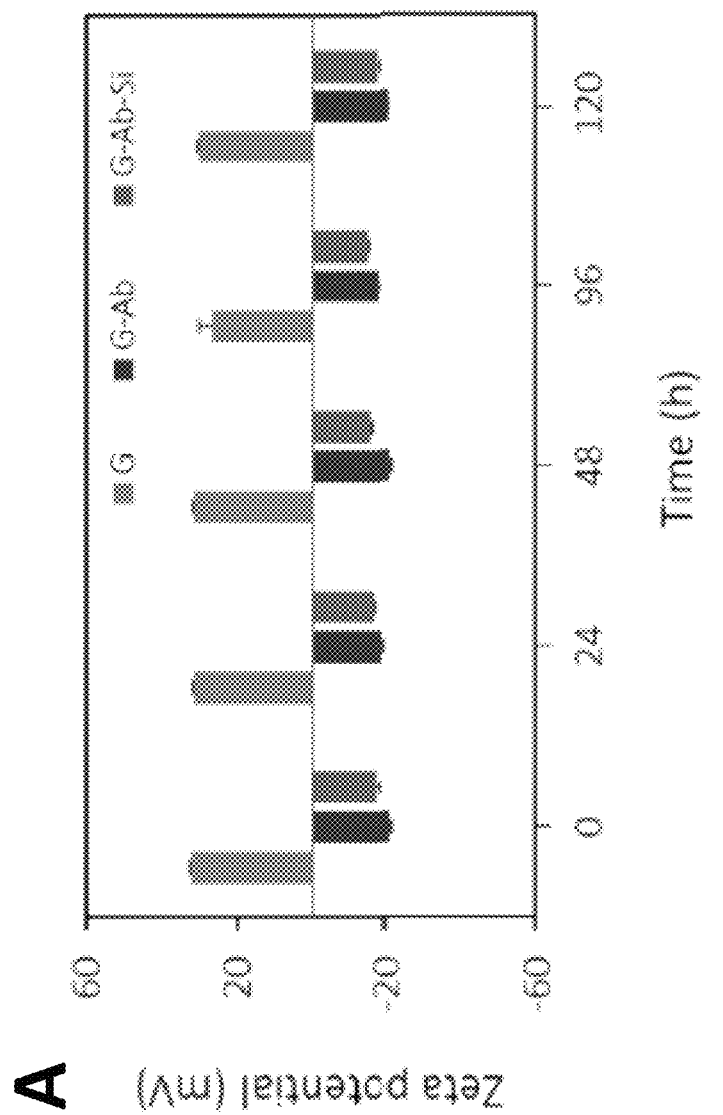
Figure 7B:
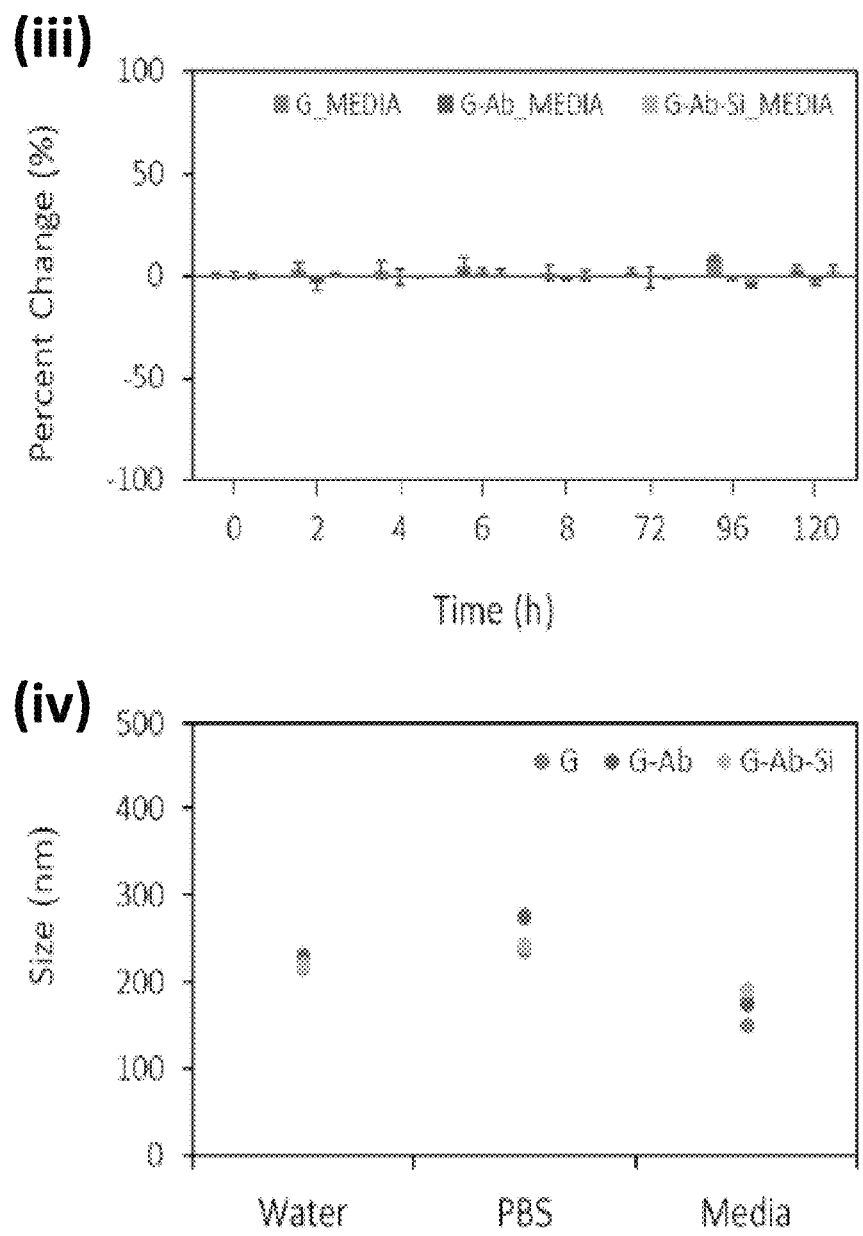

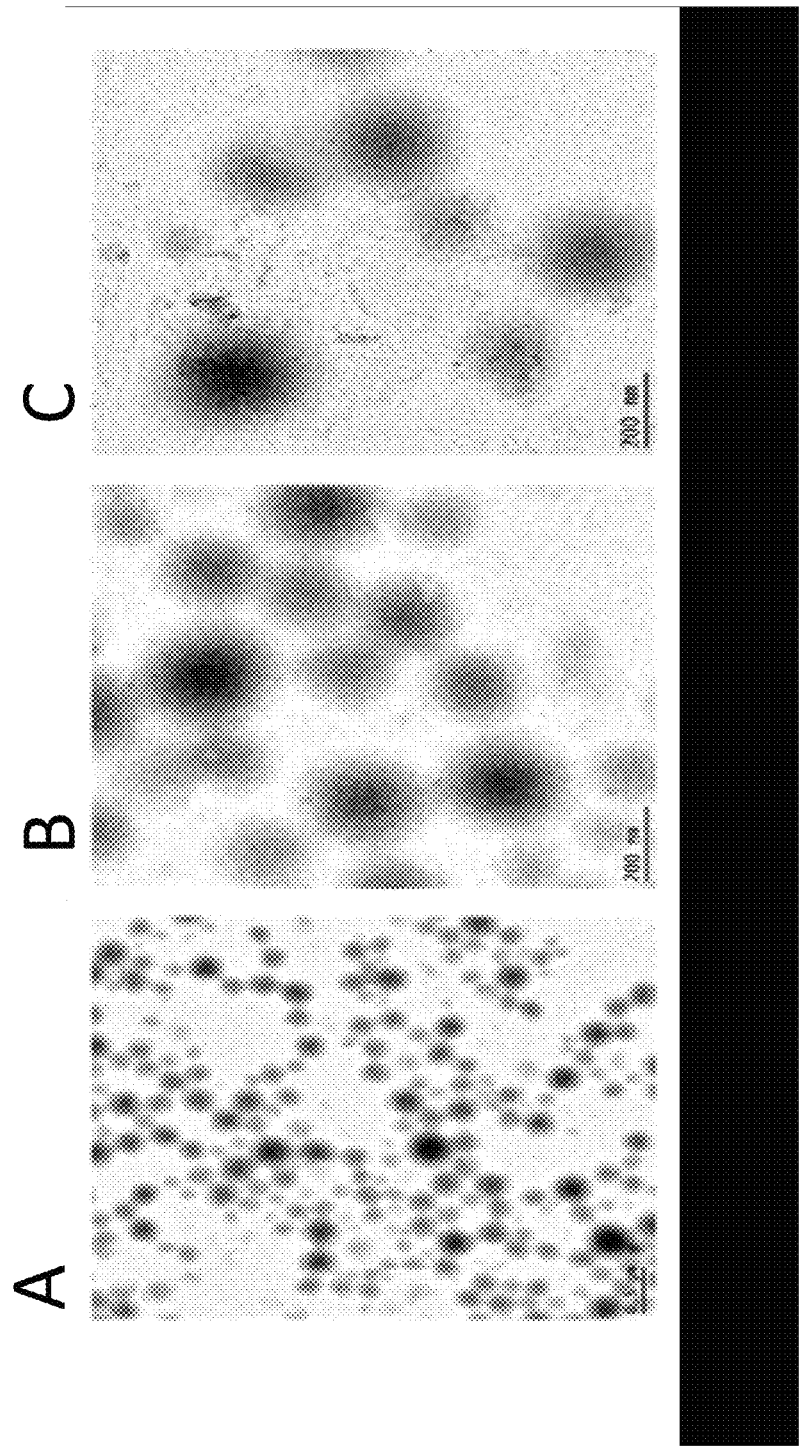
Figure 6A,B,C (i)
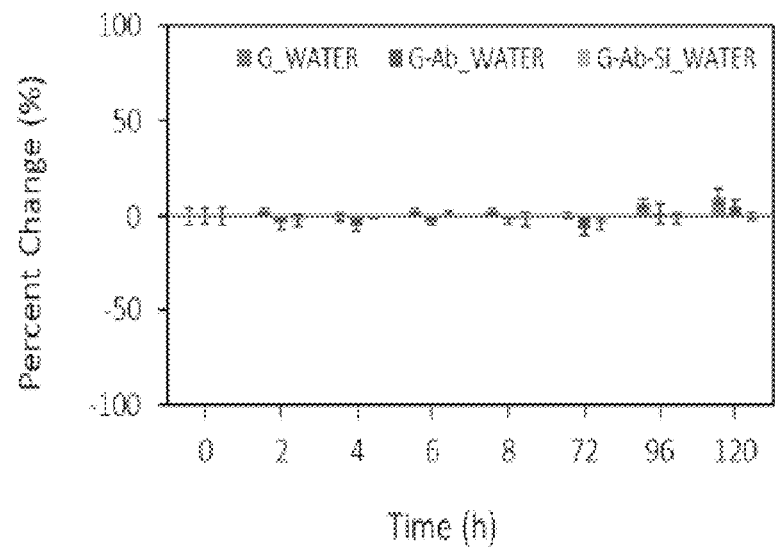
(ii)
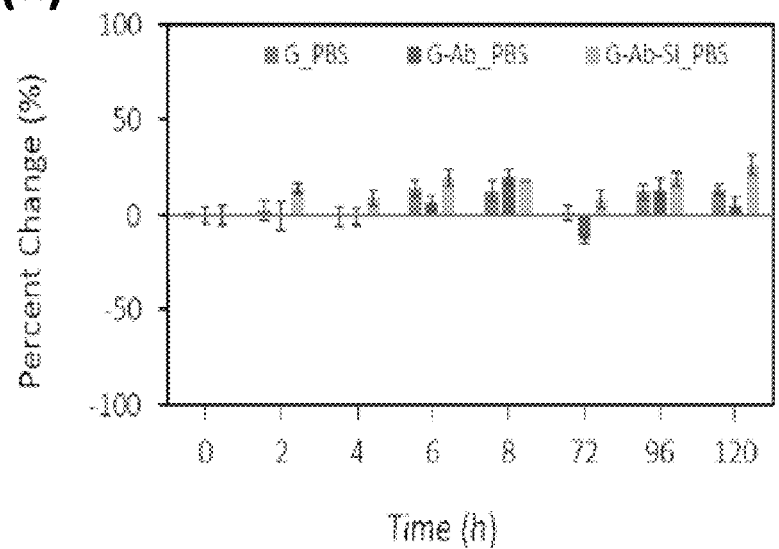
Figure 7B

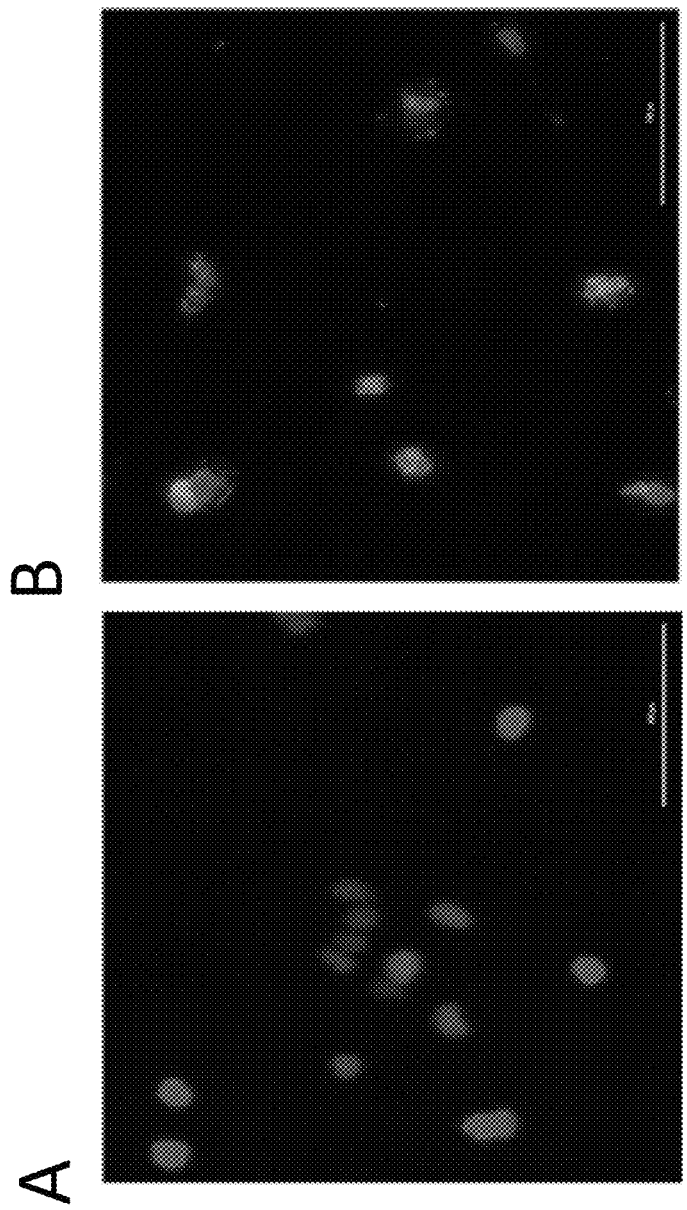
Figure 9A,B

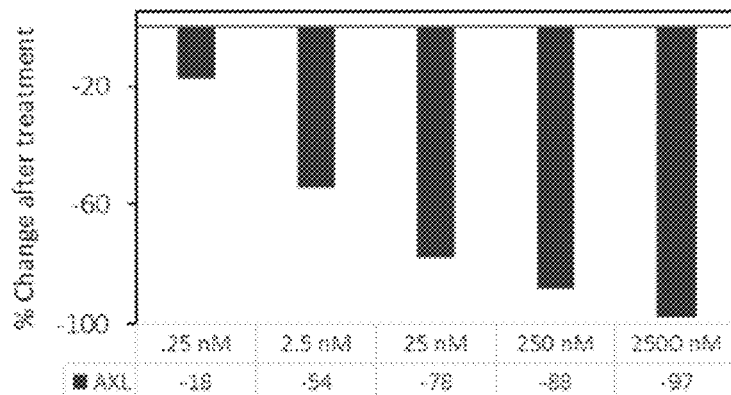
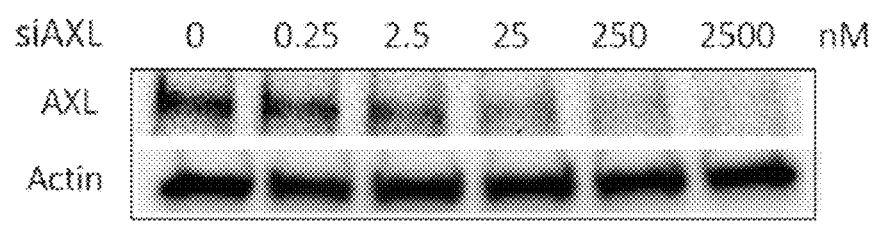
Figure 10A,B

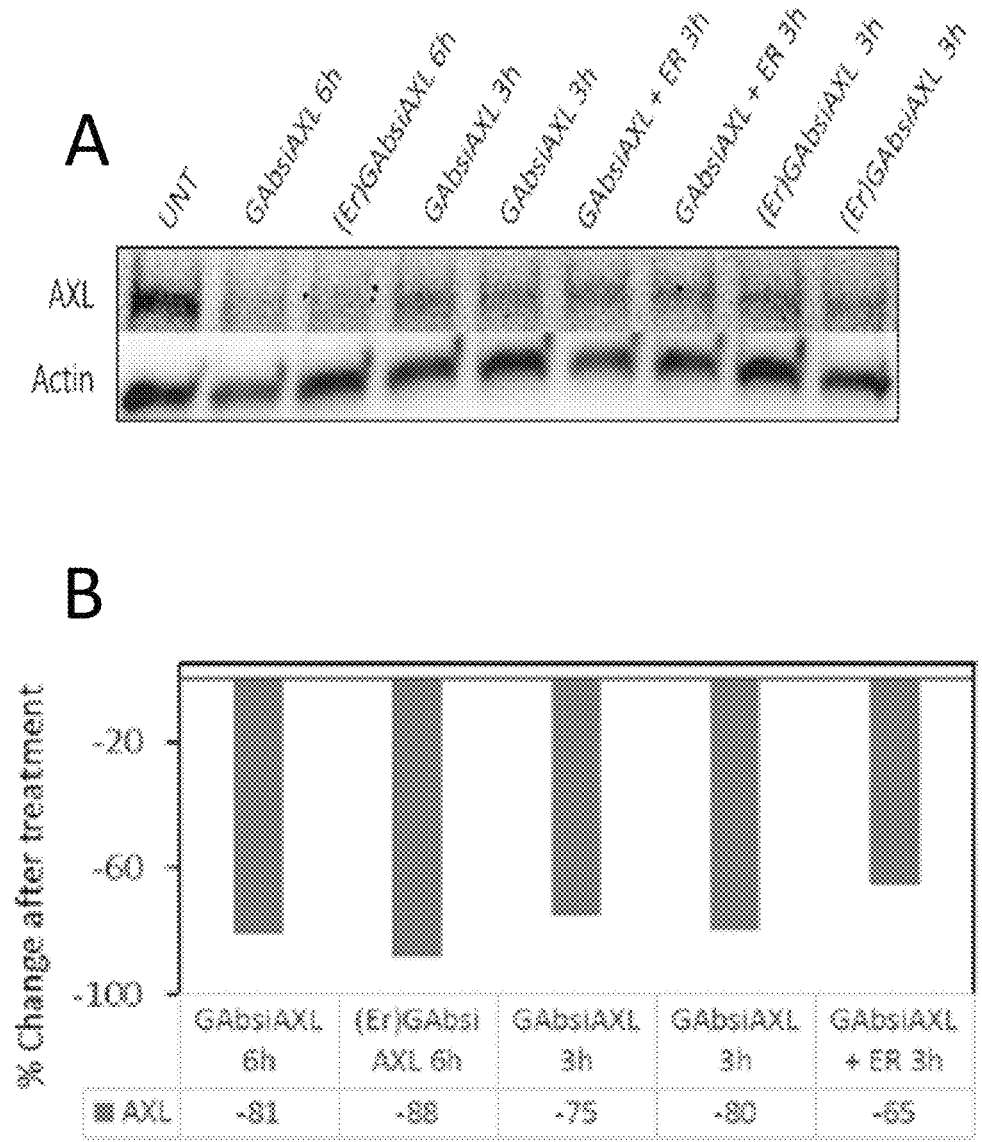
Figure 11A,B

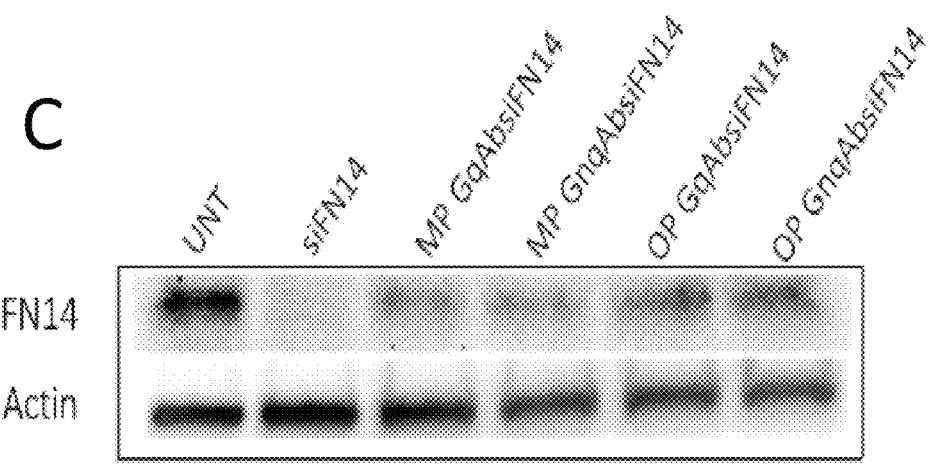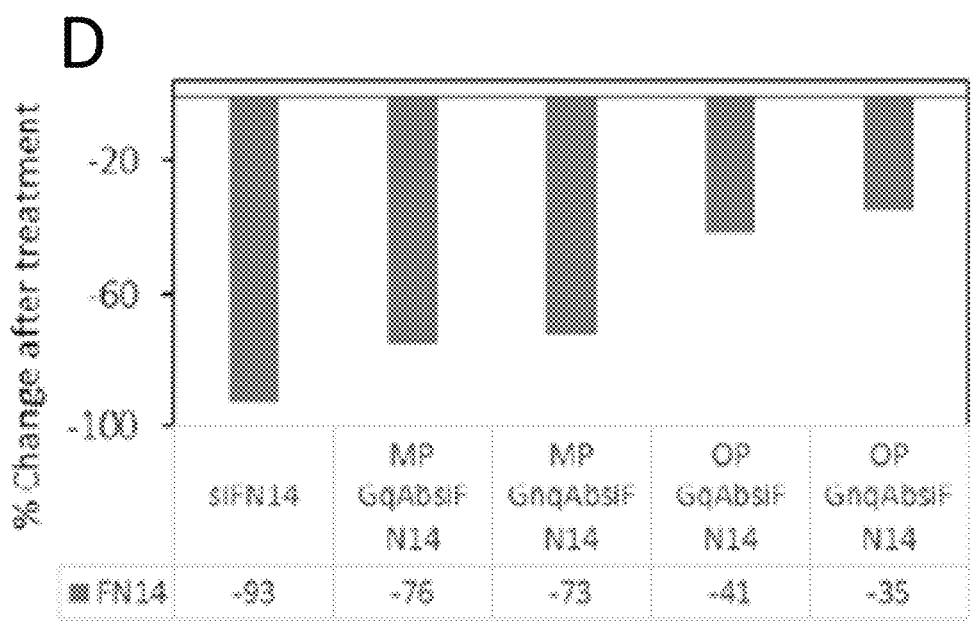
Figure 11C,D

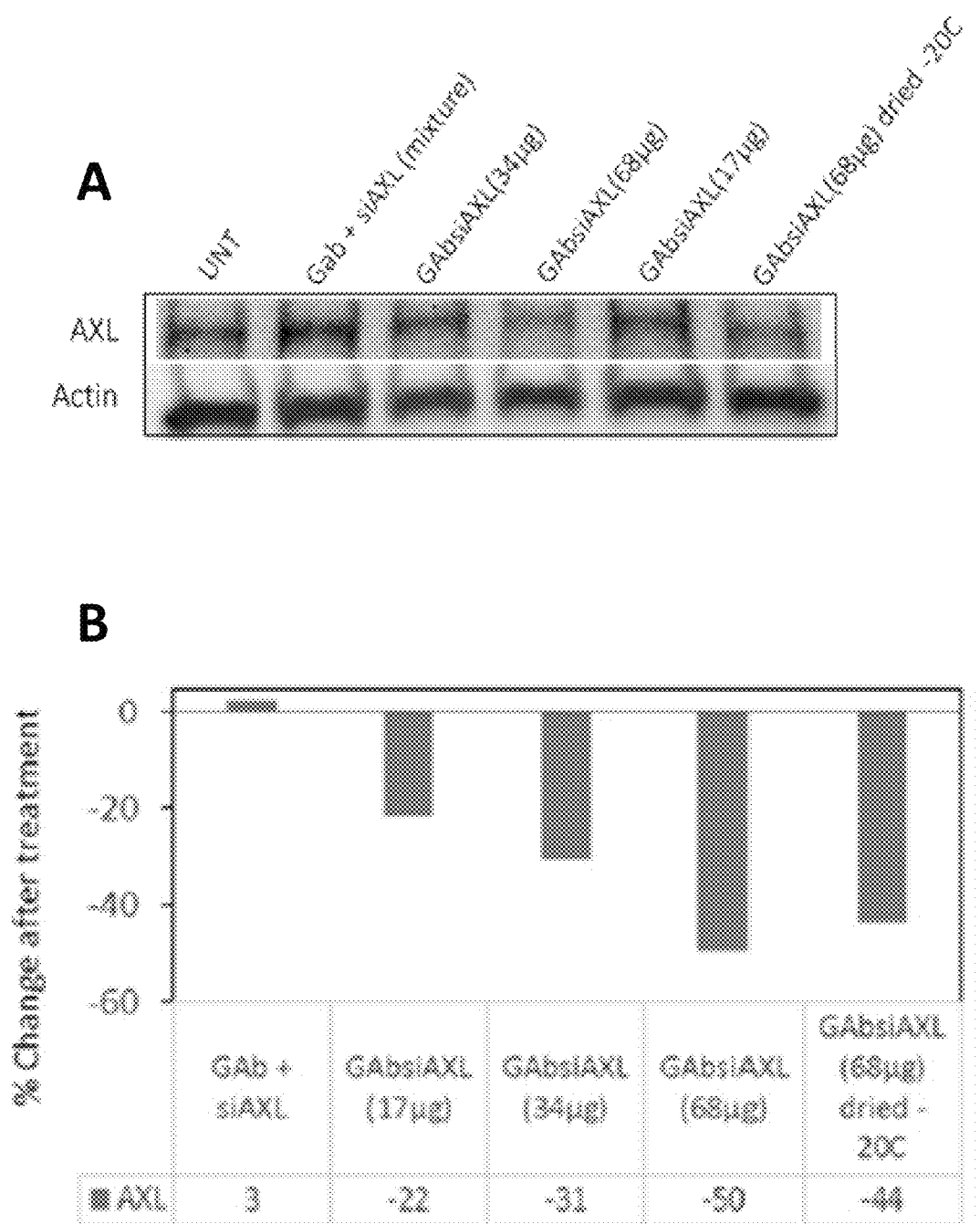
Figure 12A,B

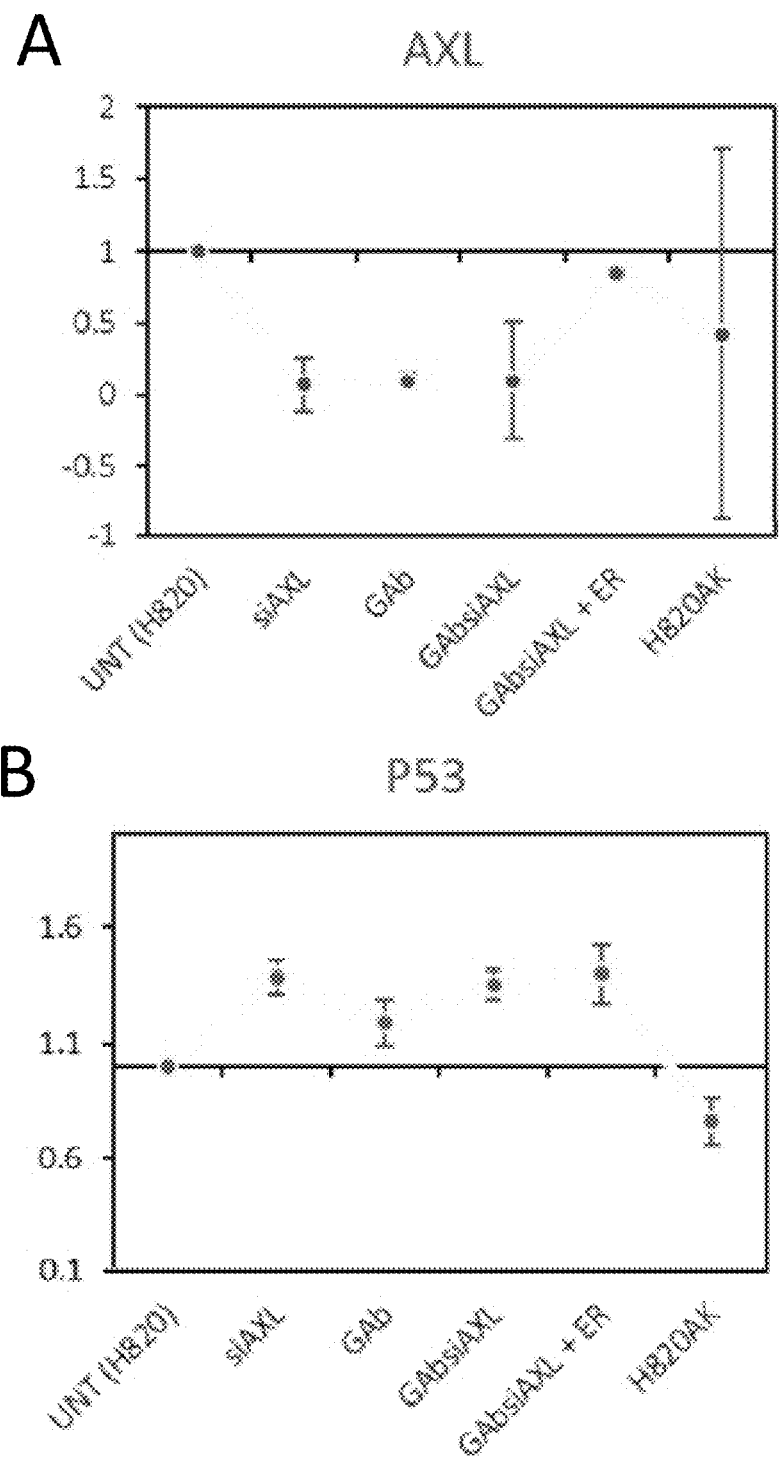
Figure 15A,B

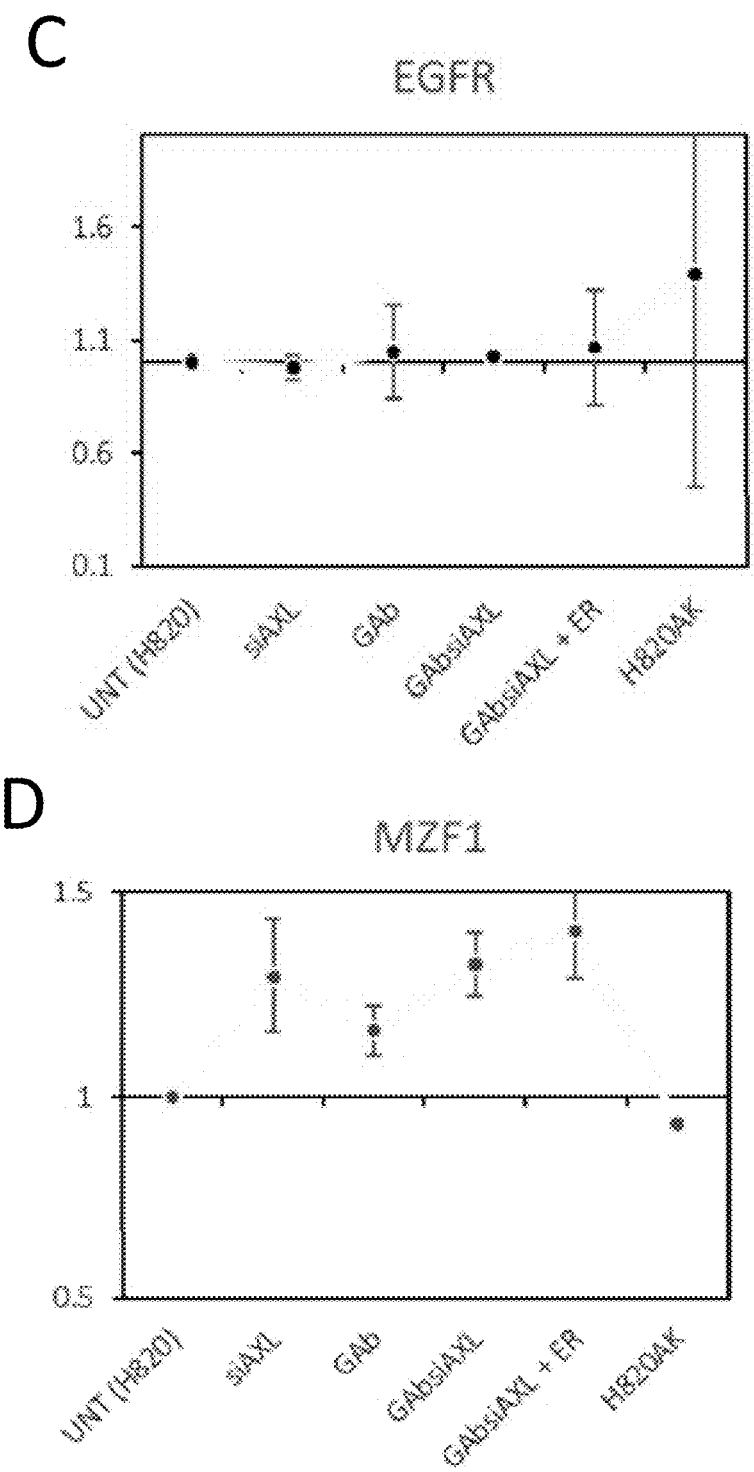
Figure 15C,D

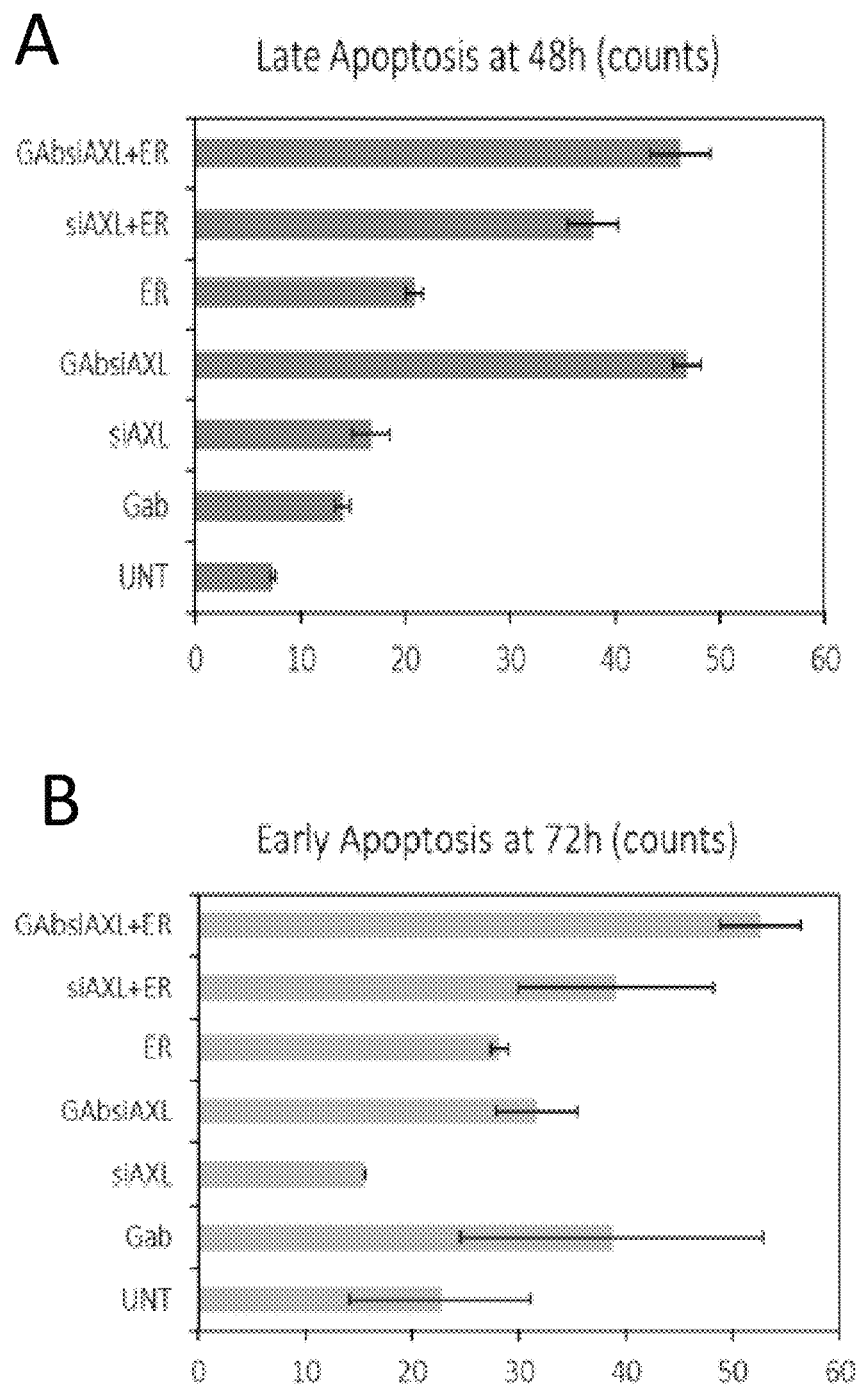
Figure 16A,B

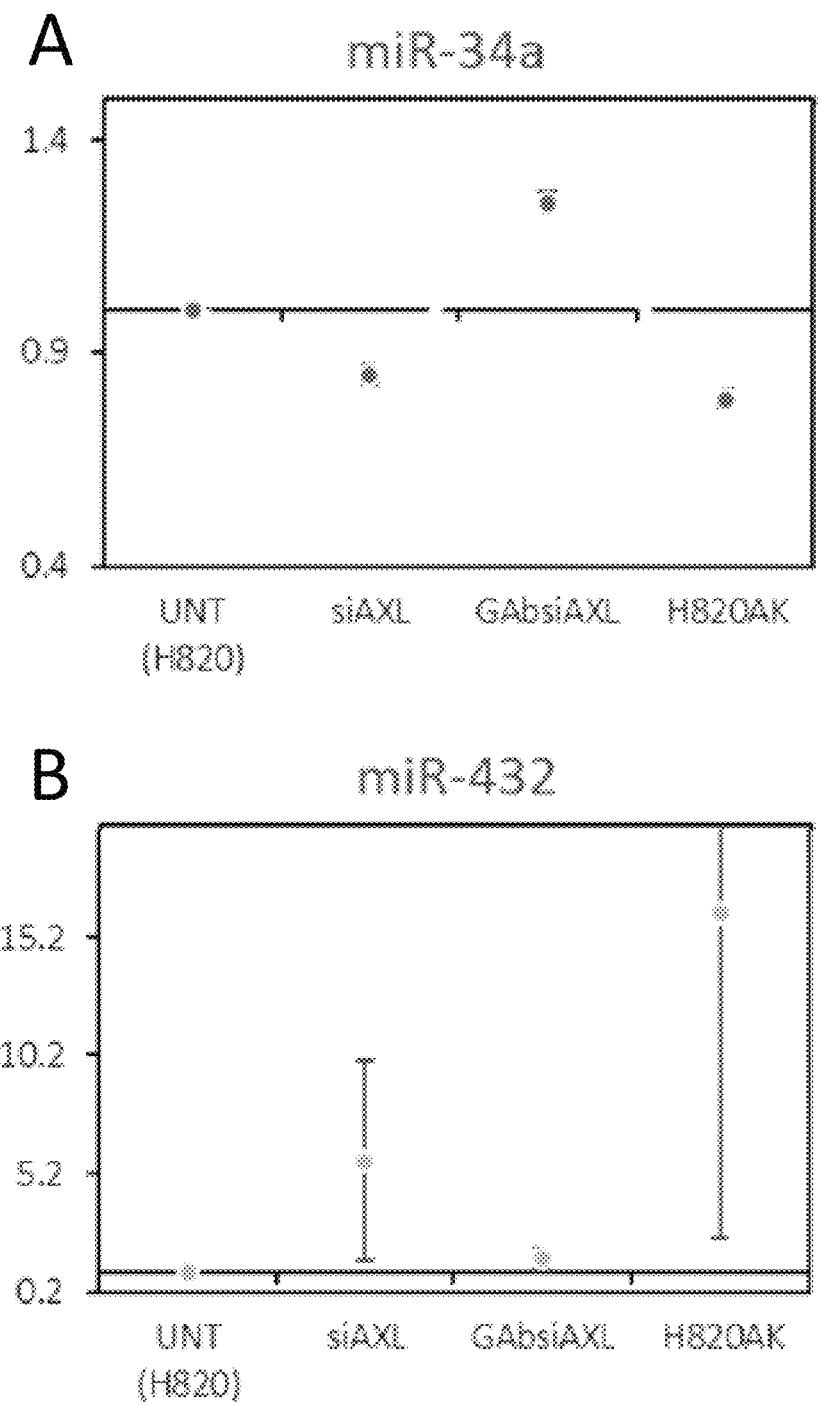
Figure 17 A,B

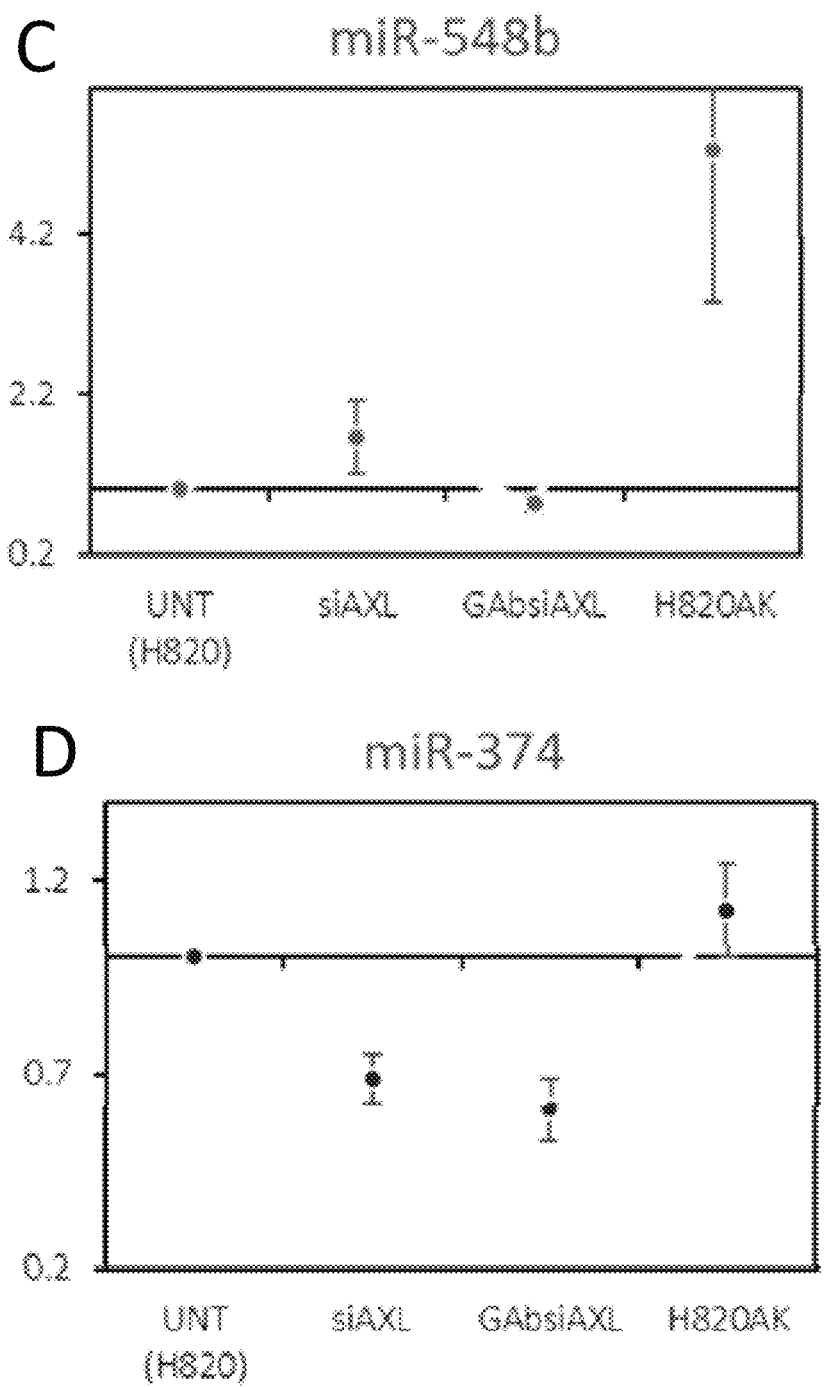
Figure 17C,D

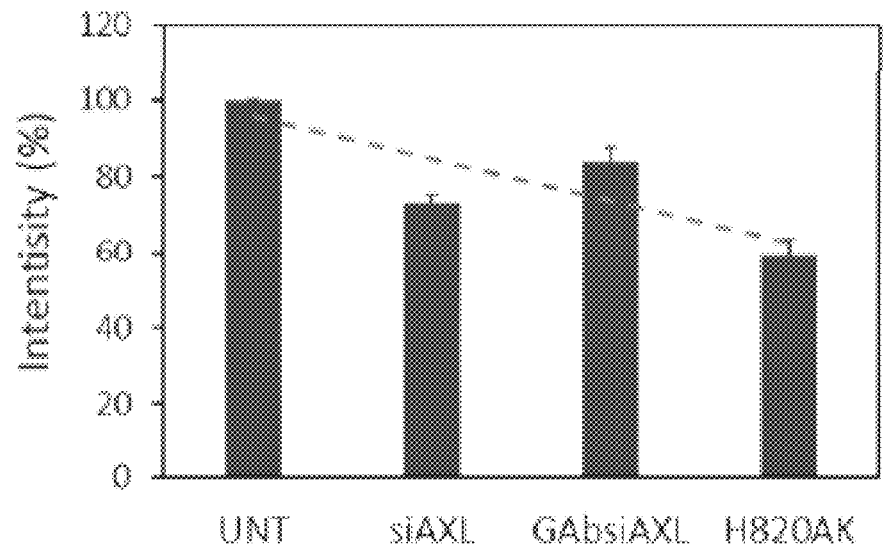
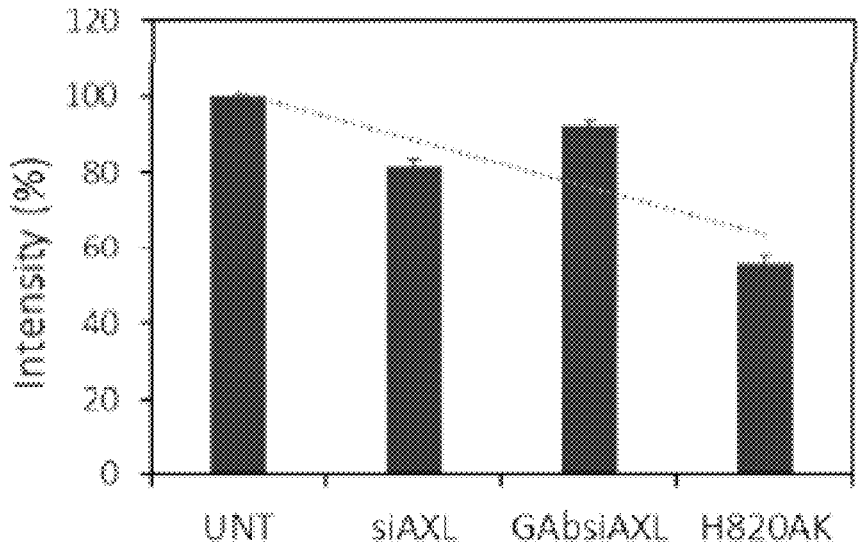
Figure 18A,B

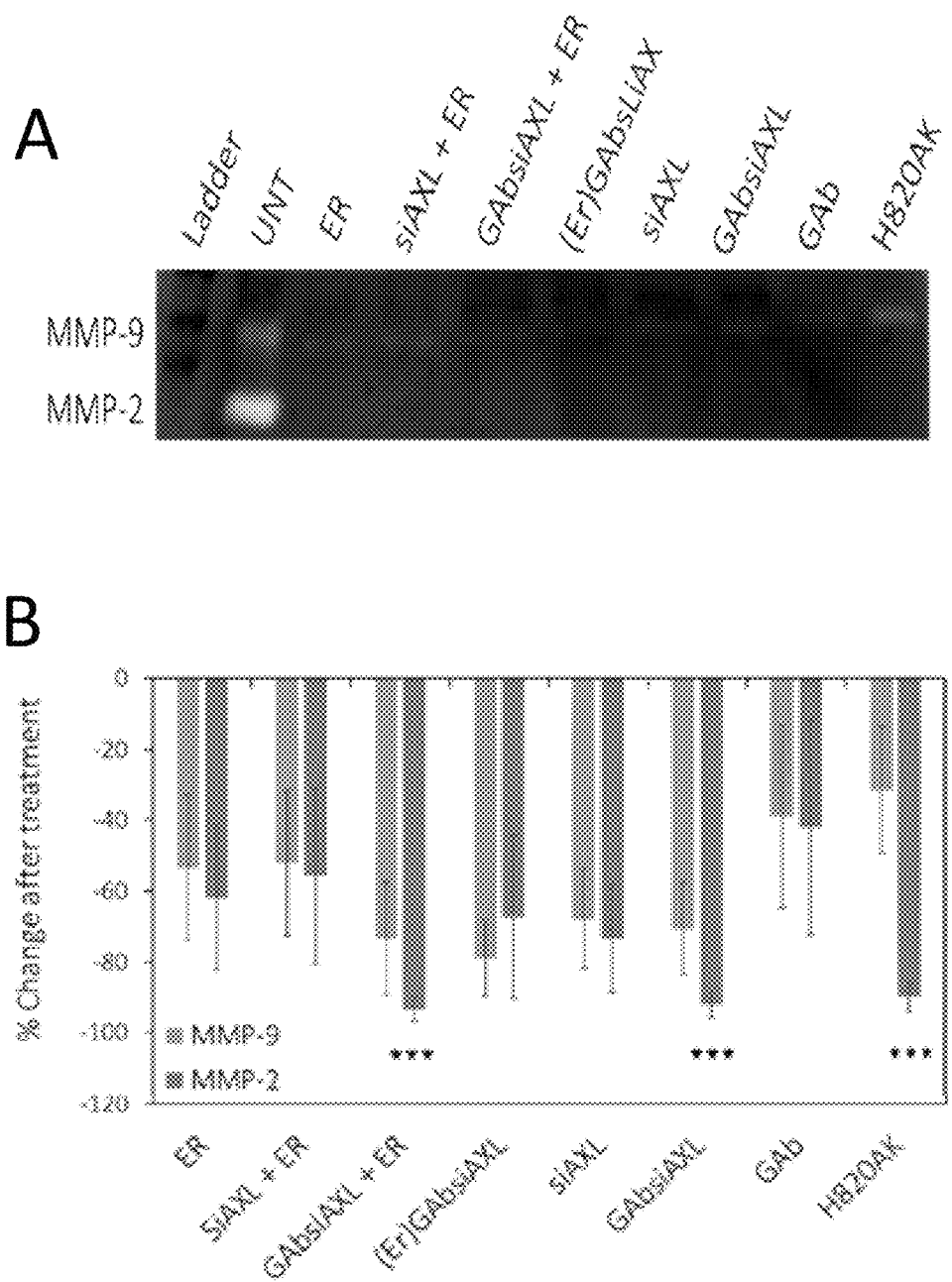
Figure 19A,B

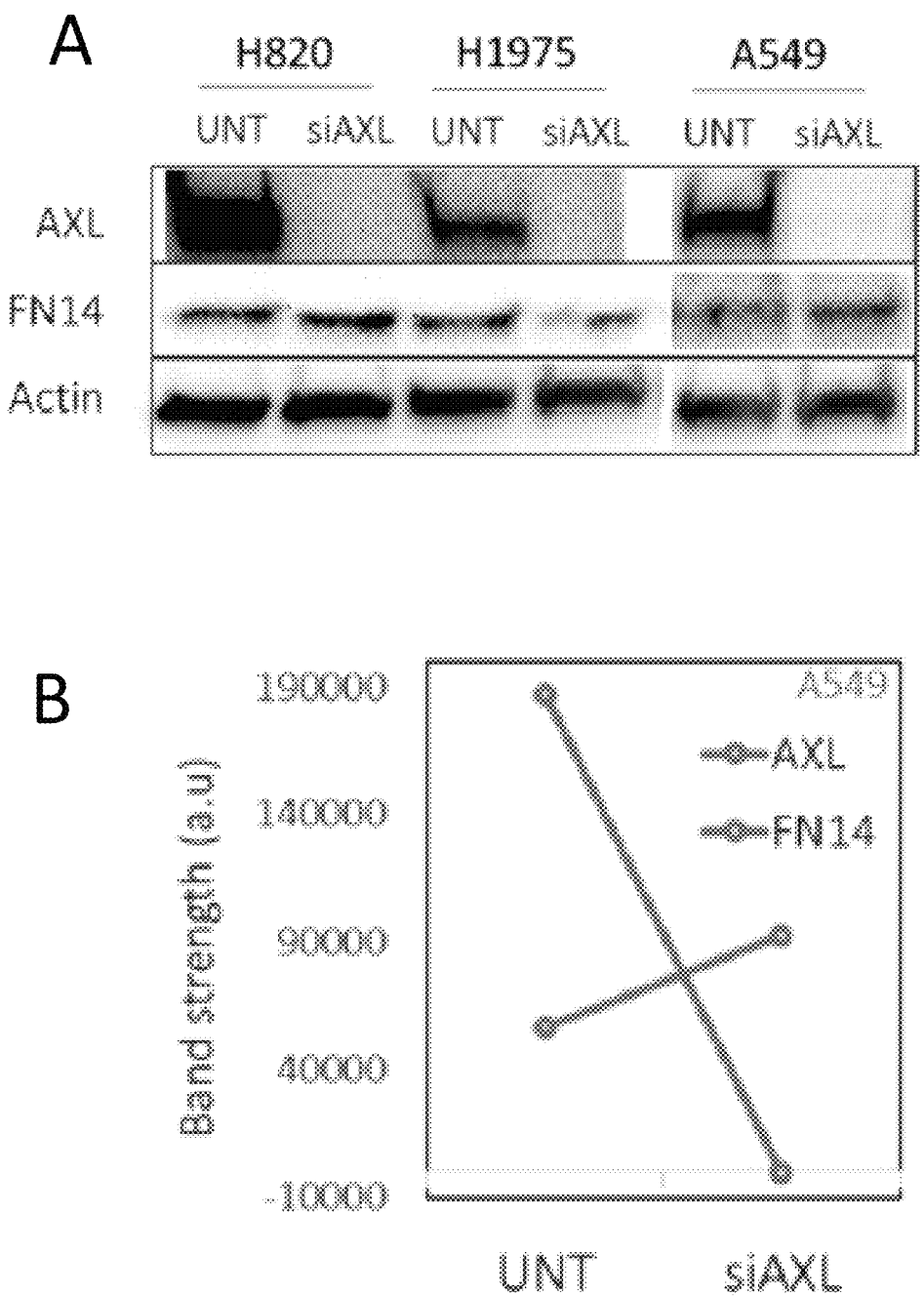
Figure 24A,B

Figure 27A,B,C,D

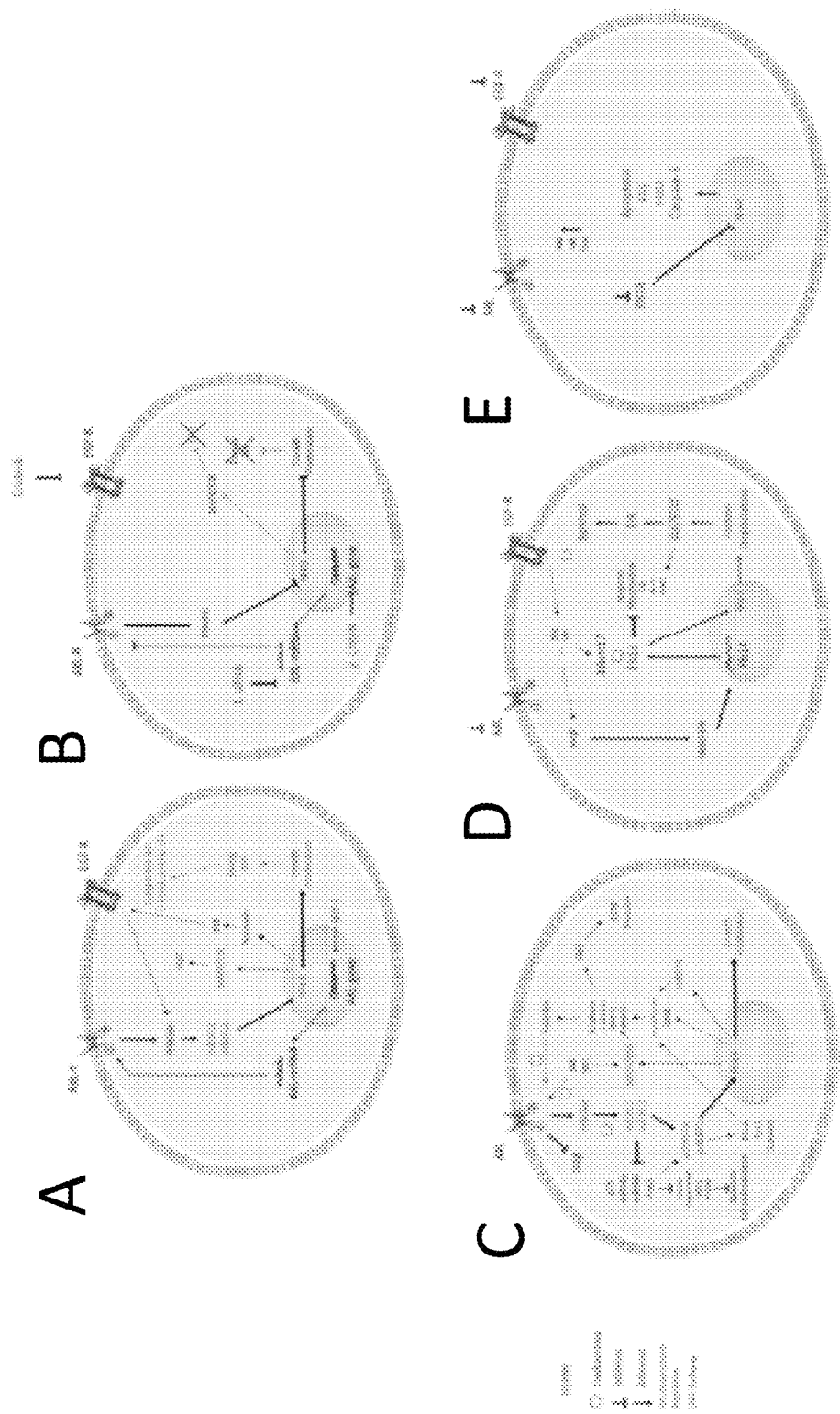
Figure 40A,B,C,D,E

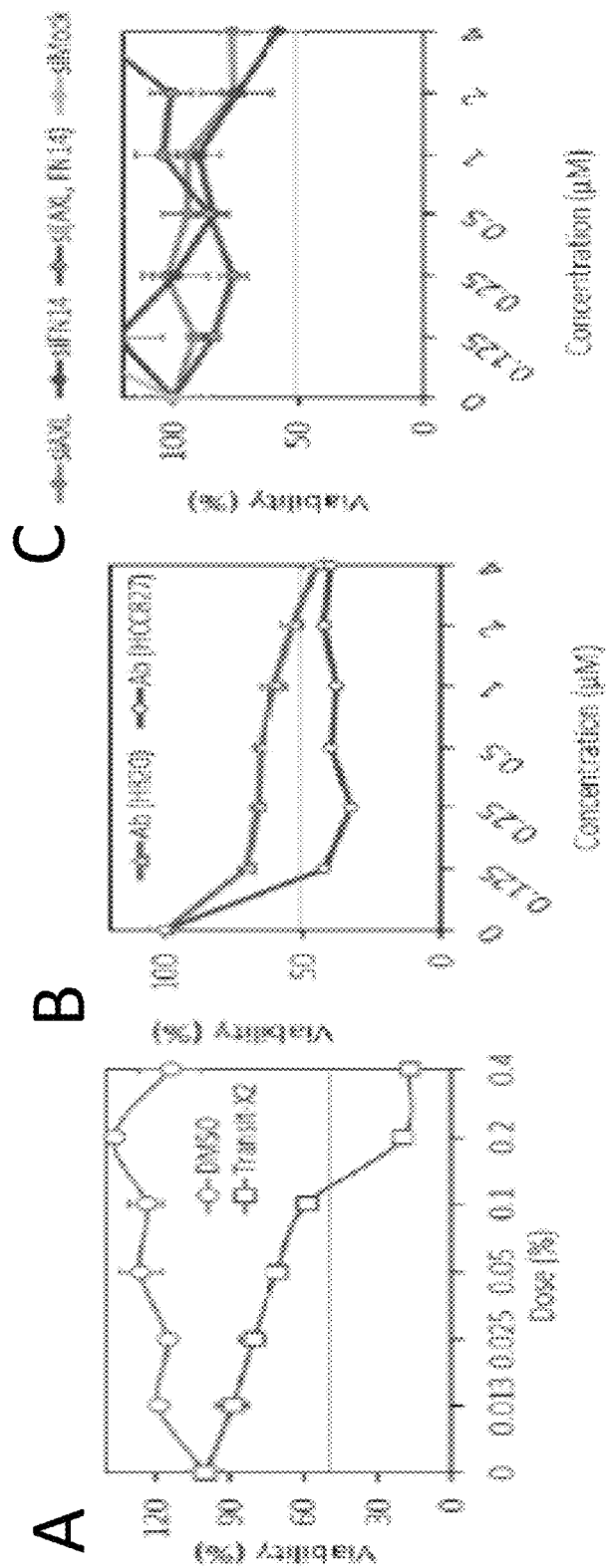
Figure 41A,B,C

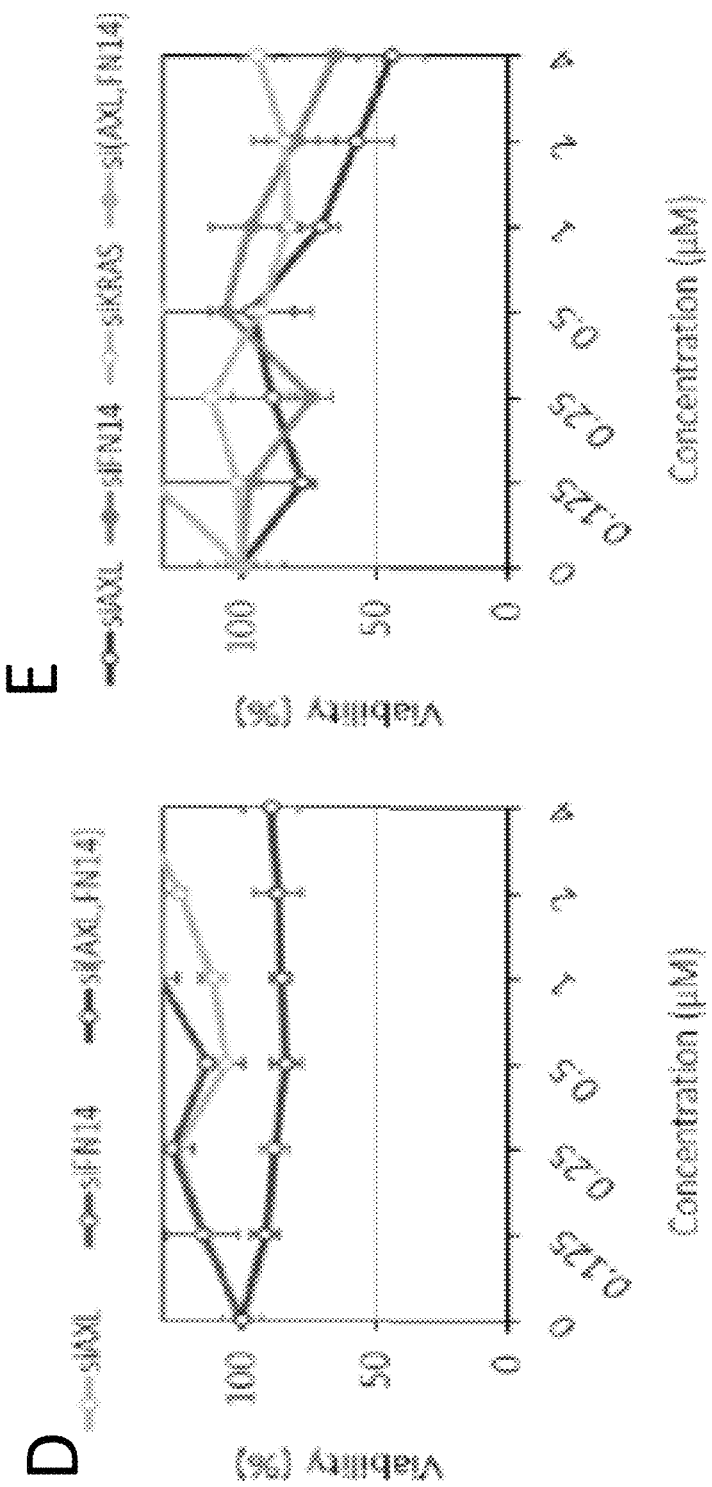
Figure 41D,E

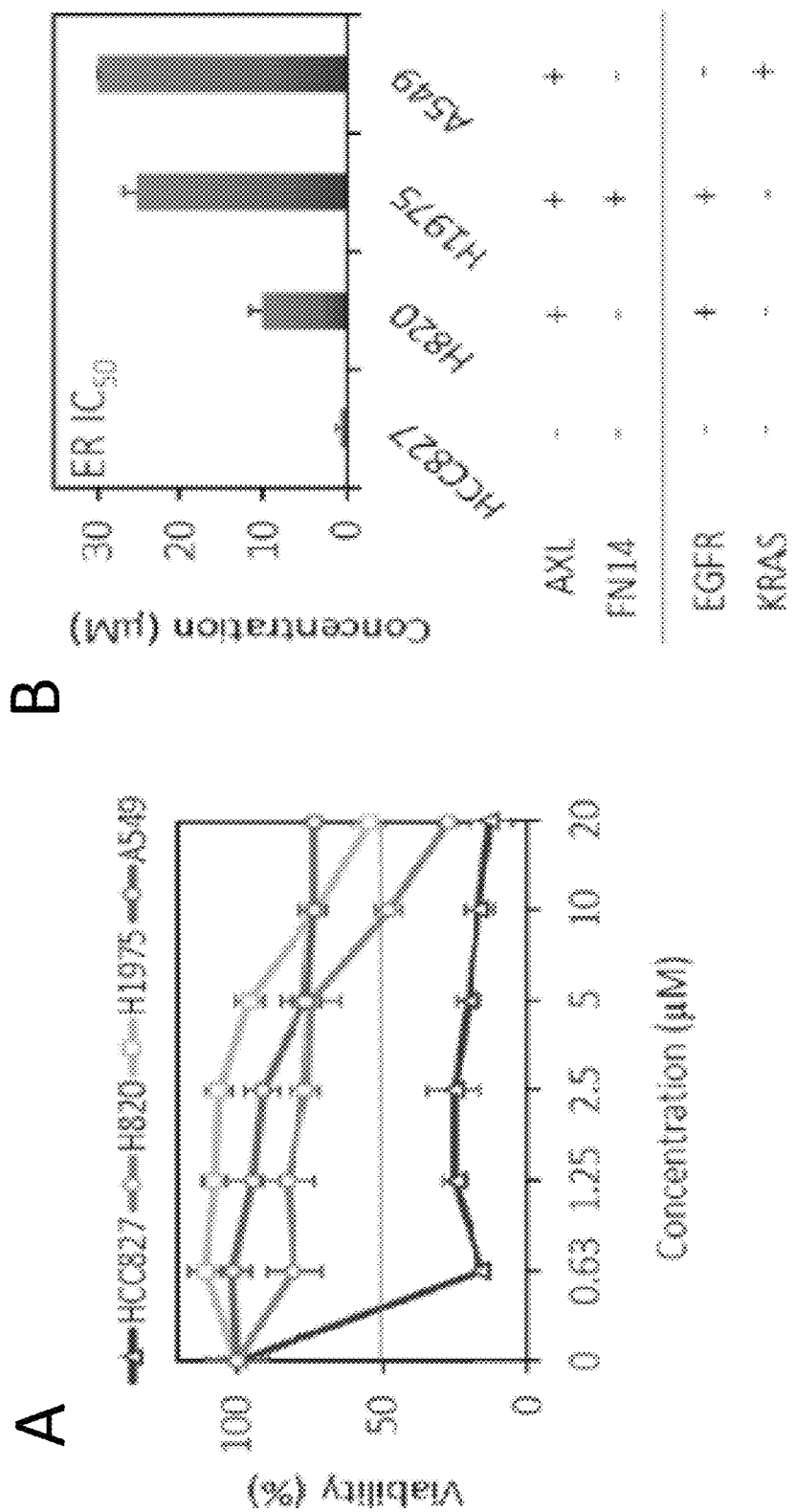
Figure 42A,B

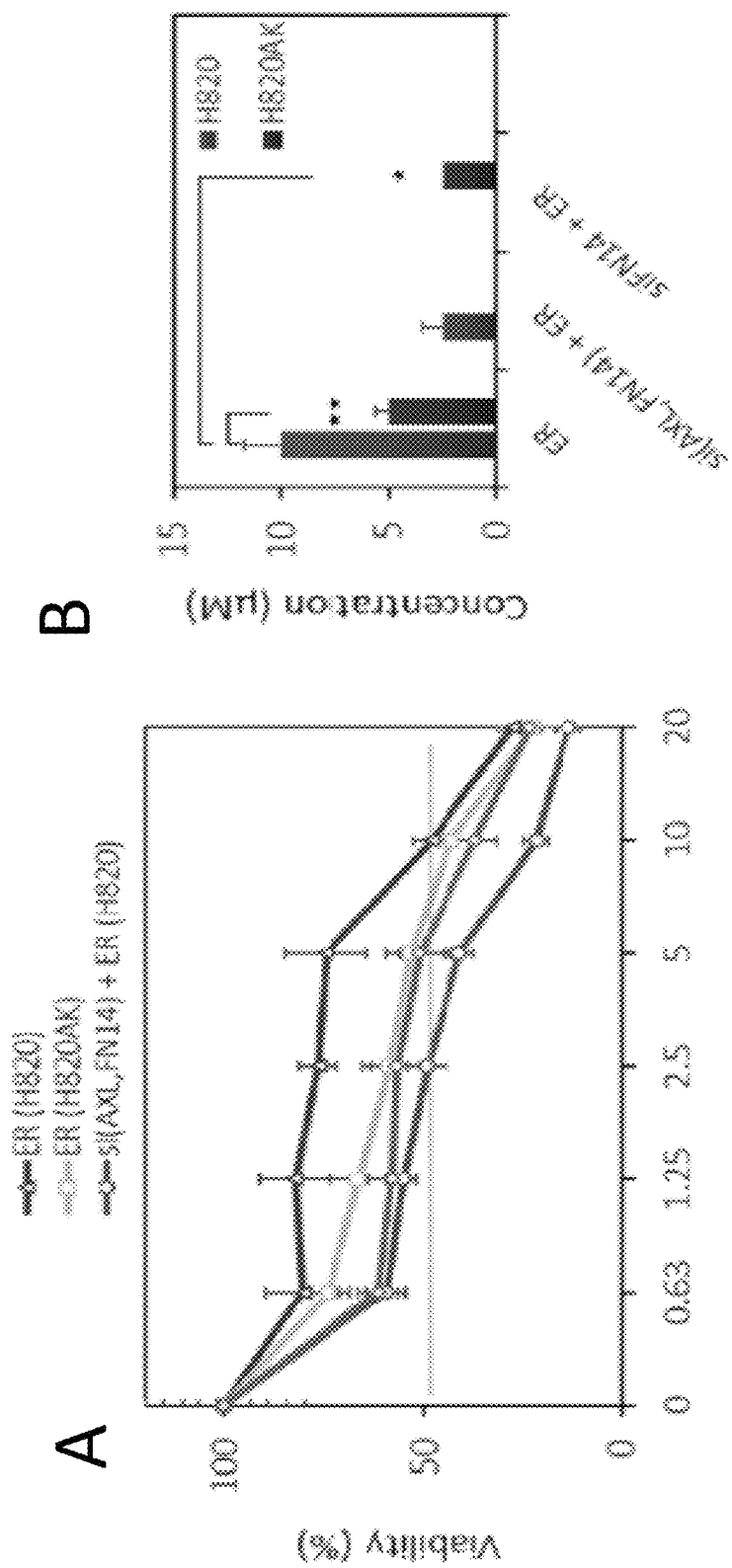
Figure 43A,B

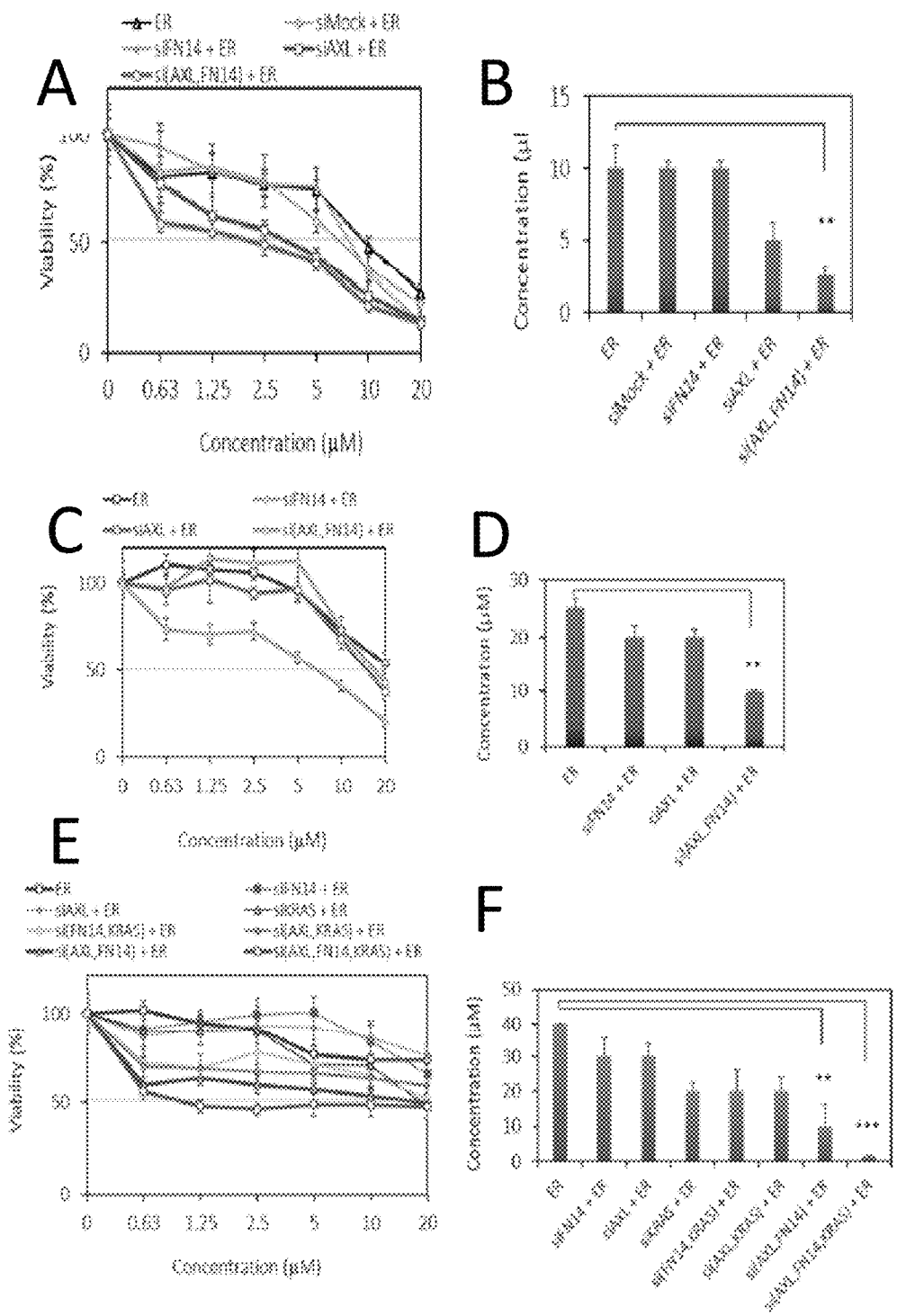
Figure 44A,B,C,D,E,F

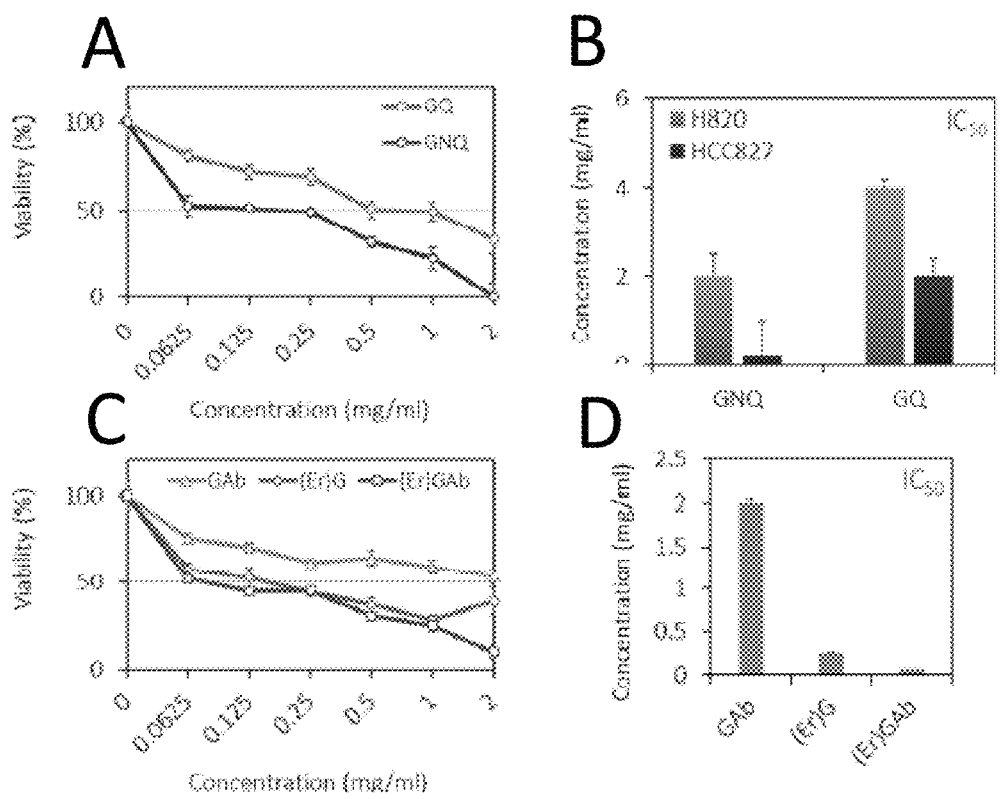
Figure 45A,B,C,D

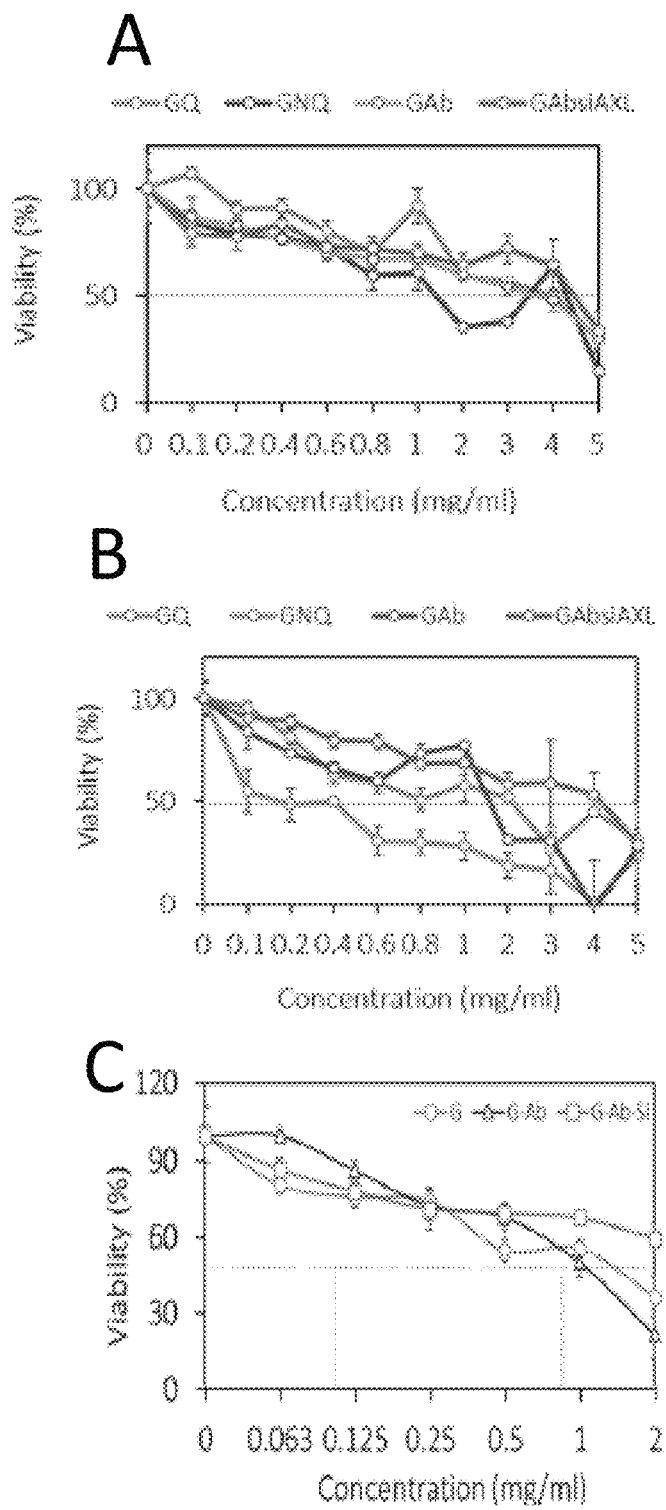
Figure 46A,B,C

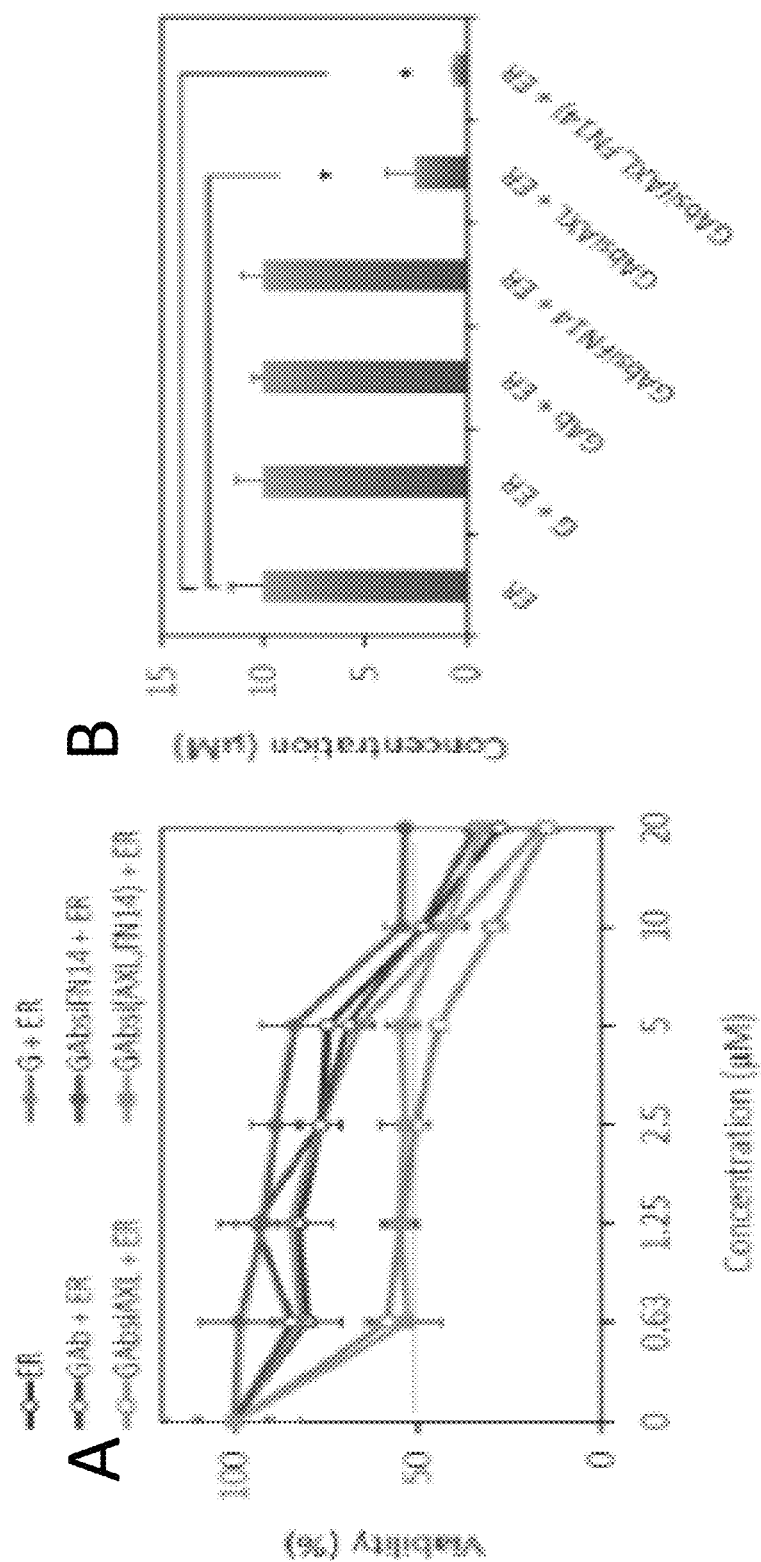
Figure 47A,B

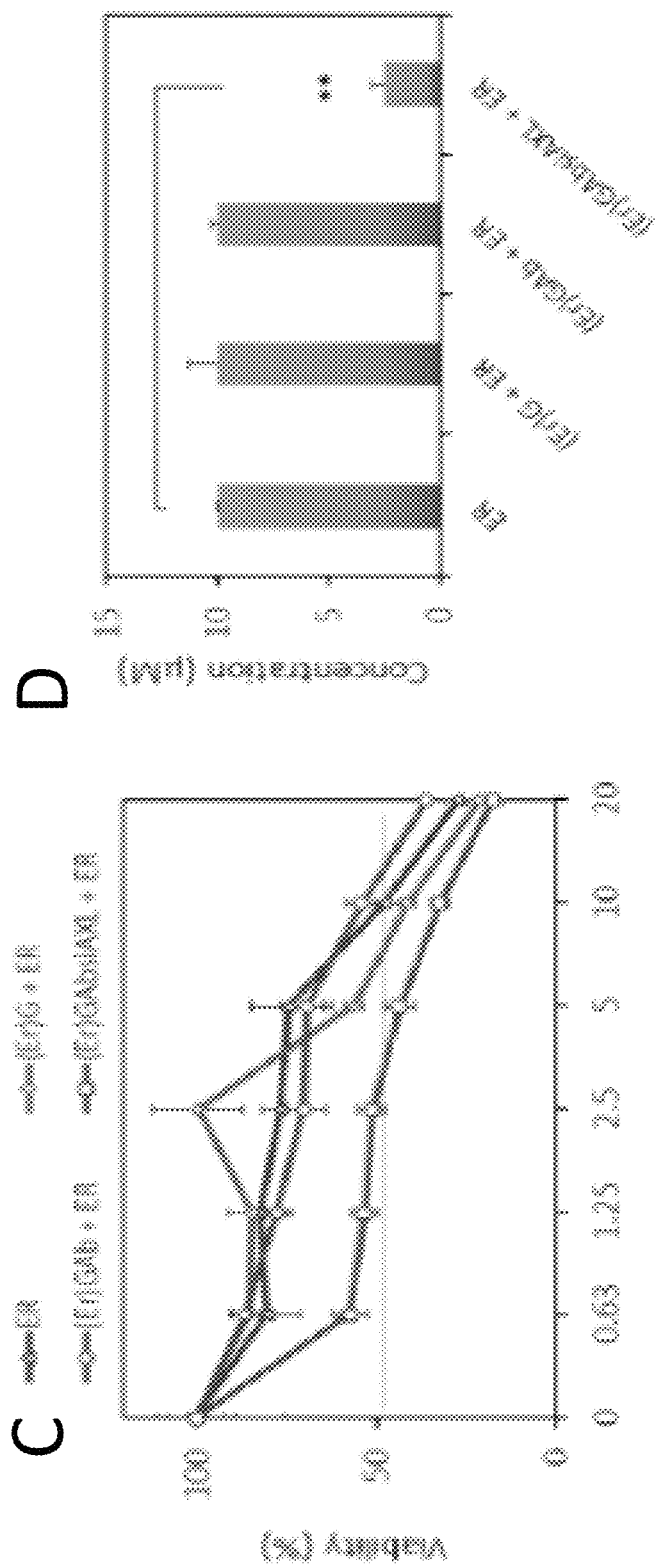
Figure 47C,D

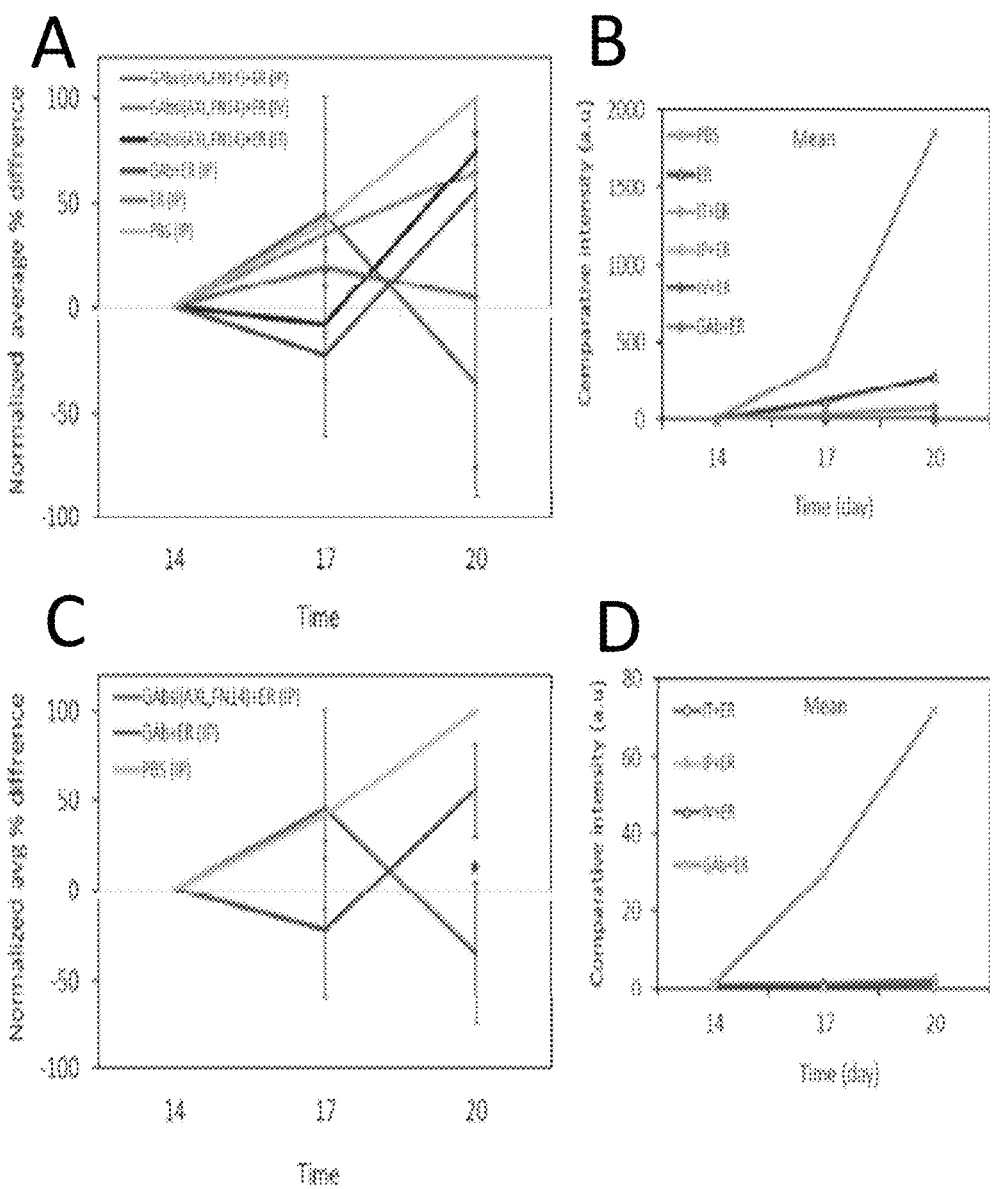
Figure 49A,B,C,D

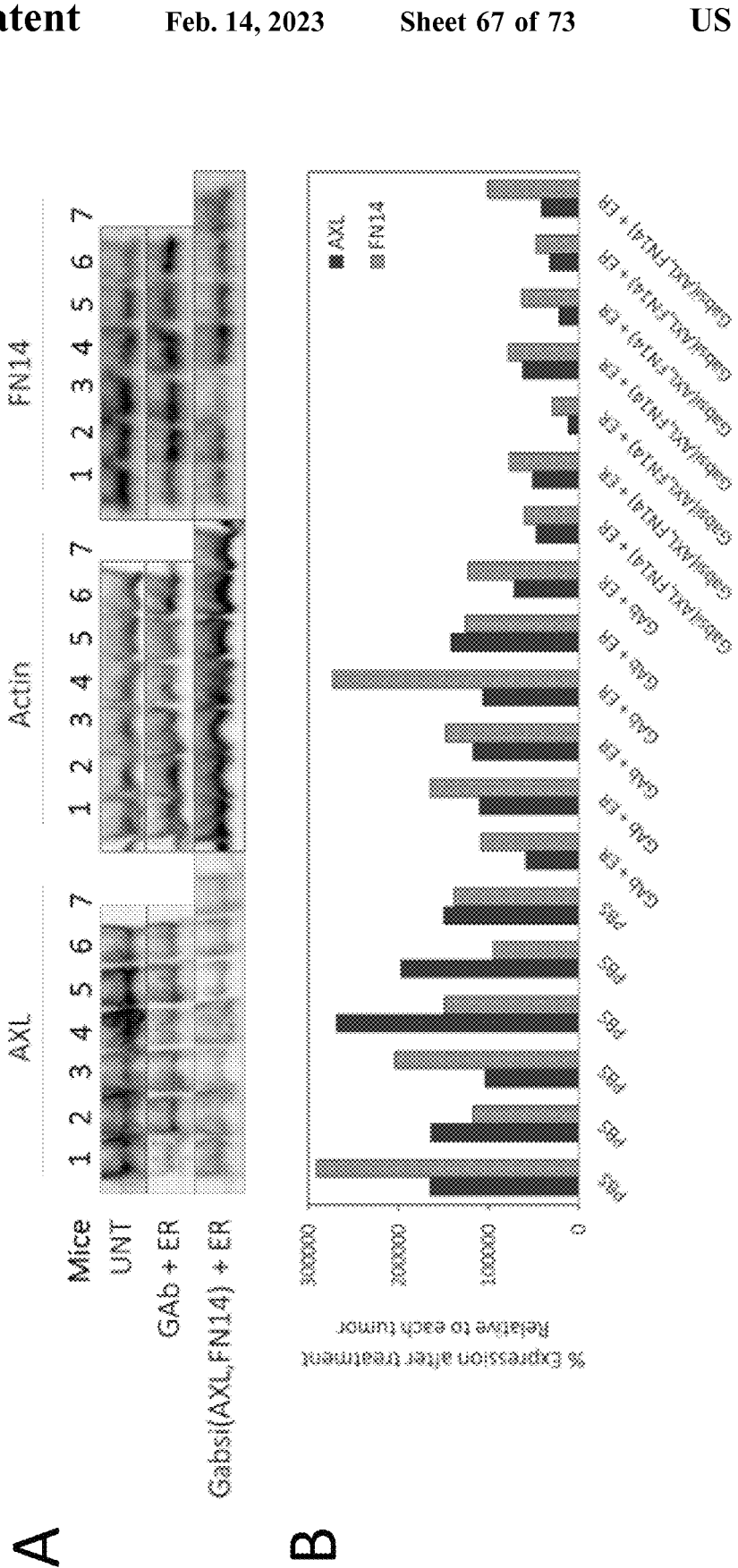
Figure 52A,B

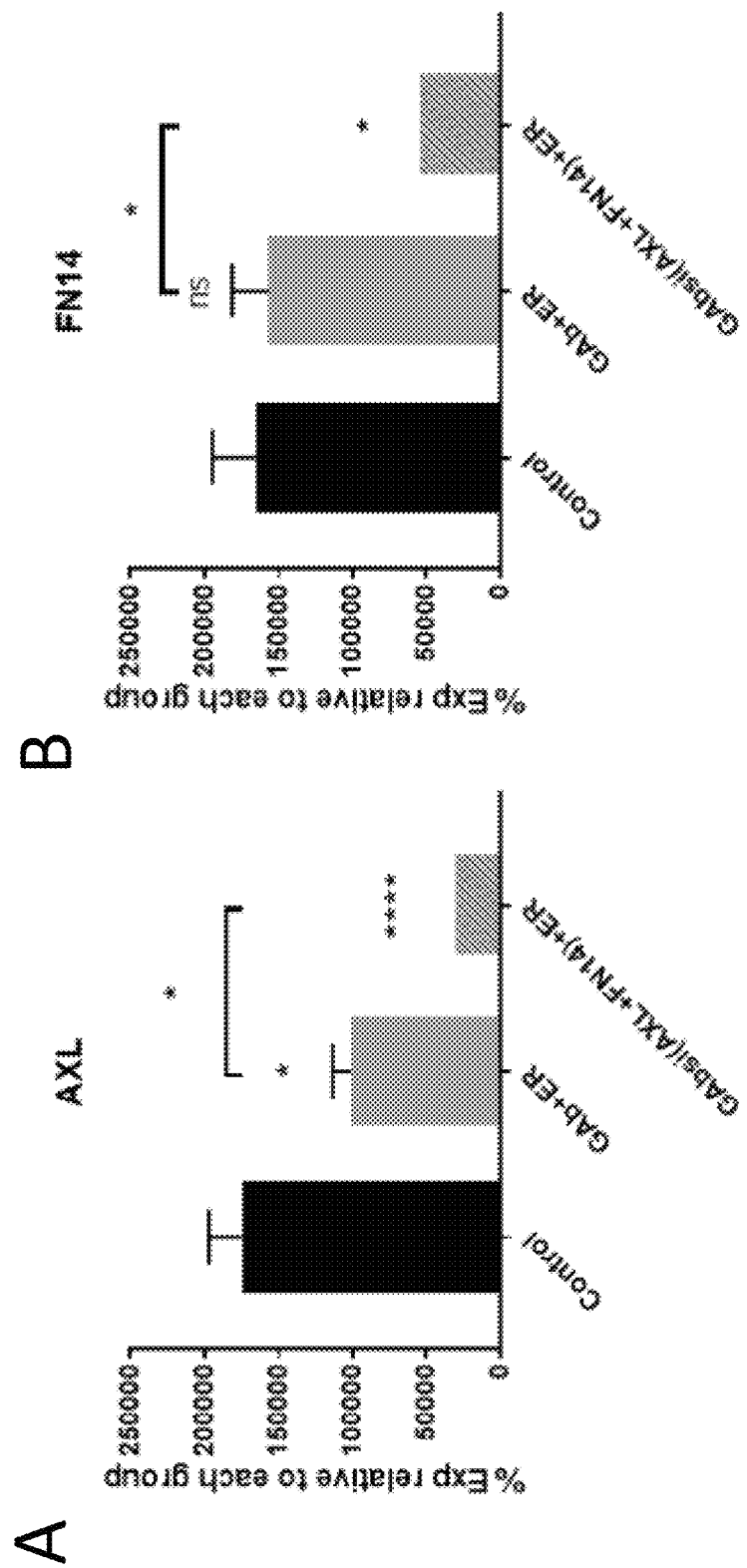
Figure 53A,B

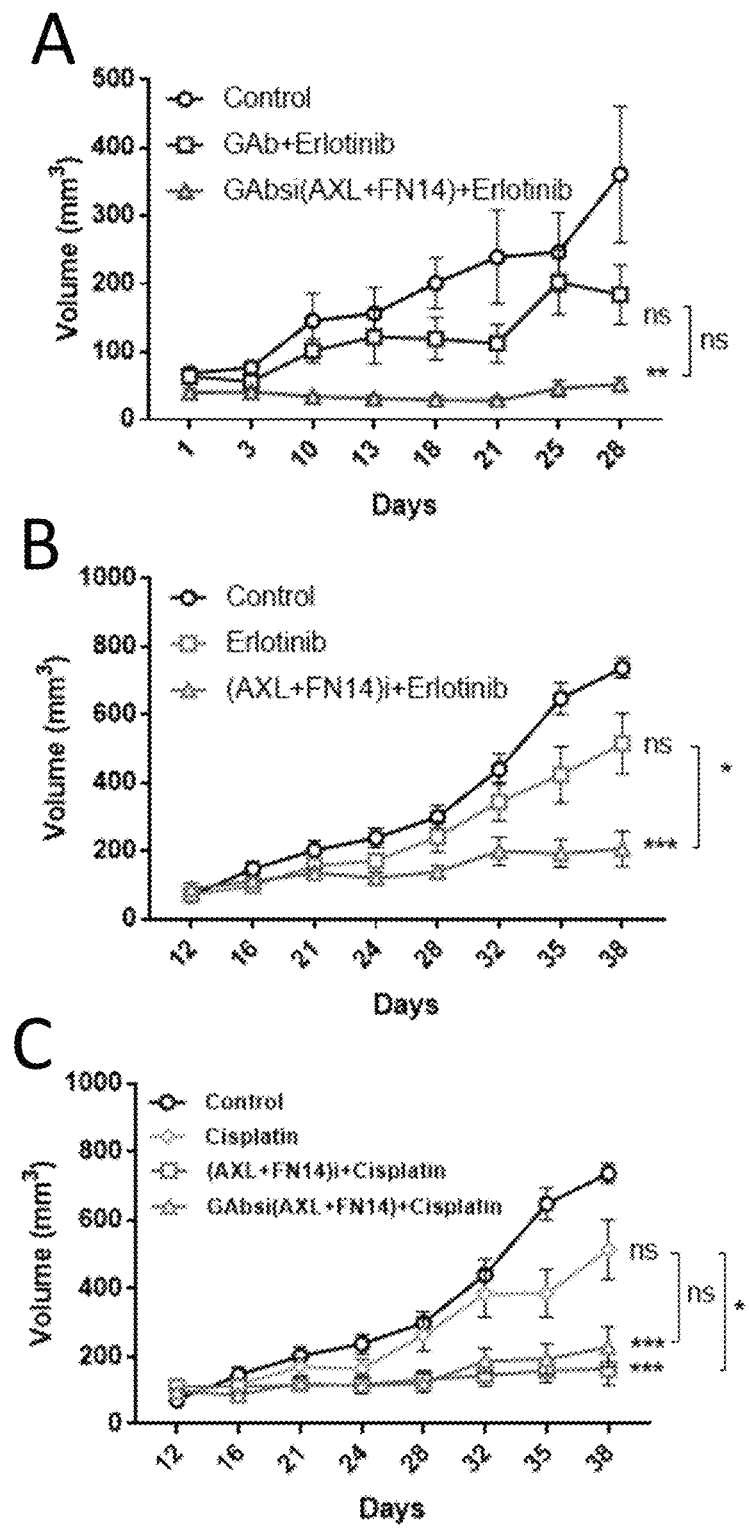
Figure 54A,B,C

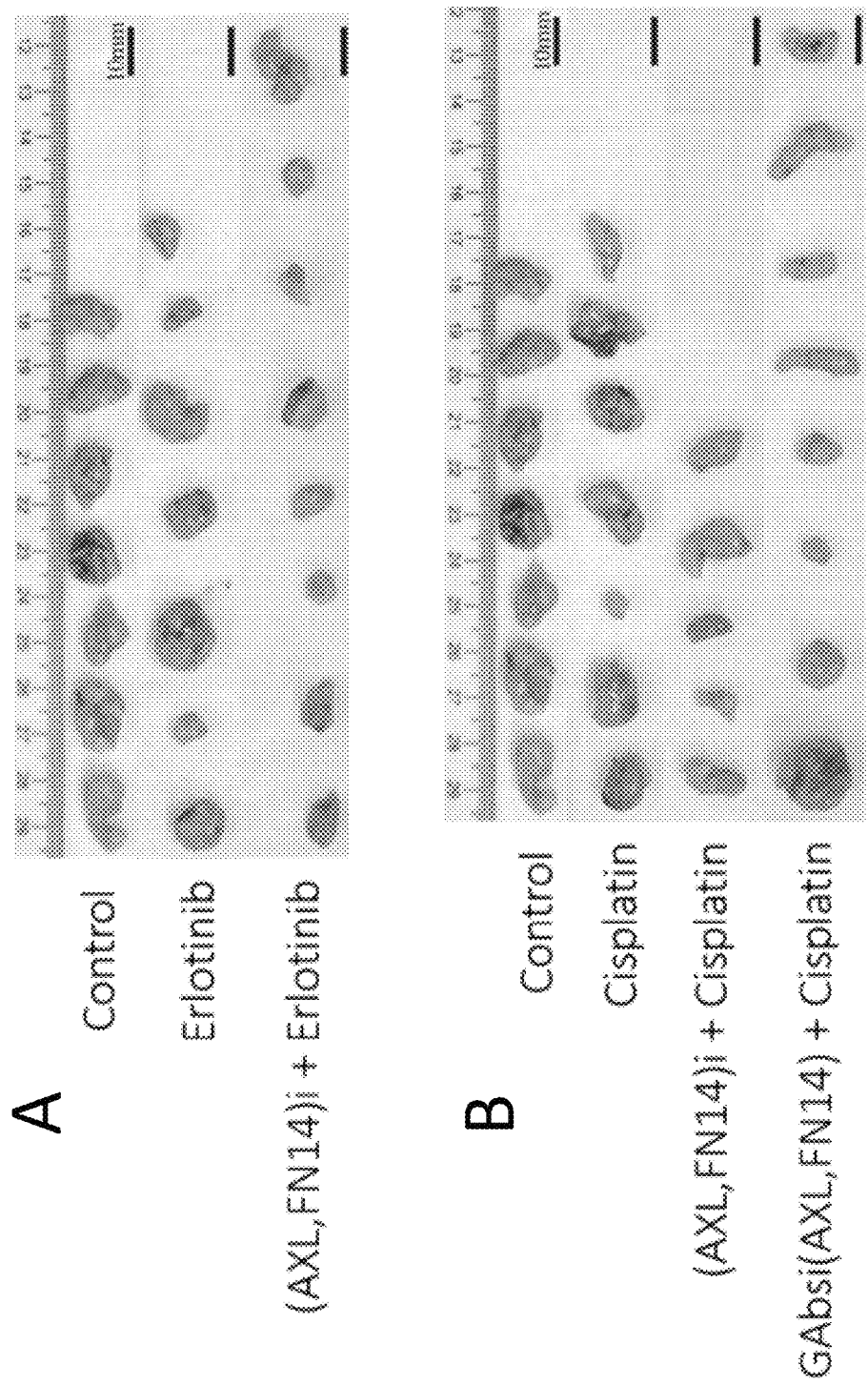
Figure 55A,B

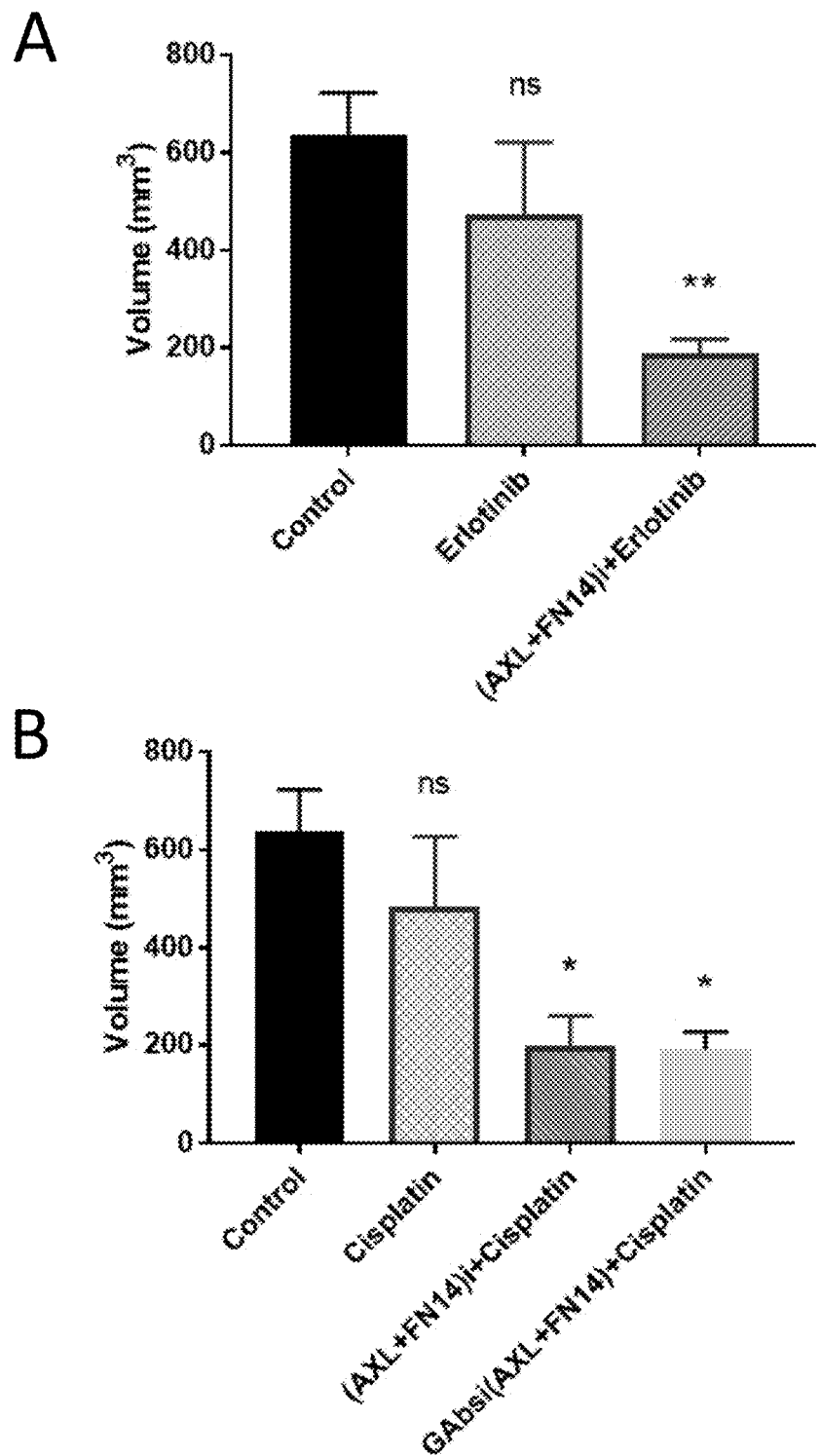
Figure 56A,B

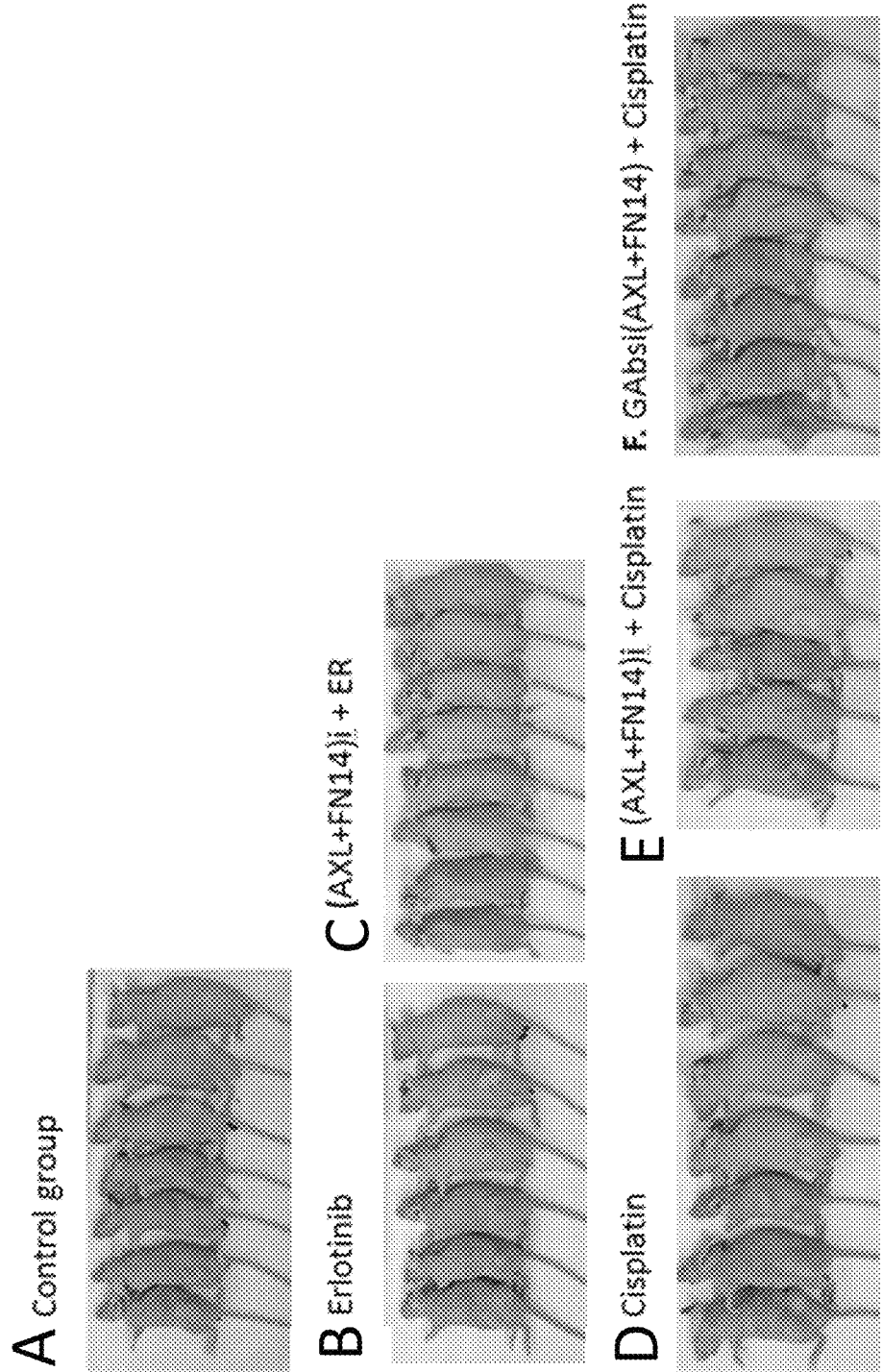
Figure 57A,B,C,D,E,F

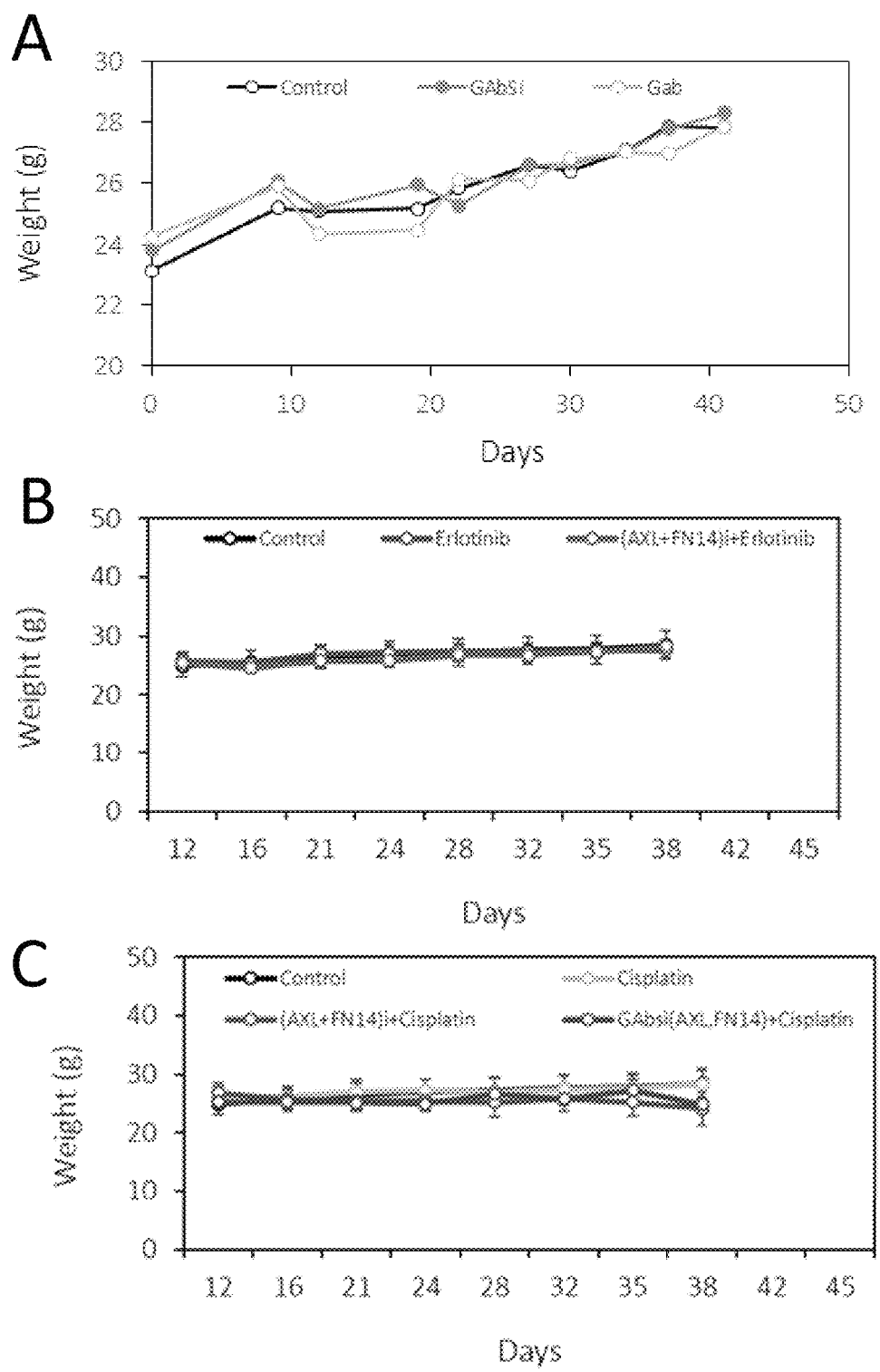
Figure 58A,B,C

COMPOSITIONS FOR THE TREATMENT OF DRUG-RESISTANT TUMORS AND METHODS OF USE THEREOF

CROSS-REFERENCE TO RELATED APPLICATIONS

This application is a 35 U.S.C. § 371 U.S. National Stage application of International Patent Application No. PCT/US2018/025544, filed Mar. 30, 2018, which claims the benefit of U.S. Provisional Patent Application Serial No. 62/479931, filed Mar. 31, 2017, both of which are incorporated by reference in their entireties.

INCORPORATION OF SEQUENCE LISTING

The content of the electronically submitted sequence listing in ASCII text file (Name: Sequence Listing_52553-173956.txt; Size: 20638 bytes; and Date of Creation: Mar. 30, 2018) filed with the application is incorporated herein by reference in its entirety.

BACKGROUND

In recent years, there have been large strides to understand drug efficacy post-treatment in cancer patients. Uramoto et al., Lung Cancer 2011; 73: 361-365. This heightened interest is primarily due to acquired drug resistance in patients. Brown et al., Nature Reviews Cancer 2014; 14: 747-753. The cause of these resistance cases is tied to poor understanding of post-treatment biochemistry. A major part of these biochemical issues partly tie with overexpressed oncogenes or mutations that compensate for the drug action in cancer cells. Frequently seen biomarkers in cancer patients include tyrosine kinase receptors families that are required for cell growth. Witton et al., J Pathol 2003; 200: 290-297. Predictably, the upregulation of these genes in cancer cells leads to uncontrolled growth of tumors. For example, epidermal growth factor receptor (EGFR), KRAS, and HER-2 are few of these upregulated oncogenes. To complicate this situation, not all of these upregulations in cancer patients are common. Ludwig et al., Nature Reviews Cancer 2005; 5: 845-856. Additionally, these genes can also exist as genetic or acquired mutations that can further change the overall function. Therefore, a drug needs to target these wild-type biomarkers and be specific to mutations as well. Of all cancers, lung cancers are mostly affected due to the sheer number of mutations that vary from patient to patient. Within lung cancer, non-small cell lung cancer (NSCLC), accounts for almost 80% of the cases (Inoue et al., Cancer Chemother Pharmacol 2015; 76: 155-161) and almost 10% of NSCLC patients harbor EGFR mutations. In addition to EGFR, other dominant mutations such as KRAS or ALK are also prevalent. Hence, efforts have been made to slowly bring personalized medicine to target the specific mutations. Of most drugs, tyrosine kinase inhibitors (TKI) are used to target these mutations. Primarily the first line and second line treatments in lung cancer cases include FDA approved cocktail of immunotherapy PD-L1 checkpoint inhibitors with TKIs such as erlotinib or gefitinib. Both these small molecule inhibitors bind to the intracellular domain of EGFR and specifically inhibits its downstream pathway. Additionally, these drugs can bind and inhibit other tyrosine kinase receptors as well albeit with low specificity. Xu Y et al., Cancer Biol Ther 2010; 9: 572-582. Both drugs target mutated EGFR that is very common in NSCLC patients. In recent years, there is a dramatic decrease in overall survival rate due to an increase in cases with treatment relapse. Much of the relapse has been tied to acquired drug resistance. Due to resistance, the drug action often fails before the end of the treatment duration. Therefore, several studies are now underway to recognize the cause of resistance in hopes to increase the drug efficacy. However, the underlying causes are still not well understood.

SUMMARY

The present disclosure is drawn to methods of sensitizing and/or resensitizing treatment-resistant cancer cells to cancer treatment. In certain aspects, the method comprises reducing the expression of at least two upregulated biomarker genes of the cancer cell. In certain aspects, the cancer treatment can be administration of an anticancer drug. In certain aspects, expression of at least one or expression of at least two of the upregulated cancer biomarker genes is reduced by the administration of an inhibitor. In certain aspects, the inhibitor is a small molecule inhibitor, an inhibitory antibody, and/or an inhibitory nucleic acid. In certain aspects, the nucleic acid can be an inhibitory siRNA. In certain aspects, two of the at least two upregulated cancer biomarkers genes are AXL and FN14.

In any aspects of the methods disclosed herein, the expression of the upregulated cancer biomarker genes can be reduced by nanoparticle delivery of inhibitory siRNAs attached to a nanoparticle. In certain aspects, the nanoparticle can be targeted to the cancer cell via an antibody or antigen-binding portion thereof specific to a cell-surface marker of the cancer cell. In certain aspects, the nanoparticle can be taken into the cell by receptor mediated endocytosis. In certain aspects, the cell-surface marker is selected from the group consisting of EGFR, cMET, HER2, HGRF, and PD-L 1.

In any aspects of the methods disclosed herein, the method further comprises administering the cancer treatment to which the treatment-resistant cancer is resistant. In certain aspects, the treatment-resistant cancer is resistant to is a tyrosine kinase inhibitor. In certain aspects, the treatment-resistant cancer is resistant to the anitcancer drug Erlotinib, Cisplatin, Gefitinib, or Dasatinib. In certain aspects, the drug can be delivered by the nanoparticle delivering at least one of the inhibitors. In certain aspects, the cancer can be non-small cell lung cancer (NSCLC), pancreatic cancer, breast cancer, or colorectal cancer.

The present disclosure also provides for methods of treating and/or preventing a cancer. In certain aspects, the method comprises administering, to a subject having a cancer and/or tumor: (i) inhibitors of at least two upregulated biomarker genes of the cancer and/or tumor and (ii) a cancer treatment. In certain aspects, the administration kills the cancer and/or delays the growth of and/or reduces the size of the tumor. In certain aspects, the growth of the tumor can be inhibited or delayed by at least about 25%, 30%, 40%, or 50% and/or the size of the tumor can be decreased by at least about 25%, 30%, 40%, or 50%, in comparison to an untreated control. In certain aspects, the growth of the tumor can be inhibited or delayed by at least about 25%, 30%, 40%, or 50% and/or the size of the tumor can be decreased by at least about 25%, 30%, 40%, or 50%, in comparison to a control treated with only one of the inhibitors and the cancer treatment. In certain aspects, the growth of the tumor can be inhibited or delayed by at least about 25%, 30%, 40%, or 50% and/or the size of the tumor can be decreased by at least about 25%, 30%, 40%, or 50%, in comparison to a control treated with the cancer treatment alone. In certain aspects, the size of the tumor can be reduced by at least about 25%, 30%, 40%, or 50%.

In any aspects of the methods disclosed herein, the death of the cancer and/or inhibition or delay of growth and/or the decrease in tumor size resulting from administration of the at least two inhibitors together, in conjunction with the cancer treatment, can be greater than the additive effect on cancer death and/or growth and/or tumor size resulting from administration of the inhibitors separately in conjunction with the cancer treatment. In other words, the method produces a synergistic effect.

In any aspects of the methods disclosed herein, the cancer treatment can be an anticancer drug. In any aspects of the methods disclosed herein, two of the at least two upregulated cancer biomarker genes can be AXL and FN14. In any aspects of the methods disclosed herein, the inhibitors can be administered by nanoparticle delivery of inhibitory siRNA attached to the surface of the nanoparticle. In certain aspects, the nanoparticle can be targeted to the tumor via an antibody or antigen-binding portion thereof specific to a cell-surface marker of a tumor cell. In certain aspects, the anticancer drug can be administered by nanoparticle delivery. In certain aspects, the same nanoparticle delivers at least one of the inhibitory siRNAs. In any aspects of the methods disclosed herein, the anticancer drug can be a tyrosine kinase inhibitor. In certain aspects, the anticancer drug can be Erlotinib, Cisplatin, Gefitinib, or Dasatinib. In any aspects of the methods disclosed herein, the cancer can be non-small cell lung cancer (NSCLC), pancreatic cancer, breast cancer, or colorectal cancer. In any aspects of the methods disclosed herein, administration of any of the inhibitors, nanoparticles, and/or anticancer drug can be intravenous.

The present disclosure also provides for compositions comprising a nanoparticle and at least one or at least two siRNAs capable of inhibiting the expression of one or more overexpressed cancer biomarker genes. In certain aspects, the composition is lyophilized. In certain aspects, the siRNAs are attached to the surface of the nanoparticle. In certain aspects, the attachment of the siRNA to the surface of the nanoparticle inhibits interaction of the siRNA with nuclease proteins and/or inhibits degradation of the siRNA. In certain aspects, this inhibition of interaction of the siRNA with nuclease proteins and/or inhibition of degradation of the siRNA can occur in the bloodstream of a subject.

In any aspects of the compositions disclosed herein, the upregulated biomarker genes can be selected from the group consisting of EGRF, KRAS, HER-2, AXL, and FN14. In certain apsects, the upregulated biomarker genes can be optionally selected from the group consisting of AXL, Her-2, and FN14. In any aspects of the compositions disclosed herein, the composition can further comprise an anticancer drug. In certain aspects, the anticancer drug can be selected from the group consisting of Erlotinib, Cisplatin, Gefitinib, and Dasatinib.

In any aspects of the compositions disclosed herein, the composition can be targeted to a cancer cell via an antibody or antigen-binding portion thereof portion thereof specific to a cell-surface marker of the cancer cell that is attached to the nanoparticle. In certain aspects, the cell-surface marker can facilitate receptor-mediated endocytosis. In any aspects of the compositions disclosed herein, the anticancer drug can be contained within the nanoparticle. In certain aspects, the nanoparticle can degrade within a cell to release the drug.

BRIEF DESCRIPTION OF THE DRAWINGS/FIGURES

FIG. 1. FIG. 1 shows activation of RISC complex using siRNA to degrade AXL mRNA in the cytoplasm.

Figure 2:
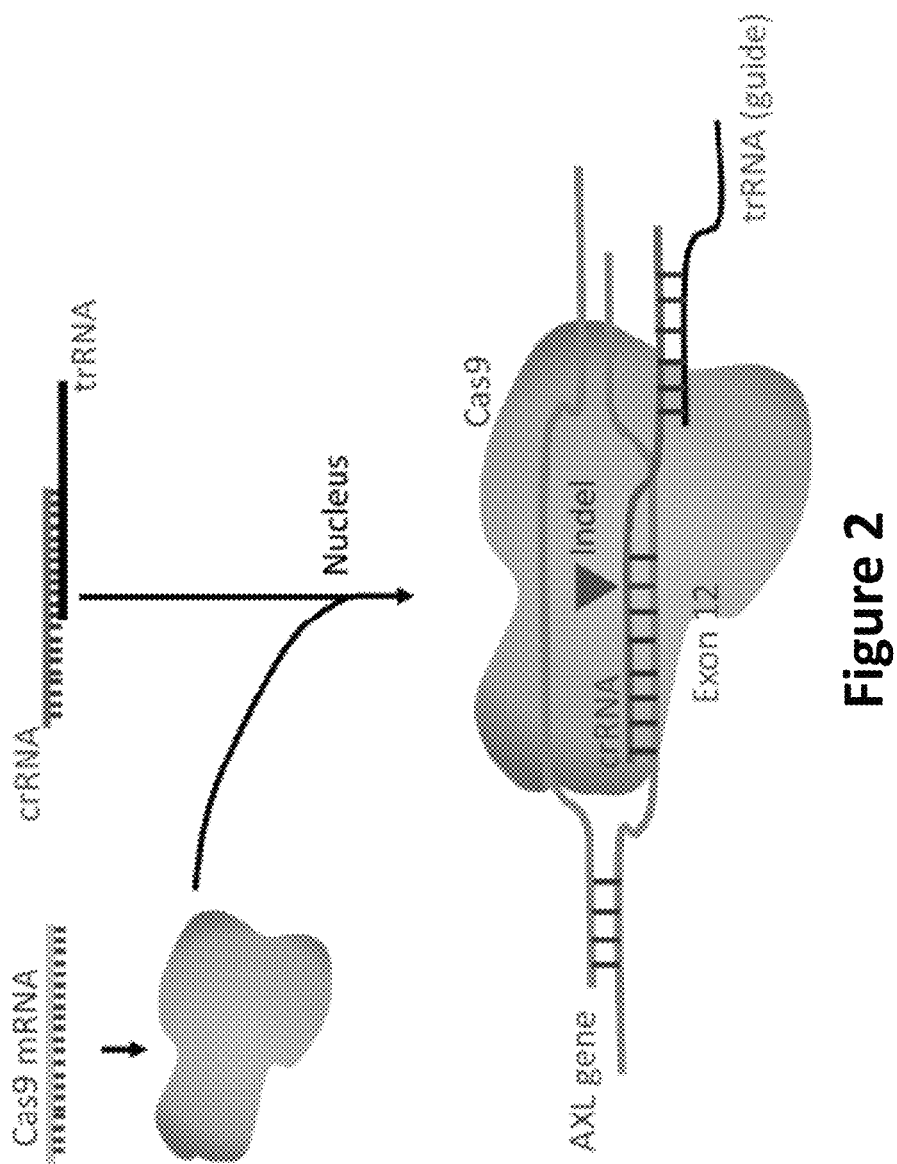

FIG. 2. FIG. 2 shows the formation of indel in the AXL gene using the complex formed by CRISPR RNA, Tracer guide RNA, and the Cas9 endonuclease protein.

Figure 3:
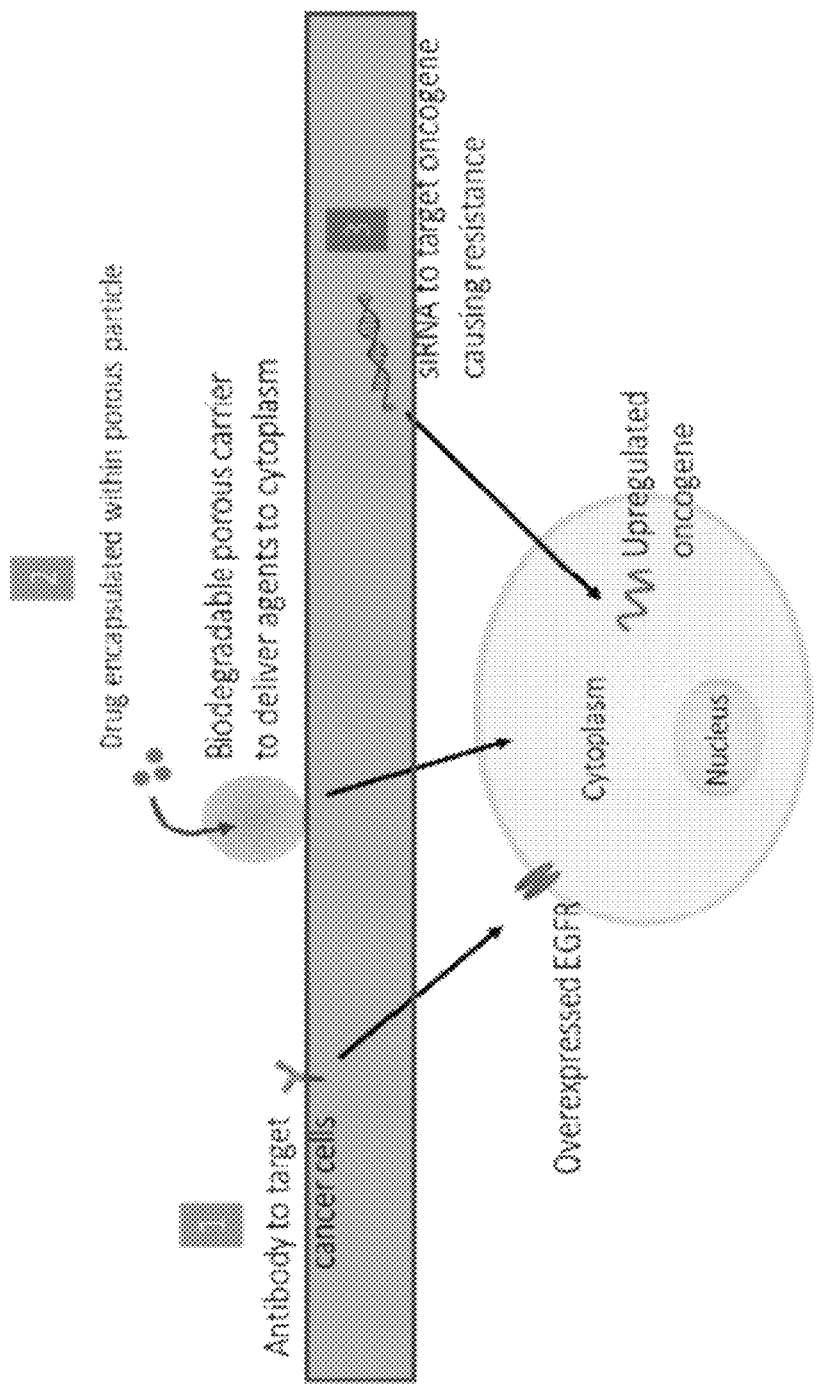

FIG. 3. FIG. 3 shows the three components needed to target, release drug and destroy resistance causing oncogenic mRNA within cell cytoplasm.

Figure 4:
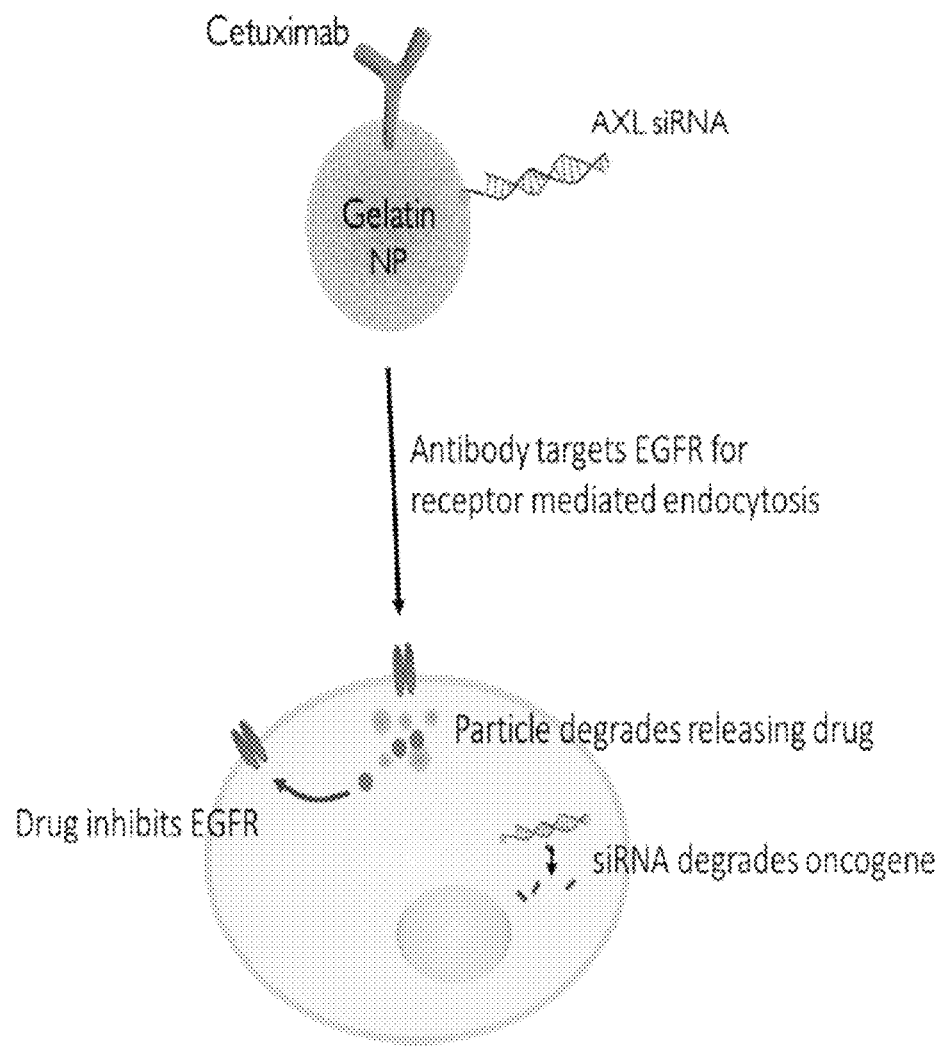

FIG. 4. FIG. 4 shows the design of an antibody conjugated porous drug encapsulated multifunctional nanoparticle with siRNA on its surface. These particles, once internalized, will degrade within the cytoplasm using proteases and release both drug and siRNA to block and inhibit EGFR pathway and AXL pathway respectively.

FIG. 5A,B. FIG. 5A and 5B show standard curves for (A) Ab-Cy5 using Cetuximab and (B) siAXL-Cy5.

FIG. 6A-C. FIG. 6A, 6B, and 6C show TEM images for (A) Gelatin nanoparticle (G) (B) antibody conjugated GAb and (C) antibody and siRNA conjugated GAbsi AXL.

FIG. 7A. FIG. 7A shows the stability of Gelatin nanoparticle constructs evaluated through change in surface potential over time.

FIG. 7B. FIG. 7B shows the stability of Gelatin nanoparticle constructs evaluated through change in hydrodynamic size over time in (panel (i)) water, (panel (ii)) 1×PBS, (panel (iii)) RPMI media. Averaged results are shown in (panel (iv)).

Figure 8A:
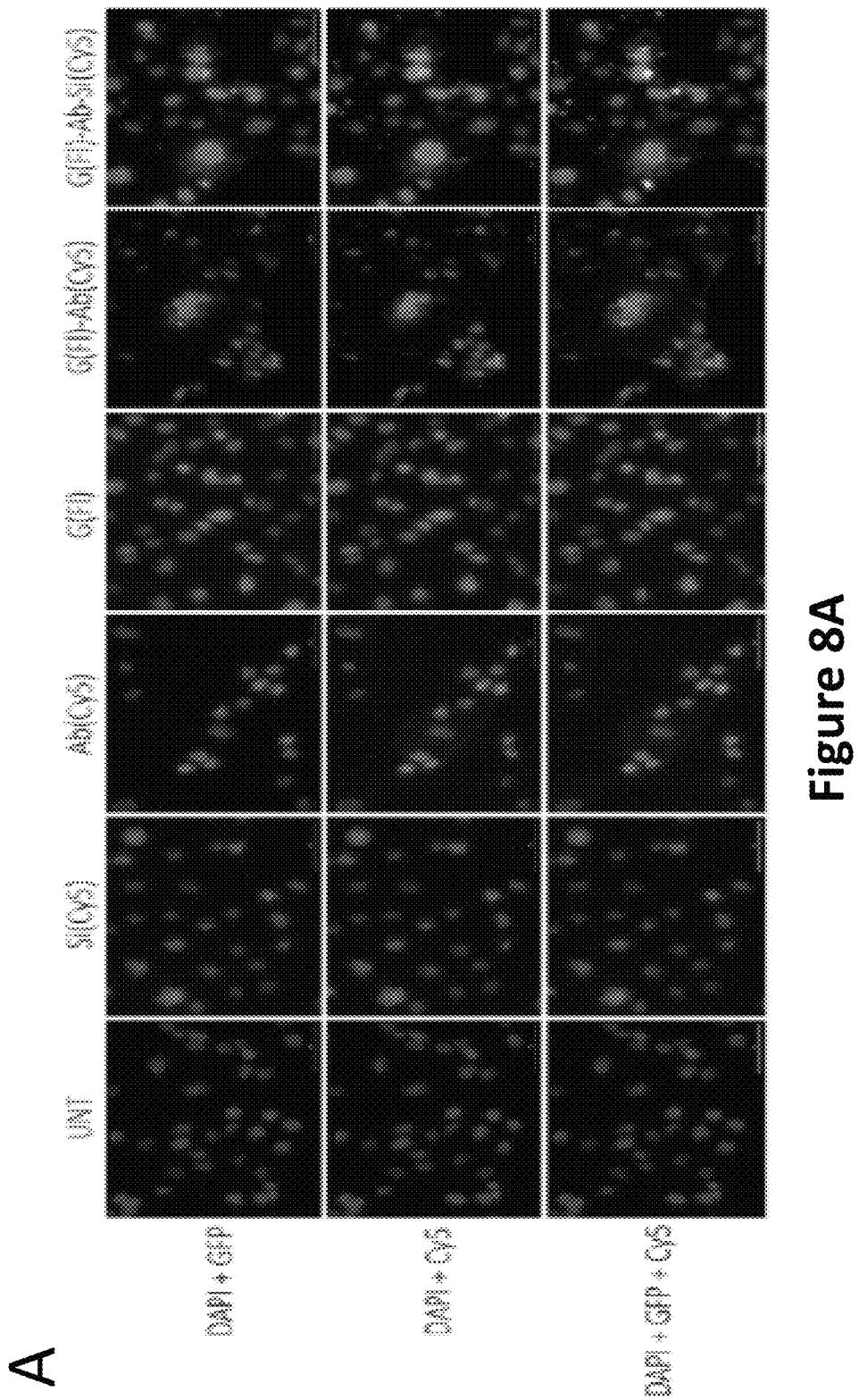
Figure 8B:
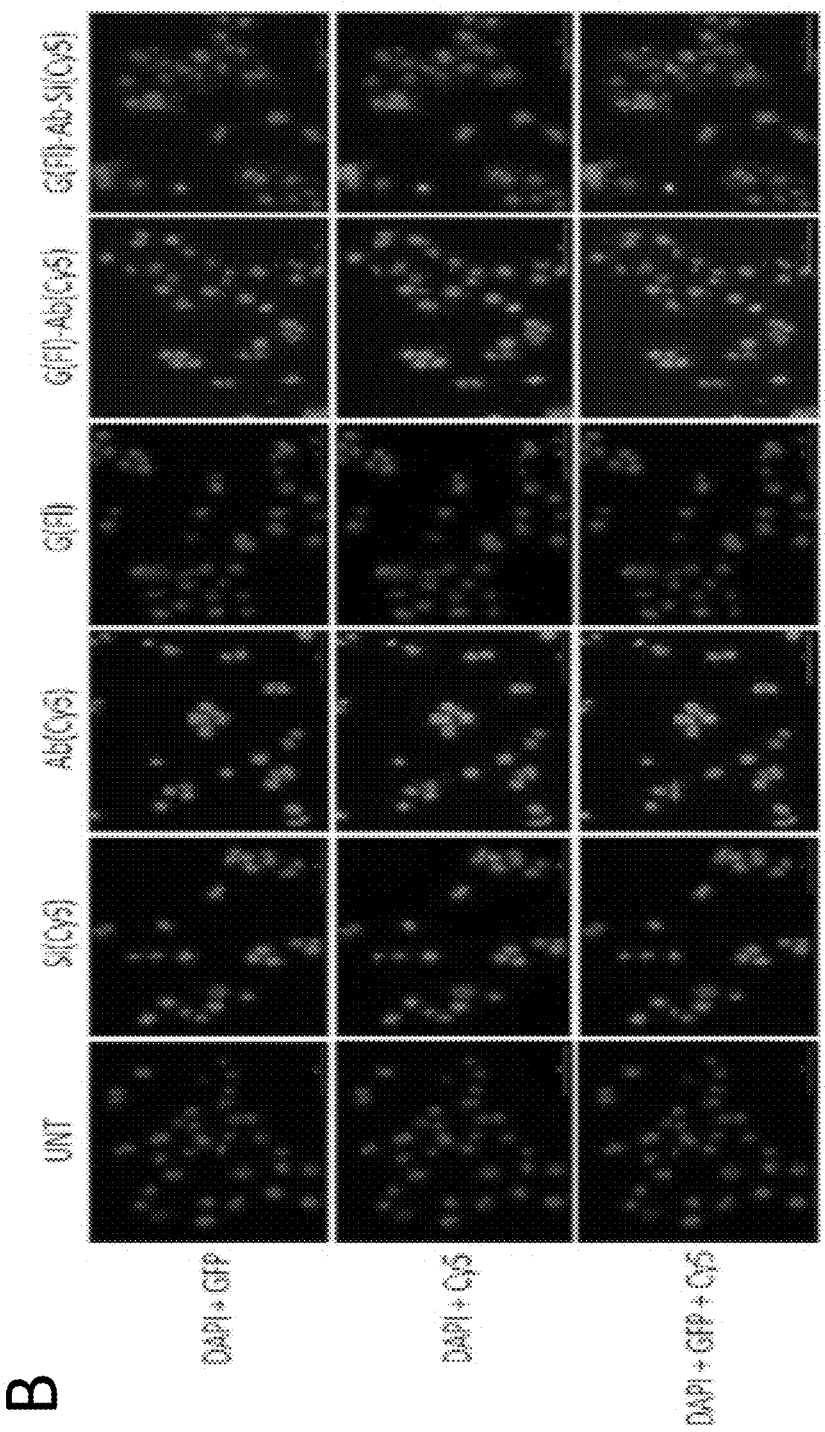

FIG. 8A,B. FIG. 8A and 8B show the internalization of targeted constructs in (A) H820 and (B) HCC827 cells (40×). Results indicate gelatin particles (Fluorescein) are only internalized when antibody is present on surface. Similarly, siRNA is internalized when gelatin particles are internalized by antibody targeting.

FIG. 9A,B. FIG. 9A and 9B show the internalization of targeted constructs in HCC827 cells: (A) GAb (B) Gabsi-AXL-Cy5 (60×). Results indicate presence of high quantities of siRNA (Cy5) in the cytoplasm of cells after internalization of construct.

FIG. 10A,B. FIG. 10A and 10B show downregulation of AXL using siRNA in H820 cells: (A) Band densitometry analysis (B) associated blot.

FIG. 11A,B. FIG. 11A and 11B show downregulation of AXL using siRNA conjugated constructs in H820 cells: (A) associated blot (B) Band densitometry analysis.

FIG. 11C,D. FIG. 11C and 11D show downregulation of FN14 using siRNA conjugated constructs in H820 cells: (C) associated blot (C) Band densitometry analysis. MP and OP stand for Modified protocol and Old protocol respectively. Gq and Gnq stand for gelatin particles with glutaraldehyde quenched and non-quenched respectively.

FIG. 12A,B. FIG. 12A and 12B show downregulation of AXL using siRNA conjugated constructs in H820 cells: (A) associated blot (B) Band densitometry analysis. Results indicate that physical mixture of GAb and siRNA does not allow downregulation. Results also show that storing lyophilized power at −20° C. does not adversely affect function of construct.

Figure 13:
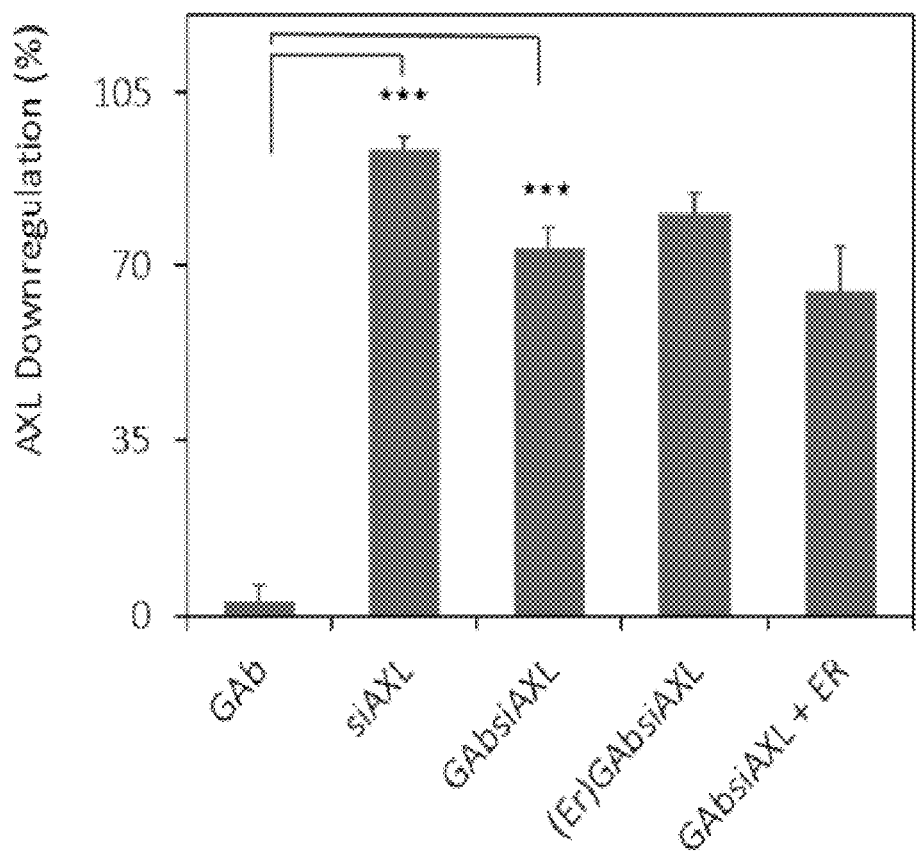

FIG. 13. FIG. 13 shows cumulative analysis of AXL downregulation using siRNA alone, siRNA conjugated constructs and synergistic treatment of GAbsiAXL with erlotinib in H820 cells. Results show siRNA was efficiently downregulating AXL when present in sample. These results suggest nanoparticle based delivery of siRNA was highly stable and efficient. As shown in figure GAb control did not affect AXL in cells. ★★★ p≤0.001, and the values were analyzed using one-way Anova.

Figure 14A:
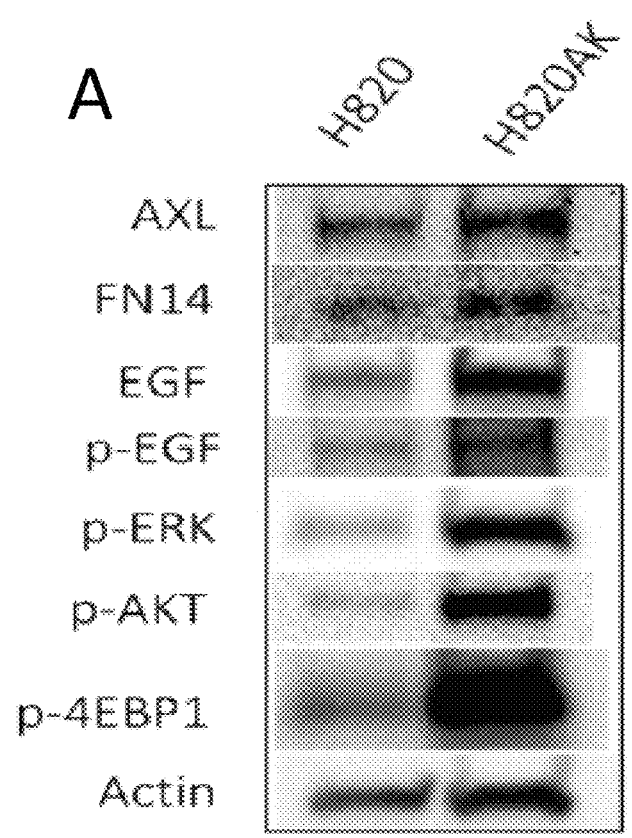

FIG. 14A. FIG. 4A shows protein analysis between H820 and CRISPR generated AXL knockout H820AK cells: (A) associated blot.

Figure 14B:
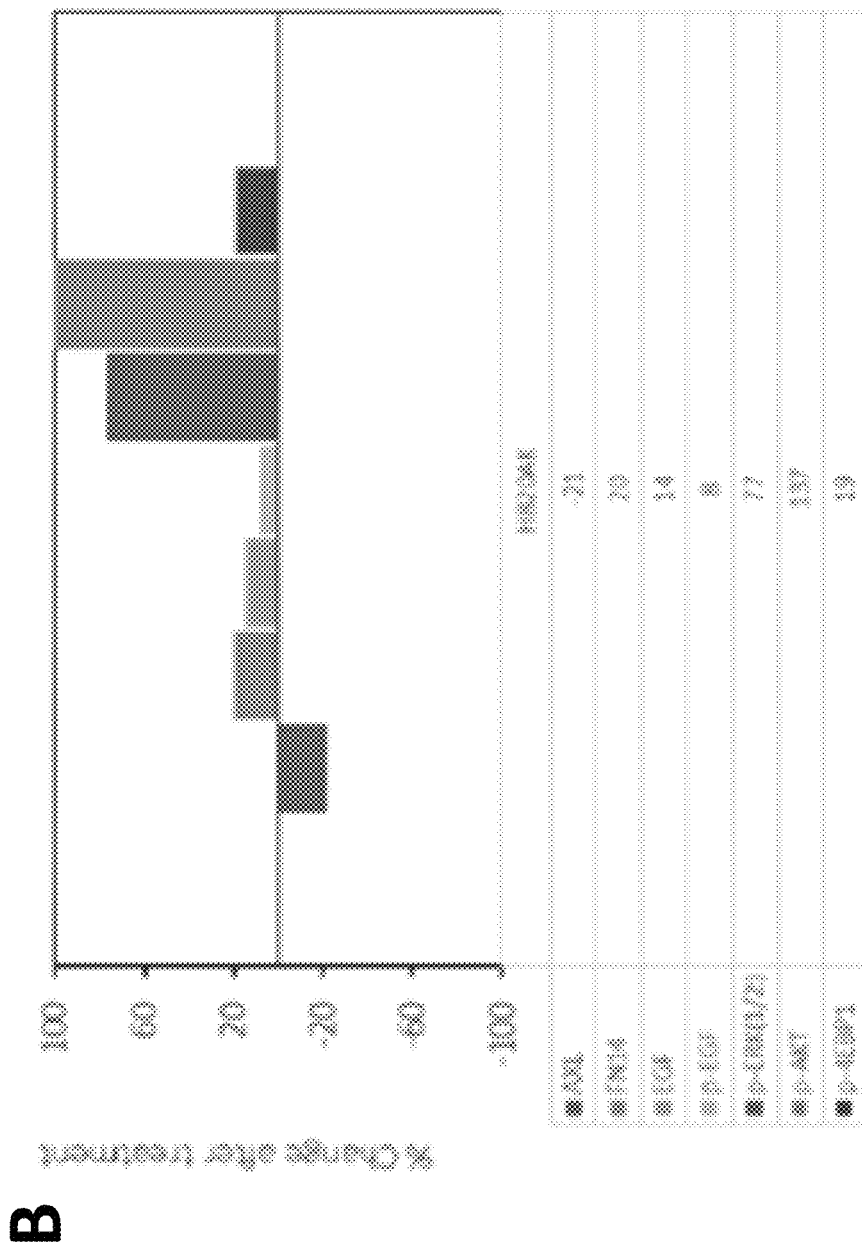

FIG. 14B. FIG. 4B shows protein analysis between H820 and CRISPR generated AXL knockout H820AK cells: (B) Band densitometry analysis for blot.

Figure 14C:
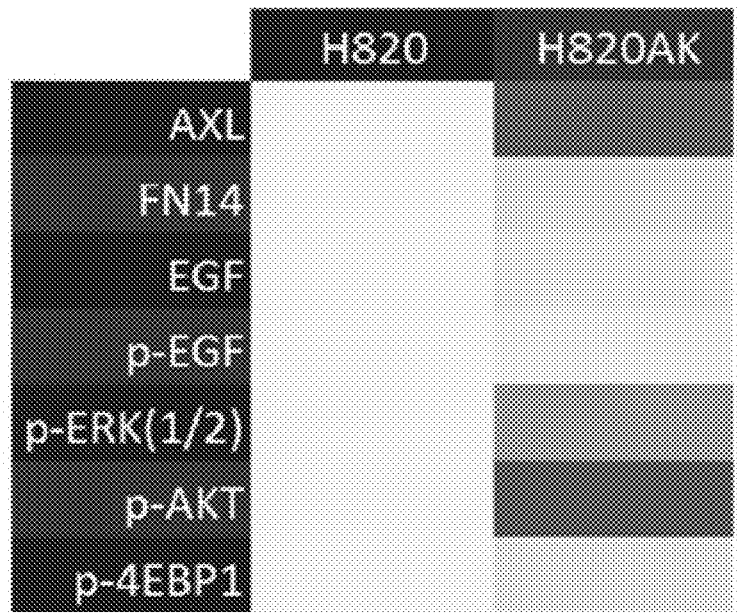

FIG. 14C. FIG. 4C shows protein analysis between H820 and CRISPR generated AXL knockout H820AK cells: (C) Representative heat map showing relative expressions (Red=high; Blue=low).

FIG. 15A,B. FIG. 15A and 15B show RT-PCR gene expression analysis for: (A) AXL and (B) P53. Results were averaged from 3 independent experiments.

FIG. 15C,D. FIG. 15C and 15D show RT-PCR gene expression analysis for: (C) EGFR and (D) MZF1. Results were averaged from 3 independent experiments.

FIG. 16A,B. FIG. 16A and 16B show apoptosis assay analysis for: (A) Late-stage at 48 h and (B) Early-stage at 72 h shows relative increase during synergistic treatment of siRNA based samples with erlotinib in H820 cells.

Figure 16C:
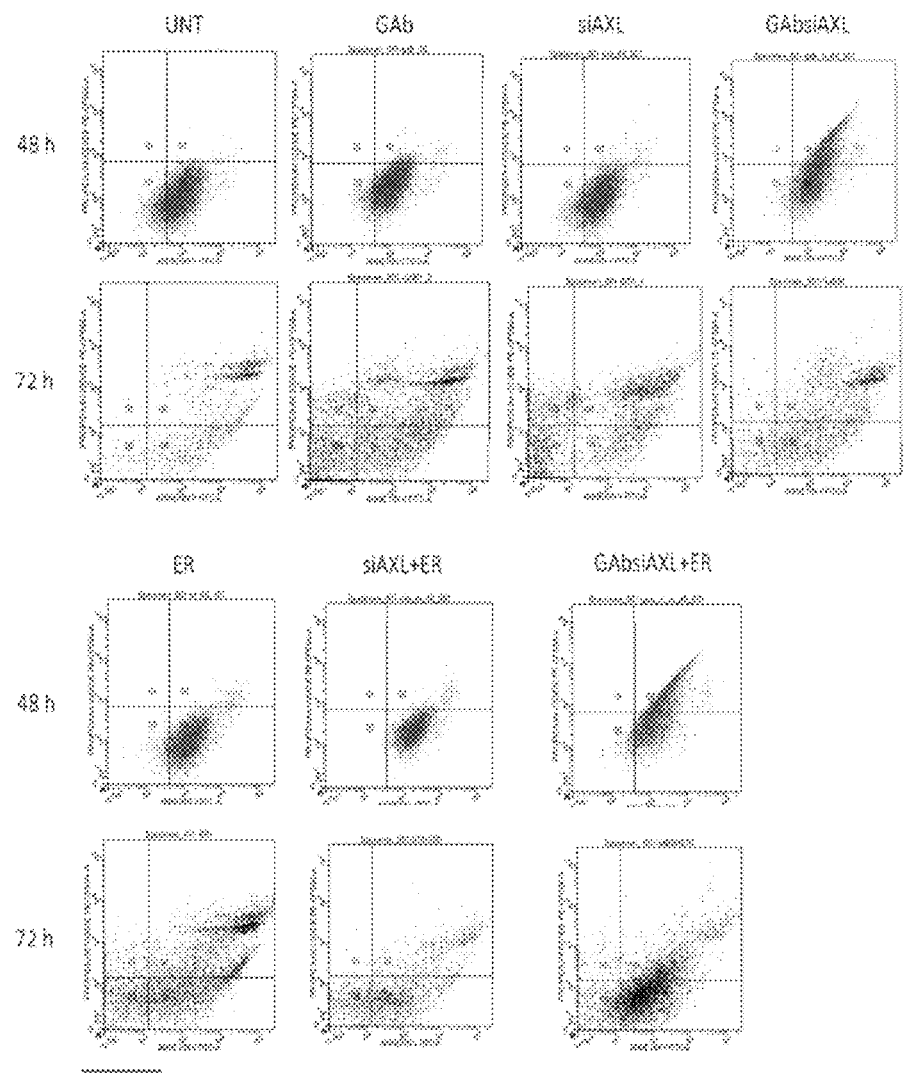

FIG. 16C. FIG. 16C shows associative flow cytometry data for apoptosis results from apoptosis assay above. Q2 and Q4 indicate late and early-stage apoptosis respectively. Results were averaged from 2 independent experiments.

FIG. 17A,B. FIG. 17A and 17B show RT-PCR micro-RNA expression analysis for: (A) miR-34a and (B) miR-432. Results were averaged from 3 independent experiments.

FIG. 17C,D. FIG. 17C and 17D show RT-PCR micro-RNA expression analysis for: (C) miR-548b and (D) miR-374. Results were averaged from 3 independent experiments.

FIG. 18A,B. FIG. 18A and 18B show proliferation analysis in H820 cells using (A) Invasion assay and (B) Migration assay.

FIG. 19A,B. FIG. 19A and 19B show zymogram analysis in H820 cells for MMP-2 and MMP-9 activity using conditioned media: (A) Associated zymograph (B) Band densitometry analysis. Results were averaged from 3 independent experiments. ★★★ p≤0.001, and the values were analyzed using one-way anova.

Figure 20A:
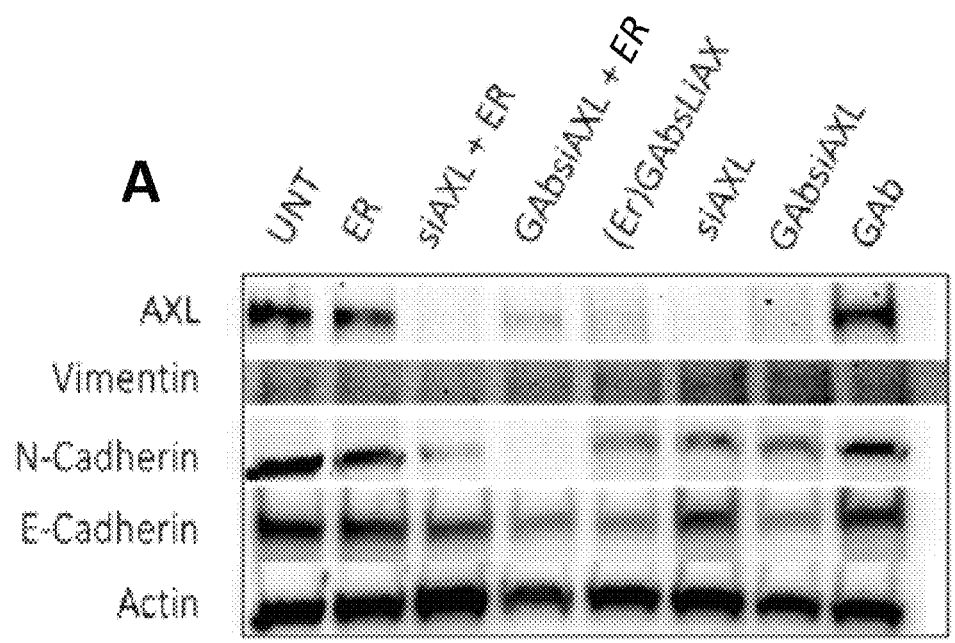

FIG. 20A. FIG. 20A shows Western blot for AXL siRNA based treatments, controls and synergistic treatment with erlotinib in H820 cells: (A) EMT pathway.

Figure 20B:
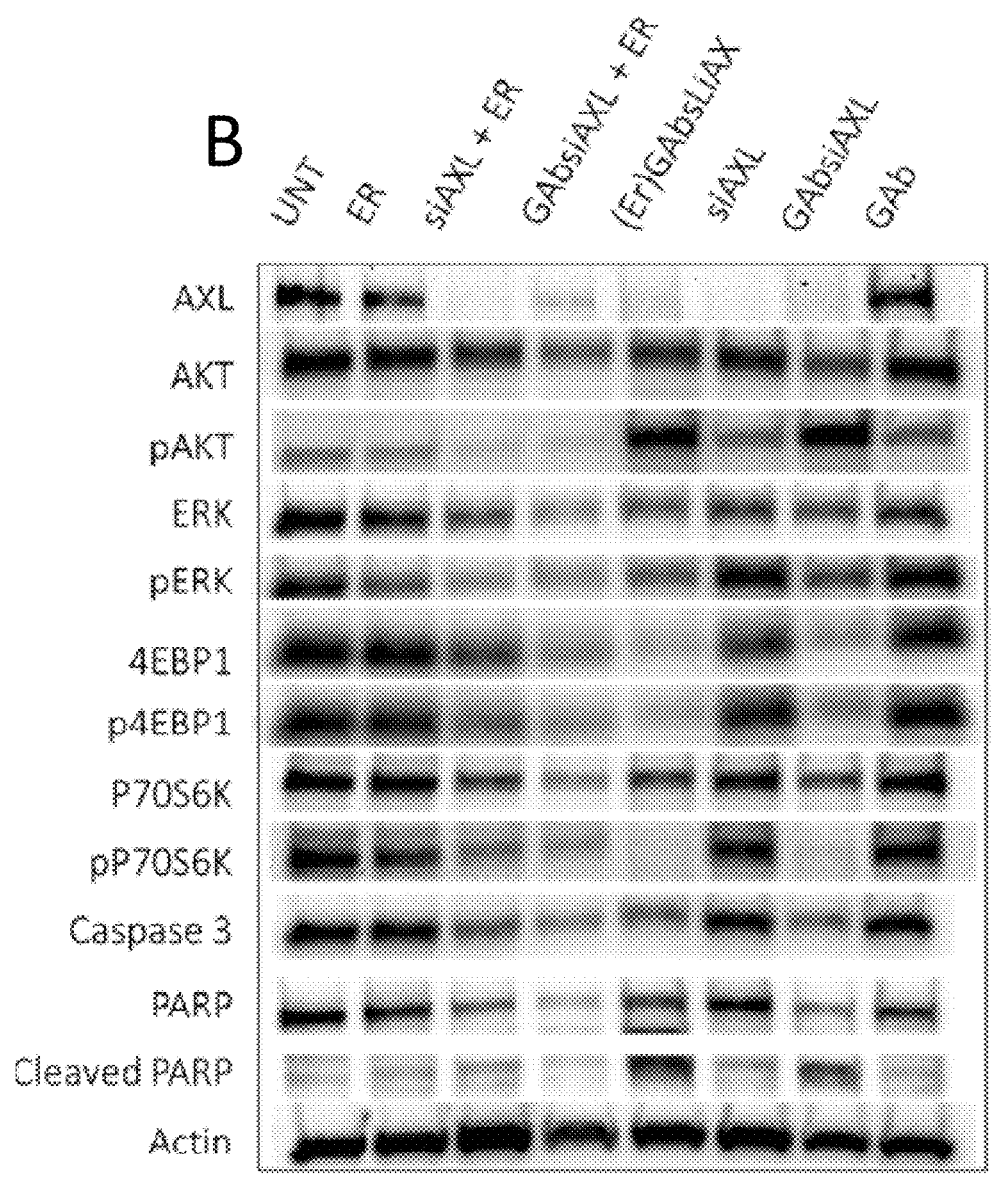

FIG. 20B. FIG. 20B shows Western blot for AXL siRNA based treatments, controls and synergistic treatment with erlotinib in H820 cells: (B) mTOR-AKT axis and apoptosis pathway.

Figure 20C:
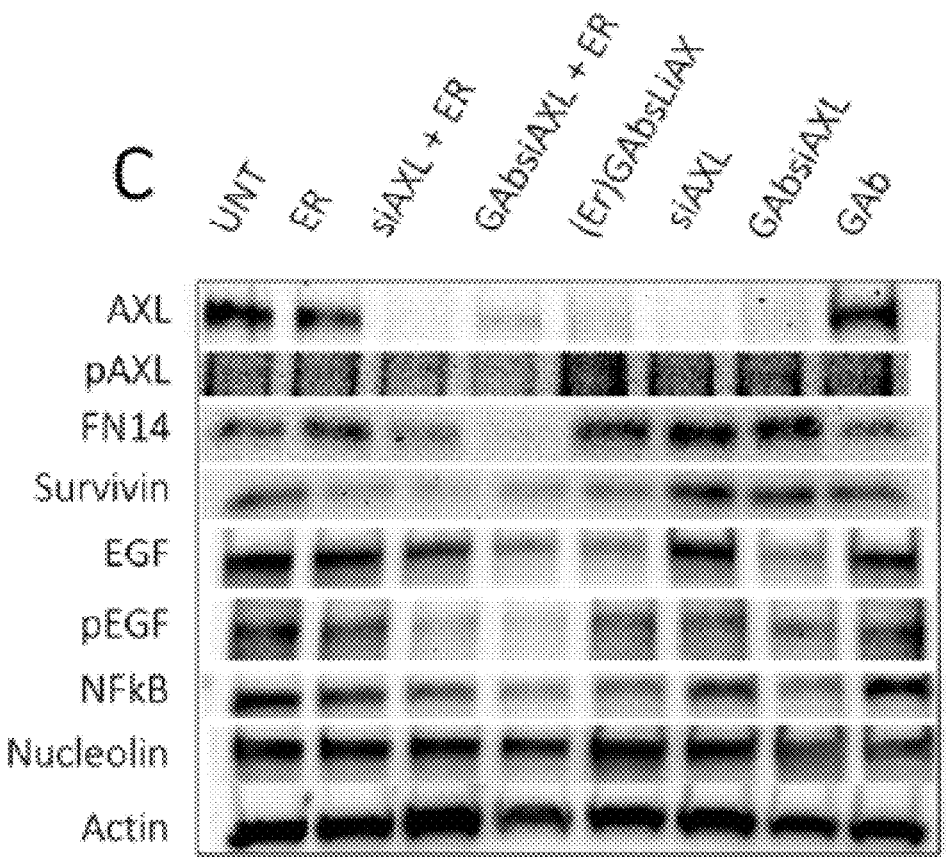

FIG. 20C. FIG. 20C shows Western blot for AXL siRNA based treatments, controls and synergistic treatment with erlotinib in H820 cells: (C) EGFR and associated survival pathways.

Figure 21:
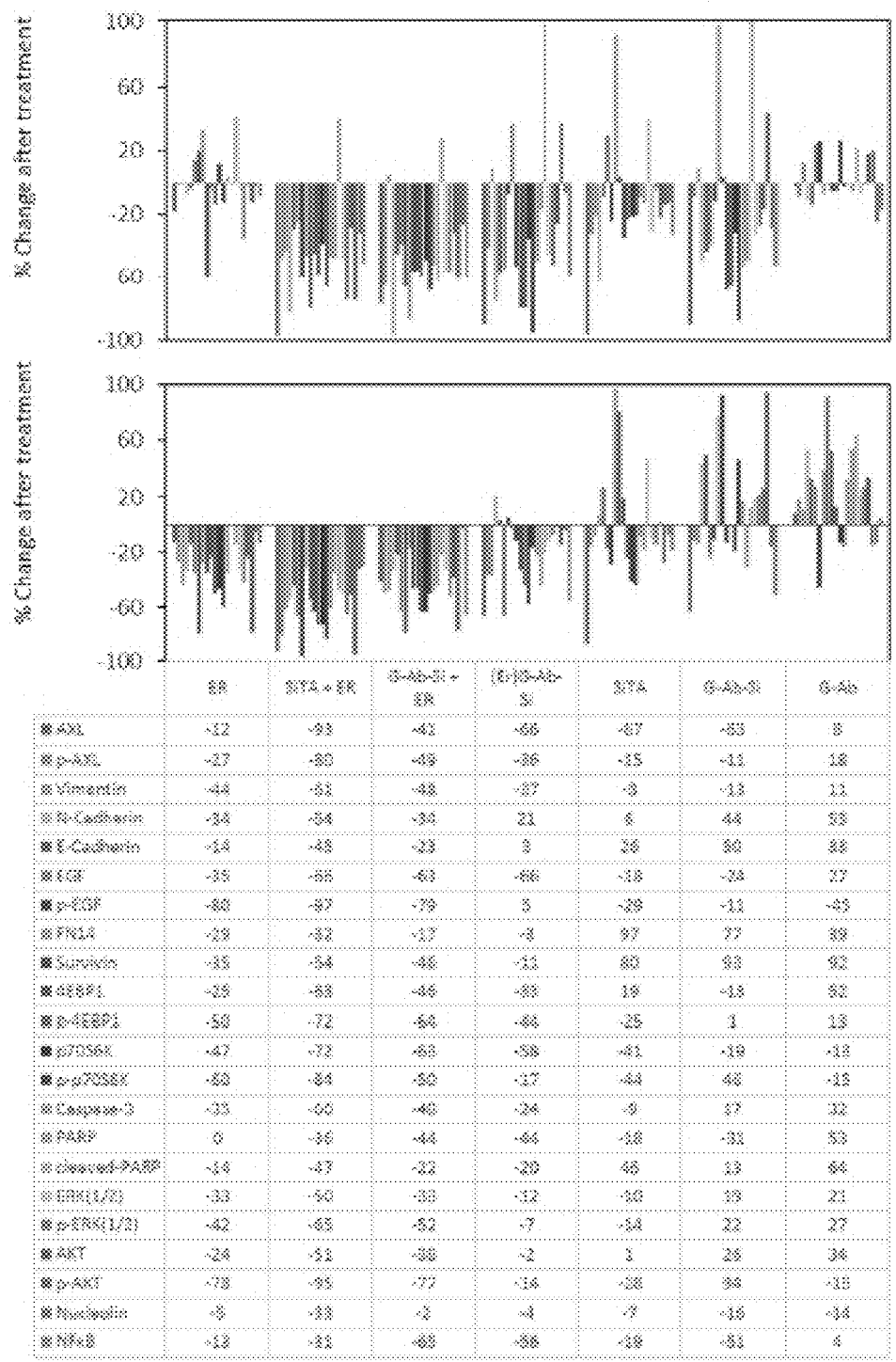

FIG. 21. FIG. 21 shows band densitometry analysis for associated blots shown in FIG. 20. Data represents protein analysis for AXL siRNA based treatments, controls and synergistic treatment with erlotinib in H820 cells.

Figure 22:
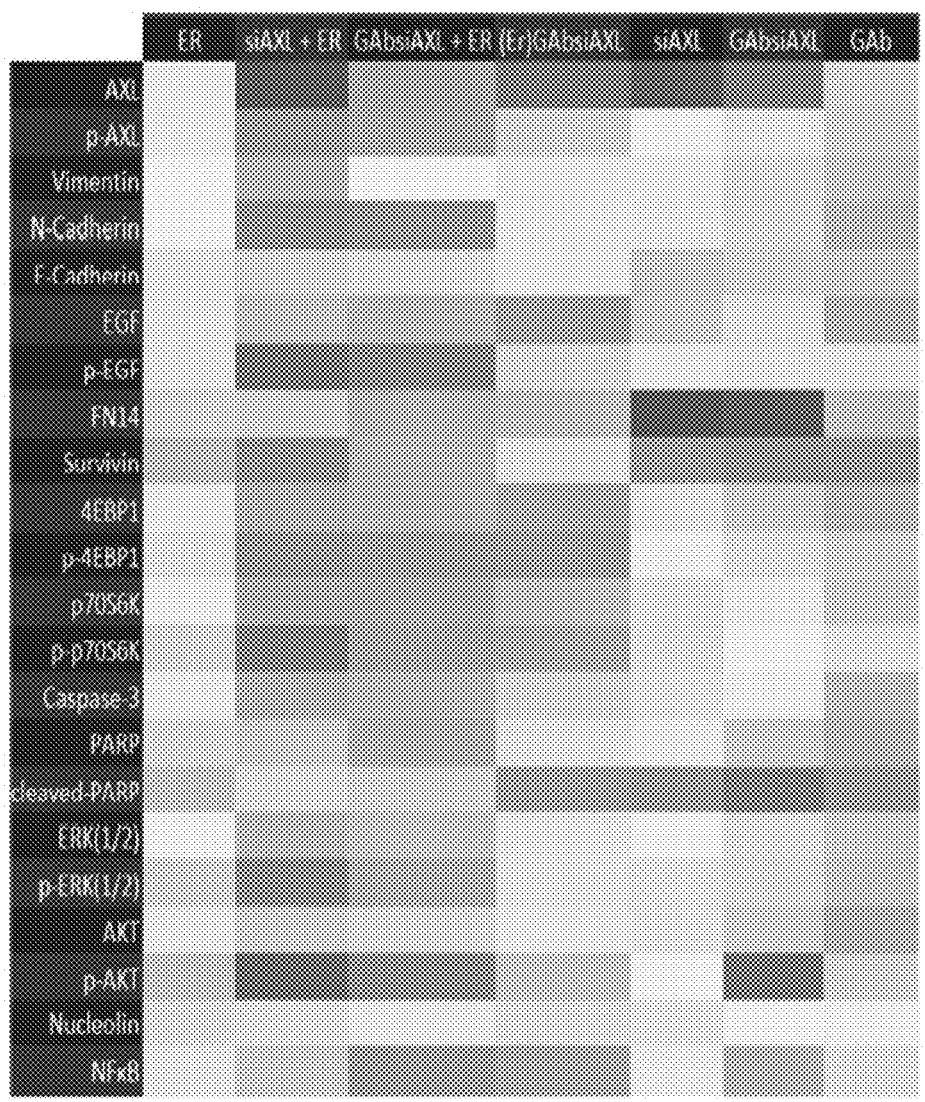

FIG. 22. FIG. 22 shows a representative heat map for data shown in FIG. 21 (Red=high; Blue=low). Data represents protein analysis for AXL siRNA based treatments, controls and synergistic treatment with erlotinib in H820 cells. Results were averaged from 2 independent experiments.

Figure 23:
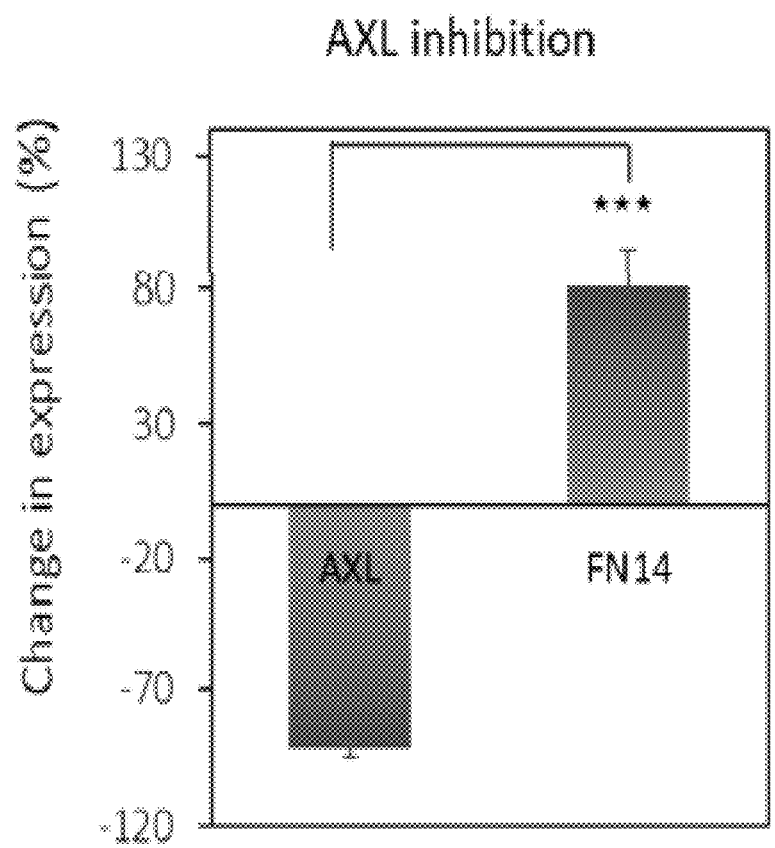

FIG. 23. FIG. 23 shows relative expression of FN14 when AXL is downregulated in H820 cells. Results were averaged from 3 independent experiments. ★★★ p <0.001, and the values were analyzed using one-way anova.

FIG. 24A,B. FIG. 24A and 24B show relative expression of FN14 when AXL is downregulated in NSCLC cells: (A) associated western blot and (B) Band densitometry analysis for A549 cells showing FN14 upregulation.

Figure 25A:
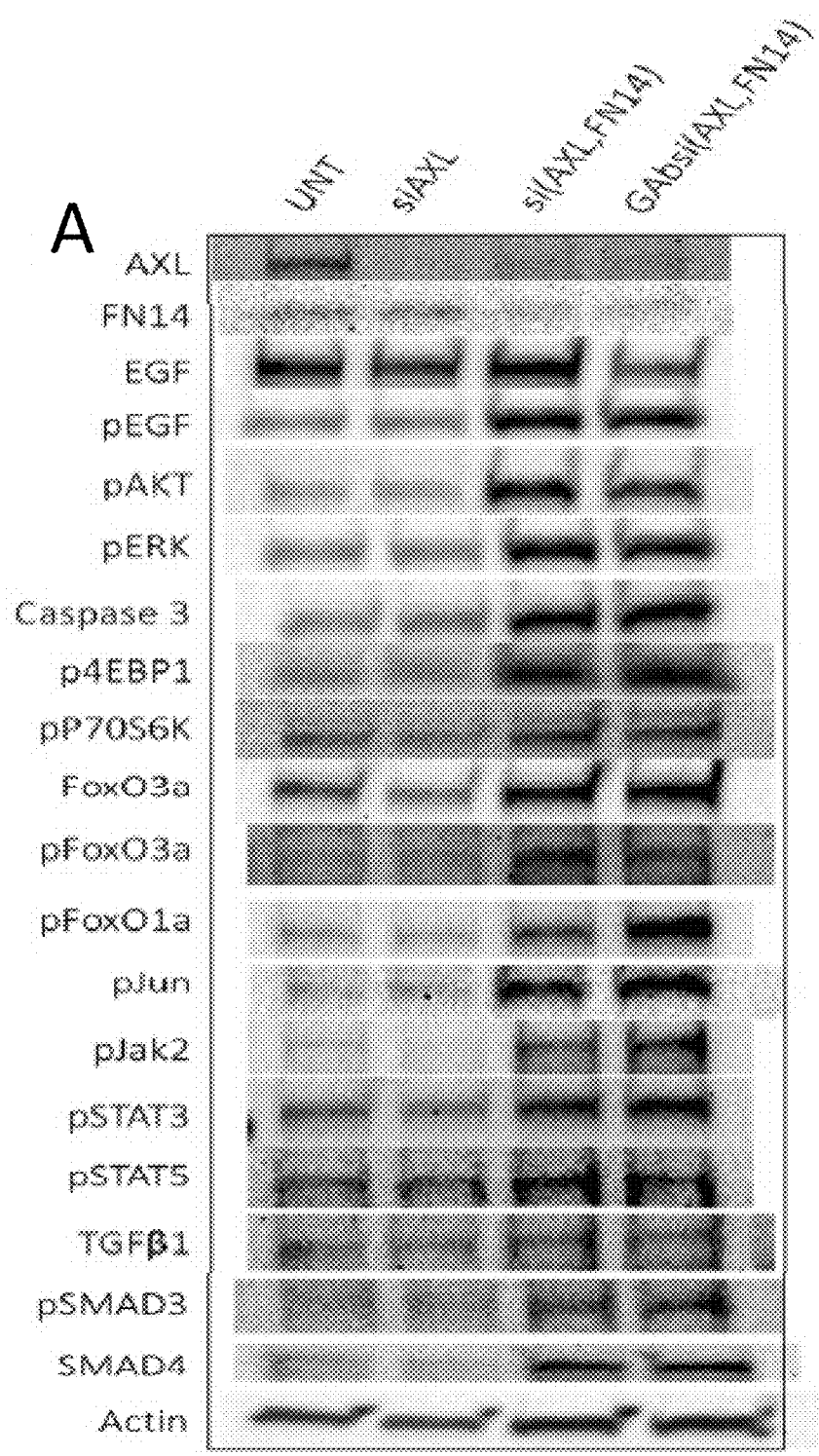

FIG. 25A. FIG. 25A shows Western blot for AXL-FN14 survival cross-talk analysis in H820 cells using siRNA and dual siRNA-construct, GAbsi(AXL,FN14) treatments.

Figure 25B:
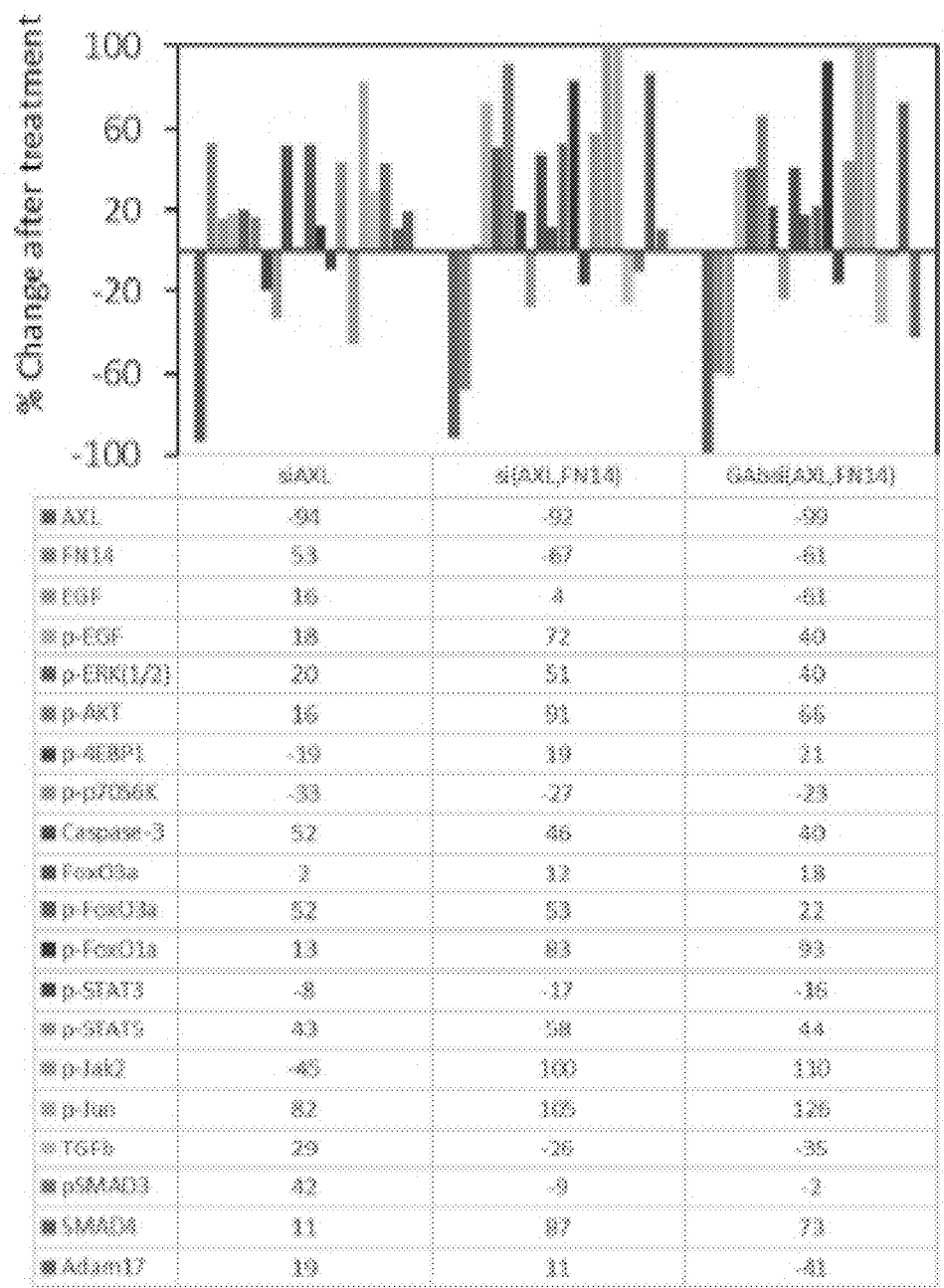

FIG. 25B. FIG. 25B shows associated band densitometry analysis for the above.

Figure 26:
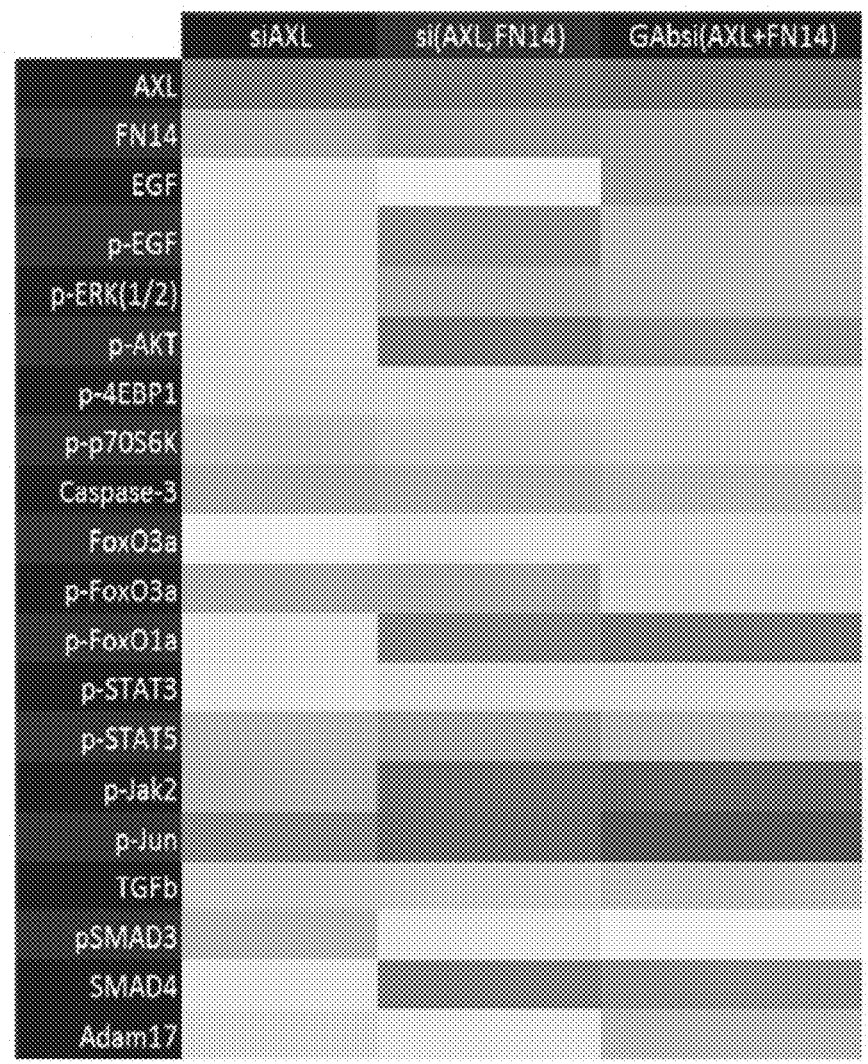
Figure 27:
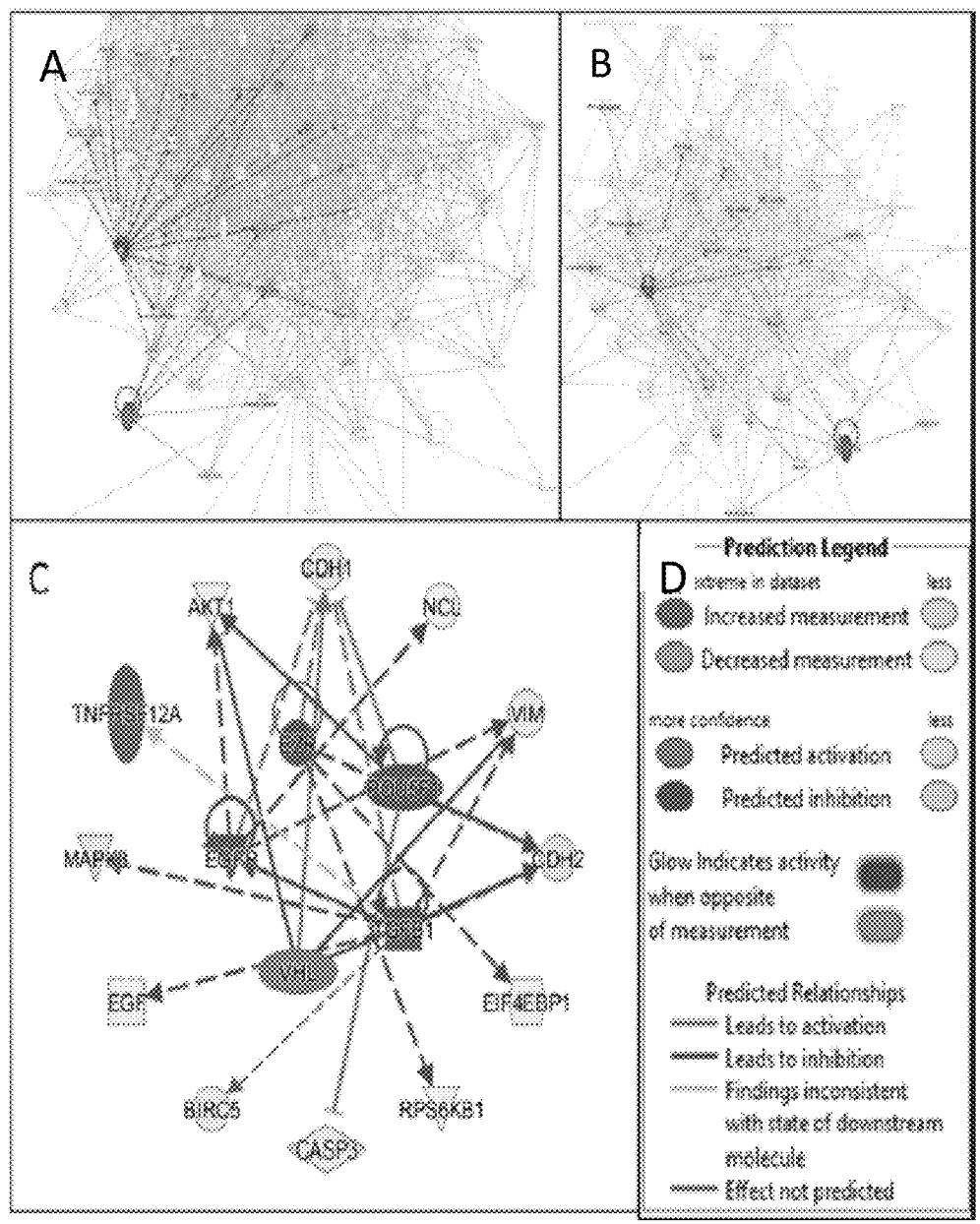

FIG. 26. FIG. 26 shows a representative heat map for data shown in FIG. 25 (Red=high; Blue=low). Data represents protein analysis for AXL and FN14 siRNA based treatments in H820 cells.

FIG. 27A-D. FIG. 27A, 27B, 27C, and 27D illustrates IPA bioinformatic protein network algorithm predicting that AXL may cross-talk with proteins related to RAS, MAPK and PTEN pathways (A) and TGFb1 could be one of the FN14 promoters when AXL is repressed (B-D).

Figure 28:
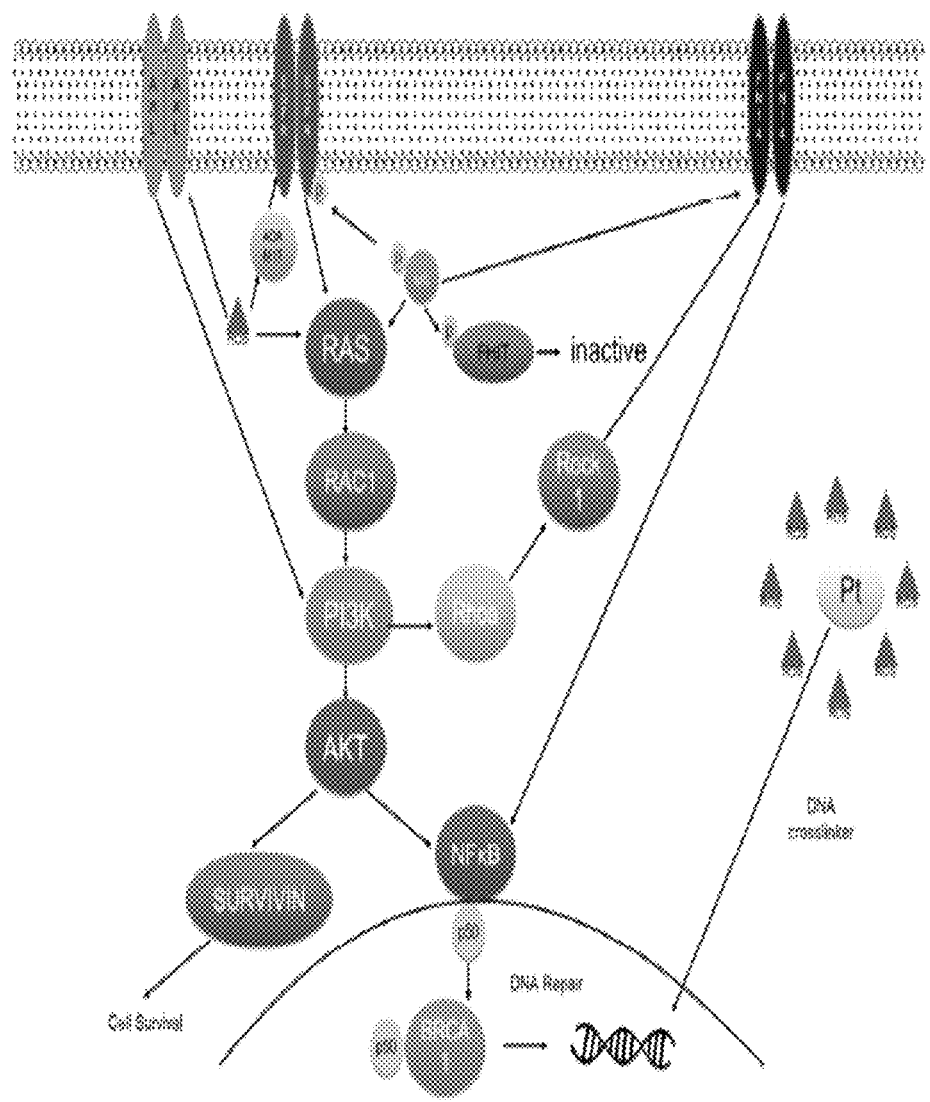

FIG. 28. FIG. 28 shows pathways effected by FN14 and AXL when active together under influence of reactive oxygen species (ROS) in cisplatin resistant cancer cells.

Figure 29:
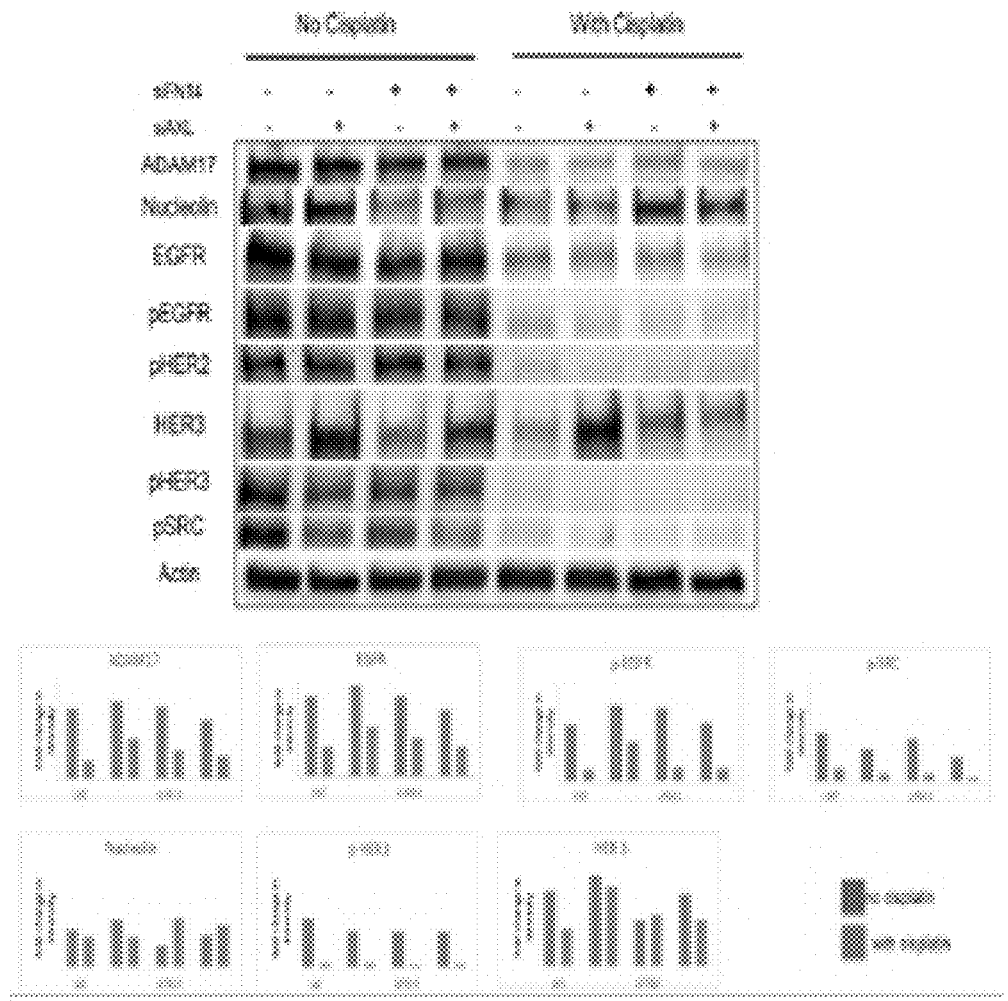

FIG. 29. FIG. 29 shows effects of AXL or FN14 siRNAs with or without cisplatin treatment on erbB family of proteins and their controllers in cisplatin resistant H1975 NSCLC cells.

Figure 30:
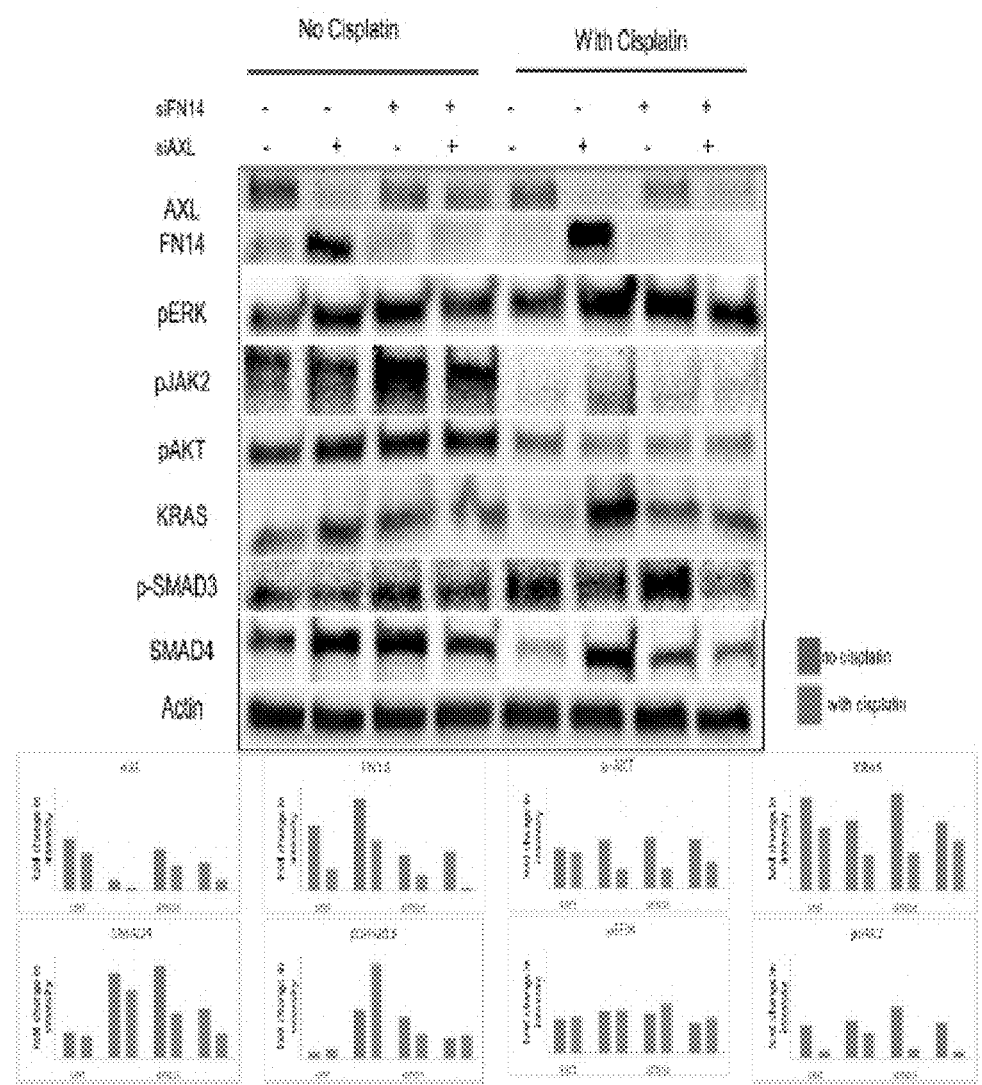

FIG. 30. FIG. 30 shows effects of AXL or FN14 siRNAs with or without cisplatin treatment on AXL, FN14, PI3K and related proteins in cisplatin resistant H1975 NSCLC cells.

Figure 31:
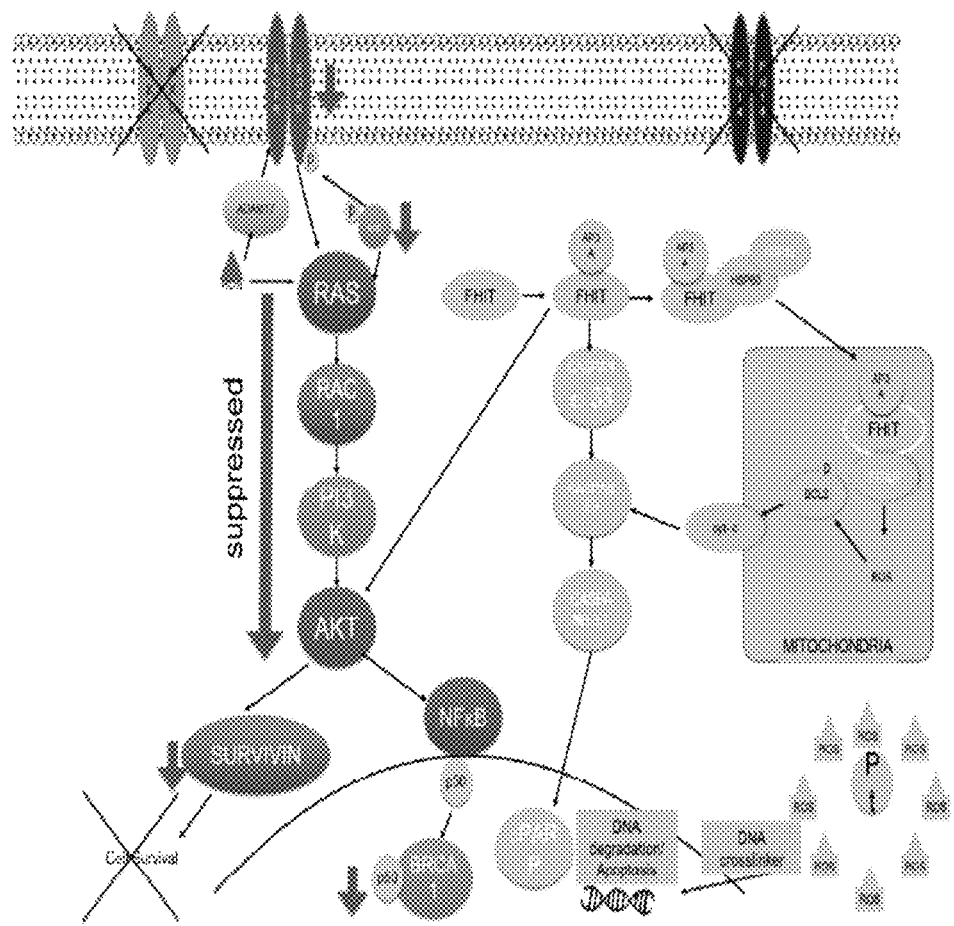

FIG. 31. FIG. 31 shows suppression of PI3K pathway after dual inhibition of AXL and FN14 proteins in cisplatin resistant cancer cells.

Figure 32:
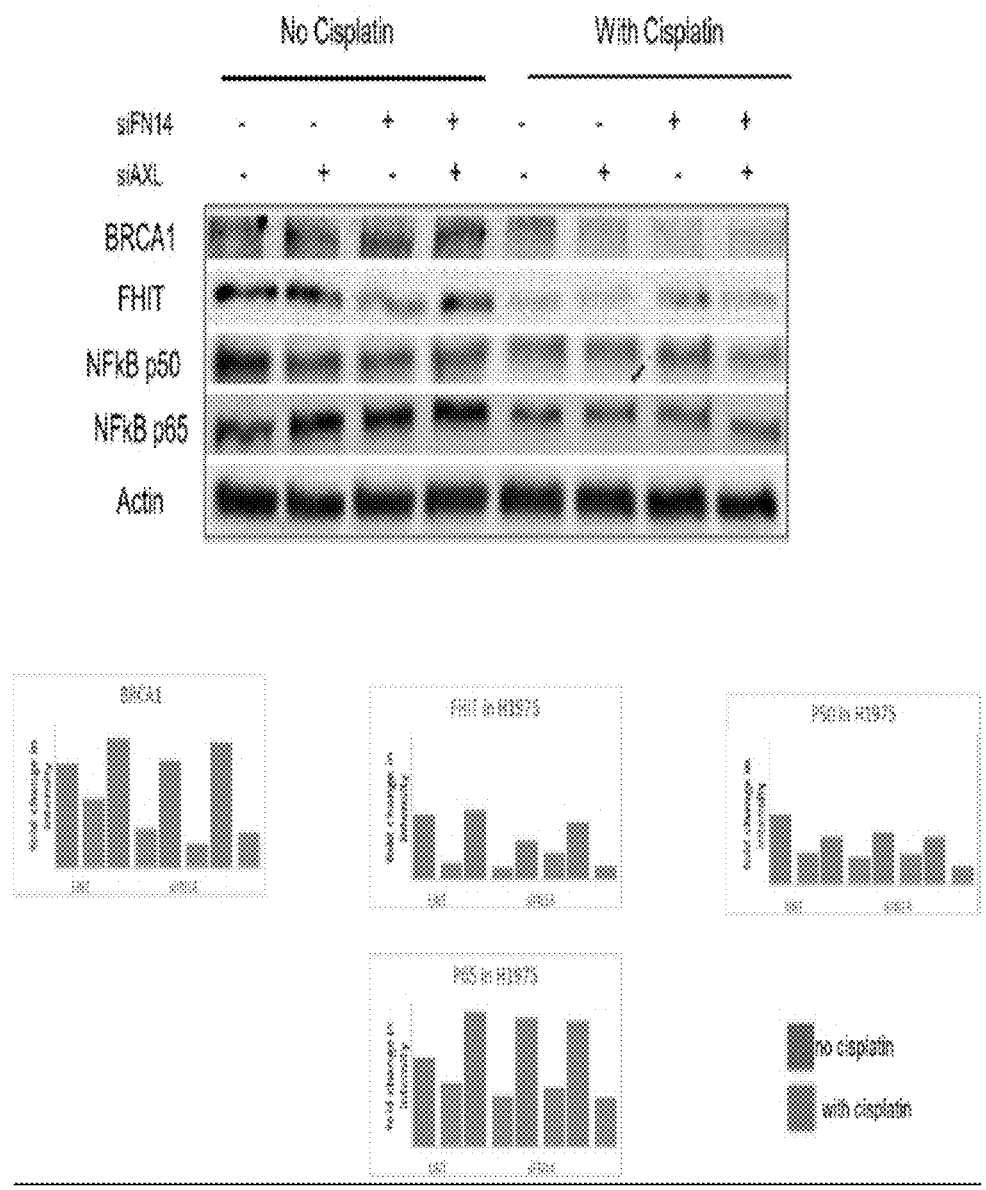

FIG. 32. FIG. 32 shows effects of AXL or FN14 siRNAs with or without cisplatin treatment on FHIT and NFkB family proteins in cisplatin resistant H1975 NSCLC cells.

Figure 33:
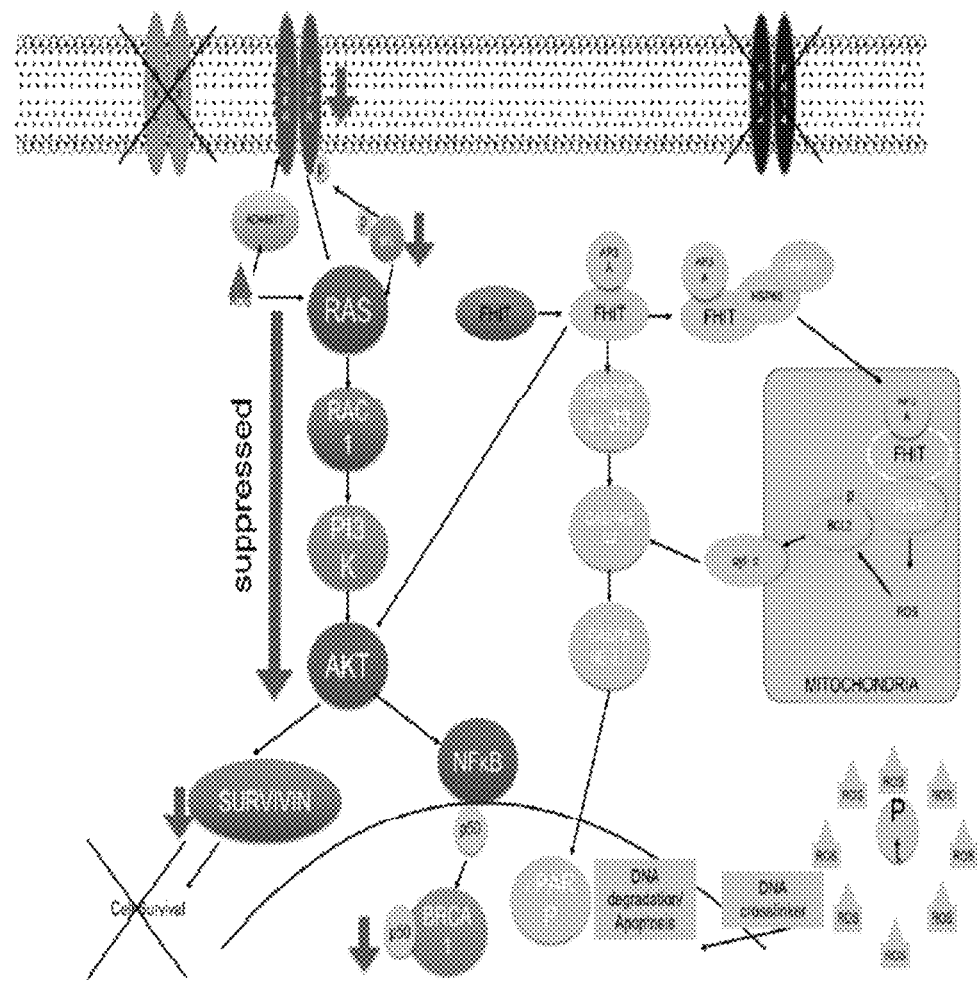

FIG. 33. FIG. 33 shows suppression of NFkB after dual inhibition of AXL and FN14 proteins.

Figure 34:
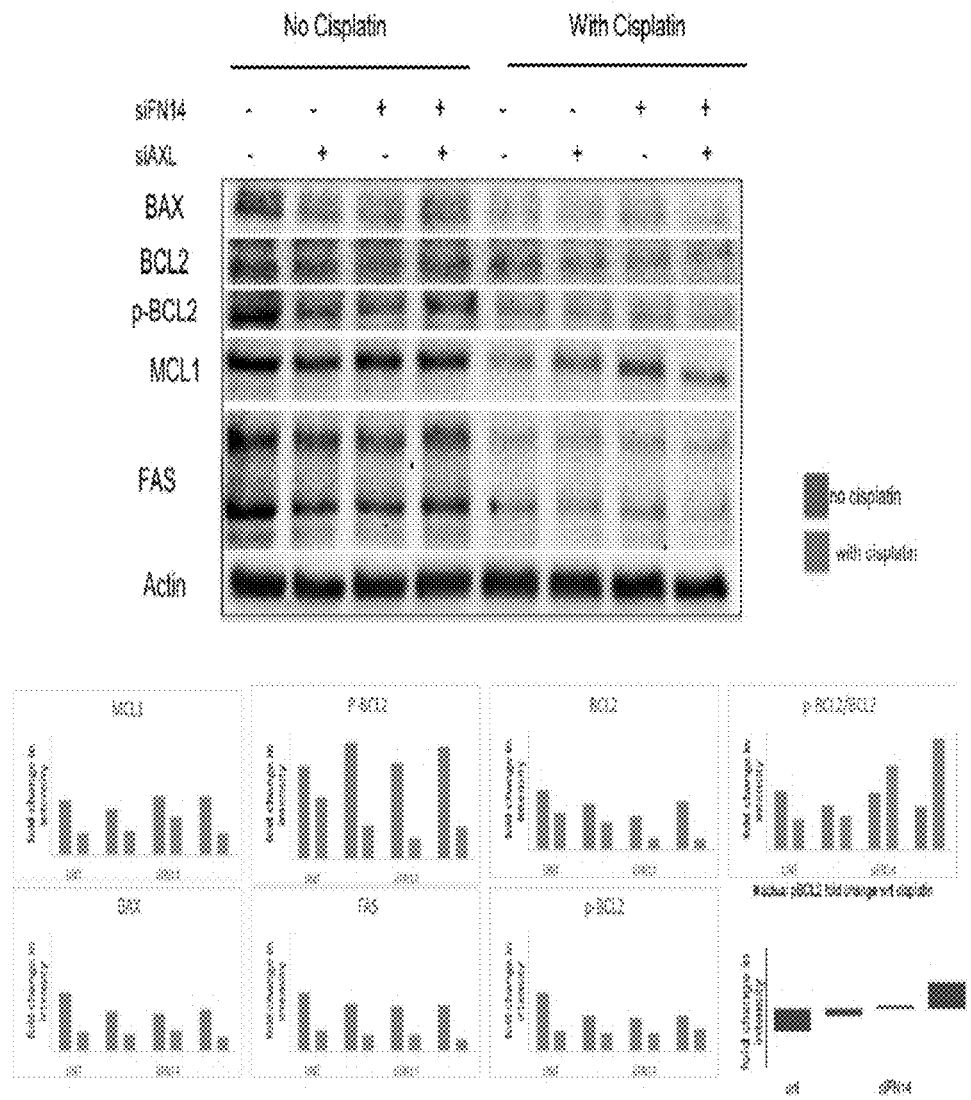

FIG. 34. FIG. 34 show effects of AXL or FN14 siRNAs with or without cisplatin treatment on BCL2 family proteins in cisplatin resistant H1975 NSCLC cells.

Figure 35:
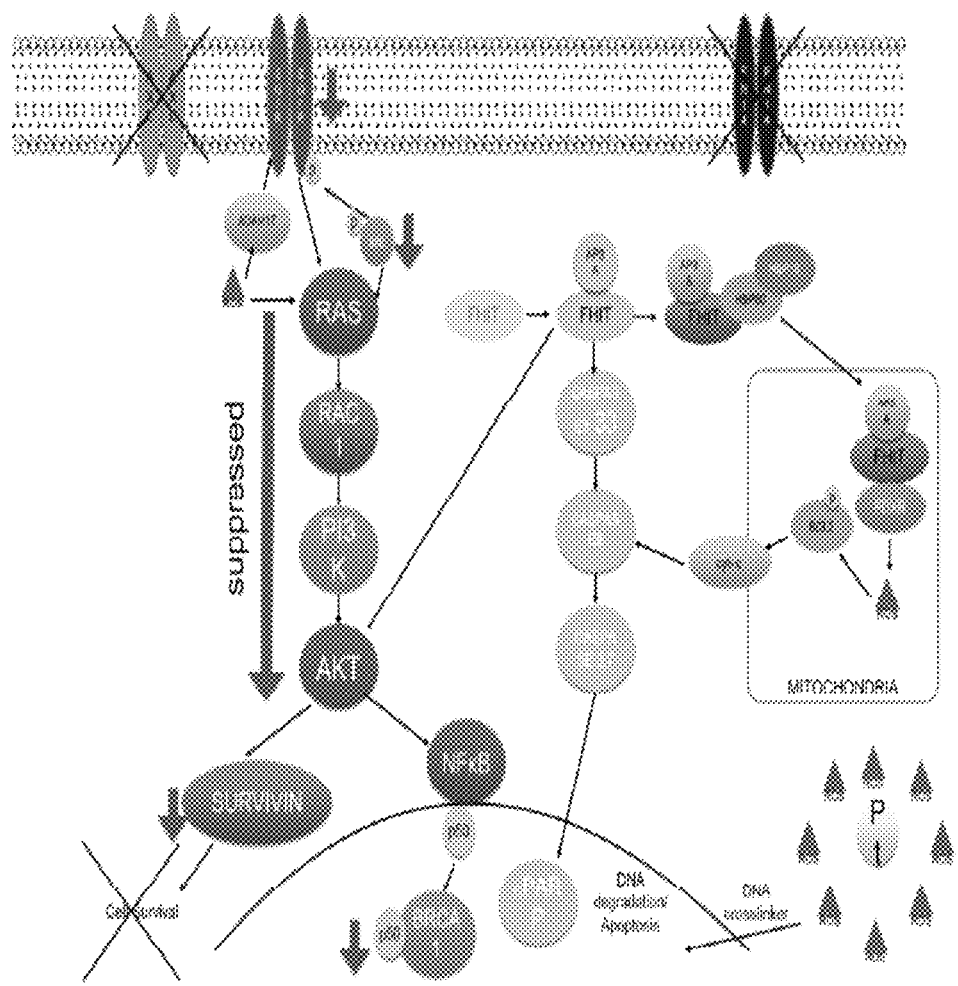

FIG. 35. FIG. 35 shows activation of FHIT and subsequent release of cytochrome-c upon dual inhibition of AXL and FN14 proteins in cisplatin resistant cancer cells.

Figure 36:
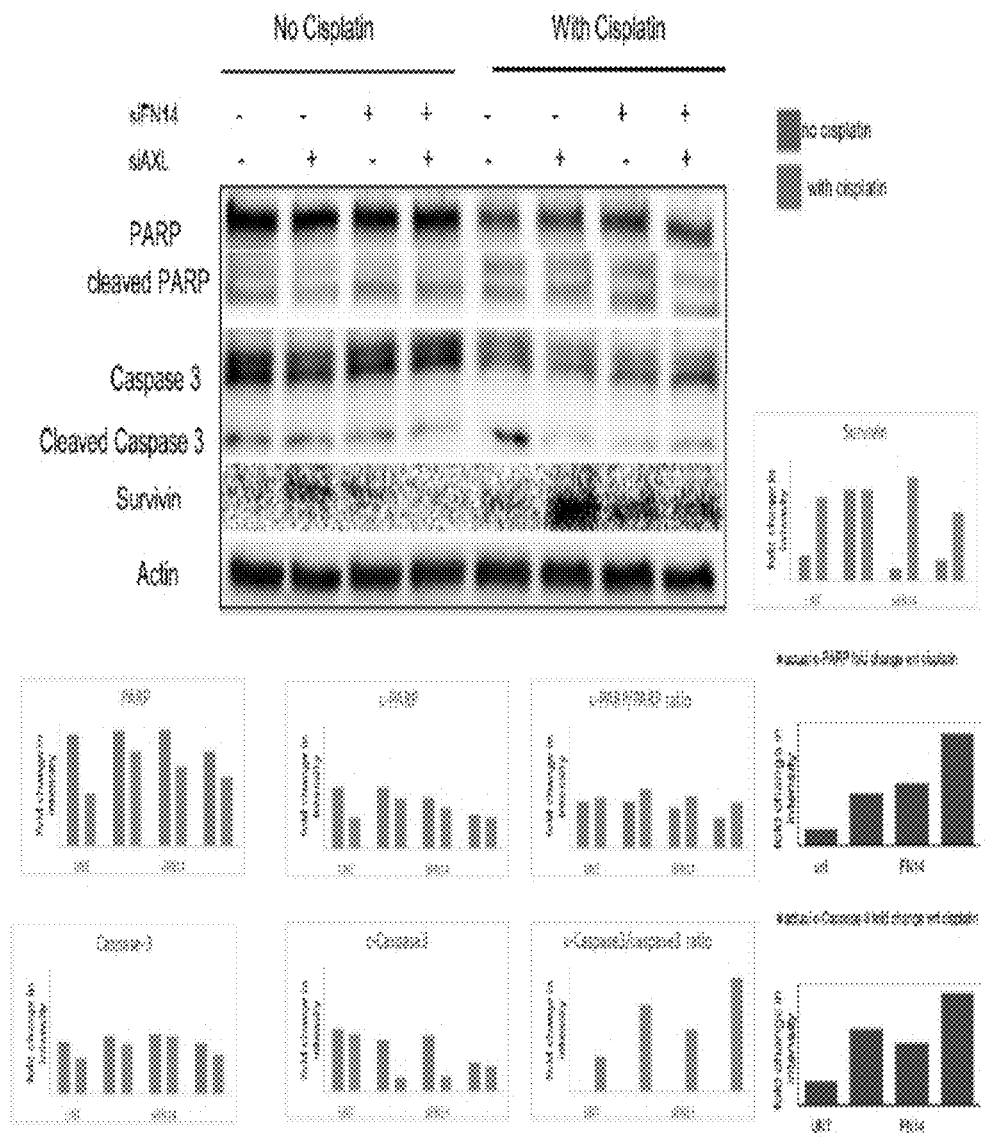

FIG. 36. FIG. 36 shows effects of AXL or FN14 siRNAs with or without cisplatin treatment on Caspase-3 and PARP and change in their its ratios in cisplatin resistant H1975 NSCLC cells.

Figure 37:
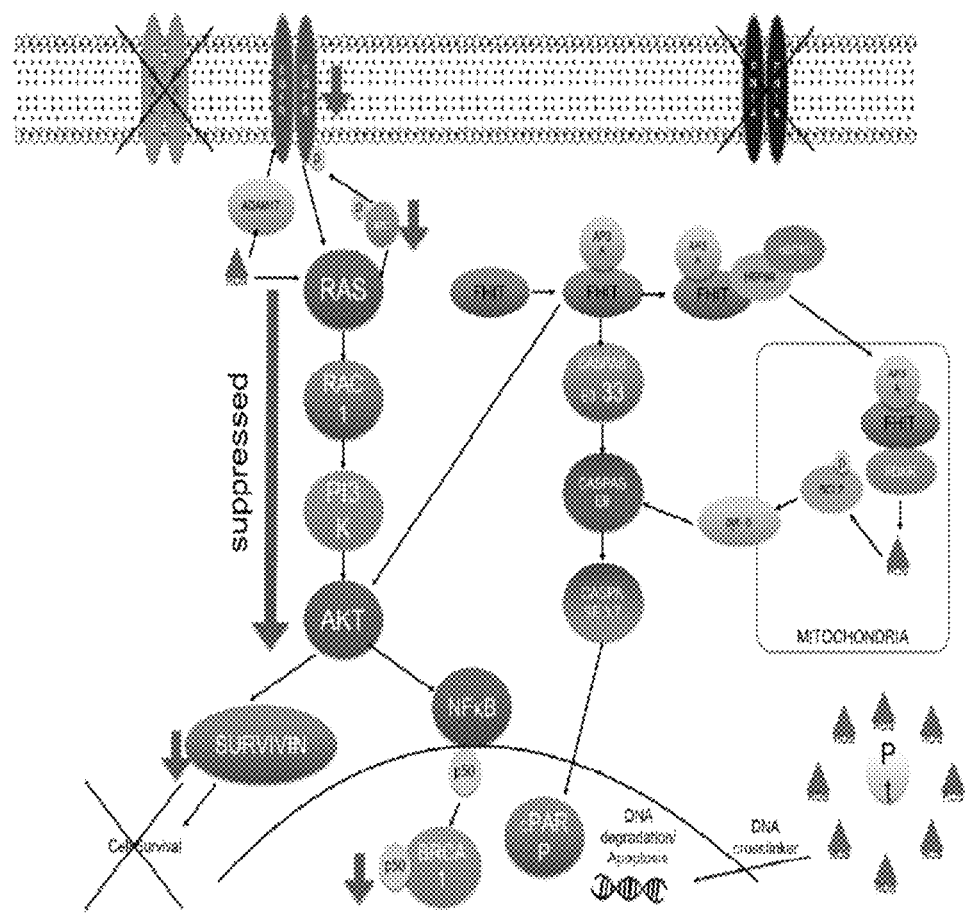

FIG. 37. FIG. 37 shows activation of Caspase-3 and PARP cleavage upon dual inhibition of AXL and FN14 protein in cisplatin resistant cancer cells.

Figure 38:
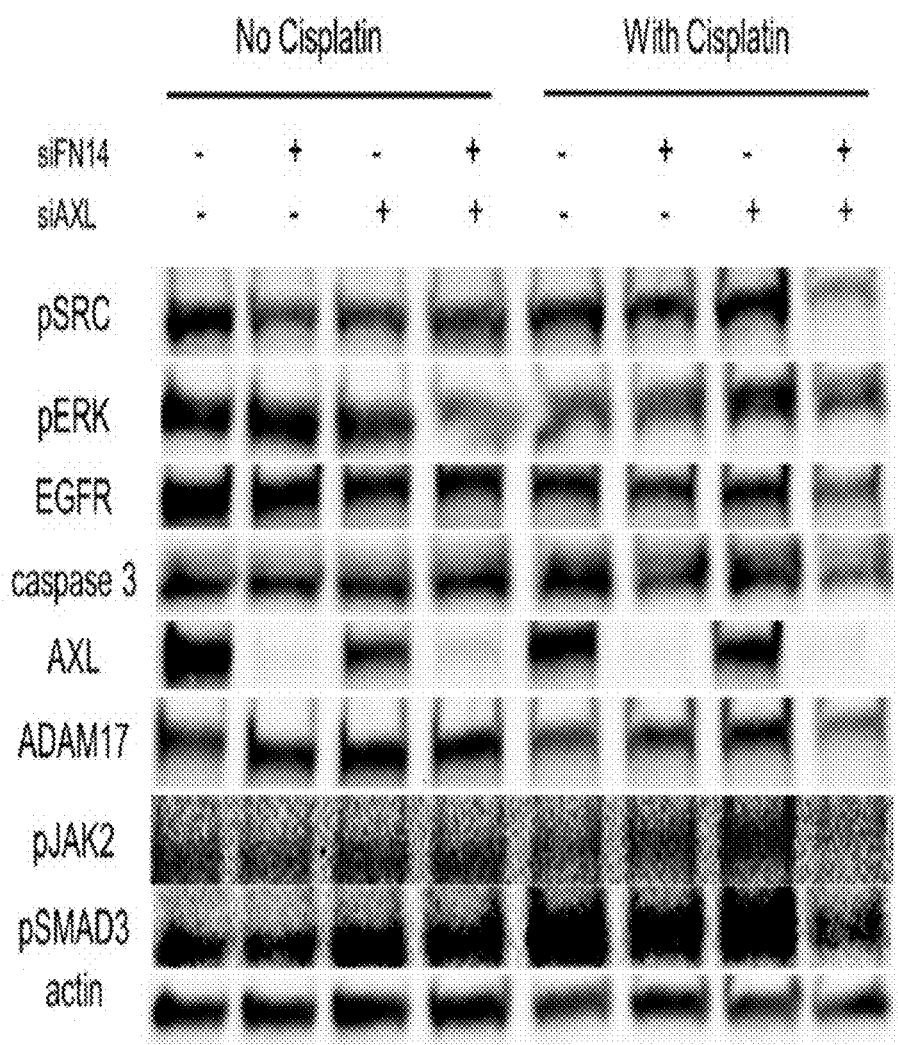

FIG. 38. FIG. 38 shows Western blot analysis of AXL or FN14 siRNAs with or without cisplatin treatment forin cisplatin resistant A549 NSCLC cells.

Figure 39:
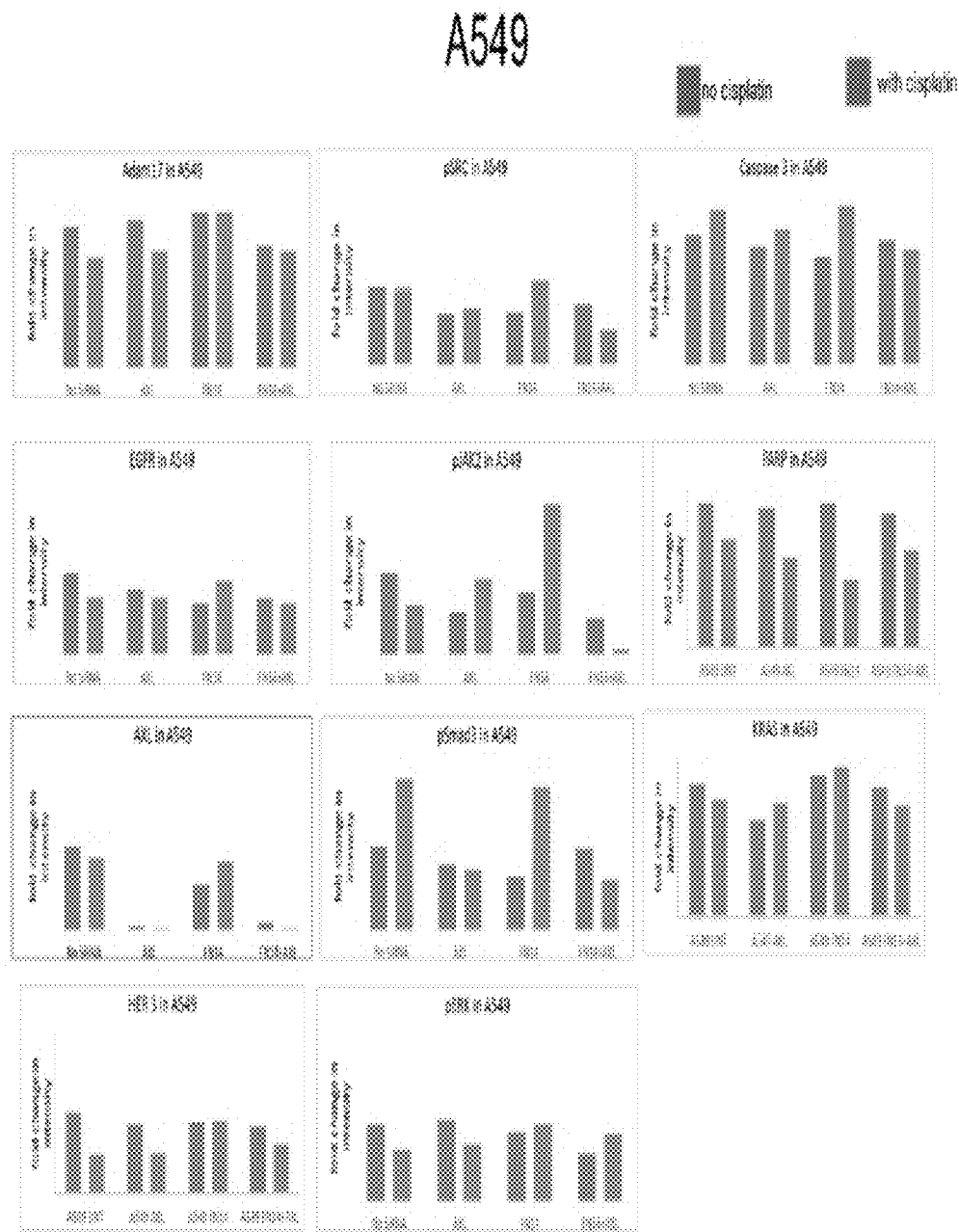

FIG. 39. FIG. 39 shows band densitometry analysis for A549 western blots of FIG. 38.

FIG. 40A-E. FIG. 40A, 40B, 40C, 40D, and 40E illustrate (A-B) AXL's possible role in resistance and solution to the problem, (C) Cell pathway network based on protein analysis in H820, (D) FN14 upregulation followed by AXL downregulation based on protein analysis in H820, (E) Synergistic inhibition of AXL/FN14 for resensitization of drug (TKI) resistant NSCLC.

FIG. 41A-C. FIG. 41A, 41B, and 42C show 72 h cell viability analysis of: (A) DMSO and Transit-X2 in H820, (B) Cetuximab antibody in H820 and HCC827, and (C) siRNA in H820.

FIG. 41D,E. FIG. 41D and 41E show 72h cell viability analysis of: (D) siRNA in H1975 and (E) siRNA in A549 cells.

FIG. 42A,B. FIG. 42A and 42B show 72 h toxicity of erlotinib in various NSCLC cells lines: (A) Cell viability plot and (B) IC50 analysis. Results were averaged from 3 independent experiments.

FIG. 43A,B. FIG. 43A and 43B show re-sensitization to erlotinib in CRISPR assisted AXL knockout H820AK cell line for 72 h. (A) Represents the cell viability plot and (B) represent the associated IC50 analysis. Results were averaged from 3 independent experiments. *$p \leq 0.05$, **$p \leq 0.01$, and the values were analyzed using one-way ANOVA.

FIG. 44A-F. FIG. 44A, 44B, 44C, 44D, 44E, and 44F show re-sensitization to erlotinib in various NSCLC cells lines by blocking AXL/FN14/KRAS pathways in H820, H1975 and A549 NSCLC cells for 72 h. (A, C, E) Represent the cell viability plot and (B, D, F) represent the associated IC50 analysis.

FIG. 45A-D. FIG. 45A, 45B, 45C, and 45D show 72 h toxicity profile for nanoparticles in H820, and HCC827 NSCLC cells. (A) Synthesized gelatin quenched and non-quenched NP and its representative (B) IC50 analysis, (C) Comparison between drug-encapsulated nanoparticles, and its representative (D) IC50 analysis. Results were averaged from 3 independent experiments.

FIG. 46A-C. FIG. 46A, 46B, and 46C show toxicity profile for siRNA conjugated nanoparticles in (A) 24 h data in H820, (B) 24 h data in HCC827, and (C) 72 h data in H820 cells. Results were averaged from 3 independent experiments. Based on the viability assay, 0.6 mg/ml was used as a treatment concentration for a period of 4 h in most MTT assays.

FIG. 47A,B. FIG. 47A and 47B show 72 h toxicity profile for synergistic drug and (A) siRNA conjugated nanoparticles and (B) erlotinib encapsulated siRNA constructs in H820 cells. (A) Viability plot and (B) representative IC50 values. Results were averaged from 3 independent experiments. *$p \leq 0.05$, ** $p \leq 0.01$, and the values were analyzed using one-way ANOVA .

FIG. 47C,D. FIG. 47C and 47D show 72 h toxicity profile for synergistic drug and (C) siRNA conjugated nanoparticles and (D) erlotinib encapsulated siRNA constructs in H820 cells. (C) Viability plot and (D) representative IC50 values. Results were averaged from 3 independent experiments. *$p \leq 0.05$, **$p \leq 0.01$, and the values were analyzed using one-way ANOVA.

Figure 48:
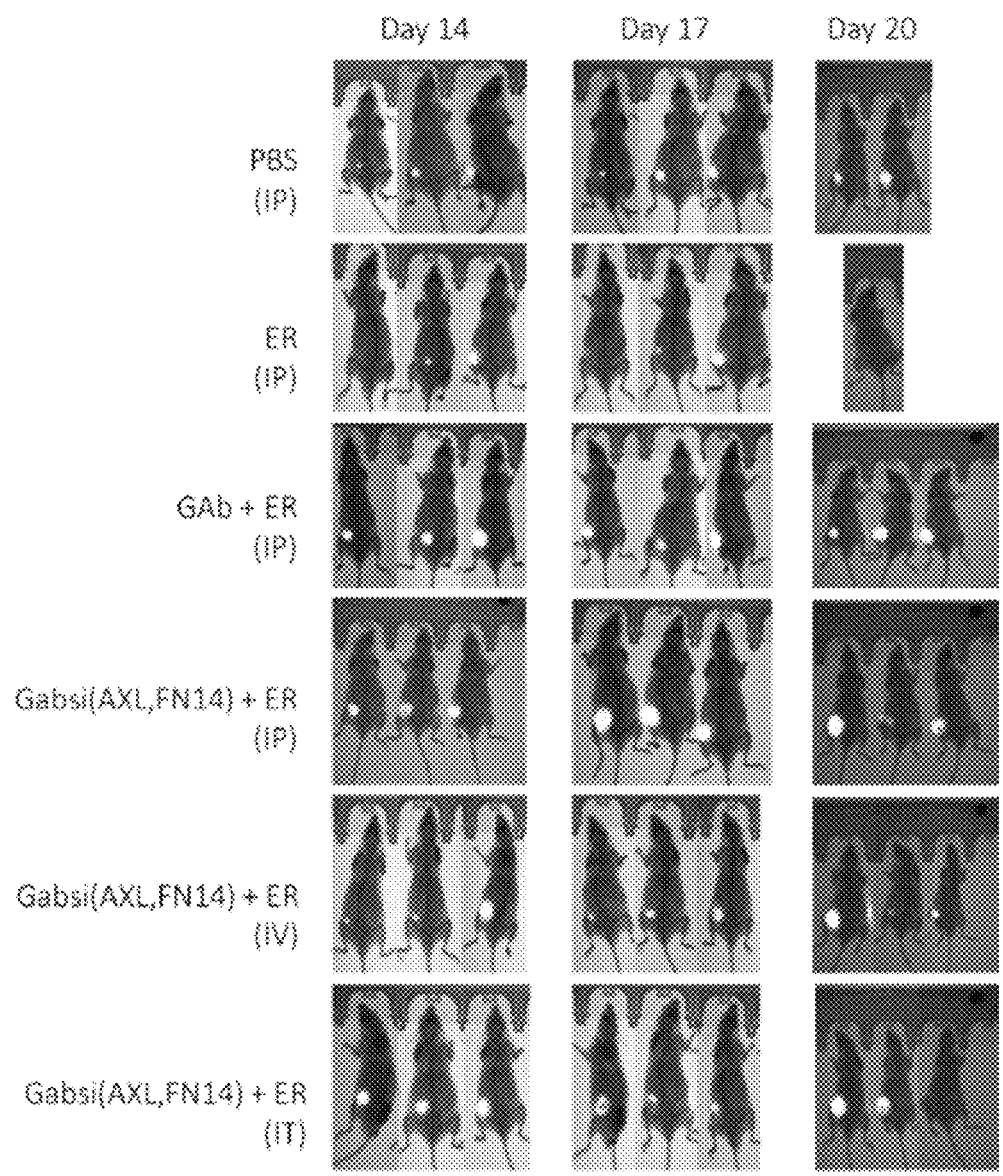

FIG. 48. FIG. 48 shows fluorescence imaging of mice treated with constructs and drug (TKI).

FIG. 49A-D. FIG. 49A, 49B, 49C, and 49D show (A,C) Total fluorescence measured from tumors and (B,D) mean fluorescence measured from tumors. IT/IP/IV+ER represent dual-siRNA construct treatments. Results were averaged from 5 mice. *$p \leq 0.05$, and the normalized percentage differences between day 17 and day 20 values were analyzed using one-way anova.

Figure 50A:
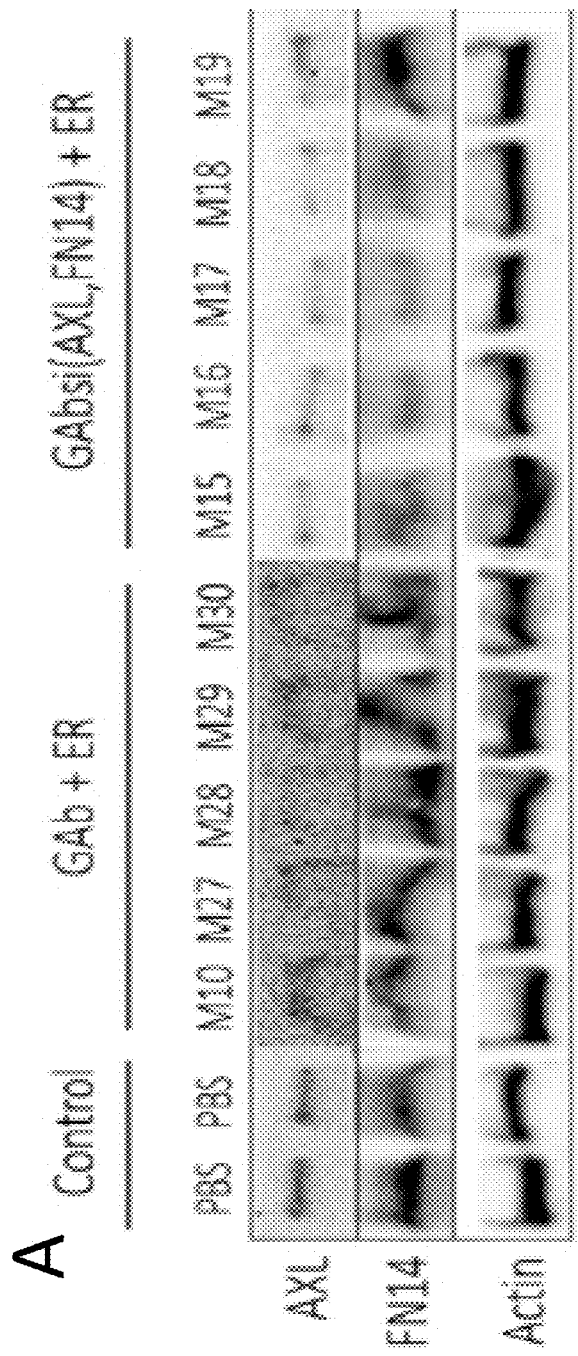
Figure 50B:
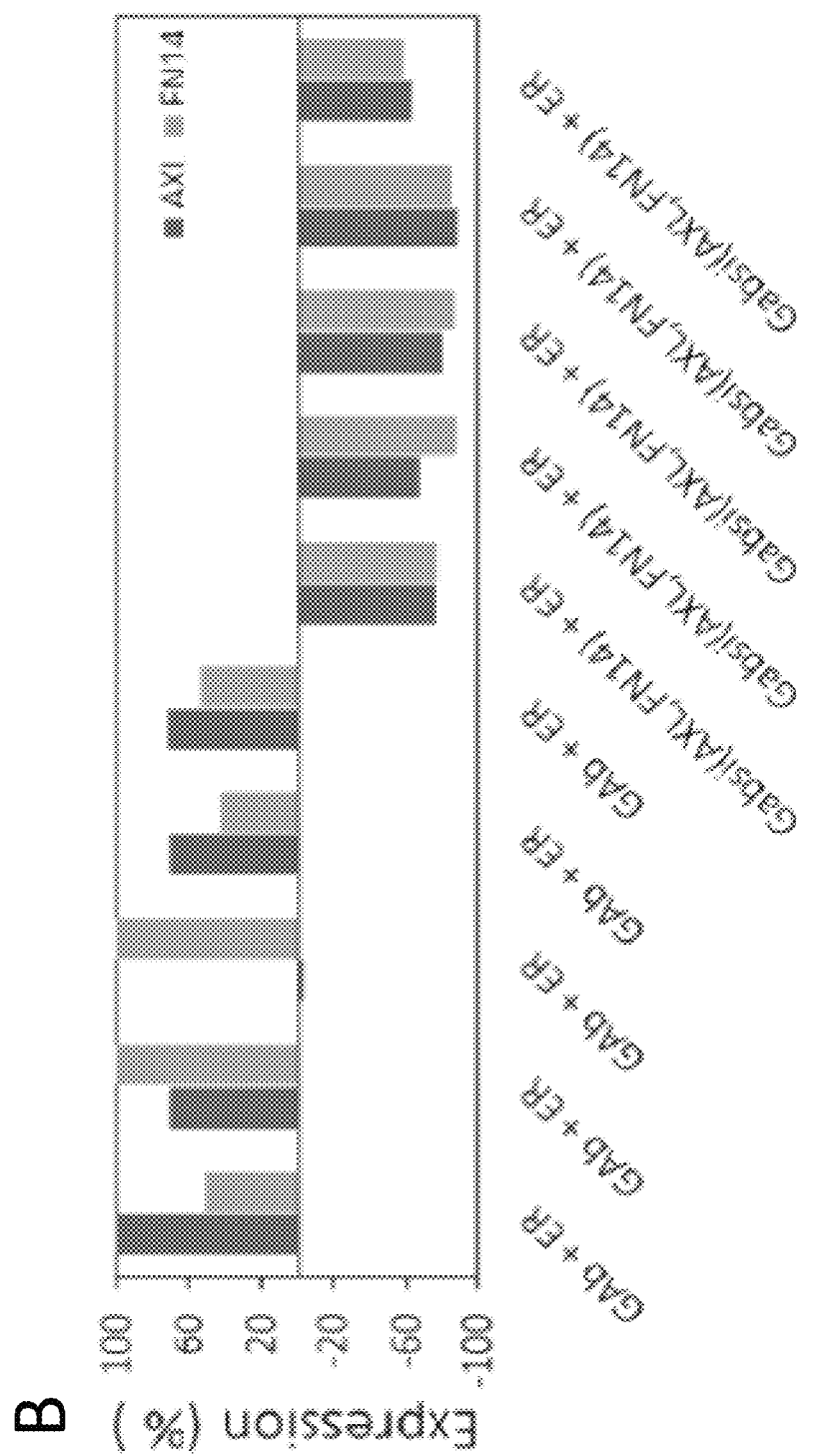

FIG. 50A. FIG. 50A shows a protein blot for AXL and FN14 expression in mice tumor samples FIG. 50B. FIG. 50B shows band densitometry analysis for the blot of FIG. 50A by normalizing values to PBS controls. Results for PBS, GAb+ER and GAbsi (AXL,FN14)+ER were averaged from 2, 5 and 5 mice tumors respectively. Results show AXL and FN14 expression is drastically reduced in siRNA conjugated gelatin nanoparticle treatment samples.

Figure 51:
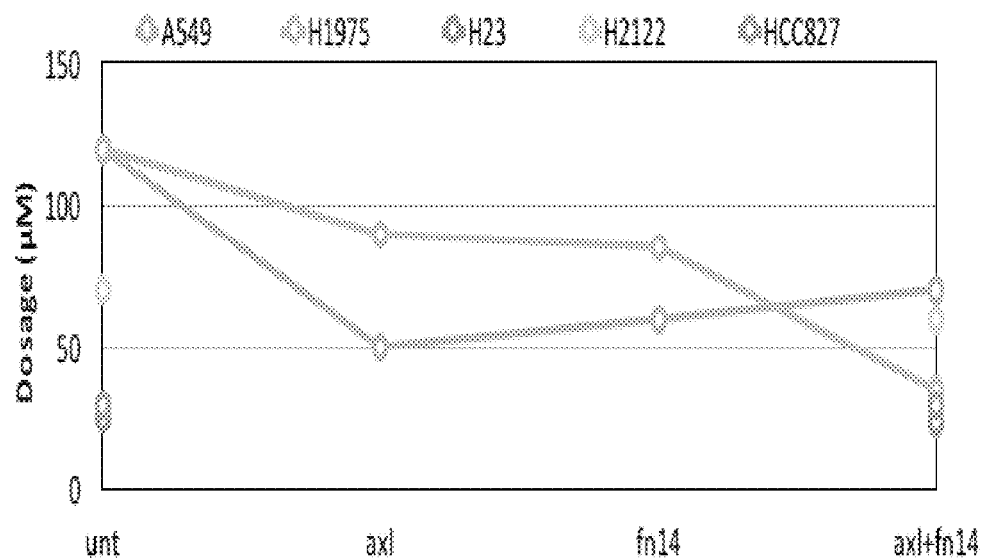

FIG. 51. FIG. 51 shows cell viability in cisplatin sensitive and resistant cell lines.

FIG. 52A,B. FIG. 52A and 52B show downregulation of AXL/FN14 using siRNA conjugated nanoparticles from excised tumor tissue. Mouse study with A549 tumor xenograft (Athymic nude mice). (A) Presence of siRNA on nanoparticles downregulate AXL/FN14 protein levels in tumor lysates of mice. Vehicle (PBS) and targeted nanoparticles without siRNA (GAb) followed by treatment with Erlotinib were used as controls. Control vehicle and nanoparticles preparations were administered by IP and Erlotinib was given by oral gavage. (B) Densitometry plot showing individual mice data for AXL and FN14 protein expression levels based on western blot. Results show that gelatin nanoparticles successfully deliver siRNA to downregulate both AXL and FN14 within tumor cells.

FIG. 53A,B. FIG. 53A and 53B show downregulation of AXL/FN14 using siRNA conjugated nanoparticles. (A,B) shows % relative expression of AXL and FN14 averaged from tumor groups presented in FIG. 52A,B. In both cases AXL ($p<0.0001$) and FN14 ($p<0.0113$) levels were significantly reduced in group treated with siRNA conjugated targeted gelatin nanoparticles compared to control groups. Results show targeted gelatin nanoparticles successfully deliver siRNA to downregulate both AXL and FN14 within tumor cells FIG. 54A,B,C. FIG. 54A, 54B, and 54C show downregulation of AXL/FN14 or AXL in TKI/Cisplatin of tumor bearing mice. AXL and FN14 were selectively inhibited using either siRNA using targeted nanoparticles or small-molecule inhibitors. For delivering siRNA, EGFR targeted gelatin nanoparticles (GAb) were used. (A) Targeting AXL/FN14 by siRNA led to erlotinib sensitization and reduction in tumor volume ($p<0.0095$). (B) Targeting AXL/FN14 by pharmacological inhibitor led to erlotinib sensitization and reduction in tumor volume ($p<0.0002$). (C) Targeting AXL/FN14 by siRNA ($p<0.0003$) and pharmacological inhibitor ($p<0.0006$) led to cisplatin sensitization and reduction in tumor volume. Results show AXL and FN14 are viable therapeutic targets for TKI and Cisplatin sensitization therapy.

FIG. 55A,B. FIG. 55A and 55B show excised tumor images after treatment period. Excised tumor images from individual groups at the end of the therapy study. Tumor images are shown with respect to individual groups. (A) Erlotinib treatment group: Treatment with AXL/FN14 pharmacological inhibitors followed by erlotinib administration (all PO) showed effective reduction of tumor volume. (B) Cisplatin treatment group: AXL/FN14-siRNA gelatin antibody conjugated nanoparticle and pharmacological inhibitors both independently showed tumor sensitization to cisplatin therapy. Successful reduction in tumor volume was observed followed by AXL/FN14 inhibition.

FIG. 56A,B. FIG. 56A and 56B show reduction in excised tumor volume. Excised-tumor image analysis of individual groups. Image analysis was performed using Image-J software to determine the tumor volume (mm$^3$). (A) Treatment with AXL/FN14 pharmacological inhibitors followed by erlotinib showed reduction in tumor volume ($p<0.0093$) in comparison with control and erlotinib-alone treated group. (B) Treatment with AXL/FN14-siRNA gelatin nanoparticle construct ($p<0.0133$) or pharmacological inhibitors ($p<0.0436$) followed by cisplatin showed reduction in tumor volume in comparison with control and cisplatin-alone treated group. Successful reduction in tumor size followed by AXL/FN14.

FIG. 57A-F. FIGS. 57A-F show images of mice from the studies.

FIG. 58A,B,C. FIG. 58A, 58B, and 58C show mouse body weight curves. Plot of body weights of tumor bearing mice during the treatment period. Animals were measured on a digital weighing scale weekly once or twice to monitor general health condition. (A) Control Group, siRNA conjugated targeted Gelatin nanoparticles (GAbsi) group, and targeted Gelatin nanoparticles (GAb) group; (B) Control Group, Erlotinib group, AXL inhibitor, FN14 inhibitor followed by Erlotinib treatment group; (C) Control Group, Cisplatin group, AXL inhibitor, FN14 inhibitor followed by Cisplatin treatment group and siRNA conjugated targeted Gelatin nanoparticles (GAbsi) followed by Cisplatin treatment group.

DETAILED DESCRIPTION

Overview

AXL belongs to class IX tyrosine kinase family and is upregulated in many cancers. Recently, AXL upregulations has been seen in patients undergoing treatment or with resistance. Zhang, et al., Nat Genet 2012; 44: 852-860. In fact, most of the biomarkers overexpressed in EGFR drug resistant cells belongs to TAM receptor family. The AXL gene is responsible for encoding proteins related to growth, proliferation and anti-inflammation in cells and AXL has been shown to activate the phosphoinositol-3 kinase signaling pathway downstream that is upregulated in almost all cancers. Ruan, G X and Kazlauskas, A, Embo J 2012; 31: 1692-1703; Lee, et al., Oncogene 2002; 21: 329-336. In a separate study, AXL was also shown to activate MAPK/ERK pathway downstream. Tai, et al., Oncogene 2008; 27: 4044-4055. Several studies have also shown that AXL is downregulated in cancer cells undergoing apoptosis. Lee, et al., Oncogene 2002; 21: 329-336.

Along with AXL, FN14 (Fn14 or the Fibroblast growth factor-inducible 14 (gene TNFRSF12A)—the smallest known member of the tumor necrosis factor (TNF) superfamily—has also been implicated in imparting cancer-treatment resistance. FN14 was previously was shown to be upregulated in cancer and had a link to cachexia. Johnston, et al., Cell 2015; 162: 1365-1378; Winkles, et al., Nature Reviews Drug Discovery 2008; 7: 411-425. Cachexia associated with muscle loss due to protein degradation, worsens disease progression in cancer patients during drug treatment. Johnston, et al., Cell 2015; 162: 1365-1378. Recently, FN14 was also implicated in drug resistance in cancer. Whitsett, et al., Am J Pathol 2012; 181: 111-120; Whitsett, et al., Mol Cancer Res 2014; 12: 550-559; Kwon, et al., International Journal of Oncology 2014; 44: 583-590. A bioinformatics analysis also suggested a link between AXL and FN14 pathways downstream. Kohn, et al., Plos One 2012; 7. Additionally, upregulation of FN14 was consistent with increased NFkB expression. Previous studies also confirmed that NFkB is a downstream target of FN14. Enwere, et al., Front Immunol 2014; 5: 34; Poveda, et al., Front Immunol 2013; 4: 447; Brown, et al., Plos One 2013; 8: e65248.

Multifunctional cytokine tumor necrosis factor-like weak inducer of apoptosis (TWEAK) is its only known ligand of FN14. Elevated FN14 expression has been observed in a number of solid tumors including hepatocellular carcinoma (Feng, et al., The American Journal of Pathology 2000; 156: 1253-1261), esophageal adenocarcinoma (Wang, et al., Oncogene 2006; 25: 3346-3356; Watts, et al., International Journal of Cancer 2007; 121: 2132-2139), glioblastoma (Tran, et al., The American Journal of Pathology 2003; 162: 1313-1321; Tran, et al., Cancer Res 2006; 66: 9535-9542), and HER2+breast cancer. Fn14 signaling upregulates cell survival through upregulation of NF-κB, Bcl-XL, Bcl-2 expression and multiple GEF-Rho GTPase activation in glioblastoma. Fortin, et al., Molecular Cancer Research: MCR 2009; 7: 1871-1881; Tran, et al., J Biol Chem 2005; 280: 3483-3492; Tran, et al., The TWEAK-Fn14 Ligand Receptor Axis Promotes Glioblastoma Cell Invasion and Survival Via Activation of Multiple GEF-Rho GTPase Signaling Systems 2013 . Fn14 signaling also upregulates glioma and breast cell invasion by activating Rac1 and NFκB. Tran, et al., Cancer Res 2006; 66: 9535-9542; Willis, et al., Molecular Cancer Research: MCR 2008; 6: 725-734. Indeed, FN14 is a possible therapeutic target for melanoma. Zhou, et al., J Invest Dermatol 2013; 133: 1052-1062. Although Fn14 expression has been observed in NSCLC specimens (Culp, et al., American Association for Cancer Research 2010; 16: 497-508), little is known about it's in this particular tumor type.

Studies have shown a link between the expressions of FN14 and EGFR and a concurrency in FN14 expressions with activating EGFR mutation. Whitsett, et al., The American Journal of Pathology 2012; 181: 111-120. FN14 expression also tends to be highly elevated in EGFR T790M mutation and can only be effected with a higher dose of TKI. Fn14 also tends to augment metastasis by up-regulation of integrin a6 (Jandova, et al., Neoplasma 2015; 62: 41-52), suggesting contribution to cell motility and invasion and eventually a new potential target for NSCLC treatment. EGFR del 19 mutation is correlated with FN14/JAK/STAT signaling pathways. Sun, et al., Oncology Reports 2016; 36: 1030-1040. FN14 tends to be a positive regulator of src and downregulation of p-SRC upon suppression of FN14 is disclosed herein as well as suppression of p-HER3. A similar correlation was also observed in MET driven NSCLC. FN14 and MET expressions significantly correlated and suppression of MET also showed suppression of FN14. Whitsett, et al., Clinical & Experimental Metastasis 2014; 31: 613-623.

It has also been observed that FN14 is upregulated via RhoA/ROCK kinase pathway and mediated NFkB activation. Chorianopoulos, et al., Basic Res Cardiol 2010; 105: 301-313; Blanco-Colio, Front Immunol 2014; 5. Suppression of FN14 appears to suppress BRCA1 expression, thus preventing DNA repair mechanism. However, increased expression of AXL during suppression of FN14 is disclosed herein. Upregulation of FN14 promotes NADPH oxidase activation, thus promoting oxidative stress. Madrigal-Matute, et al., Cardiovascular Research 2015; 108: 139-147. Targeting FN14 appeared to induce cachexia. Johnson, et al., Cell 2015; 162: 1365-1378. As disclosed herein, suppression of FN14, under the influence of cisplatin, upregulates FHIT which triggers subsequent apoptosis through Bcl-2 phosphorylation.

FN14 may be dependent to Mcl-1. Whitsett, et al., Molecular Cancer Research : MCR 2014; 12: 550-559. The majority of adenocarcinoma and squamous cell carcinomas show expressions of Mcl-1, also correlating to higher tumor stages and poor outcomes. Mcl-1 is mitochondria associated pro-survival Bcl-2 family member which binds to pro apoptotic Noxa, BAK and BAX, thus retaining them to their inactive state and limiting apoptotic signaling. Tran, et al., J Biol Chem 2005; 280: 3483-3492; Zhang, et al., Oncogene 2011; 30: 1963-1968. Indeed, it is disclosed herein that under the influence of cisplatin, when FN14 was suppressed, there was an increase in the rate of cleavage of Caspase-3 and subsequently, PARP.

Both AXL and Fn14 can up-regulate p50 by canonical NFkB pathway and suppressing any one of them generates a feedback to over-express the other. Dual inhibition negates this feedback and thus p50-BRCA1 complex gets down regulated, resulting to suppression of DNA repair and re-sensitization to cisplatin.

EGFR is over-expressed when either FN14 or AXL is suppressed. EGFR alone can up-regulate p50 through Pi3K-PKC-NFkB downstream pathway. However, the expression falls below the untreated level, once both FN14 and AXL are inhibited. Co-inhibition of AXL and FN14 significantly inhibits p-SRC, which makes EGFR redundant. Suppressed p-SRC leads to unchecked increase in FHIT-AP3F complex and subsequent rupture of mitochondrial wall by ROS (produced by cisplatin) to release cyt-c.

Definitions

To the extent necessary to provide descriptive support, the subject matter and/or text of the appended claims is incorporated herein by reference in their entirety.

The headings provided herein are solely for ease of reference and are not limitations of the various aspects or aspects of the disclosure, which can be had by reference to the specification as a whole.

It will be understood by all readers of this written description that the exemplary aspects and embodiments described and claimed herein may be suitably practiced in the absence of any recited feature, element or step that is, or is not, specifically disclosed herein.

It is to be noted that the term "a" or "an" entity refers to one or more of that entity; for example, "a compound," is understood to represent one or more compounds. As such, the terms "a" (or "an"), "one or more," and "at least one" can be used interchangeably herein.

Furthermore, "and/or" where used herein is to be taken as specific disclosure of each of the specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects or embodiments: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, technical and scientific terms used herein have the same meaning as commonly understood by one of ordinary skill in the art to which this disclosure is related. Numeric ranges are inclusive of the numbers defining the range. Even when not explicitly identified by "and any range in between," or the like, where a list of values is recited, e.g., 1, 2, 3, or 4, the disclosure specifically includes any range in between the values, e.g., 1 to 3, 1 to 4, 2 to 4, etc.

The terms defined immediately below are more fully defined by reference to the specification in its entirety.

As used herein, the term "non-naturally occurring" condition, substance, polypeptide, polynucleotide, composition, entity, plant, organism, individual, and/or any combination thereof, or any grammatical variants thereof, is a conditional term that explicitly excludes, but only excludes, those forms that are well-understood by persons of ordinary skill in the art as being "naturally-occurring," or that are, or might be at any time, determined or interpreted by a judge or an administrative or judicial body to be, "naturally-occurring."

As used herein, the term "identity," e.g., "percent identity" to an amino acid sequence or to a nucleotide sequence disclosed herein refers to a relationship between two or more nucleotide sequences or between two or more amino acid sequences. When a position in one sequence is occupied by the same nucleic acid base or amino acid in the corresponding position of the comparator sequence, the sequences are said to be "identical" at that position. The percentage "sequence identity" is calculated by determining the number of positions at which the identical nucleic acid base or amino acid occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window. In order to optimally align sequences for comparison, the portion of a nucleotide or amino acid sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using, e.g., the program "BLAST" which is available from the National Center for Biotechnology Information, and which program incorporates the programs BLASTN (for nucleotide sequence comparison) and BLASTP (for amino acid sequence comparison), which programs are based on the algorithm of Karlin and Altschul (Proc. Natl. Acad. Sci. USA 90(12):5873-5877, 1993).

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a polypeptide subunit contained in a vector is considered isolated as disclosed herein. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "coding region" is a portion of nucleic acid comprising codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode a selection marker gene and a gene of interest. In addition, a vector, polynucleotide, or nucleic acid can encode heterologous coding regions, either fused or unfused to a nucleic acid encoding a polypeptide subunit or fusion protein as provided herein.

Heterologous coding regions include without limitation specialized elements or motifs, such as a secretory signal peptide or a heterologous functional domain.

In certain aspects, the polynucleotide or nucleic acid is DNA. In the case of DNA, a polynucleotide comprising a nucleic acid that encodes a polypeptide normally can include a promoter and/or other transcription or translation regulatory elements operably associated with one or more coding regions. An operable association or linkage can be when a coding region for a gene product, e.g., a polypeptide, can be associated with one or more regulatory sequences in such a way as to place expression of the gene product under the influence or control of the regulatory sequence(s). Two DNA fragments (such as a polypeptide coding region and a promoter associated therewith) can be "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription regulatory elements, besides a promoter, for example enhancers, operators, repressors, and transcription termination signals, can be operably associated with the polynucleotide to direct cell-specific transcription.

A variety of transcription regulatory regions are known to those skilled in the art. These include, without limitation, transcription regulatory regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription regulatory regions include those derived from vertebrate genes such as actin, heat shock protein, bovine growth hormone and rabbit B-globin, as well as other sequences capable of controlling gene expression in eukaryotic cells. Additional suitable transcription regulatory regions include tissue-specific promoters and enhancers.

Similarly, a variety of translation regulatory elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other aspects, a polynucleotide can be RNA, for example, in the form of messenger RNA (mRNA).

Polynucleotide and nucleic acid coding regions can be associated with additional coding regions which encode secretory or signal peptides, which direct the secretion of a polypeptide encoded by a polynucleotide as disclosed herein. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain aspects, the native signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse B-glucuronidase.

A "vector" is nucleic acid molecule as introduced into a host cell, thereby producing a transformed host cell. A vector can include nucleic acid sequences that permit it to replicate in a host cell, such as an origin of replication. A vector can also include one or more selectable marker gene and other genetic elements known in the art. Illustrative types of vectors include plasmids, phages, viruses and retroviruses.

A "transformed" cell, or a "host" cell, is a cell into which a nucleic acid molecule has been introduced by molecular biology techniques. As used herein, the term transformation encompasses those techniques by which a nucleic acid molecule can be introduced into such a cell, including transfection with viral vectors, transformation with plasmid vectors, and introduction of naked DNA by electroporation, lipofection, and particle gun acceleration. A transformed cell or a host cell can be a bacterial cell or a eukaryotic cell.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide that is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

The term "pharmaceutical composition" refers to a preparation that is in such form as to permit the biological activity of the active ingredient to be effective, and that contains no additional components that are unacceptably toxic to a subject to which the composition would be administered. Such composition can be sterile.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

Method of Sensitizing a Cancer Cell to Treatment

TKI treatments often involve systemic use for eight to twenty months. Thress et al., Nat Med 2015; 21: 560-562. Frequent use of the drug kills the tumor cells, but generates some cells that become immune to the drug. These TKI immune cells eventually grow to overtake the existing set of cancer cells and form drug-resistant tumors. For example, patients treated with erlotinib often develop acquired resistance within nine to fourteen months. Thress et al., Nat Med 2015; 21: 560-562. The immunity to drug in these cells are established by forming resistant mutations that affect the drug action. Typically, TKIs bind to the intracellular ATP binding region of the EGFR receptor by competitive binding. Giovannetti et al., Mol Pharmacol 2008; 73: 1290-1300. Studies have shown that these mutations may cause an increased affinity to ATP at the biding site by switching amino acids. Also correlated increased ATP concentration in cells to increased competitive binding with erlotinib to the region. This is reasoned due to ability of irreversible drugs such as CL-387785 to covalently bind and inhibit EGFR in resistant cells. Xu Y et al., Cancer Biol Ther 2010; 9: 572-582. Overall, these mutational responses are a means of cancer cell survival.

AXL derives its name from the Greek word anexelekto—that means uncontrolled—and is present in most cells. The human AXL gene is located on chromosome 19q13.2 comprised of 20 exons. AXL belongs to class IX tyrosine kinase family and has documented to be upregulated in many cancers. Recently, AXL upregulations has been seen in patients undergoing treatment or with resistance. Zhang et al., Nat Genet 2012; 44: 852-860. Most importantly, AXL affects the phosphoinositol-3 kinase And MAPK/ERK signaling pathway downstream. AXL also is overexpressed during epithelial to mesenchymal transition (EMT). Asiedu et al., Oncogene 2014; 33: 1316-1324. The end result of upregulated EMT includes high motility of cells. The upregulation of EMT tied with AKT pathway can enhance cell proliferation and decrease cell apoptosis mechanisms. Lee et al., Oncogene 2002; 21: 329-336. Studies have shown a link between regulation of mTOR proteins and upregulated AKT pathways, wherein mTOR expression overrides normal cell-cycle regulatory pathways leading to uncontrolled growth. Khan et al., Chin J Cancer 2013; 32: 253-265. All these downstream functions have been shown to be linked to NFkB that regulates gene expression within the nucleus. Elkabets et al., Cancer Cell 2015; 27: 533-546. Interestingly, these effects caused by EMT is commonly observed in patients with acquired resistance. Uramoto et al., Anticancer Research 2010; 30: 2513-2517. These evidence strongly supports the case for AXL's role in resistance causing mechanisms. However, little is known about this mechanism and warrants further understanding. As disclosed herein, it has been discovered that inhibition of AXL downregulates cell proliferation and resensitizes cells back to EGFR treatment modality. To demonstrate the role of Axl in drug resistance, two representative approaches were used: (a) Downregulate AXL mRNA using siRNA delivery and understand the protein levels; and (b) Knockout Axl gene using CRISPR-CAS9 in drug resistant cancer cells and understand the cellular functions.

By synthesizing an artificial siRNA complementary to AXL mRNA sequence (FIG. 1) AXL can be specifically target within the cell cytoplasm. Therefore, an siRNA (GGA ACU GCA UGC UGA AUG A) (SEQ ID NO: 1) was used specific to the AXL mRNA within human cells. This sequence is a short hairpin loop sequence and is very stable. Axl-siRNA was delivered using nanoparticle (covalent linking) and also by traditional transfection agent (electrostatic binding) and the mechanistic effects were studied in detail. Separately, similar to RNAi pathway, the CRISPR system was used (FIG. 2) to target the AXL gene and cause a mutation. This mutation is believed to lead to a transcription of a non-functional mRNA, and a non-functional protein within the cell. Therefore, CRISPR induced AXL knockdown should inhibit the AXL downstream actions permanently. This allowed for a careful genetic analysis of AXL actions before and after knockout within the cell.

To confirm the data, results for FN14 analysis were repeated and showed a consistent upregulation of ~80% every time AXL was downregulated. This proved that FN14 is closely related to EGFR and was part of AXL survival cross talk. Therefore targeting the AXL/FN14 axis simultaneously should deprive the resistant cancer cells of any growth and survival factors that impart drug resistance. NSCLC drug resistant cell lines (for example H820, H1975, A549 cell lines) showed high associations with both AXL and FN14 (FIG. 24). In fact, AXL associations had higher scores than EGFR in several of these cell lines. Based on this detailed protein analysis it was beleived that AXL-FN14 compensatory axis can exist in multiple drug resistant NSCLC cell lines. Therefore, the synergistic effect of AXL and FN14 to overcomes drug resistance in NSCLC cell lines (For ex. TK and cisplatin drug resistance) was investigated.

Drug treatment and pathway inhibition were combined and the effect of drug resensitization in cells was determined. The required concentration of DMSO and transfection agent needed for drug and siRNA treatments was first optimized by testing their toxicity in H820 cells (FIG. 41). Additionally, cells were checked for sensitivity to anti-EGFR antibody (Cetuximab). Results showed that T790M mutant H820 cells were more resistant to antibody than HCC827 cells (FIG. 41). Next it was established that siRNA alone had no effect on multiple cell lines (FIG. 41).

The $IC_{50}$ of erlotinib was investigated in multiple cell lines based on their AXL and FN14 expressions and EGFR/KRAS mutant status (FIG. 42). Results showed that HCC827 that carries the E746-A750 deletion were highly sensitive while H820 that has both the drug sensitive del E746-E749 and resistant T790M mutation was resistant to erlotinib ($IC_{50}$ >10 µM). Similarly, the T790M mutant H1975 and KRAS mutant A549 were highly resistant to erlotinib ($IC_{50}$ >10 µM). The independent and combined effects of AXL and FN14 siRNAs were also examined. siRNA and siRNA based constructs for treatment and studied variation in $IC_{50}$ of erlotinib in multiples drug resistant cell lines were used.

Downregulation of AXL resensitized H820 cells to erlotinib by decreasing $IC_{50}$ by half (FIG. 44). Similarly, AXL knocked out H820 cells also showed a reduced $IC_{50}$ confirming role of AXL and FN14 in imparting overall resistance (FIG. 43). Similar results were published in another study. Rho, et al., Cancer Res 2014; 74: 253-262. In A549, downregulation of AXL or FN14 was able to slightly decrease $IC_{50}$ (FIG. 44). It is thought that the KRAS mutation can still allow active downstream signaling in these cells. Srikar, et al., Sci Rep 2016; 6: 30245. Therefore, KRAS was also downregulated using a G12S mutation specific siRNA and determined that, $IC_{50}$ for erlotinib had further decreased (FIG. 44). However, when both AXL (protein synthesis for proliferation) and FN14 (protein degradation for survival) were knocked off, the $IC_{50}$ for erlotinib decreased in all the three cell lines by half or more (FIG. 44). In H1975, that already had FN14 upregulated, a combination of AXL and FN14 seemed to resensitize the cells (FIG. 44). In addition, by downregulating all three pathways in A549, total resensitization of cells towards the drug was observed (FIG. 44). Together, these results suggest AXL is playing a role in erlotinib resistance in NSCLC. These results also signify AXL-FN14 axis can induce survival mechanism in drug resistant cells delaying action of drug.

The present disclosure provides for methods of sensitizing, or in certain aspects resensitizing, a cancer cell to a cancer treatment. For purposes of this disclosure, sensitizing a cancer cell to a cancer treatment means making the cell more susceptible to the treatment than it would be without applying the method of sensitization. For example, a sensitized cancer cell and/or cancer, tumor, or the like can exhibit greater inhibition, remission, and/or reduction in response to a treatment or require, for example, a lower dose of an anticancer drug for effective treatment. In certain aspects the cancer cell is treatment resistant. Treatment resistant cancer is sometimes referred to as refractory cancer. In some aspects, the cancer cell begins as resistant to a treatment and in some aspects, the cancer cell acquires resistant to a treatment, such as acquiring resistance to an anticancer drug as a response to the treatment. Thus, it will be understood by one of ordinary skill in the art that treatment resistant can refer to cancer that may be resistant at the beginning of treatment and/or becomes resistant during treatment. In some cases, a resistant cancer can fail to respond to treatment at all or can respond but start to grow again.

As disclosed herein, a method of sensitizing and/or resensitizing a cancer cell to a cancer treatment comprises modifying the expression of at least two biomarkers of the cancer cell. In certain aspects, the biomarker expression modification can be an enhancement or reduction of expression, i.e., upregulation or downregulation of expression. In certain aspects, the modification is a reduction of expression. In certain aspects, the biomarker is a cancer biomarker gene. It will be understood by one of ordinary skill in the art that reducing expression can be a partial or complete reduction in expression. A reduction in expression can be achieved, for example, by deleting, knocking out, disrupting, or the like a biomarker gene. A reduction in expression can also be achieved by inhibiting expression. In certain aspects, the reduction in expression is achieved by inhibiting the expression of one or more cancer biomarkers. In certain aspects, the reduction in expression is achieved by inhibiting the expression of two or more cancer biomarkers. In certain aspects, the reduction in expression is achieved by inhibiting the expression of three or more cancer biomarkers.

A cancer biomarker for purposed of this disclosure is a substance or process that is indicative of a cell being or having the potential to become a cancer cell and/or of the presence of a cancer in a subject. Cancer biomarkers include biological molecules for the indication of physiological and/or pathological characteristics. Cancer biomarkers include oncogenes. Cancer biomarkers also include biological molecules that are informative of a pharmacological response to a therapeutic intervention. In certain aspects, a cancer biomarker is the expression of a gene that in a particular biological context is not normally expressed or the upregulation or increased or overexpression of a gene. For example, AXL upregulations has been seen in patients undergoing cancer treatment or with resistance (Zhang et al., Nat Genet 2012; 44: 852-860) and FN14 was previously was shown to be upregulated in cancer and had a link to cachexia (Johnston, et al., Cell 2015; 162: 1365-1378; Winkles, et al., Nature Reviews Drug Discovery 2008; 7: 411-425). Further, biomarkers can be variations at the sequence level of DNA, for example, insertions, deletions, point mutations, polymorphisms, single nucleotide polymorphisms (SNPs), translocations, and/or short tandem repeats. Biomarkers can also be epigenetic changes that can affect gene expression patterns without altering the actual genetic sequence. In certain aspects, these epigenetic changes can include, for example, modification of histone proteins, chromatin, scaffold proteins, and/or DNA methylation status. In certain aspects, biomarkers can be identified at the molecular or cellular level (e.g. DNA, RNA, and/or protein), by utilizing biological specimens (e.g. plasma, serum, and/or urines), tissues, radiological assessments, and the like.

For purposes of the present disclosure, a cancer treatment can comprise any anticancer and/or cancer-preventative, therapy, drug, protocol, radiation therapy, chemotherapy, or the like. In certain aspects, the cancer treatment can be an anticancer drug or the administration of an anticancer drug. In certain aspects, the drug can be an inactive prodrug that becomes pharmacologically active after administration and after having been metabolized. It will be understood by one of ordinary skill in the art that prodrugs can be activated either intracellularly or extracellularly. In certain aspects, the drug can be a co-drug, comprising at least two chemically linked prodrugs. While not limited by the term, but for illustrative purposes, anticancer drugs can be used in chemotherapy and referred to as chemotherapeutic agents. In certain aspects, chemotherapeutic agents include alkylating agents, anthracyclines, cytoskeletal disruptors (taxanes), epothilones, histone deacetylase inhibitors, inhibitors of Topoisomerase I or II, kinase inhibitors, nucleotide analogs and precursor analogs, peptide antibiotics, platinum-based agents, retinoids, and/or vinca alkaloids and derivatives.

As noted, in certain aspects, the reduction in expression of at least two cancer biomarkers is achieved by inhibiting the expression of one or more cancer biomarkers, such as achieved by the administration of one or more inhibitors. Reduction in expression refers to any method that can result in less expression of the biomarker including, for example, disrupting or knocking out a gene or inhibiting expression of the gene and/or its gene product. In certain aspects, an inhibitor can be a drug—such as small molecule (less than ~900 daltons or less than 500 daltons), an antibody, a nucleic acid, and/or nucleic acid-protein complex (e.g. RNA-induced silencing complex (RISC)), or any combination or compound comprising such inhibitors. In certain aspects, a nucleic acid can be, for example, an anti-sense DNA, double-stranded RNA, a small interfering RNA (siRNA), microRNA (miRNA), piwi-interacting RNA (piRNA), repeat associated small interfering RNA (rasiRNA), small nuclear ribonucleic acid (snRNA), small nuclear ribonucleoproteins (snRNP), and/or small nucleolar RNA (snoRNA). For example, in certain aspects, one or more, two or more, or three or more, of the inhibitors is an siRNA. In certain aspects, at least one of the at least two, two of the at least two, or three of the at least two, of the at least two upregulated cancer biomarkers are the AXL, FN14, EGRF, KRAS, and/or HER-2 genes. In certain aspects, inhibitory siRNAs inhibit expression of the AXL, FN14, EGRF, KRAS, and/or HER-2 genes. In certain aspects, inhibitory siRNAs inhibit expression of the AXL, FN14, and/or KRAS genes. In certain aspects, inhibitory siRNAs inhibit expression of the AXL and/or FN14.

In certain aspects, the expression of the upregulated cancer biomarkers, such as upregulated biomarker genes, is reduced by delivery of an inhibitor associated with a nanoparticle, i.e., nanoparticle delivery. In certain aspects, one or more, two or more, or three or more, of the inhibitors are an inhibitory nucleic acid, for example, an inhibitory siRNA. In certain aspects the inhibitor, such as an inhibitory siRNA, is conjugated to the nanoparticles as described anywhere herein. In certain aspects, the inhibitor is conjugated to the surface of the nanoparticle. In certain aspects the inhibitor is a drug incorporated within a nanoparticle. Illustrative examples of nanoparticles of this disclosure include, for example, gelatin nanoparticle, silica and silicon-based nanoparticles, metal and metal oxides nanoparticles, carbon nanotubes, graphene, dendrimers, polymers, cyclodextrins, lipids, hydrogels, and/or semiconductor nanocrystals. Nanoparticles are also referred to in the art as ultrafine particles. A nanoparticle of this disclosure can be between about 1 and 1,000 nanometers in hydrodynamic size, between about 10 and 1,000 nanometers in hydrodynamic size, between about 100 and 1,000 nanometers in hydrodynamic size, between about 1 and 500 nanometers in hydrodynamic size, between about 10 and 500 nanometers in hydrodynamic size, between about 100 and 500 nanometers in hydrodynamic size, between about 1 and 300 nanometers in hydrodynamic size, between about 10 and 300 nanometers in hydrodynamic size, between about 100 and 300 nanometers in hydrodynamic size, or between about 200 and 300 nanometers in hydrodynamic size. In certain aspects, conjugation of an inhibitor, such as an inhibitory siRNA, can be through intermolecular attractions between the nanoparticle and biomolecule, e.g., via covalent bonding, chemisorption, and/or noncovalent interactions. In certain aspects, the inhibitor is covalently bonded to the nanoparticle. Before exerting a therapeutic effect, a nanoparticle may need to cross or elude various barriers and/or defenses in biological systems including, for example, nuclease degradation, opsonization, and elimination by the phagocyte system, non-specific distribution, interstitial fluid pressure, cellular internalization, and/or cellular efflux pumps. It has been discovered that one advantage of nanoparticle delivery of an inhibitor is that association with a nanoparticle can stabilize and/or prevent degradation, prevent inactivation, and/or clearance of an inhibitor, for example both prior to and when administered into the body of a subject. For example, it has been discovered that conjugation of siRNA to a nanoparticle inhibits interaction of the siRNA with nuclease proteins and/or inhibits degradation of the siRNA, for example, in the bloodstream of a subject. Further, it is known to those of ordinary skill in the art that chemical modifications of nucleic acids can increase their stability, including in vivo stability. For example, illustrative modifications include modification of the sugar-phosphate backbone by, 2'-fluoro and 4'-thio modifications, incorporation of locked nucleic acids (nucleic acids having ribose moiety modified with an extra bridge connecting the 2' oxygen and 4' carbon that locks the base in the C3'-endo position), phosphorothioation, and/or methyl phosphonation.

In certain aspects, a nanoparticle for the delivery of an inhibitor and/or anticancer drug is targeted to a cancer cell and/or tumor via an antibody or antigen-binding portion thereof that recognizes, binds to, is directed to, is specific for, and the like, a cell-surface marker of a cancer cell. Numerous such cancer cell-surface markers are known in the art, as well as antibodies to them. Illustrative examples of cancer cell-surface markers include EGFR, cMET, HER2, HGRF, and PD-L1. In certain aspects, the antibody or antigen-binding portion thereof is conjugated to the surface of the nanoparticle, such as covalently attached. Thus, in certain aspects, a nanoparticle can be associated with both one or more inhibitors, such as inhibitory siRNA, and an antibody or antigen-binding portion thereof. Further, in certain aspects, a nanoparticle can also comprise an anticancer drug. In certain aspects, the targeted nanoparticle is taken into the cell via receptor mediated endocytosis, for example, as illustrated in FIG. 4.

In certain aspects, the method of sensitizing and/or re-sensitizing a treatment-resistant cancer cell to a cancer treatment, as described anywhere herein, further comprises administering to a cancer treatment to which the treatment-resistant cancer is resistant. For purposes of this disclosure, a cancer treatment can be for the treatment of any animal cancer, including any human cancer. Illustrative examples of cancers include non-small cell lung cancer (NSCLC), pancreatic cancer, breast cancer, and colorectal cancer. Further examples include carcinoma, sarcoma, lymphoma, leukemia, germ cell tumor, blastoma, desmoplastic small-round-cell tumor, liposarcoma, and/or epithelioid hemangioendothelioma. In certain aspects, the treatment to which the treatment-resistant cancer is resistant to is chemotherapy and/or an anticancer drug. In certain aspects, the treatment to which the treatment-resistant cancer is resistant to is a tyrosine kinase inhibitor. In certain aspects, the treatment to which the treatment-resistant cancer is resistant to is the anticancer drug Erlotinib, Cisplatin, Gefitinib, or Dasatinib. In certain aspects, the cancer treatment is administered separately and/or independently of any biomarker inhibitor(s). In certain aspects, the cancer treatment is administered in conjunction with one or more cancer biomarker inhibitors. By "in conjunction with" it is understood that the cancer treatment is administered at a time and in a manner such that its action corresponds with the action of the cancer biomarker inhibitor(s). For example, the cancer treatment and cancer biomarker inhibitor(s) are administered at the same time or close enough in time such that they exert their biological effects on the cancer cell at least in part simultaneously. In certain aspects, the inhibitor(s) can be administered first, such as to allow time for reduction in cancer biomarker expression before the administration of the cancer treatment. In certain aspects, the cancer treatment can be administered first and the inhibitor(s) afterwards, such as to increase the effectiveness of the treatment if needed. In certain aspects, both the cancer treatment and the inhibitor(s) are administered by the same route of delivery such as in the same pill or tablet, from the same inhaler, from the same transdermal patch, from the same syringe, from the same IV infusion, and the like. In certain aspects, an anticancer drug is delivered to a cancer cell as a component of the same nanoparticle used to deliver at least one of the inhibitors, such as a nucleic acid, such as an inhibitory siRNA, to the cancer cell and/or tumor. It should be understood that methods of sensitizing and/or resensitizing a cancer cell are not limited to in vivo administration or administration to a subject, of inhibitors and cancer treatments, but also include administration in vitro, ex vivo, etc.

Method of Treating and/or Preventing Cancer

The present disclosure also provides for methods of treating a cancer and/or preventing an increase or spread of cancer. In certain aspects, the method comprises administering, to a subject with cancer: (i) inhibitors of at least one or at least two upregulated cancer biomarker genes of the cancer and (ii) a cancer treatment. In certain aspects, the method comprises administering, to a subject with a tumor: (i) inhibitors of at least one or at least two upregulated cancer biomarker genes of the tumor cells and (ii) a cancer treatment. For example, in certain aspects, two of the at least two upregulated cancer biomarker genes are AXL, FN14, EGRF, KRAS, and/or HER-2 genes. In certain aspects, two of the at least two upregulated cancer biomarker genes ALX and FN14. In certain aspects, the method kills the cancer. In certain aspects, the method results in delayed growth, inhibited growth, and/or reduced size of a tumor. In certain aspects, the growth of the tumor is inhibited or delayed by at least about 10%, 20%, 25%, 30%, 40%, or 50% and/or the size of the tumor is decreased by at least about 10%, 20%, 25%, 30%, 40%, or 50%, in comparison to an untreated control. In certain aspects, the growth of the tumor is inhibited or delayed by from any of about 10%, 20%, 25%, 30%, 40%, or 50% to any of about 20%, 25%, 30%, 40%, 50%, 60%, or 75% and/or the size of the tumor is decreased from any of about 10%, 20%, 25%, 30%, 40%, or 50% to any of about 20%, 25%, 30%, 40%, 50%, 60%, or 75%, in comparison to an untreated control. In certain aspects, the growth of the tumor is inhibited or delayed by at least about 10%, 20%, 25%, 30%, 40%, or 50% and/or the size of the tumor is decreased by at least about 10%, 20%, 25%, 30%, 40%, or 50%, in comparison to a control treated with only one of the inhibitors and the cancer treatment. In certain aspects, the growth of the tumor is inhibited or delayed by from any of about 10%, 20%, 25%, 30%, 40%, or 50% to any of about 20%, 25%, 30%, 40%, 50%, 60%, or 75% and/or the size of the tumor is decreased from any of about 10%, 20%, 25%, 30%, 40%, or 50% to any of about 20%, 25%, 30%, 40%, 50%, 60%, or 75%, in comparison to a control treated with only one of the inhibitors and the cancer treatment. In certain aspects, the growth of the tumor is inhibited or delayed by at least about 10%, 20%, 25%, 30%, 40%, or 50% and/or the size of the tumor is decreased by at least about 10%, 20%, 25%, 30%, 40%, or 50%, in comparison to a control treated with the cancer treatment alone. In certain aspects, the growth of the tumor is inhibited or delayed by from any of about 10%, 20%, 25%, 30%, 40%, or 50% to any of about 20%, 25%, 30%, 40%, 50%, 60%, or 75% and/or the size of the tumor is decreased from any of about 10%, 20%, 25%, 30%, 40%, or 50% to any of about 20%, 25%, 30%, 40%, 50%, 60%, or 75%, in comparison to a control treated with the cancer treatment alone. In certain aspects, the size of the tumor is reduced by at least about 10%, 20%, 25%, 30%, 40%, 50%, 60%, or 75% from the size of the tumor before treatment. In certain aspects, the size of the tumor is reduced from any of about 10%, 20%, 25%, 30%, 40%, or 50% to any of about 20%, 25%, 30%, 40%, 50%, 60%, 75%, 80%, 90%, 95%, 98%, 99%, or 100% from the size of the tumor before treatment. In certain aspects, the size of the tumor is reduced by at least about 25%, 30%, 40%, or 50% from the size of the tumor before treatment. It is understood that the time during which any of the above is determined is generally measured over the time that one of ordinary skill in the art would expect the subject cancer treatment to be administered and/or exhibit an effect and can be over, for example, any of about or between any of about 1 day, 2 days, 3 days, 4 days, 5 days, 6 days, 7 days, 8 days, 9 days, 10 days, 2 weeks, 3 weeks, 4 weeks, 5 weeks, 6 weeks, 1 month, 2 month, 3 month, 4 month, 5 month 6 months, 9 months, 1 year, 2 years, 3 years, 4 years, or 5 years.

In certain aspects, the amount of cancer cell death, inhibition, prevention, delay of growth, decrease in tumor size, and the like, resulting from administration of at least two inhibitors of upregulated cancer biomarkers, such as cancer biomarker genes, and cancer treatment, as disclosed anywhere herein, is greater than the additive effect resulting from administration of each inhibitor alone in conjunction with the cancer treatment. That is, the use of two or more inhibitors results in a synergistic effect.

In certain aspects, an inhibitor disclosed herein can be administered by nanoparticle delivery. In certain aspects, the inhibitor is associated with, such as conjugated to, a nanoparticle (as a nanoparticle, nanoparticle delivery, and association with a nanoparticle are described in detail elsewhere herein). In certain aspects, one or more inhibitory siRNA is attached to the surface of the nanoparticle, such as by covalent bonding. Also as described elsewhere herein in greater detail, in certain aspects, delivery of the nanoparticle is targeted to a cancer cell and/or tumor via an antibody or antigen-binding portion thereof that is specific to a cell-surface maker of a tumor cell.

In certain aspects, a cancer treatment can include an anticancer, and/or cancer-preventative, therapy, drug, protocol, and/or chemotherapy. For example, surgery, chemotherapy, radiation therapy, hormonal therapy, targeted therapies (e.g. immunotherapy, such as monoclonal antibody therapy), angiogenesis inhibition, synthetic lethality, and/or collateral lethality. In certain aspects, the cancer treatment is an anticancer drug or the administration of an anticancer drug. In certain aspects, the anticancer drug is administered by nanoparticle delivery, for example as associated with a nanoparticle such as conjugated and/or incorporated into the nanoparticle. In certain aspects, the anticancer drug is delivered to the target cancer cell and/or tumor with the same nanoparticle used to deliver at least one of the inhibitory siRNAs or with the same nanoparticle used to deliver at least two inhibitory siRNAs. By at least two inhibitory siRNAs it is understood that the two inhibitory siRNAs each target a different upregulated cancer biomarker gene.

In certain aspects, a method of treating and/or preventing a cancer disclosed herein can be for the treatment or prevention of any animal cancer, including any human cancer, as described in detail elsewhere herein.

In certain aspects, the administration of inhibitors, nanoparticles, and/or anticancer drugs can be by any known delivery route, for example, oral, mucosal, intravenous, intramuscular, enteral (gastrointestinal), parenteral, local, topical, and/or inhalation. It will be understood by one of ordinary skill in the art that delivery can be accomplished by any known pharmaceutical delivery method, for example, via pill, tablet, capsule, enema, suppository, injection, surface application (e.g., patch), insufflation, and/or infusion.

Compositions Comprising a Nanoparticle and Methods of Delivery of siRNA Using Nanoparticles The Holy Grail of nanomedicine is selective delivery of inhibitors or targeting agents to the cytoplasm of cancer cells within the organism. To achieve this, different type of nanoparticles can be developed to target and traffic drug molecules in cancer cells. Several studies have shown that nanoparticles are capable of diffusing through the tumor by EPR. Albanese et al., Annu Rev Biomed Eng 2012; 14: 1-16. Nanoparticles can be made porous for drugs to be encapsulated and be designed to attach different targeting biomolecules (antibodies, peptides, aptamers and others) on the surface and encapsulation of drug molecules for targeted delivery. However, delivery of siRNA has always met significant barriers. Whitehead et al., Nature Reviews Drug Discovery 2009; 8: 129-138. This is thought to be because siRNA is easily subjected to degradation in bodily fluids due to presence of nucleases, for example, RNases. Whitehead et al., Nature Reviews Drug Discovery 2009; 8: 129-138. These endogenous enzymes are present not only inside the body, but present on surfaces outside as well. Thus nucleic acids, such as siRNA, are potent targets for degradation in both environments. For this purpose, a porous biodegradable protein based gelatin nanoparticle was developed. Because of its biodegradable nature, the nanoparticle should be highly cytocompatible. The protein structure allows encapsulation of drug and surface functionalization using targeting antibodies/peptides. Additionally, the cross-linked nature of gelatin matrix can protect short strands of siRNA and thereby enabling nucleic acid, such as siRNA, delivery. For example, an FDA approved anti-EGFR antibody (Cetuximab) was functionalized on the nanoparticle surface to target overexpressed EGFR receptors in cells. Without being bound by theory, it is thought that the large structure of antibody gives additional protection to short siRNA on the gelatin matrix. Furthermore, custom modified siRNA 5' (AXL, FN14 and KRAS) end were utilized with a thiol group to conjugate to the gelatin nanoparticle. The thiol group was protected to avoid dimer formation. Therefore, three components were combined to form a multifunctional nanoparticle that can target, internalize, degrade to release drug, and release siRNA to downregulate AXL mRNA (FIG. 3). This multifunctional nanoparticle can internalize via receptor mediated endocytosis, while the gelatin protein is degraded by proteases within the cell cytoplasm to deliver both drug and siRNA (FIG. 4). The siRNA is thus freely available within the cytoplasm to form RISC complexes to degrade intracellular mRNA (e.g., from a cancer biomarker gene, e.g., AXL and/or FN14 mRNA) thereby downregulating gene expression such as cancer biomarker gene expression (e.g., AXL and/or FN14 gene expression).

The present disclosure provides for a composition comprising a nanoparticle and at least one nucleic acid or nucleic acid-protein complex. In certain aspects, the composition can comprise a nanoparticle and at least two nucleic acids of nucleic acid-protein complexes. In certain aspects, the nanoparticle is a gelatin nanoparticle, such as a having a gelatin matrix. In certain aspects, the gelatin nanoparticle is porous and/or biodegradable. Gelatin nanoparticles can be synthesized using A two-step desolvation process (Srikar et al., Sci Rep 2016; 6: 30245), such as described in the non-limiting Examples below. In certain aspects, a biomolecule functional group, such as an antibody or nucleic acid, can be conjugated to the surface of the nanoparticle. For example, conjugated via activation of carboxyl groups on the nanoparticle surface. In certain aspects, sulfhydryl groups of siRNA can be covalently linking to free malemide groups on the nanoparticle surface, and in certain aspects, conjugated via a linker. In certain aspects, nanoparticles can be cross-linked using the ε-amino residues available in the gelatin backbone. Thus, in certain aspects, siRNAs are attached to the surface of the nanoparticle.

A nanoparticle of this disclosure, in some cases including associated functional groups, can be between about 1 and 1,000 nanometers in hydrodynamic size, between about 10 and 1,000 nanometers in hydrodynamic size, between about 100 and 1,000 nanometers in hydrodynamic size, between about 1 and 500 nanometers in hydrodynamic size, between about 10 and 500 nanometers in hydrodynamic size, between about 100 and 500 nanometers in hydrodynamic size, between about 1 and 300 nanometers in hydrodynamic size, between about 10 and 300 nanometers in hydrodynamic size, between about 100 and 300 nanometers in hydrodynamic size, or between about 200 and 300 nanometers in hydrodynamic size (e.g., Table 1 in the Examples below).

It has been discovered that in certain aspects, conjugation of nucleic acids or nucleic acid-protein complexes (e.g., inhibitor siRNA) to nanoparticles can inhibit interaction with nucleases, inhibit degradation, inhibit inactivation, and/or inhibit clearance. In certain aspects, such protection can occur before and/or after administration of the nanoparticle. In some aspects, nanoparticle mediated protection of the nucleic acid occurs after administration to a subject, such as in the bloodstream or tissue of a subject.

In certain aspects, as described elsewhere herein in greater detail, an antibody or antigen-binding fragment thereof is attached to the nanoparticle. In certain aspects, the antibody or antigen-binding fragment thereof is specific to, directed to, binds to, recognizes, etc., a cell-surface marker of a cancer cell and/or tumor. Thus, such an antibody can help target the nanoparticle to the cancer cell expressing the cell-surface marker. In certain aspects, the cell-surface marker facilitates receptor-mediated endocytosis.

In certain aspects, the composition comprising the nanoparticle comprises an anticancer drug. For example, in certain aspects, the anticancer drug can be Erlotinib, Cisplatin, Gefitinib, or Dasatinib. In certain aspects, the anticancer drug is contained in and/or incorporated into the nanoparticle. In certain aspects, the nanoparticle when administered is internalized by a cell, such as by receptor-mediated endocytosis, and is degraded within the cell to release the anticancer drug (FIG. 4).

Thus, in certain aspects, a nanoparticle comprises a nanoparticle with one or more, or two or more, inhibitory siRNAs attached, one or more antibodies or antigen-binding fragments thereof attached, and incorporating an anticancer drug.

EXAMPLES

Antibody conjugated gelatin nanoparticles effectively targets EGFR receptors on drug resistant NSCLC cells. Targeted delivery of siRNA specific to AXL or FN14, or both were evaluated in cells. The downregulation of pathways related to AXL in multiple drug resistant NSCLC was studied in detail. Data provides evidence of a survival cross-talk with FN14 post AXL knockdown (FIG. 40). Similar results were seen after knocking the AXL gene in H820 cells. In vitro and in vivo studies in NSCLC cell and mouse models confirm AXL-FN14 cross-talk and drug resensitization upon knockdown. Additionally, this present study validates stable delivery of siRNA stably into cells using nanoparticles. Overall, the study establishes AXL and FN14 as important oncogenes that influences acquired drug resistance in NSCLC.

Example 1

Methods
siRNA and crRNA Agents

To inhibit protein expression of certain pathways, siRNA was used to target and downregulate AXL, FN14, and KRAS mRNA. For this purpose AXL siRNA (Sense: 5' GGAACUGCAUGCUGAAUGAUU 3') (SEQ ID NO: 2), FN14 siRNA (Sense: 5' CUCAGAUGUCCUGAAAUUC-CAUU 3') (SEQ ID NO: 3), and KRAS siRNA for G12S mutation (Sense: 5' CAGCUAAUUCAGAAUCAUUUU 3') (SEQ ID NO: 4)was used.

For purposes of conjugation, a disulfide group was introduced at the 5' position of oligonucleotide sequence. This disulfide group was de-protected or reduced to —SH for further conjugation. An example of the structure of a disulfide group such an "S-S-oligo" is:

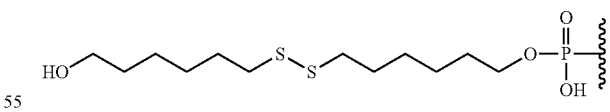

For estimation of conjugated siRNA and fluorescence imaging in vitro, Cy5 was conjugated to the anti-sense 3' end of AXL siRNA.

AXL crRNA was designed to target TTCAGTGGTCCGACGACTGT (SEQ ID NO: 5) at genomic location and PAM: hg38|-chr19:41243678-41243700 AGG, in human NSCLC NCI-H820 to generate AXL knockout cell-line (H820AK). The respective crRNA targets include Exon 12 (NM_021913), Exon 11(NM_001699) and Exon 9 (NM_001278599).

Synthesis of Gelatin Nanoparticles

Gelatin nanoparticles were synthesized using two step desolvation process. Srikar et al., Sci Rep 2016; 6: 30245. 500 mg of Gelatin type A was dissolved in 11 ml of DI water in a 100 ml beaker at 50° C. for 1 h (300 RPM). After complete dissolution, first step of desolvation using rapid addition of 20 ml acetone was initiated for 30 s. Low mol. wt. solids in the supernatant were discarded and the remaining white precipitate at the bottom of the flask was dissolved again in 12 ml of DI water at 50° C. for 2 h (300 RPM). After complete dissolution, the solution was transferred to a 20 ml glass vial and pH was adjusted to 2.8 using 1M HCl. Now the solution was transferred into a 100 ml round bottom flask and kept for stirring (300 RPM) in an oil bath at 50° C. for 1 h. Subsequently the second step of desolvation was initiated by adding acetone drop wise (100 ml/h) using a 20 ml syringe in a syringe pump. Once solution turned opaque white, addition of acetone was stopped. After 10 min, 200 µl of 25% glutaraldehyde (cross-linker) was added to the RBF and the reaction was kept at 50° C. for 15 h (300 RPM). After 15 h, solution turned pale yellow indicating cross-linked gelatin nanoparticles that was cooled to room temperature. 20 µl of 1M Tris glycine solution was quickly added to solution to quench excess glutaraldehyde followed by immediate centrifugation (40 min, 12° C. at 20,000 g). Pellet was resuspended and washed 5 times in DI water. Final suspension was passed through a 0.45 µM cellulose acetate filter and stored at 4° C. (5 mg/ml). Non quenched particles were labeled as $G_{NQ}$ and quenched particles were labeled at $G_Q$. For all experiments $G_Q$ was used, unless indicated. For erlotinib encapsulated nanoparticles, 1 mg of erlotinib dissolved in DMSO was added to the reaction solution prior to pH adjusting before the second desolvation step. These nanoparticles were labelled as (Er)G. In a similar fashion 1 mg of fluorescein was dissolved during the synthesis step to yield fluorescein encapsulated gelatin nanoparticles labeled as G(F1).

Conjugation of antibody and siRNA 10 mg of Gelatin nanoparticle solution was centrifuged and the pellet was washed with 1 ml of 0.1M MES buffer (pH 4.5). Final pellet was resuspended in 0.5 ml MES buffer in a 2 ml eppendorf tube. To this tube, 200 µl of (10 mg/ml) EDC and 300 µl of (10 mg/ml) sulfo-NHS was quickly added and solution was kept in a shaker (850 RPM) for 3.5 h at 28° C. This allowed activation of carboxyl groups on the nanoparticle surface. Activated nanoparticles were centrifuged (10,000 g for 10 min) and the pellet was quickly resuspended in 600 µl of 2 mg/ml Cetuximab (Ab) solution. Solution was kept in a shaker (800 RPM) for 15 h at 23° C. for conjugation of Ab. Resulting reaction solution was then centrifuged (10,000 g for 10 min) and the pellet was washed once with 1 ml sterile 1× PBS. Final nanoparticle solution (in 1× PBS; 5 mg/ml) was stored at 4° C. This reaction yielded two types of nanoconstructs labeled as GAb and (Er)Gab which were then used for siRNA functionalization.

5 mg of GAb or (Er)GAb solution in 1× PBS was taken in 1 ml RNAse free microcentrifuge tube. To this 0.75 mg of sulfo-SMCC dissolved in 200 µl of RNAse free water was added. Reaction solution (pH 7.4) was kept in a shaker (800 RPM) for 2 h at 23° C. This allowed the NHS ester group of the SMCC crosslinker to covalently link with available amines on the nanoparticle as well as Ab. After reaction, solution was centrifuged (10,000 g for 10 min) and the pellet was resuspended in 600 µl of RNAse free water. The pH of the resulting suspension was adjusted to 6.9 (electrode surface was cleaned with RNAse Away wipes prior use), and 50 µl of 50 µM thiol modified siRNA was added. Reaction solution was kept in shaker (650 RPM) for 2 h at 22° C. This allowed the sulfhydryl group of siRNA to covalently link to the free malemide group of the SMCC cross-linker on the nanoparticle surface. After reaction, solution was centrifuged (10,000 g for 10 min) and the pellet was washed with 1ml of RNAse free water to remove excess SMCC. Pellet was resuspended in 1ml sterile RNAse free water and pH was adjusted to 7.4. Final solution labelled as GAbsi or (Er) GAbsi was stored at 4° C. Depending on type of siRNA particles were labelled as GAbsiAXL or GAbsiFN14 or GAbsiKRAS for further experiments. For estimating the amount of siRNA conjugated, GAbsiAXL-Cy5 was utilized. For animal studies equal amounts (25 µl of 50 µM) of AXL and FN14 siRNA was reacted with gelatin nanoparticles. These particles were labelled GAbsi(AXL,FN14).

Conjugation of Antibody with NHS-Cy5 Ester

300 µl of $NaHCO_3$ and 52 µl of 10 mM NaOH was added to 1.2 ml of Cetuximab Ab (2.4 mg). After adjusting pH to 8.5, 79 µl of Cy5-NHS ester (1 mg/ml in DMSO) was added to achieve a Ab:Cy5 ratio of 1:8. Reaction solution was kept in a shaker (800 RPM) for 2 h at 23° C. and then 13 h at 4° C. Final solution (2 mg/ml Ab-Cy5) was used for conjugation with gelatin nanoparticles.

Results

Nanoparticle Synthesis and Characterization

Gelatin nanoparticles were synthesized using a two-step desolvation process. Size analysis by TEM and DLS confirmed formation of uniform nanoparticles with a size of ~200 nm (FIG. 6 and Table 1).

Nanoparticle formed during synthesis were cross-linked using the ε-amino residues available in the gelatin backbone with a cross-linking efficiency to be around 60%. The carboxyl groups on the surface of gelatin nanoparticles were activated and conjugated with EGFR targeting antibody. Fluorescence based estimation, indicated a 20% conjugation efficiency. The rest of available amine groups on the surface of gelatin was used to conjugate the siRNA using a SMCC linker. To increase the cross-reactivity of the functional groups reaction protocol was modified. The modified process decreased the reaction time to 2 h from 15 h, and improved the conjugation efficiency and stability of siRNA. Results from fluorescence based quantification revealed a very high conjugation efficiency up to 98%. The changes in zeta potential upon antibody and siRNA conjugation confirmed the formation of the respective conjugates (Table 1).

TABLE 1

Physicochemical properties of gelatin NP constructs.

| Construct Name | Hydrodynamic size (d.nm) | Zeta (mV) |
| --- | --- | --- |
| Gelatin | 227 | 16 |
| GAb | 261 | −9 |
| GAbsiAXL | 228 | −28 |

The stability of the conjugates was monitored by measuring the zeta potential and hydrodynamic size in biologically relevant media at different time points. Both measurements indicate that high stability for over a week period. (FIG. 7A and FIG. 7B).

Nanoparticle Targeting and Delivery

In order to test the ability of the antibody conjugated gelatin nanoparticles to target cancer cells, the receptor-mediated endocytosis of nanoconstructs in multiple NSCLC cells was evaluated in in vitro. For this study, particles were allowed to internalize in cells and endocytosis was analyzed using the fluorescent-labelled antibody. Fluorescence microcopy images confirm internalization of GAb and GAbsiRNA conjugates through EGFR antibody in spite of its negative surface potential (FIG. 8 and Table 1 above). As predicted, when cells were treated with nanoparticles without antibody no internalization was observed. Similarly, the internalization of siRNA using fluorescent tag was studied. Fluorescence microscopy images show that siRNA internalized in very high quantities within the cytoplasm when antibody targeted particles were used (FIG. 8 and FIG. 9). The fluorescent data validates the targeting and siRNA delivering capabilities of nanoconjugates within the cytoplasm of the cells. An earlier study also confirmed the nature this endocytosis process and the presence of nanoparticle within the cytoplasm. Srikar et al., Langmuir 2016; 32: 4877-4885. The results also suggests that the nanoparticle are very effective in transporting in siRNA to the cytoplasm without any degradation. Srikar et al., Sci Rep 2016; 6: 30245. As majority of RNA transport occur near endoplasmic reticulum within the cytoplasm. It is contemplated that the delivered siRNA should be able to knockdown the pathway very effectively in cells.

Downregulation of AXL Using siRNA and Generation of Knockout Cell Line

In order to investigate the role of AXL in drug resistance, Axl was downregulated to study related pathways. Earlier studies showed that siRNA plays an important role in post transcriptional gene silencing within the cell by utilizing the RNAi pathways. Engels J W, New Biotechnol 2013; 30: 302-307. Therefore, specific siRNA was used to target gene sequence, to silence and degrade the AXL mRNA within the cell. siRNA was first tested in NSCLC cells to evaluate downregulation of pathways. For this study, AXL siRNA was delivered into cells using transfection agent and the amount of siRNA need to achieve a high downregulation was estimated. Results indicate a concertation of 0.0025 mM was sufficient to achieve a knockdown efficiency of up to 97% in cells (FIG. 10). This siRNA concentration was chosen for conjugation and optimization strategies. To study the knockdown capabilities of siRNA by the internalized nanoparticles, the protein expression in H820 drug resistant cancer cells was investigated. For this study, multiple siRNAs that target different pathways such as AXL and FN14 within the cell were used. Results showed a very high knockdown efficiency achieved by the constructs as compared to controls (FIG. 11). Additionally, the modified protocol had a higher knockdown efficiency (FIG. 11).

The lyophilized siRNA conjugated particles (stored at −20° C. for an extended period of time) were stable and effective in silencing AXL mRNA (FIG. 12). Overall, these results also indicate very high siRNA stability post conjugation with gelatin nanoparticles (FIG. 13). Based on these experiments, specific mRNA can be efficiently targeted within the cell and target downstream activity of proteins.

An effective therapy based on siRNA would require frequent administration of siRNA to stop the protein translation activity. To work around these limitation, the functionality of the gene responsible for mRNA transcription was directly targeted. crRNA (CRISPR) was used for knocking down the AXL gene within H820 cells to generate AXL knockdown cells (H820AK). This allows the AXL gene to be mutated permanently and produce a non-functioning AXL protein that will consequently stop the functionality of the pathway. In this study, Cas9 mRNA was artificially transfected into cells and cas9 protein was allowed to be translated in the cytoplasm. A trRNA-crRNA complex (guideRNA-CRISPR) was simultaneously transfected that associates with the cas9 protein to cleave the AXL gene fragment at exon 12. Indeed, a reduction of AXL protein synthesis was observed within these cells after the gene was knocked down in H820 lung cancer cells (FIG. 14). To further evaluate the gene expression of both siRNA and crRNA knockdown cells, RT-PCR analysis was performed to cross examine with our protein analysis.

mRNA and miRNA Expression of Different Oncogenic Factors Towards AXL

RT-PCR were performed to analyze the effect of AXL down regulation. Western blots results suggest that AXL protein was affected by both siRNA and crRNA. Although a change was observed in protein levels required for pathways to function, several studies have documented presence of feedback loops to resist such changes. These feedback mechanisms are closely associated with mRNA expression in cells. Because AXL is upstream of AKT pathway that can activate mTOR, AXL could theoretically restrict the P53 gene expression required for normal autophagy processes. Wu et al., Oncotarget 2014; 5: 9546-9576. Moreover, studies have also confirmed links between non-coding DNAs (ncDNA) in regulating compensatory feedback loops. Mouraviev et al., Prostate Cancer P D 2016; 19: 14-20. The ncDNA and their counterpart miRNAs within the cells, can directly promote gene expression within the cell nucleus. Han et al. Biomed Res Int 2015, 2015: 672759. Therefore, the expression of certain mRNAs and miRNAs associated with AXL was investigated. For this study the difference in AXL and P53 mRNA levels within the cells both before and after AXL downregulation was first investigated. Additionally, the effect of synergistic drug treatment was also examined. Similar to protein analysis, results from RT-PCR show that AXL gene expression is downregulated after treatment with siRNA or crRNA (FIG. 15). Interestingly, P53 expression increased when AXL was downregulated by siRNA, suggesting that autophagy processes could be restored after siRNA treatment (FIG. 15). Apoptosis assay results performed using annexin and flow cytometry showed an increase in late stage apoptosis in cell corroborating RT-PCR analysis (FIG. 16). Still, P53 expression remain unchanged in CRISPR treated cells, that meant a compensatory activation could be restricting P53 expression. These activations may be controlled by other proliferation related oncogenes such as EGFR. Furthermore, studies have shown that EGFR is linked with regulation of AXL through certain downstream pathways. Wu et al., Oncotarget 2014; 5: 9546-9576. This linkage may be a part of a feedback loop to promote AXL expression in the nucleus.

Interestingly, an earlier work suggested the role of Myeloid zinc finger 1 (MZF1) in directly promoting the AXL gene within the nucleus. Mudduluru et al., Mol Cancer Res 2010; 8: 159-169. Additionally, MZF1 has been shown to be responsible for regulating proliferation and invasion that is closely related to drug resistance in cells. Mudduluru et al., Mol Cancer Res 2010; 8: 159-169. Based on these studies, it is plausible for EGFR to upregulate when AXL is downregulated. It is also possible for MZF1 to upregulate in order to equilibrate AXL expression in cells. Therefore, it was decided to investigate EGFR and MZF1 mRNA levels that have an association with AXL or drug resistance. However, the EGFR levels remained unchanged in siRNA treatments except for crRNA treatment (FIG. 15). Results showed 1.3 fold increase for EGFR expression in H820AK cells. This data suggests a compensatory behavior through EGFR in cells. Conversely, a decreased expression was noticed for MZF1 in H820AK cells, wherein the gene was mutated and non-functional (FIG. 15). Additionally, MZF-1 expression increased for synergistic drug treatments. This data suggests MZF1 association with AXL might be affected in CRISPR treated cells. Both these results suggest a compensatory behavior when the AXL gene is knocked down. As a next step the change in multiple miRNA associated with AXL was investigated. Firstly, miR-34a that is controlled by P53 was examined. Interestingly, the expression levels of miR-34a increased in cells when targeted by siRNA conjugated construct (FIG. 17). This result suggests that antibody and siRNA had independent or mutual roles affecting and allowing miR34a to regain control. In a previous study, it was shown that miR-34a could directly deregulate AXL protein levels in cells. The result signifies that miR34 regulation is related to P53 upregulation when AXL is targeted using antibody targeted construct, GAbsiAXL. However, the expression of miR34a did not increase in CRISPR treated cells correlating with P53 expression. Along with miR-34a, an earlier study on AXL upregulated cancer cells confirmed the link of two miRNAs; miR432 and miR548b that negatively regulate EMT. However, even though results showed that there was an increase in miR-432 and miR-548b for both siRNA and crRNA treated samples; the overall expression was minimal (FIG. 17). Interestingly, a study showed that miR-548b is deregulated in drug resistant NSCLC and its expression is often targeted by miR-374. Wang et al. Cell Death Dis 2014; 5: e1227. Therefore, miR-374 that has been shown to upregulate EMT in cancer cells was investigated. Indeed, RT-PCR results show a decreased expression of miR-374 in siRNA and crRNA treated samples (FIG. 17). Again, in CRISPR treated cells, the miR374 was slightly upregulated. These results suggest that, there are wider compensatory mechanisms at play and therefore several other proteins might be influencing these expressions. However, when the AXL mRNA is downregulated using siRNA, results suggest that the compensatory changes are relatively less. Therefore, in order to understand if these cells still had inherent proliferative potential after any compensatory activation, it is important to investigate downstream EMT regulation. To confirm this, the invasion/migration related pathways that could be regulated by AXL was next investigated.

AXL Regulates MMP-2 and MMP-9 in Drug Resistant NSCLC

Invasion/migration assay to assess the EMT potential were performed. Results showed a down trend when AXL was targeted by siRNA or crRNA (FIG. 18). However, the decrease in siRNA treatments was not significant. This can be due to the fact that these assays involve quantification of nucleic acids after lysing the cells. Since siRNA based treatments were performed in the upper chambers of the assay, there could be false positive signals. MMP-2 and MMP-9 levels in the cells were invenstigated using zymography. Several studies have shown that AXL expression was correlated with high MMP expression in cells. Rho et al., Cancer Res 2014; 74: 253-262. MMP expression was directly related to invasiveness and migratory capacity in cells. In fact, MPP are highly expressed in cell undergoing EMT required for metastases. Therefore, by investigating MMP expression in cells both before and after treatments with siRNA based constructs, the role of AXL could be accurately investigate. For this study, MMP expression in synergistic treatments with drug, and expression in CRISPR treated H820AK cells was investigated. Strikingly, a decrease in both MMP-2 and MMP-9 levels in the cells was observed (FIG. 19). The results obtained were similar to those reported in literature, wherein they showed AXL could upregulate MMP-9. Similarly, in another study AXL was shown to regulate MMP-2 in mucoepidermoid carcinoma. Chiu et al., J Oral Pathol Med 2014; 43: 538-544. Interestingly, a sharp decrease of MMP-2 in H820AK cells with non-functional AXL gene was also observed (FIG. 19). These results indicate AXL is directly responsible for regulating MMP-2 expression and partly regulating MMP-9 expression in drug resistant H820. For understanding how AXL affects the EMT pathway associated proteins such as Vimentin, N-cadherin and E-cadherin post AXL knockdown were also analyzed. This whole study comprised 2 treatment groups and three controls. The 2 groups included (1) siRNA and siRNA based construct treatment and (2) synergistic treatment of siRNA and siRNA based constructs along with drug. Controls comprises untreated cells and drug treated cells and Gab without siRNA. For analysis of protein all samples were compared to untreated control. Remarkably, protein analysis showed a reduction in Vimentin and N-cadherin expression corroborating zymogram data (FIGS. 20, 21 and 22). Based on earlier studies, the results confirm that EMT pathway was downregulated. Thus by regulating EMT and MMP levels, AXL might be increasing the proliferative abilities of the cell. These abilities require high energy consumption and protein synthesis. Bonaldo et al., Dis Model Mech 2013; 6: 25-39. Several studies have shown that AXL regulated mTOR and mTOR pathway which increases protein synthesis. Elkabets et al., Cancer Cell 2015; 27: 533-546. Consequently, several proteins downstream of mTOR pathway after targeting AXL were investigated.

sAXL Knockdown Deregulates mTOR Pathway in NSCLC

AXL has been shown to upregulate the AKT pathway downstream. Ruan et al., Embo J 2012; 31: 1692-1703. In turn AKT pathway activates the mTOR pathway. The mTOR complexes that get activated are known to phosphorylate 2 major proteins, 4EBP1 and p70S6K. Xiao et al. The role of mTOR and phospho-p70S6K in pathogenesis and progression of gastric carcinomas: an immunohistochemical study on tissue microarray. Xiao et al., J Exp Clin Canc Res 2009; 28. This phosphorylation results directs protein synthesis, cell growth and energy production by glycolysis. This effect is also known to be part of the Warburg hypothesis in cancer cells, wherein the normal mitochondrial energy cycle is arrested. In normal cells, 4EBP1 binds to eIF4F complex that controls and recruit's ribosomal proteins. However, in cancer cells, phosphorylation of 4EBP1 inactivates this process. On the other hand, phosphorylation of p70S6K mediates mitogenic signals by arresting the G to S phase checkpoint for normal cell cycle regulation. Both these processes contribute to proliferation. In order to investigate the effect of AXL on mTOR, 4EBP1, p70S6K and their phosphorylated counterparts were therefor studied. Furthermore, the activation of mTOR complexes is known to arrest the P53 pathway that controls normal cell growth factors and cell death substrates. In normal cells these substrates, caspase-3 and poly(ADP-ribose)polymerase (PARP) are activated for execution of apoptosis. Cardnell et al. Plos One 2016; 11: e0152584. Typically, it leads to cleavage of PARP that initiates apoptosis. However, during mTOR upregulation, these cell death and repair mechanism are suspended and therefore growth is unchecked. These proteins that are required for the normal cell death processes were also investigated. H820 cells were treated with same treatment groups used for EMT analysis. Results from erlotinib treated cells showed minimal effect (FIG. 20, FIG. 21, and FIG. 22). However synergistic siRNA treatment with drug, downregulated most of the mTOR associated downstream proteins (FIGS. 20, 21 and 22). siRNA treated cells showed an upregulation for normal 4EBP1 and a decrease in phosphorylated p70S6K. On the other hand, GAb showed an upregulation in most proteins (FIGS. 20, 21 and 22). Similarly, siRNA based constructs with antibody did not decrease mTOR associated proteins. This signifies antibody treatment might also have a synergistic effect. Interestingly, even CRISPR treated AXL knockout cells showed relatively higher amounts of phospho-4EBP1 (FIG. 14). However, the cleaved PARP levels required for normal apoptosis function increased in siRNA and siRNA based constructs (FIG. 20, FIG. 21, and FIG. 22). These results indicate that AXL downregulation affects the mTOR pathway and upregulates normal apoptosis functions in drug resistant NSCLC.

Next, upstream activators of mTOR that are ERK and AKT pathways were investigated. Both EGFR and AXL are known to activate these pathways. Results show that synergistic treatment of EGFR inhibitor along with AXL siRNA downregulated both these pathways as compared to drug control (FIG. 20, FIG. 21, and FIG. 22). On the other hand, AXL knockout cells, H820AK showed an upregulation of both phospho-ERK and phospho-AKT (FIG. 14). The analysis from H820AK show that a new pathway upstream of AKT and ERK had been activated. Additionally, downstream proteins often associated with nuclear gene promoters such as nucleolin and NFkB were also investigated. Tai et al., Oncogene 2008; 27: 4044-4055. Results showed that NFkB a downstream target of AKT, was downregulated in all drug-siRNA based treatments (FIG. 20, FIG. 21, and FIG. 22). These results suggest that NFkB was being controlled by AXL and downregulation of both EGFR and AXL had a combined effect. Similarly, siRNA and antibody based construct also showed a downregulation (FIGS. 20, 21 and 22). However, when treated independently with erlotinib or GAb NFkB was upregulated (FIGS. 20, 21 and 22). Surprisingly, siRNA treatment alone had minimal change (FIG. 20, FIG. 21, and FIG. 22). Together these results signify that a pathway downstream of EGFR was initiating a pro-survival signal. This signal was strong enough that, the siRNA treatment alone had minimal change of NFkB levels (FIG. 20, FIG. 21, and FIG. 22). When EGFR levels were examined, most samples showed minimal change except synergistic treatments (FIG. 20, FIG. 21, and FIG. 22). Furthermore, even CRISPR generated H820AK cells showed upregulated EGF protein (FIG. 14). Therefore, based on these results it was ascertained that AXL survival cross-talk was in play and the pathway in question was related to EGFR.

In order to investigate this possibility, oncogenic survival factors were investigated, namely survivin and FN14 that are associated with EGFR. Whitsett et al. 2012; 181: 111. Survivin was an inhibitor of apoptosis while FN14 was a wound healing gene. Recently, FN14 was shown to be upregulated in cancer and had a link to cachexia. Johnston et al., Cell 2015; 162: 1365-1378. Cachexia associated with muscle loss due to protein degradation, worsens disease progression in cancer patients during drug treatment. Johnston et al., Cell 2015; 162: 1365-1378. Additionally, FN14 was also implicated in drug resistance in cancer. Whitsett et al., Am J Pathol 2012; 181: 111-120. Remarkably, protein analysis showed that both survivin and FN14 where upregulated when AXL was inhibited (FIG. 20, FIG. 21, and FIG. 22). Additionally, upregulation of FN14 was consistent with increased NFkB expression (FIG. 20, FIG. 21, and FIG. 22). To confirm the data, the results for FN14 analysis was repeated, and results showed a consistent upregulation of ~80% every time AXL was downregulated (FIG. 23).

AXL Crosstalk with FN14 May be Independent of EGFR Mutant Status

AXL-FN14 cross-talk was investigated in several other cells. FN14 was found to be upregulated along with AKT, ERK, EGF and downstream mTOR protein in H820AK gene knockout cells (FIG. 14). The downregulation of AXL in KRAS mutant A549 NSCLC cells resulted in upregulation of FN14 (FIG. 24). AXL was also downregulated in another EGFR T790 mutant similar to H820, H1975 that was known to have upregulated FN14. In H1975, FN14 upregulation was not significant (FIG. 24). These results signify that the AXL-FN14 cross-talk axis is EGFR mutant independent. Also, if FN14 was already upregulated in H1975 cells, FN14 might be part of a cross-talk involving other pathways rather than AXL. Overall, these results suggested that downregulation of AXL led to FN14 upregulation in order for cells to survive. This survival strategy by FN14 leads to protein degradation in drug resistant NSCLC, and was EGFR mutant independent.

Mechanism of AXL-FN14 and Its Role in TKI Resistance

To understand how FN14 upregulates proteins that may be regulated both by AXL and FN14 independently were investigated. Importantly, a previous study had found FN14 to be downstream of TGFβ pathway. Chen et al. Plos One 2015, 10: e0143802. In this study, TGFβ via SMAD4 was shown to increase FN14 gene expression. Indeed, several studies have shown AXL via JNK pathway could control SMAD3 proteins as well. Reichl et al., Hepatology 2015; 61: 930-941. It is known that SMAD3 and SMAD4 can form complexes to translocate into the nucleus. Furthermore, in AXL upregulated cells, it was shown that AXL deregulates TGFβ in an earlier study. Reichl et al., Hepatology 2015; 61: 930-941. This step ceases TGFβ induced apoptosis regime. Together the results from these studies suggest, TGFβ might upregulate in absence of AXL and could directly regulate FN14 to kick-start a survival mechanism. several of these proteins and other nuclear transcriptor proteins implied in this process were investigated. Specifically, 4EBP1 that is associated with mTOR, and FoxO family proteins. Similar to SMAD, FoxO proteins have a fork head DNA binding domain that can directly regulate cell growth genes. Generally, in cancer cells, these proteins are phosphorylated by the AKT pathway and taken out of the nucleus. Therefore, if these proteins are deregulated it would signify that AKT or ERK pathway may have been re-initiated in AXL downregulated cells. Indeed, protein analysis revealed an upregulation of both TGFβ and SMAD proteins (FIGS. 25 and 126). Interestingly, Adam17 a sheddase protein that is part of a positive feedback loop controlled by FN14 increased it expression as well (FIG. 25 and FIG. 26). Results also indicated an increase in phospho-Jun that is part of the SAPK/JNK pathway (FIG. 25 and FIG. 26). Importantly, when FN14 was upregulated, a slight increase in both AKT and ERK proteins are seen. These data indicate increased activity in SAPK/JNK, AKT and ERK pathways that might be regulated by EGFR. Results also showed a decrease in phospho-4EBP1 and phospho-p70S6K, and an increase in Caspase3, indicating an increase in normal cell cycle control when AXL pathway is inhibited. This data was similar to the previous protein analysis (FIG. 20, FIG. 21 and FIG. 22). On the other hand, when both AXL and FN14 were downregulated using siRNA and siRNA conjugated constructs, an increase in ERK and AKT activity was observed, and phosphorylation of 4EBP1 and FoxO family proteins (FIG. 25 and FIG. 26). Also noticed was an uptick in JAK/STAT proteins that communicates with FN14, and phospho-EGF (FIG. 25 and FIG. 26). These results suggest EGFR may be compensating for the loss of both AXL and FN14. Compared to siRNA treatment, antibody conjugated constructs had minimal difference (FIG. 25 and FIG. 26). These results suggest that EGFR blocking might be reducing the effect of phosphorylation in the cells. Alternatively, these results also suggest that other pathways may be involved in compensatory feedback loops. Looking at associative relations between the present data with other genes and miRNAs, bioinformatics analysis was also utilized. For this study, associations with several genes and miRNAs were analyzed using the upregulation/downregulation factors based on AXL and FN14. Using gene modelling, associative biochemical pathways and metabolic factors were analyzed. AXL and FN14 axis has high association with Rapl, MAPK, Ras and chemokine signaling pathways. Moreover, FN14 belongs to a chemokine pathway. Winkles JA, Nature Reviews Drug Discovery 2008; 7: 411-425. Additionally, AXL may have a downstream effect on PTEN. Interestingly, a prior study experimentally observed that PTEN was upregulated when AXL was downregulated. Papadakis et al., J Invest Dermatol 2011; 131: 509-517. Furthermore, RT-PCR gene expression data analysis points out at miR-92a as a possible target. miR-92a could have high associations with AXL, P53 as well as MZF1. It is possible to suggest that miR-92 could be a target for AXL induced resistance in cancer cells. Interestingly, a recent study showed evidence of miR-92a in directly deregulating AXL and TGFβ. Zhu et al., Am J Transl Res 2016; 8: 3460-3470. Based on the IPA bioinformatics, interpretation of the results (FIG. 27) signify the need to investigative several of these association to fully understand the role of AXL in NSCLC drug resistance. The results also confirm that AXL may have an important role in inducing and regulating several of these genes and miRNAs to impart resistance in NSCLC cells. In order to investigate the possibility of AXL-FN14 associations in lung cancer, gene associations in several lung cancer cell lines were analyzed. Based on the protein analysis, NSCLC cell lines showed high associations with both AXL and FN14. In fact, AXL associations had higher scores than EGFR in several of these cell lines.

FN14 as Target for Cisplatin

Fn14 or the Fibroblast growth factor-inducible 14 (gene TNFRSF12A) is the smallest known member of the tumor necrosis factor (TNF) superfamily. Winkles J A, Nature reviews Drug discovery 2008; 7: 411-425. Multifunctional cytokine tumor necrosis factor-like weak inducer of apoptosis (TWEAK) is its only known ligand. Elevated FN14 expression has been observed in a number of solid tumors including hepatocellular carcinoma (Feng et al., The American Journal of Pathology 2000; 156: 1253-1261), esophageal adenocarcinoma (Wang et al., Oncogene 2006; 25: 3346-3356), glioblastoma (Tran et al., The American Journal of Pathology 2003; 162: 1313-1321), and HER2+breast cancer. Fn14 signaling upregulates cell survival through upregulation of NF-κB, Bcl-XL, Bcl-2 expression and multiple GEF-Rho GTPase activation in glioblastoma. Tran et al., 2013. Fn14 signaling also upregulates glioma and breast cell invasion by activating Rac1 and NFκB. Tran et al., Cancer Res 2006; 66: 9535-9542. Indeed, FN14 is a possible therapeutic target for melanoma. Zhou et al., J Invest Dermatol 2013; 133: 1052-1062. Although Fn14 expression has been observed in NSCLC specimens (Culp et al., American Association for Cancer Research 2010; 16: 497-508), little is known about its role in this particular tumor type. Studies show that there is a link between the expressions of FN14 and EGFR and a concurrency in FN14 expressions with activating EGFR mutation. Whitsett et al., The American Journal of Pathology 2012; 181: 111-120. FN14 expressions also tend to be highly elevated in EGFR T790M mutation and can only be effected with a higher dose of TKI. Fn14 also tends to augment metastasis by up-regulation of integrin a6 (Jandova et al., Neoplasma 2015; 62: 41-52), suggesting contribution to cell motility and invasion and eventually a new potential target for NSCLC treatment. EGFR del 19 mutation is correlated with FN14/JAK/STAT signaling pathways. Sun et al., Oncology reports 2016; 36: 1030-1040. FN14 tends to be a positive regulator of src and in the experiment, and downregulation of p-SRC upon suppression of FN14 was observed. Suppression of p-HER3 was also observed. A similar correlation was also observed in MET driven NSCLC. FN14 and MET expressions significantly correlated and suppression of MET also showed suppression of FN14. It has also been observed that FN14 is upregulated via RhoA/ROCK kinase pathway and mediated NFkB activation. Chorianopoulos et al., Basic Res Cardiol 2010; 105: 301-313. Suppression of FN14 seems to suppress BRCA1 expression, thus preventing DNA repair mechanism. However, it was also noticed an increase in the expression of AXL during suppression of FN14. Upregulation of FN14 promotes NADPH oxidase activation, thus promoting oxidative stress. Madrigal-Matute et al., Cardiovascular Research 2015; 108: 139-147. Targeting FN14 seems to induce cachexia. Johnston et al., Cell 2015; 162: 1365-1378. Our research shows that suppression of FN14, under the influence of cisplatin, upregulates FHIT which triggers subsequent apoptosis through Bcl-2 phosphorylation. Study suggests that FN14 may be dependent to Mcl-1. Majority of adenocarcinoma and squamous cell carcinoma show expressions of Mcl-1, also correlating to higher tumor stages and poor outcomes. Mcl-1 is mitochondria associated pro-survival Bcl-2 family member which binds to pro apoptotic Noxa, BAK and BAX, thus retaining them to their inactive state and limiting apoptotic signaling. Zhang et al., Oncogene 2011; 30: 1963-1968. Indeed, it was observed that under the influence of cisplatin, when FN14 was suppressed, there was an increase in the rate of cleavage of Caspase 3 and subsequently, PARP.

Dual Expression of AXL and FN14 Leads to Drug Resistance

Cisplatin is a major ROS inducer and a DNA cross-linker. However, oxidative stress enhances Axl-mediated cell migration through an Aktl/Rac1-dependent mechanism. Oncogenic H-Ras enhances DNA repair through the Ras/phosphatidylinositol 3-kinase/ Rac1 pathway in NIH3T3 cells and up-regulates ERCC1, one of the key enzymes involved in nucleotide excision repair, to protect against platinum- based anticancer agents and associated ROS. RhoA/ROCK pathway regulated FN14. Thus, ROS induced up-regulation of RhoA and ROCK also up-regulated FN14. RhoA/ROCK is also directly involved in crosstalk with src—thus probably further up-regulating both EGFR and FN14. This is probably how the cell becomes resistant to cisplatin and over-expression of AXL and FN14 initiates Example 2

Targeting AXL-FN14 Using Nanoparticles In Vitro

Based on results from siRNA+drug toxicity studies, downregulated AXL-FN14 axis in H820 cells by treatment with siRNA-conjugated nanoconstructs was investigated. For this study toxicity of gelatin nanoparticles in H820 and HCC827 cells was initially tested. Results showed that particles after glutaraldehyde quenching were non-toxic (FIG. 45). The studies also confirmed the ability of gelatin nanoparticles to deliver drug through encapsulation in HCC827 drug sensitive cells (FIG. 45).

Cytotoxicity assays also confirmed that synthesized siRNA conjugates were non-toxic (FIG. 46). As a next step drug resensitization in H820 cells using dual-siRNA AXL-FN14 constructs was investigated. Similar results to that of siRNA-based treatments were achieved (FIG. 47). The results demonstrate that nanoparticles can be utilized for targeting these pathways and can be an important step in translating therapies in higher organisms. Targeting AXL-FN14 using nanoparticles in A549 mice xenografts In order to translate the in vitro findings to an in vivo model, mice were treated with luciferase expressing A549 xenograft tumors with our siRNA-conjugated constructs. Both AXL and FN14 were synergistically targeted using a single construct along with erlotinib and monitored tumor volume reduction by fluorescence imaging (FIG. 48). Results indicated that targeted treatment using siRNA-constructs injected intraperitoneally reduced the tumor size by 50% with time (at the third treatment day) as compared to nanoparticle devoid of siRNA (FIG. 49). Controls treated with mice such as PBS or drug showed either a rapid increase or minimal reduction in tumor size (FIG. 49).

To confirm the downregulation of AXL-FN14 in tumors, protein analysis was performed on the tumor tissues. AXL and FN14 was found to be downregulated in tumor tissues treated with dual-siRNA construct GAbsi(AXL,FN14) as compared to controls (FIG. 50). These results confirm resensitization of drug resistant tumors towards erlotinib (TKI) therapy. The in vivo studies demonstrate the use of nanoparticles for siRNA delivery to tumors, and drug resensitization.

In Vitro Cytotoxicity

Cytotoxicity in cisplatin sensitive and resistant cell lines (FIG. 51) upon down regulation of AXL and FN14 were investigated. Co-inhibition of AXL and FN14 in cisplatin resistant cell lines decreases $IC_{50}$ values by 300 folds (FIG. 51).

Summary

Targeted delivery of siRNA specific to AXL or FN14, or both were evaluated in cells. The downregulation of pathways related to AXL in multiple drug resistant NSCLC has been studied in detail. Our data provide evidence of a survival cross talk with FN14 post AXL knockdown. Similar results were seen after knocking the AXL gene in H820 cells. In vitro and in vivo studies in NSCLC cell and mouse models confirm AXL-FN14 cross talk and drug resensitization upon knockdown. Additionally, this present study validates stable delivery of siRNA stably into cells using nanoparticles. Overall, the study establishes AXL and FN14 as important oncogenes that influence acquired drug resistance in NSCLC. The mechanisms suggested in this study can help develop new treatment strategies to combat drug resistance in cancer. Table 2 and Table 3 below show current AXL and FN14 drugs, respectively, in clinical trial.

TABLE 2

Known AXL associated targeting agents or direct inhibitors.

| Name | Type | Company | Year | Status | Comments |
|---|---|---|---|---|---|
| R428 | SMI | Rigel Pharma | 2011 | Published | |
| BGB324 | SMI | BergenBio | 2015 | Clinical trial P1/P2 | Recruiting |
| S49076 | SMI | Servier | 2013 | Clinical trial P1 | Unknown results |
| TP-0903 | SMI | Tolero Pharma | 2013 | Preclinical/P1 | Preclinical success |
| MGCD265 (Glesatinib) | SMI | Mirati Therapeutics | | Clinical trial P2 | Recruiting/Termination Preclinical completed |
| LY2801653 (Merestinib) | SMI | Eli Lilly | 2014 | Clinical trial P2 | Recruiting |
| LY3009806 (Ramucirumab) | SMI | Eli Lilly | 2014 | Clinical trial P2 | Recruiting |
| MP-470 (Amuvatinib) | SMI | Astex Pharma | 2011 | Clinical trial P2 | Unknown results |
| SKI-606 (Bosutinib) | SMI | Pfizer | 2005 | Preclinical | Unknown results |
| ASP2215 | SMI | Astellas Pharma | 2015 | Clinical trial P1 | Terminated (Adverse effects in ER combo) |
| XL184 (Cabozantinib) | SMI | Exelixis | 2008 | Clinical trial P1b/2 | Completed |
| GSK1363089 (XL880) | SMI | GlaxoSmithKline | 2008 | Clinical trial P2 | Completed |
| SGI-7079 | SMI | Tolero Pharma | 2013 | Preclinical | Completed |
| AXL1717 | SMI | Axelar AB | 2011 | Clinical trial P1 | Completed |
| BPI-9016M | SMI | Betta Pharma | 2015 | Clinical trial P1 | Recruiting |
| MGCD516 | SMI | Mirati Pharma | 2014 | Clinical trial P1 | Recruiting |
| TAB-058CL | Ab | Creative Biolabs | | In vitro | |
| TAB-0138CL | Ab | Creative Biolabs | | In vitro | |
| TAB-0139CL | Ab | Creative Biolabs | | In vitro | |
| TAB-0140CL | Ab | Creative Biolabs | | In vitro | |
| TAB-0188CL | Ab | Creative Biolabs | | In vitro | |
| TAB-1093CL | Ab | Creative Biolabs | | In vitro | |
| TAB-1094CL | Ab | Creative Biolabs | | In vitro | |
| 20G7-D9 | Ab | Creative Biolabs | | Published | |
| GL21.T | RNA | Aptagen | 2012 | Published | |

SMI: Small Molecule Inhibitor
Ab: Antibody
RNA: Ribonucleic acid

TABLE 3

Known FN14 associated targeting agents or direct inhibitors.

| Agent | Type | Status | Developer | Reference |
|---|---|---|---|---|
| RG7212 (RO5458640) | Neutralizing mAb | Phase I trial Completed | Hoffmann-La Roche | NCT01383733 |
| Fn14-TRAIL (KAHR-101) | Signal converter protein | Pre-clinical | KAHR Medical | |
| BIIB036 (P4A8) | Agonistic mAb | | | |
| BIIB023 | Neutralizing mAb | Pre-clinical | | |
| 18D1 | Agonistic mAb | Phase 1 Completed Phase 2 ongoing | Biogen Idec Biogen Idec | NCT00771329 NCT01499355 |
| PDL192 (enavatuzumab) | Agonistic mAb | Pre-clinical | University Hospital of Würzburg/arGEN-X | |
| ITEM4-recombinant gelonin | Immunotoxin conjugate | Phase I trial Completed Pre-clinical | Abbot | NCT00738764 |
| hSGZ | Immunotoxin fusion protein | | MD Anderson Cancer Center | |
| GranzymeB-TWEAK | Ligand-apoptotic factor fusion protein | Pre-clinical Pre-clinical Pre-clinical | " | |
| Fn14-Fc | Decoy receptor Signal converter protein | Pre-clinical | Emory University School of Medicine | — |
| Fn14-TRAIL (KAHR-101) | | | | |

Additional Sequences:

```
AXL siRNA Sequence:
Sense
                            (SEQ ID NO: 2)
    5' GGAACUGCAUGCUGAAUGAUU 3'
```

There are three mRNA transcript variants this sequence targets to:

*Homo sapiens* AXL receptor tyrosine kinase (AXL), transcript variant 1, mRNA Accession: NM_021913.4:

```
                                              (SEQ ID NO: 6)
    1   gtgagggaag gaggcagggg tgctgagaag gcggctgctg ggcagagccg gtggcaaggg 61   cctcccctgc cgctgtgcca ggcaggcagt gccaaatccg gggagcctgg agctgggggg 121   agggccgggg acagcccggc cctgccccct ccccgctgg gagcccaaca acttctgagg 181   aaagtttggc acccatggcg tgcggtgcc ccaggatggg cagggtcccg ctggcctggt 241   gcttggcgct gtgcggctgg gcgtgcatgg ccccaggggg cacgcaggct gaagaaagtc 301   ccttcgtggg caacccaggg aatatcacag gtgcccgggg actcacgggc acccttcggt 361   gtcagctcca ggttcaggga gagcccccg aggtacattg gcttcgggat ggacagatcc 421   tggagctcgc ggacagcacc cagacccagg tgccctggg tgaggatgaa caggatgact 481   ggatagtggt cagccagctc agaatcacct ccctgcagct ttccgacacg ggacagtacc 541   agtgtttggt gtttctggga catcagacct tcgtgtccca gcctggctat gttgggctgg 601   agggcttgcc ttacttcctg gaggagcccg aagacaggac tgtggccgcc aacacccct 661   tcaacctgag ctgccaagct cagggacccc cagagccgt ggacctactc tggctccagg 721   atgctgtccc cctggccacg gctccaggtc acggccccca gcgcagcctg catgttccag 781   ggctgaacaa gacatcctct ttctcctgcg aagcccataa cgccaagggg gtcaccacat 841   cccgcacagc caccatcaca gtgctccccc agcagcccg taacctccac ctggtctccc 901   gccaacccac ggagctggag gtggcttgga ctccaggcct gagcggcatc taccccctga 961   cccactgcac cctgcaggct gtgctgtcag acgatgggat gggcatccag gcgggagaac
```

-continued

```
1021   cagaccccc agaggagccc ctcacctcgc aagcatccgt gccccccat cagcttcggc
1081   taggcagcct ccatcctcac accccttatc acatccgcgt ggcatgcacc agcagccagg
1141   gcccctcatc ctggacccac tggcttcctg tggagacgcc ggagggagtg ccctgggcc
1201   ccctgagaa cattagtgct acgcggaatg ggagccaggc cttcgtgcat tggcaagagc
1261   cccgggcgcc cctgcagggt accctgttag ggtaccggct ggcgtatcaa ggccaggaca
1321   ccccagaggt gctaatggac atagggctaa ggcaagaggt gaccctggag ctgcaggggg
1381   acgggtctgt gtccaatctg acagtgtgtg tggcagccta cactgctgct ggggatggac
1441   cctggagcct cccagtaccc ctggaggcct ggcgcccagg gcaagcacag ccagtccacc
1501   agctggtgaa ggaaccttca actcctgcct tctcgtggcc ctggtggtat gtactgctag
1561   gagcagtcgt ggccgctgcc tgtgtcctca tcttggctct cttccttgtc caccggcgaa
1621   agaaggagac ccgttatgga gaagtgtttg aaccaacagt ggaaagaggt gaactggtag
1681   tcaggtaccg cgtgcgcaag tcctacagtc gtcggaccac tgaagctacc ttgaacagcc
1741   tgggcatcag tgaagagctg aaggagaagc tgcgggatgt gatggtggac cggcacaagg
1801   tggccctggg gaagactctg ggagagggag agtttggagc tgtgatggaa ggccagctca
1861   accaggacga ctccatcctc aaggtggctg tgaagacgat gaagattgcc atctgcacga
1921   ggtcagagct ggaggatttc ctgagtgaag cggtctgcat gaaggaattt gaccatccca
1981   acgtcatgag gctcatcggt gtctgtttcc agggttctga acgagagagc ttcccagcac
2041   ctgtggtcat cttaccttc atgaaacatg gagacctaca cagcttcctc ctctattccc
2101   ggctcgggga ccagccagtg tacctgccca ctcagatgct agtgaagttc atggcagaca
2161   tcgccagtgg catggagtat ctgagtacca gagattcat acccgggac ctggcggcca
2221   ggaactgcat gctgaatgag aacatgtccg tgtgtgtggc ggacttcggg ctctccaaga
2281   agatctacaa tggggactac taccgccagg gacgtatcgc caagatgcca gtcaagtgga
2341   ttgccattga gagtctagct gaccgtgtct acaccagcaa gagcgatgtg tggtccttcg
2401   gggtgacaat gtgggagatt gccacaagag gccaaacccc atatccgggc gtggagaaca
2461   gcgagattta tgactatctg cgccagggaa atcgcctgaa gcagcctgcg gactgtctgg
2521   atggactgta tgccttgatg tcgcggtgct gggagctaaa tccccaggac cggccaagtt
2581   ttacagagct gcgggaagat ttggagaaca cactgaaggc cttgcctcct gcccaggagc
2641   ctgacgaaat cctctatgtc aacatggatg agggtggagg ttatcctgaa cccctggag
2701   ctgcaggagg agctgacccc ccaacccagc cagaccctaa ggattcctgt agctgcctca
2761   ctgcggctga gtccatcct gctggacgct atgtcctctg cccttccaca accctagcc
2821   ccgctcagcc tgctgatagg ggctcccag cagccccagg gcaggaggat ggtgcctgag
2881   acaaccctcc acctggtact ccctctcagg atccaagcta agcactgcca ctggggaaaa
2941   ctccaccttc ccactttccc accccacgcc ttatcccac ttgcagccct gtcttcctac
3001   ctatcccacc tccatcccag acaggtccct cccctttctct gtgcagtagc atcaccttga
3061   aagcagtagc atcaccatct gtaaaaggaa ggggttggat tgcaatatct gaagccctcc
3121   caggtgttaa cattccaaga ctctagagtc caaggtttaa agagtctaga ttcaaaggtt
3181   ctaggtttca aagatgctgt gagtctttgg ttctaaggac ctgaaattcc aaagtctcta
3241   attctattaa agtgctaagg ttctaaggcc tacttttttt ttttttttt ttttttttt
3301   ttttgcgata gagtctcact gtgtcaccca ggctggagtg cagtggtgca atctcgcctc
3361   actgcaacct tcacctaccg agttcaagtg attttcctgc cttggcctcc caagtagctg
3421   ggattacagg tgtgtgccac cacacccggc taatttttat attttttagta gagacagggt
```

-continued

```
3481  ttcaccatgt tggccaggct ggtctaaaac tcctgacctc aagtgatctg cccacctcag
3541  cctcccaaag tgctgagatt acaggcatga gccactgcac tcaaccttaa gacctactgt
3601  tctaaagctc tgacattatg tggttttaga ttttctggtt ctaacatttt tgataaagcc
3661  tcaaggtttt aggttctaaa gttctaagat tctgatttta ggagctaagg ctctatgagt
3721  ctagatgttt attcttctag agttcagagt ccttaaaatg taagattata gattctaaag
3781  attctatagt tctagacatg gaggttctaa ggcctaggat tctaaaatgt gatgttctaa
3841  ggctctgaga gtctagattc tctggctgta aggctctaga tcataaggct tcaaaatgtt
3901  atcttctcaa gttctaagat tctaatgatg atcaattata gtttctgagg ctttatgata
3961  atagattctc ttgtataaga tcctagatcc taagggtcga aagctctaga atctgcaatt
4021  caaaagttcc aagagtctaa agatggagtt tctaaggtcc ggtgttctaa gatgtgatat
4081  tctaagactt actctaagat cttagattct ctgtgtctaa gattctagat cagatgctcc
4141  aagattctag atgattaaat aagattctaa cggtctgttc tgtttcaagg cactctagat
4201  tccattggtc caagattccg gatcctaagc atctaagtta taagactctc acactcagtt
4261  gtgactaact agacaccaaa gttctaataa tttctaatgt tggacacctt taggttcttt
4321  gctgcattct gcctctctag gaccatggtt aagagtccaa gaatccacat ttctaaaatc
4381  ttatagttct aggcactgta gttctaagac tcaaatgttc taagtttcta agattctaaa
4441  ggtccacagg tctagactat taggtgcaat ttcaaggttc taaccctata ctgtagtatt
4501  ctttggggtg cccctctcct tcttagctat cattgcttcc tcctcccccaa ctgtgggggt
4561  gtgccccctt caagcctgtg caatgcatta gggatgcctc ctttcccgca ggggatggac
4621  gatctcccac ctttcgggcc atgttgcccc cgtgagccaa tccctcacct tctgagtaca
4681  gagtgtggac tctggtgcct ccagaggggc tcaggtcaca taaaactttg tatatcaacg
4741  agaaaaaaaa
```

*Homo sapiens* AXL receptor tyrosine kinase (AXL), transcript variant 2, mRNA Accession: NM_001699.5:

(SEQ ID NO: 7)
```
  1  gtgagggaag gaggcagggg tgctgagaag gcggctgctg ggcagagccg gtggcaaggg
 61  cctcccctgc cgctgtgcca ggcaggcagt gccaaatccg gggagcctgg agctgggggg
121  agggccgggg acagcccggc cctgccccct ccccgctgg gagcccaaca acttctgagg
181  aaagtttggc acccatggcg tggcggtgcc ccaggatggg cagggtcccg ctggcctggt
241  gcttggcgct gtgcggctgg gcgtgcatgg cccccagggg cacgcaggct gaagaaagtc
301  ccttcgtggg caacccaggg aatatcacag gtgcccgggg actcacgggc acccttcggt
361  gtcagctcca ggttcaggga gagcccccg aggtacattg gcttcgggat ggacagatcc
421  tggagctcgc ggacagcacc cagacccagg tgccctggg tgaggatgaa caggatgact
481  ggatagtggt cagccagctc agaatcaccc cctgcagct tccgacacg ggacagtacc
541  agtgtttggt gtttctggga catcagacct tcgtgtccca gcctggctat gttgggctgg
601  agggcttgcc ttacttcctg gaggagcccc aagacaggac tgtggccgcc aacacccct
661  tcaacctgag ctgccaagct cagggaccc cagagccgt ggacctactc tggctccagg
721  atgctgtccc cctggccacg gctccaggtc acggccccca gcgcagcctg catgttccag
781  ggctgaacaa gacatcctct ttcctcctgcg aagcccataa cgccaagggg gtcaccacat
841  cccgcacagc caccatcaca gtgctccccc agcagcccg taacctccac ctggtctccc
```

-continued

```
 901   gccaacccac ggagctggag gtggcttgga ctccaggcct gagcggcatc tacccctga
 961   cccactgcac cctgcaggct gtgctgtcag acgatgggat gggcatccag gcgggagaac
1021   cagacccccc agaggagccc ctcacctcgc aagcatccgt gccccccat cagcttcggc
1081   taggcagcct ccatcctcac accccttatc acatccgcgt ggcatgcacc agcagccagg
1141   gcccctcatc ctggacccac tggcttcctg tggagacgcc ggagggagtg ccctgggcc
1201   cccctgagaa cattagtgct acgcggaatg ggagccaggc cttcgtgcat tggcaagagc
1261   cccgggcgcc cctgcagggt accctgttag ggtaccggct ggcgtatcaa ggccaggaca
1321   ccccagaggt gctaatggac atagggctaa ggcaagaggt gaccctggag ctgcagggg
1381   acgggtctgt gtccaatctg acagtgtgtg tggcagccta cactgctgct ggggatggac
1441   cctggagcct cccagtaccc ctggaggcct ggcgcccagt gaaggaacct tcaactcctg
1501   ccttctcgtg gccctggtgg tatgtactgc taggagcagt cgtggccgct gcctgtgtcc
1561   tcatcttggc tctcttcctt gtccaccggc gaaagaagga gacccgttat ggagaagtgt
1621   ttgaaccaac agtggaaaga ggtgaactgg tagtcaggta ccgcgtgcgc aagtcctaca
1681   gtcgtcggac cactgaagct accttgaaca gcctgggcat cagtgaagag ctgaaggaga
1741   agctgcggga tgtgatggtg gaccggcaca aggtggccct ggggaagact ctgggagagg
1801   gagagtttgg agctgtgatg aaggccagc tcaaccagga cgactccatc ctcaaggtgg
1861   ctgtgaagac gatgaagatt gccatctgca cgaggtcaga gctggaggat ttcctgagtg
1921   aagcggtctg catgaaggaa tttgaccatc ccaacgtcat gaggctcatc ggtgtctgtt
1981   tccagggttc tgaacgagag agcttcccag cacctgtggt catcttacct ttcatgaaac
2041   atggagacct acacagcttc ctcctctatt cccggctcgg ggaccagcca gtgtacctgc
2101   ccactcagat gctagtgaag ttcatggcag acatcgccag tggcatggag tatctgagta
2161   ccaagagatt catacaccgg gacctggcgg ccaggaactg catgctgaat gagaacatgt
2221   ccgtgtgtgt ggcggacttc gggctctcca gaagatcta caatggggac tactaccgcc
2281   agggacgtat cgccaagatg ccagtcaagt ggattgccat tgagagtcta gctgaccgtg
2341   tctacaccag caagagcgat gtgtggtcct tcggggtgac aatgtgggag attgccacaa
2401   gaggccaaac cccatatccg ggcgtggaga acagcgagat ttatgactat ctgcgccagg
2461   gaaatcgcct gaagcagcct gcggactgtc tggatggact gtatgccttg atgtcgcggt
2521   gctgggagct aaatccccag accggccaa gttttacaga gctgcgggaa gatttggaga
2581   acacactgaa ggccttgcct cctgcccagg agcctgacga atcctctat gtcaacatgg
2641   atgagggtgg aggttatcct gaaccccctg gagctgcagg aggagctgac ccccaaccc
2701   agccagaccc taaggattcc tgtagctgcc tcactgcggc tgaggtccat cctgctggac
2761   gctatgtcct ctgcccttcc acaacccta gccccgctca gctgctgat aggggctccc
2821   cagcagcccc agggcaggag gatggtgcct gagacaaccc tccacctggt actccctctc
2881   aggatccaag ctaagcactg ccactgggga aaactccacc ttcccacttt cccaccccac
2941   gccttatccc cacttgcagc cctgtcttcc tacctatccc acctccatcc cagacaggtc
3001   cctccccttc tctgtgcagt agcatcacct tgaaagcagt agcatcacca tctgtaaaag
3061   gaaggggttg gattgcaata tctgaagccc tccaggtgt taacattcca agactctaga
3121   gtccaaggtt taaagagtct agattcaaag gttctaggtt tcaaagatgc tgtgagtctt
3181   tggttctaag gacctgaaat tccaaagtct ctaattctat taaagtgcta aggttctaag
3241   gcctactttt tttttttttt tttttttttt tttttttgcg atagagtctc actgtgtcac
```

-continued

```
3301  ccaggctgga gtgcagtggt gcaatctcgc ctcactgcaa ccttcaccta ccgagttcaa
3361  gtgattttcc tgccttggcc tcccaagtag ctgggattac aggtgtgtgc caccacaccc
3421  ggctaatttt tatattttta gtagagacag ggtttcacca tgttggccag gctggtctaa
3481  aactcctgac ctcaagtgat ctgcccacct cagcctccca aagtgctgag attacaggca
3541  tgagccactg cactcaacct taagacctac tgttctaaag ctctgacatt atgtggtttt
3601  agattttctg gttctaacat ttttgataaa gcctcaaggt tttaggttct aaagttctaa
3661  gattctgatt ttaggagcta aggctctatg agtctagatg tttattcttc tagagttcag
3721  agtccttaaa atgtaagatt atagattcta aagattctat agttctagac atggaggttc
3781  taaggcctag gattctaaaa tgtgatgttc taaggctctg agagtctaga ttctctggct
3841  gtaaggctct agatcataag gcttcaaaat gttatcttct caagttctaa gattctaatg
3901  atgatcaatt atagtttctg aggctttatg ataatagatt ctcttgtata agatcctaga
3961  tcctaagggt cgaaagctct agaatctgca attcaaaagt tccaagagtc taaagatgga
4021  gtttctaagg tccggtgttc taagatgtga tattctaaga cttactctaa gatcttagat
4081  tctctgtgtc taagattcta gatcagatgc tccaagattc tagatgatta aataagattc
4141  taacggtctg ttctgtttca aggcactcta gattccattg gtccaagatt ccggatccta
4201  agcatctaag ttataagact ctcacactca gttgtgacta actagacacc aaagttctaa
4261  taatttctaa tgttggacac ctttaggttc tttgctgcat tctgcctctc taggaccatg
4321  gttaagagtc caagaatcca catttctaaa atcttatagt tctaggcact gtagttctaa
4381  gactcaaatg ttctaagttt ctaagattct aaaggtccac aggtctagac tattaggtgc
4441  aatttcaagg ttctaaccct atactgtagt attctttggg gtgcccctct ccttcttagc
4501  tatcattgct tcctcctccc caactgtggg ggtgtgcccc cttcaagcct gtgcaatgca
4561  ttagggatgc ctcctttccc gcagggatg gacgatctcc cacctttcgg gccatgttgc
4621  ccccgtgagc caatccctca ccttctgagt acagagtgtg gactctggtc cctccagagg
4681  ggctcaggtc acataaaact ttgtatatca acgagaaaaa aaa
```

40

*Homo sapiens* AXL receptor tyrosine kinase (AXL), transcript variant 3, mRNA Accession: NM_001278599.1.

(SEQ ID NO: 8)
```
  1  agcacacgcg taaacaacac gcagaactgc agtcgcactt acaagacttg gtcccagggc
 61  cgggcaccga gtggctctgc ctgcgatcca gcactttggg aggccgaggc gggaggatcg
121  cttggggcca gaagtttgag agcagcctgg gcaacgtggg ctgaacaaga catcctcttt
181  ctcctgcgaa gcccataacg ccaaggggt caccacatcc cgcacagcca ccatcacagt
241  gctcccccag cagccccgta acctccacct ggtctcccgc caacccacgg agctggaggt
301  ggcttggact ccaggcctga gcggcatcta cccctgacc cactgcaccc tgcaggctgt
361  gctgtcagac gatgggatgg catccaggc gggagaacca gaccccccag aggagcccct
421  cacctcgcaa gcatccgtgc cccccatca gcttcggcta ggcagcctcc atcctcacac
481  cccttatcac atccgcgtgg catgcaccag cagccagggc ccctcatcct ggacccactg
541  gcttcctgtg agacgccgg agggagtgcc cctgggcccc ctgagaaca ttagtgctac
601  gcggaatggg agccaggcct tcgtgcattg gcaagagccc cgggcgcccc tgcagggtac
661  cctgttaggg taccggctgg cgtatcaagg ccaggacacc ccagaggtgc taatggacat
721  agggctaagg caagaggtga ccctggagct gcagggggac gggtctgtgt ccaatctgac
```

-continued

```
 781   agtgtgtgtg gcagcctaca ctgctgctgg ggatggaccc tggagcctcc cagtacccct
 841   ggaggcctgg cgcccagggc aagcacagcc agtccaccag ctggtgaagg aaccttcaac
 901   tcctgccttc tcgtggccct ggtggtatgt actgctagga gcagtcgtgg ccgctgcctg
 961   tgtcctcatc ttggctctct tccttgtcca ccggcgaaag aaggagaccc gttatgagaa
1021   agtgtttgaa ccaacagtgg aaagaggtga actggtagtc aggtaccgcg tgcgcaagtc
1081   ctacagtcgt cggaccactg aagctacctt gaacagcctg gcatcagtg aagagctgaa
1141   ggagaagctg cgggatgtga tggtggaccg gcacaaggtg gccctgggga agactctggg
1201   agagggagag tttggagctg tgatggaagg ccagctcaac caggacgact ccatcctcaa
1261   ggtggctgtg aagacgatga agattgccat ctgcacgagg tcagagctgg aggatttcct
1321   gagtgaagcg gtctgcatga aggaatttga ccatcccaac gtcatgaggc tcatcggtgt
1381   ctgtttccag ggttctgaac gagagagctt cccagcacct gtggtcatct acctttcat
1441   gaaacatgga gacctacaca gcttcctcct ctattcccgg ctcggggacc agccagtgta
1501   cctgcccact cagatgctag tgaagttcat ggcagacatc gccagtggca tggagtatct
1561   gagtaccaag agattcatac accgggacct ggcggccagg aactgcatgc tgaatgagaa
1621   catgtccgtg tgtgtggcgg acttcgggct ctccaagaag atctacaatg gggactacta
1681   ccgccaggga cgtatcgcca agatgccagt caagtggatt gccattgaga gtctagctga
1741   ccgtgtctac accagcaaga gcgatgtgtg gtccttcggg gtgacaatgt gggagattgc
1801   cacaagaggc caaaccccat atccgggcgt ggagaacagc gagatttatg actatctgcg
1861   ccagggaaat cgcctgaagc agcctgcgga ctgtctggat ggactgtatg ccttgatgtc
1921   gcggtgctgg gagctaaatc cccaggaccg gccaagtttt acagagctgc gggaagattt
1981   ggagaacaca ctgaaggcct tgcctcctgc ccaggagcct gacgaaatcc tctatgtcaa
2041   catggatgag ggtggaggtt atcctgaacc ccctggagct gcaggaggag ctgacccccc
2101   aacccagcca gaccctaagg attcctgtag ctgcctcact gcggctgagg tccatcctgc
2161   tggacgctat gtcctctgcc cttccacaac ccctagcccc gctcagcctg ctgatagggg
2221   ctccccagca gcccagggc aggaggatgg tgcctgagac aaccctccac ctggtactcc
2281   ctctcaggat ccaagctaag cactgccact ggggaaaact ccaccttccc actttcccac
2341   cccacgcctt atccccactt gcagccctgt cttcctacct atcccacctc catcccagac
2401   aggtccctcc ccttctctgt gcagtagcat caccttgaaa gcagtagcat caccatctgt
2461   aaaaggaagg ggttggattg caatatctga agccctccca ggtgttaaca ttccaagact
2521   ctagagtcca aggtttaaag agtctagatt caaaggttct aggtttcaaa gatgctgtga
2581   gtctttggtt ctaaggacct gaaattccaa agtctctaat tctattaaag tgctaaggtt
2641   ctaaggccta cttttttttt ttttttttt ttttttttt ttgcgataga gtctcactgt
2701   gtcacccagg ctggagtgca gtggtgcaat ctcgcctcac tgcaaccttc acctaccgag
2761   ttcaagtgat tttcctgcct tggcctccca agtagctggg attacaggtg tgtgccacca
2821   cacccggcta atttttatat ttttagtaga cagggtttt caccatgttg gccaggctgg
2881   tctaaaactc ctgacctcaa gtgatctgcc cacctcagcc tcccaaagtg ctgagattac
2941   aggcatgagc cactgcactc aaccttaaga cctactgttc taaagctctg acattatgtg
3001   gttttagatt ttctggttct aacatttttg ataaagcctc aaggttttag gttctaaagt
3061   tctaagattc tgattttagg agctaaggct ctatgagtct agatgtttat tcttctagag
3121   ttcagagtcc ttaaaatgta agattataga ttctaaagat tctatagttc tagacatgga
3181   ggttctaagg cctaggattc taaaatgtga tgttctaagg ctctgagagt ctagattctc
```

-continued

```
3241  tggctgtaag gctctagatc ataaggcttc aaaatgttat cttctcaagt tctaagattc
3301  taatgatgat caattatagt ttctgaggct ttatgataat agattctctt gtataagatc
3361  ctagatccta agggtcgaaa gctctagaat ctgcaattca aaagttccaa gagtctaaag
3421  atggagtttc taaggtccgg tgttctaaga tgtgatattc taagacttac tctaagatct
3481  tagattctct gtgtctaaga ttctagatca gatgctccaa gattctagat gattaaataa
3541  gattctaacg gtctgttctg tttcaaggca ctctagattc cattggtcca agattccgga
3601  tcctaagcat ctaagttata agactctcac actcagttgt gactaactag acaccaaagt
3661  tctaataatt tctaatgttg acacccttta ggttctttgc tgcattctgc ctctctagga
3721  ccatggttaa gagtccaaga atccacattt ctaaaatctt atagttctag cactgtagt
3781  tctaagactc aaatgttcta agtttctaag attctaaagg tccacaggtc tagactatta
3841  ggtgcaattt caaggttcta accctatact gtagtattct ttggggtgcc cctctccttc
3901  ttagctatca ttgcttcctc ctccccaact gtggggggtgt gccccccttca agcctgtgca
3961  atgcattagg gatgcctcct ttcccgcagg ggatggacga tctcccacct ttcgggccat
4021  gttgcccccg tgagccaatc cctcaccttc tgagtacaga gtgtggactc tggtgcctcc
4081  agagggggctc aggtcacata aaactttgta tatcaacgag aaaaaaaa FN14 siRNA Sequence:
     Sense
                               (SEQ ID NO: 3)
     5' CUCAGAUGUCCUGAAAUUCCAUU 3'.
```

*Homo sapiens* TNF receptor superfamily member 12A (TNFRSF12A), mRNA Accession: NM_016639.2.

```
                                                       (SEQ ID NO: 9)
   1   aaggcggggg cgggggcggg gcggcggccg tgggtccctg ccggccggcg gcgggcgcag
  61   acagcggcgg gcgcaggacg tgcactatgg ctcggggctc gctgcgccgg ttgctgcggc
 121   tcctcgtgct ggggctctgg ctggcgttgc tgcgctccgt ggccggggag caagcgccag
 181   gcaccgcccc ctgctcccgc ggcagctcct ggagcgcgga cctggacaag tgcatggact
 241   gcgcgtcttg cagggcgcga ccgcacagcg acttctgcct gggctgcgct gcagcacctc
 301   ctgccccctt ccggctgctt tggcccatcc ttggggcgc tctgagcctg accttcgtgc
 361   tggggctgct ttctggcttt ttggtctgga gacgatgccg caggagagag aagttcacca
 421   cccccataga ggagaccggc ggagagggct gcccagctgt ggcgctgatc cagtgacaat
 481   gtgccccctg ccagccgggg ctcgcccact catcattcat tcatccattc tagagccagt
 541   ctctgcctcc cagacgcggc gggagccaag ctcctccaac cacaaggggg gtgggggcg
 601   gtgaatcacc tctgaggcct gggcccaggg ttcaggggaa ccttccaagg tgtctggttg
 661   ccctgcctct ggctccagaa cagaaaggga gcctcacgct ggctcacaca aaacagctga
 721   cactgactaa ggaactgcag catttgcaca ggggaggggg gtgccctcct tcctagaggc
 781   cctgggggcc aggctgactt ggggggcaga cttgacacta ggccccactc actcagatgt
 841   cctgaaattc caccacgggg gtcaccctgg ggggttaggg acctattttt aacactaggg
 901   ggctggccca ctaggagggc tggccctaag atacagaccc ccccaactcc ccaaagcggg
 961   gaggagatat ttatttttggg gagagtttgg aggggaggga gaatttatta ataaaagaat
1021   ctttaacttt aaaaaaaaaa aaaaaaaa
```

The breadth and scope of the present disclosure should not be limited by any of the above-described exemplary aspects and embodiments, but should be defined only in accordance with the following claims and their equivalents.

What is claimed is:

1. A method of treating a cancer, the method comprising administering, to a subject having non-small cell lung cancer (NSCLC), pancreatic, breast, or colorectal cancer and/or tumor: (i) inhibitors of at least the two biomarker genes AXL and FN14, and (ii) a cancer treatment, wherein the administration kills the cancer and/or delays the growth of and/or reduces the size of the tumor.

2. The method of claim 1, wherein the size of the tumor is reduced by at least about 30%.

3. The method of claim 1, wherein the cancer treatment is an anticancer drug.

4. The method of claim 3, wherein the anticancer drug is a tyrosine kinase inhibitor.

5. The method of claim 4, wherein the anticancer drug is Erlotinib, Cisplatin, Gefitinib, or Dasatinib.

6. The method of claim 1, wherein the AXL inhibitor and FN14 inhibitor are administered by nanoparticle delivery of inhibitory siRNA attached to the surface of a nanoparticle.

7. The method of claim 6, wherein the cancer treatment is an anticancer drug and wherein the anticancer drug is administered by nanoparticle delivery.

8. The method of claim 7, wherein the anticancer drug is administered by nanoparticle delivery with the same nanoparticle delivering at least one of the inhibitory siRNAs.

9. The method of claim 6, wherein the both the AXL inhibitory siRNA and FN14 inhibitory siRNA are administered by nanoparticle delivery of inhibitory siRNA attached to the surface of the same nanoparticle.

10. The method of claim 9, wherein the anticancer drug is administered by nanoparticle delivery with the same nanoparticle delivering both the AXL inhibitory siRNA and the FN14 inhibitory siRNA.

11. The method of claim 6, wherein the nanoparticle is targeted to the tumor via an antibody or antigen-binding portion thereof specific to a cell-surface marker of a tumor cell.

12. The method of claim 1, wherein administration of any of the inhibitors, nanoparticles, and/or anticancer drug is intravenous.

13. The method of claim 1, wherein the growth of the tumor is inhibited or delayed by at least about 30% and/or the size of the tumor is decreased by at least about 30% in comparison to an untreated control.

14. The method of claim 1, wherein the growth of the tumor is inhibited or delayed by at least about 30% and/or the size of the tumor is decreased by at least about 30% in comparison to a control treated with only one of the inhibitors and the cancer treatment.

15. The method of claim 1, wherein the growth of the tumor is inhibited or delayed by at least about 30% and/or the size of the tumor is decreased by at least about 30% in comparison to a control treated with the cancer treatment alone.

* * * * *

```
                          SEQUENCE LISTING

<160> NUMBER OF SEQ ID NOS: 9

<210> SEQ ID NO 1
<211> LENGTH: 19
<212> TYPE: RNA
<213> ORGANISM: Artificial Sequence
<220> FEATURE:
<223> OTHER INFORMATION: Synthetic

<400> SEQUENCE: 1
ggaacugcau gcugaauga                                              19

<210> SEQ ID NO 2
<211> LENGTH: 21
<212> TYPE: RNA
<213> ORGANISM: Artificial Sequence
<220> FEATURE:
<223> OTHER INFORMATION: Synthetic

<400> SEQUENCE: 2
ggaacugcau gcugaaugau u                                           21

<210> SEQ ID NO 3
<211> LENGTH: 23
<212> TYPE: RNA
<213> ORGANISM: Artificial Sequence
<220> FEATURE:
<223> OTHER INFORMATION: Synthetic

<400> SEQUENCE: 3
cucagauguc cugaaauucc auu                                         23

<210> SEQ ID NO 4
<211> LENGTH: 21
<212> TYPE: RNA
<213> ORGANISM: Artificial Sequence
<220> FEATURE:
<223> OTHER INFORMATION: Synthetic

<400> SEQUENCE: 4
cagcuaauuc agaaucauuu u                                           21

<210> SEQ ID NO 5
<211> LENGTH: 20
<212> TYPE: DNA
<213> ORGANISM: Homo sapiens

<400> SEQUENCE: 5
ttcagtggtc cgacgactgt                                             20

<210> SEQ ID NO 6
<211> LENGTH: 4750
<212> TYPE: DNA
<213> ORGANISM: Homo sapiens

<400> SEQUENCE: 6
gtgagggaag gaggcagggg tgctgagaag gcggctgctg ggcagagccg gtggcaaggg    60
cctcccctgc cgctgtgcca ggcaggcagt gccaaatccg gggagcctgg agctgggggg   120
agggccgggg acagcccggc cctgcccct ccccgctgg gagcccaaca acttctgagg    180
aaagtttggc acccatggcg tggcggtgcc ccaggatggg cagggtcccg ctggcctggt   240
```

-continued

```
gcttggcgct gtgcggctgg gcgtgcatgg cccccagggg cacgcaggct gaagaaagtc      300
ccttcgtggg caacccaggg aatatcacag gtgcccgggg actcacgggc acccttcggt      360
gtcagctcca ggttcaggga gagcccccg  aggtacattg gcttcgggat ggacagatcc      420
tggagctcgc ggacagcacc cagacccagg tgcccctggg tgaggatgaa caggatgact      480
ggatagtggt cagccagctc agaatcacct ccctgcagct ttccgacacg ggacagtacc      540
agtgtttggt gtttctggga catcagacct tcgtgtccca gcctggctat gttgggctgg      600
agggcttgcc ttacttcctg gaggagcccg aagacaggac tgtggccgcc aacacccct       660 tcaacctgag ctgccaagct cagggacccc cagagcccgt ggacctactc tggctccagg      720
atgctgtccc cctggccacg gctccaggtc acggccccca gcgcagcctg catgttccag      780
ggctgaacaa gacatcctct ttctcctgcg aagcccataa cgccaagggg gtcaccacat      840
cccgcacagc caccatcaca gtgctccccc agcagccccg taacctccac ctggtctccc      900
gccaacccac ggagctggag gtggcttgga ctccaggcct gagcggcatc taccccctga      960
cccactgcac cctgcaggct gtgctgtcag acgatgggat gggcatccag gcgggagaac     1020
cagacccccc agaggagccc ctcacctcgc aagcatccgt gcccccccat cagcttcggc     1080
taggcagcct ccatcctcac acccttatc  acatccgcgt ggcatgcacc agcagccagg     1140
gcccctcatc ctggacccac tggcttcctg tggagacgcc ggaggagtg  cccctgggcc     1200 cccctgagaa cattagtgct acgcggaatg ggagccaggc cttcgtgcat ggcaagagc      1260 cccgggcgcc cctgcagggt accctgttag ggtaccggct ggcgtatcaa ggccaggaca     1320
ccccagaggt gctaatggac atagggctaa gcaagaggt gaccctggag ctgcaggggg      1380
acgggtctgt gtccaatctg acagtgtgtg tggcagccta cactgctgct ggggatggac     1440
cctggagcct cccagtaccc ctggaggcct ggcgcccagg gcaagcacag ccagtccacc     1500
agctggtgaa ggaaccttca actcctgcct tctcgtggcc ctggtggtat gtactgctag     1560
gagcagtcgt ggccgctgcc tgtgtcctca tcttggctct cttccttgtc caccggcgaa     1620
agaaggagac ccgttatgga gaagtgtttg aaccaacagt ggaaagaggt gaactggtag     1680
tcaggtaccg cgtgcgcaag tcctacagtc gtcggaccac tgaagctacc ttgaacagcc     1740
tgggcatcag tgaagagctg aaggagaagc tgcgggatgt gatggtggac cggcacaagg     1800
tggccctggg gaagactctg ggagagggag agtttggagc tgtgatggaa ggccagctca     1860
accaggacga ctccatcctc aaggtggctg tgaagacgat gaagattgcc atctgcacga     1920
ggtcagagct ggaggatttc ctgagtgaag cggtctgcat gaaggaattt gaccatccca     1980
acgtcatgag gctcatcggt gtctgttttc agggttctga acgagagagc ttcccagcac     2040
ctgtggtcat cttaccttc  atgaaacatg gagacctaca cagcttcctc ctctattccc     2100
ggctcgggga ccagccagtg tacctgccca ctcagatgct agtgaagttc atggcagaca     2160
tcgccagtgg catggagtat ctgagtacca agagattcat acaccgggac ctggcggcca     2220
ggaactgcat gctgaatgag aacatgtccg tgtgtgtggc ggacttcggg ctctccaaga     2280
agatctacaa tggggactac taccgccagg acgtatcgc  caagatgcca gtcaagtgga     2340
ttgccattga gagtctagct gaccgtgtct acaccagcaa gagcgatgtg tggtccttcg     2400
gggtgacaat gtgggagatt gccacaagag gccaaacccc atatccgggc gtggagaaca     2460
gcgagattta tgactatctg cgccaggaa  atcgcctgaa gcagcctgcg gactgtctgg     2520
atggactgta tgccttgatg tcgcggtgct gggagctaaa tccccaggac cggccaagtt     2580
ttacagagct gcgggaagat ttggagaaca cactgaaggc cttgcctcct gcccaggagc     2640
```

```
ctgacgaaat cctctatgtc aacatggatg agggtggagg ttatcctgaa cccctggag    2700
ctgcaggagg agctgacccc ccaacccagc cagaccctaa ggattcctgt agctgcctca    2760
ctgcggctga ggtccatcct gctggacgct atgtcctctg cccttccaca accctagcc    2820
ccgctcagcc tgctgatagg ggctccccag cagcccagg gcaggaggat ggtgcctgag    2880
acaaccctcc acctggtact ccctctcagg atccaagcta agcactgcca ctggggaaaa    2940
ctccaccttc ccactttccc accccacgcc ttatccccac ttgcagccct gtcttcctac    3000
ctatcccacc tccatcccag acaggtccct cccttctct gtgcagtagc atcaccttga    3060
aagcagtagc atcaccatct gtaaaaggaa ggggttggat tgcaatatct gaagccctcc    3120
caggtgttaa cattccaaga ctctagagtc caaggtttaa agagtctaga ttcaaaggtt    3180
ctaggtttca aagatgctgt gagtctttgg ttctaaggac ctgaaattcc aaagtctcta    3240
attctattaa agtgctaagg ttctaaggcc tacttttttt tttttttttt tttttttttt    3300
ttttgcgata gagtctcact gtgtcaccca ggctggagtg cagtggtgca atctcgcctc    3360
actgcaacct tcacctaccg agttcaagtg attttcctgc cttggcctcc caagtagctg    3420
ggattacagg tgtgtgccac cacacccggc taatttttat attttttagta gagacagggt    3480
ttcaccatgt tggccaggct ggtctaaaac tcctgacctc aagtgatctg cccacctcag    3540
cctcccaaag tgctgagatt acaggcatga gccactgcac tcaaccttaa gacctactgt    3600
tctaaagctc tgacattatg tggttttaga ttttctggtt ctaacatttt tgataaagcc    3660
tcaaggtttt aggttctaaa gttctaagat tctgatttta ggagctaagg ctctatgagt    3720
ctagatgttt attcttctag agttcagagt ccttaaaatg taagattata gattctaaag    3780
attctatagt tctagacatg gaggttctaa ggcctaggat tctaaaatgt gatgttctaa    3840
ggctctgaga gtctagattc tctggctgta aggctctaga tcataaggct tcaaaatgtt    3900
atcttctcaa gttctaagat tctaatgatg atcaattata gtttctgagg ctttatgata    3960
atagattctc ttgtataaga tcctagatcc taagggtcga agctctaga atctgcaatt    4020
caaaagttcc aagagtctaa agatggagtt tctaaggtcc ggtgttctaa gatgtgatat    4080
tctaagactt actctaagat cttagattct ctgtgtctaa gattctagat cagatgctcc    4140
aagattctag atgattaaat aagattctaa cggtctgttc tgtttcaagg cactctagat    4200
tccattggtc caagattccg gatcctaagc atctaagtta taagactctc acactcagtt    4260
gtgactaact agacaccaaa gttctaataa tttctaatgt tggacacctt taggttcttt    4320
gctgcattct gcctctctag gaccatggtt aagagtccaa gaatccacat ttctaaaatc    4380
ttatagttct aggcactgta gttctaagac tcaaatgttc taagtttcta agattctaaa    4440
ggtccacagg tctagactat taggtgcaat ttcaaggttc taaccctata ctgtagtatt    4500
ctttggggtg cccctctcct tcttagctat cattgcttcc tcctcccaa ctgtggggt    4560
gtgccccctt caagcctgtg caatgcatta gggatgcctc ctttcccgca ggggatggac    4620
gatctcccac ctttcgggcc atgttgcccc cgtgagccaa tccctcacct tctgagtaca    4680
gagtgtggac tctggtgcct ccagagggc tcaggtcaca taaaactttg tatatcaacg    4740
agaaaaaaaa                                                           4750
```

<210> SEQ ID NO 7
<211> LENGTH: 4723
<212> TYPE: DNA
<213> ORGANISM: Homo sapiens

<400> SEQUENCE: 7

```
gtgagggaag gaggcagggg tgctgagaag gcggctgctg ggcagagccg gtggcaaggg      60
cctcccctgc cgctgtgcca ggcaggcagt gccaaatccg gggagcctgg agctgggggg     120
agggccgggg acagcccggc cctgccccct ccccgctgg gagcccaaca acttctgagg      180
aaagtttggc acccatggcg tggcggtgcc ccaggatggg cagggtcccg ctggcctggt     240
gcttggcgct gtgcggctgg gcgtgcatgg cccccagggg cacgcaggct gaagaaagtc     300
ccttcgtggg caacccaggg aatatcacag gtgcccgggg actcacgggc acccttcggt     360
gtcagctcca ggttcaggga gaccccccg aggtacattg gcttcgggat ggacagatcc      420
tggagctcgc ggacagcacc cagacccagg tgcccctggg tgaggatgaa caggatgact     480
ggatagtggt cagccagctc agaatcacct ccctgcagct ttccgacacg ggacagtacc     540
agtgtttggt gtttctggga catcagacct tcgtgtccca gcctggctat gttgggctgg     600
agggcttgcc ttacttcctg gaggagcccg aagacaggac tgtggccgcc aacaccccct     660
tcaacctgag ctgccaagct cagggacccc cagagcccgt ggacctactc tggctccagg     720
atgctgtccc cctggccacg gctccaggtc acggccccca gcgcagcctg catgttccag     780
ggctgaacaa gacatcctct ttctcctgcg aagcccataa cgccaagggg gtcaccacat     840
cccgcacagc caccatcaca gtgctccccc agcagccccg taacctccac ctggtctccc     900
gccaacccac ggagctggag gtggcttgga ctccaggcct gagcggcatc taccccctga     960
cccactgcac cctgcaggct gtgctgtcag acgatgggat gggcatccag gcgggagaac    1020
cagaccccca agaggagccc ctcacctcgc aagcatccgt gcccccccat cagcttcggc    1080
taggcagcct ccatcctcac accccttatc acatccgcgt ggcatgcacc agcagccagg    1140
gcccctcatc ctggacccac tggcttcctg tggagacgcc ggagggagtg cccctgggcc    1200
cccctgagaa cattagtgct acgcggaatg ggagccaggc cttcgtgcat tggcaagagc    1260
cccgggcgcc cctgcagggt accctgttag ggtaccggct ggcgtatcaa ggccaggaca    1320
ccccagaggt gctaatggac atagggctaa ggcaagaggt gaccctggag ctgcagggga    1380
acgggtctgt gtccaatctg acagtgtgtg tggcagccta cactgctgct ggggatggac    1440
cctggagcct cccagtaccc ctggaggcct ggcgcccagt gaaggaacct tcaactcctg    1500
ccttctcgtg gccctggtgg tatgtactgc taggagcagt cgtggccgct gcctgtgtcc    1560
tcatcttggc tctcttcctt gtccaccggc gaaagaagga gacccgttat ggagaagtgt    1620
ttgaaccaac agtggaaaga ggtgaactgg tagtcaggta ccgcgtgcgc aagtcctaca    1680
gtcgtcggac cactgaagct accttgaaca gcctgggcat cagtgaagag ctgaaggaga    1740
agctgcggga tgtgatggtg gaccggcaca ggtggcccct ggggaagact ctgggagagg    1800
gagagtttgg agctgtgatg gaaggccagc tcaaccagga cgactccatc ctcaaggtgg    1860
ctgtgaagac gatgaagatt gccatctgca cgaggtcaga gctggaggat ttcctgagtg    1920
aagcggtctg catgaaggaa tttgaccatc ccaacgtcat gaggctcatc ggtgtctgtt    1980
tccagggttc tgaacgagag agcttcccag cacctgtggt catcttacct ttcatgaaac    2040
atggagacct acacagcttc ctcctctatt cccggctcgg ggaccagcca gtgtacctgc    2100
ccactcagat gctagtgaag ttcatggcag acatcgccag tggcatggag tatctgagta    2160
ccaagagatt catacaccgg gacctggcgg ccaggaactg catgctgaat gagaacatgt    2220
ccgtgtgtgt ggcggacttc gggctctcca agaagatcta caatgggggac tactaccgcc    2280
agggacgtat cgccaagatg ccagtcaagt ggattgccat tgagagtcta gctgaccgtg    2340
```

```
tctacaccag caagagcgat gtgtggtcct tcggggtgac aatgtgggag attgccacaa    2400
gaggccaaac cccatatccg ggcgtggaga acagcgagat ttatgactat ctgcgccagg    2460
gaaatcgcct gaagcagcct gcggactgtc tggatggact gtatgccttg atgtcgcggt    2520
gctgggagct aaatccccag gaccggccaa gttttacaga gctgcgggaa gatttggaga    2580
acacactgaa ggccttgcct cctgcccagg agcctgacga atcctctat gtcaacatgg     2640 atgagggtgg aggttatcct gaaccccctg gagctgcagg aggagctgac ccccaaccc    2700 agccagaccc taaggattcc tgtagctgcc tcactgcggc tgaggtccat cctgctggac    2760
gctatgtcct ctgcccttcc acaaccccta gccccgctca gcctgctgat aggggctccc    2820
cagcagcccc agggcaggag gatggtgcct gagacaaccc tccacctggt actccctctc    2880
aggatccaag ctaagcactg ccactgggga aaactccacc ttcccacttt cccaccccac    2940
gccttatccc cacttgcagc cctgtcttcc tacctatccc acctccatcc cagacaggtc    3000
cctccccttc tctgtgcagt agcatcacct tgaaagcagt agcatcacca tctgtaaaag    3060
gaaggggttg gattgcaata tctgaagccc tcccaggtgt taacattcca agactctaga    3120
gtccaaggtt taaagagtct agattcaaag gttctaggtt tcaaagatgc tgtgagtctt    3180
tggttctaag gacctgaaat tccaaagtct ctaattctat taaagtgcta aggttctaag    3240
gcctactttt tttttttttt tttttttttt tttttttgcg atagagtctc actgtgtcac    3300
ccaggctgga gtgcagtggt gcaatctcgc tcactgcaa ccttcaccta ccgagttcaa     3360
gtgattttcc tgccttggcc tcccaagtag ctgggattac aggtgtgtgc caccacaccc    3420
ggctaatttt tatattttta gtagagacag ggtttcacca tgttggccag gctggtctaa    3480
aactcctgac ctcaagtgat ctgcccacct cagcctccca aagtgctgag attacaggca    3540
tgagccactg cactcaacct taagacctac tgttctaaag ctctgacatt atgtggtttt    3600
agattttctg gttctaacat ttttgataaa gcctcaaggt tttaggttct aaagttctaa    3660
gattctgatt ttaggagcta aggctctatg agtctagatg tttattcttc tagagttcag    3720
agtccttaaa atgtaagatt atagattcta aagattctat agttctagac atggaggttc    3780
taaggcctag gattctaaaa tgtgatgttc taaggctctg agagtctaga ttctctggct    3840
gtaaggctct agatcataag gcttcaaaat gttatcttct caagttctaa gattctaatg    3900
atgatcaatt atagtttctg aggctttatg ataatagatt ctcttgtata agatcctaga    3960
tcctaagggt cgaaagctct agaatctgca attcaaaagt tccaagagtc taaagatgga    4020
gtttctaagg tccggtgttc taagatgtga tattctaaga cttactctaa gatcttagat    4080
tctctgtgtc taagattcta gatcagatgc tccaagattc tagatgatta aataagattc    4140
taacggtctg ttctgtttca aggcactcta gattccattg gtccaagatt ccggatccta    4200
agcatctaag ttataagact ctcacactca gttgtgacta actagacacc aaagttctaa    4260
taatttctaa tgttggacac ctttaggttc tttgctgcat tctgcctctc taggaccatg    4320
gttaagagtc caagaatcca catttctaaa atcttatagt tctaggcact gtagttctaa    4380
gactcaaatg ttctaagttt ctaagattct aaaggtccac aggtctagac tattaggtgc    4440
aatttcaagg ttctaaccct atactgtagt attcctttggg gtgcccctct ccttcttagc    4500
tatcattgct tcctcctccc caactgtggg ggtgtgcccc cttcaagcct gtgcaatgca    4560
ttagggatgc ctcctttccc gcaggggatg gacgatctcc cacctttcgg gccatgttgc    4620
```

| | | | | | |
|---|---|---|---|---|---|
| cccgtgagc | caatccctca | ccttctgagt | acagagtgtg | gactctggtg | cctccagagg | 4680 |
| ggctcaggtc | acataaaact | ttgtatatca | acgagaaaaa | aaa | | 4723 |

<210> SEQ ID NO 8
<211> LENGTH: 4128
<212> TYPE: DNA
<213> ORGANISM: Homo sapiens

<400> SEQUENCE: 8

| | | | | | |
|---|---|---|---|---|---|
| agcacacgcg | taaacaacac | gcagaactgc | agtcgcactt | acaagacttg | gtcccagggc | 60 |
| cgggcaccga | gtggctctgc | ctgcgatcca | gcactttggg | aggccgaggc | gggaggatcg | 120 |
| cttggggcca | gaagtttgag | agcagcctgg | gcaacgtggg | ctgaacaaga | catcctcttt | 180 |
| ctcctgcgaa | gccataacg | ccaagggggt | caccacatcc | cgcacagcca | ccatcacagt | 240 |
| gctcccccag | cagccccgta | acctccacct | ggtctcccgc | caacccacgg | agctggaggt | 300 |
| ggcttggact | ccaggcctga | gcggcatcta | cccctgacc | cactgcaccc | tgcaggctgt | 360 |
| gctgtcagac | gatgggatgg | gcatccaggc | gggagaacca | gacccccag | aggagcccct | 420 |
| cacctcgcaa | gcatccgtgc | cccccatca | gcttcggcta | gcagcctcc | atcctcacac | 480 |
| cccttatcac | atccgcgtgg | catgcaccag | cagccagggc | ccctcatcct | ggacccactg | 540 |
| gcttcctgtg | gagacgccgg | agggagtgcc | cctgggcccc | cctgagaaca | ttagtgctac | 600 |
| gcggaatggg | agccaggcct | tcgtgcattg | gcaagagccc | cgggcgcccc | tgcagggtac | 660 |
| cctgttaggg | taccggctgg | cgtatcaagg | ccaggacacc | ccagaggtgc | taatggacat | 720 |
| agggctaagg | caagaggtga | ccctggagct | gcaggggac | gggtctgtgt | ccaatctgac | 780 |
| agtgtgtgtg | gcagcctaca | ctgctgctgg | ggatggaccc | tggagcctcc | cagtaccct | 840 |
| ggaggcctgg | cgcccaggc | aagcacagcc | agtccaccag | ctggtgaagg | aaccttcaac | 900 |
| tcctgccttc | tcgtggccct | ggtggtatgt | actgctagga | gcagtcgtgg | ccgctgcctg | 960 |
| tgtcctcatc | ttggctctct | tccttgtcca | ccggcgaaag | aaggagaccc | gttatggaga | 1020 |
| agtgtttgaa | ccaacagtgg | aaagaggtga | actggtagtc | aggtaccgcg | tgcgcaagtc | 1080 |
| ctacagtcgt | cggaccactg | aagctacctt | gaacagcctg | gcatcagtg | aagagctgaa | 1140 |
| ggagaagctg | cgggatgtga | tggtggaccg | gcacaaggtg | gccctgggga | agactctggg | 1200 |
| agagggagag | tttggagctg | tgatggaagg | ccagctcaac | caggacgact | ccatcctcaa | 1260 |
| ggtggctgtg | aagacgatga | agattgccat | ctgcacgagg | tcagagctgg | aggatttcct | 1320 |
| gagtgaagcg | gtctgcatga | aggaatttga | ccatccaac | gtcatgaggc | tcatcggtgt | 1380 |
| ctgtttccag | ggttctgaac | gagagagctt | cccagcacct | gtggtcatct | acctttcat | 1440 |
| gaaacatgga | gacctacaca | gcttcctcct | ctattcccgg | ctcggggacc | agccagtgta | 1500 |
| cctgcccact | cagatgctag | tgaagttcat | ggcagacatc | gccagtggca | tggagtatct | 1560 |
| gagtaccaag | agattcatac | accgggacct | ggcggccagg | aactgcatgc | tgaatgagaa | 1620 |
| catgtccgtg | tgtgtggcgg | acttcgggct | ctccaagaag | atctacaatg | ggactacta | 1680 |
| ccgccaggga | cgtatcgcca | agatgccagt | caagtggatt | gccattgaga | gtctagctga | 1740 |
| ccgtgtctac | accagcaaga | gcgatgtgtg | gtccttcggg | gtgacaatgt | gggagattgc | 1800 |
| cacaagaggc | caaaccccat | atccgggcgt | ggagaacagc | gagatttatg | actatctgcg | 1860 |
| ccagggaaat | cgcctgaagc | agcctgcgga | ctgtctggat | ggactgtatg | ccttgatgtc | 1920 |
| gcggtgctgg | gagctaaatc | cccaggaccg | gccaagtttt | acagagctgc | gggaagattt | 1980 |

```
ggagaacaca ctgaaggcct tgcctcctgc ccaggagcct gacgaaatcc tctatgtcaa    2040
catggatgag ggtggaggtt atcctgaacc ccctggagct gcaggaggag ctgacccccc    2100
aacccagcca gaccctaagg attcctgtag ctgcctcact gcggctgagg tccatcctgc    2160
tggacgctat gtcctctgcc cttccacaac ccctagcccc gctcagcctg ctgatagggg    2220
ctccccagca gccccagggc aggaggatgg tgcctgagac aaccctccac ctggtactcc    2280
ctctcaggat ccaagctaag cactgccact ggggaaaact ccaccttccc actttcccac    2340
cccacgcctt atccccactt gcagccctgt cttcctacct atcccacctc catcccagac    2400
aggtccctcc ccttctctgt gcagtagcat caccttgaaa gcagtagcat caccatctgt    2460
aaaaggaagg ggttggattg caatatctga agccctccca ggtgttaaca ttccaagact    2520
ctagagtcca aggtttaaag agtctagatt caaaggttct aggtttcaaa gatgctgtga    2580
gtctttggtt ctaaggacct gaaattccaa agtctctaat tctattaaag tgctaaggtt    2640
ctaaggccta cttttttttt ttttttttt ttttttttt ttgcgataga gtctcactgt    2700
gtcacccagg ctggagtgca gtggtgcaat ctcgcctcac tgcaaccttc acctaccgag    2760
ttcaagtgat tttcctgcct tggcctccca agtagctggg attacaggtg tgtgccacca    2820
cacccggcta attttatat ttttagtaga cagggtttt caccatgttg gccaggctgg    2880
tctaaaactc ctgacctcaa gtgatctgcc cacctcagcc tcccaaagtg ctgagattac    2940
aggcatgagc cactgcactc aaccttaaga cctactgttc taaagctctg acattatgtg    3000
gttttagatt ttctggttct aacattttg ataaagcctc aaggttttag gttctaaagt    3060
tctaagattc tgattttagg agctaaggct ctatgagtct agatgtttat tcttctagag    3120
ttcagagtcc ttaaaatgta agattataga ttctaaagat tctatagttc tagacatgga    3180
ggttctaagg cctaggattc taaaatgtga tgttctaagg ctctgagagt ctagattctc    3240
tggctgtaag gctctagatc ataaggcttc aaaatgttat cttctcaagt tctaagattc    3300
taatgatgat caattatagt ttctgaggct ttatgataat agattctctt gtataagatc    3360
ctagatccta agggtcgaaa gctctagaat ctgcaattca aagttccaa gagtctaaag    3420 atggagtttc taaggtccgg tgttctaaga tgtgatattc taagacttac tctaagatct    3480
tagattctct gtgtctaaga ttctagatca gatgctccaa gattctagat gattaaataa    3540
gattctaacg gtctgttctg tttcaaggca ctctagattc cattggtcca agattccgga    3600
tcctaagcat ctaagttata agactctcac actcagttgt gactaactag acaccaaagt    3660
tctaataatt tctaatgttg gacacccttta ggttctttgc tgcattctgc ctctctagga    3720
ccatggttaa gagtccaaga atccacattt ctaaaatctt atagttctag gcactgtagt    3780
tctaagactc aaatgttcta agtttctaag attctaaagg tccacaggtc tagactatta    3840
ggtgcaattt caaggttcta accctatact gtagtattct ttggggtgcc cctctccttc    3900
ttagctatca ttgcttcctc ctccccaact gtggggtgt gcccccttca agcctgtgca    3960
atgcattagg gatgcctcct ttcccgcagg ggatggacga tctcccacct ttcgggccat    4020
gttgcccccg tgagccaatc cctcaccttc tgagtacaga gtgtggactc tggtgcctcc    4080 agagggctc aggtcacata aaactttgta tatcaacgag aaaaaaaa              4128
```

<210> SEQ ID NO 9
<211> LENGTH: 1048
<212> TYPE: DNA
<213> ORGANISM: Homo sapiens

<400> SEQUENCE: 9

```
aaggcggggg cggggcggg gcggcggccg tgggtccctg ccggccggcg gcgggcgcag      60
acagcggcgg gcgcaggacg tgcactatgg ctcgggctc gctgcgccgg ttgctgcggc     120
tcctcgtgct ggggctctgg ctggcgttgc tgcgctccgt ggccggggag caagcgccag    180
gcaccgcccc ctgctcccgc ggcagctcct ggagcgcgga cctggacaag tgcatggact    240
gcgcgtcttg cagggcgcga ccgcacagcg acttctgcct gggctgcgct gcagcacctc    300
ctgccccctt ccggctgctt tgcccatcc ttgggggcgc tctgagcctg accttcgtgc    360
tggggctgct ttctggcttt ttggtctgga gacgatgccg caggagagag aagttcacca    420
cccccataga ggagaccggc ggagagggct gcccagctgt ggcgctgatc cagtgacaat    480 gtgcccctg ccagccgggg ctcgcccact catcattcat tcatccattc tagagccagt    540
ctctgcctcc cagacgcggc gggagccaag ctcctccaac cacaaggggg gtgggggcg    600 gtgaatcacc tctgaggcct gggcccaggg ttcaggggaa ccttccaagg tgtctggttg    660
ccctgcctct ggctccagaa cagaaaggga gcctcacgct ggctcacaca aaacagctga    720
cactgactaa ggaactgcag catttgcaca ggggagggg gtgccctcct tcctagaggc    780
cctgggggcc aggctgactt ggggggcaga cttgacacta ggcccactc actcagatgt    840 cctgaaattc caccacgggg gtcaccctgg gggttaggg acctatttt aacactaggg    900 ggctggccca ctaggagggc tggccctaag atacagaccc ccccaactcc ccaaagcggg    960
gaggagatat ttattttggg gagagtttgg aggggaggga gaatttatta ataaaagaat   1020
ctttaacttt aaaaaaaaaa aaaaaaa                                      1048
```